US008431704B2

(12) United States Patent
Love et al.

(10) Patent No.: US 8,431,704 B2
(45) Date of Patent: Apr. 30, 2013

(54) QUINOLINE OR ISOQUINOLINE SUBSTITUTED P2X7 ANTAGONISTS

(75) Inventors: Christopher John Love, Hampshire (GB); Joseph Elisabeth Leenaerts, Rijkevorsel (BE); Ludwig Paul Cooymans, Beerse (BE); Donald Alec Lebsack, San Diego, CA (US); Bryan James Branstetter, Oceanside, CA (US); Jason Christopher Rech, San Diego, CA (US); Elizabeth Ann Gleason, La Mesa, CA (US); Jennifer Diane Venable, Solana Beach, CA (US); Danielle Wiener, La Jolla, CA (US); Deborah Margaret Smith, San Diego, CA (US); James Guy Breitenbucher, Escondido, CA (US)

(73) Assignee: Janssen Pharmaceutica NV, Beerse (BE)

( * ) Notice: Subject to any disclaimer, the term of this patent is extended or adjusted under 35 U.S.C. 154(b) by 297 days.

(21) Appl. No.: 12/988,891

(22) PCT Filed: Apr. 21, 2009

(86) PCT No.: PCT/US2009/041249
§ 371 (c)(1),
(2), (4) Date: Dec. 17, 2010

(87) PCT Pub. No.: WO2009/132000
PCT Pub. Date: Oct. 29, 2009

(65) Prior Publication Data
US 2011/0092481 A1 Apr. 21, 2011

(30) Foreign Application Priority Data
Apr. 22, 2008 (EP) .................... 08154909

(51) Int. Cl.
*C07D 215/38* (2006.01)
(52) U.S. Cl.
USPC .......................... 546/146; 546/169
(58) Field of Classification Search .......... 546/146, 546/169
See application file for complete search history.

(56) References Cited

U.S. PATENT DOCUMENTS

2006/0217448 A1 9/2006 Kelly et al.
2006/0293337 A1 12/2006 Evans et al.

FOREIGN PATENT DOCUMENTS

WO WO 2006 080884 A1 8/2006
WO WO 2006 110516 A1 10/2006

OTHER PUBLICATIONS

Database Chemcats Ryan Scientific Screening library database accession 2042676574 (Jan. 25, 2008).*
European Search Report for corresponding EP Application 08154909.9 mailed on Jun. 20, 2008.
International Search Report for corresponding PCT Application PCT/US2009/041249 mailed on Jul. 31, 2009.
Hudson et al "Methodological Implications of Simultaneous Solid-Phase Peptide Syntehsis. 1. Comparison of Different Coupling Procedures" J Org Chem 1988 vol. 53 pp. 617-624.
Dyatkin et al "Determination of the Absolute Configuration of a Key Tricyclic Component of a Novel Vasopressing Receptor Antagonist by Use of Vibrational Circular Dichroism" Chirality 2002 vol. 14 pp. 215-219.
Database Chemcats Enamine Screening Library Database Accession 2035772210 Jan. 17, 2008.
Database Chemcats Ukrorgsynthesis Screeing Collection Accession 2033253463 Mar. 6, 2007.
Database Chemcats Ryan Scientific Screening Library Database Accession 2042676574 Jan. 25, 2008.
Database Chemcats Ambinter Stock Screeing Collection Database Accession 2046454718 Feb. 13, 2008.
Database Chemcats Ryan Scientific Screening Library Database Accession 2043876860 Jan. 25, 2008.
Database Chemcats Ryan Scientific Screening Library Database Accession 2042637020 Jan. 25, 2008.
Database Chemcats Ryan Scientific Screening Library Database Accession 2042634059 Jan. 25, 2008.
Database Chemcats Ambinter Stock Screening Collection Database Accession 2040548370 Feb. 13, 2008.
Database Chemcats Ambinter Stock Screening Collection Database Accession 2040381923 Feb. 13, 2008.
Database Chemcats Ambinter Stock Screening Collection Database Accession 2040033692 Feb. 13, 2008.
Database Chemcats Aurora Screening Library Database Accession 2037938546 Sep. 6, 2007.

* cited by examiner

*Primary Examiner* — D M Seaman
(74) *Attorney, Agent, or Firm* — Michael J. Atkins

(57) ABSTRACT

The present invention is related to novel compounds of formula (I) having P2X7 antagonistic properties, pharmaceutical compositions comprising these compounds, chemical processes for preparing these compounds and their use in the treatment or prophylaxis of diseases associated with P2X7 receptor activity in animals, in particular humans. (I).

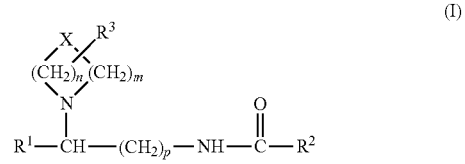

12 Claims, No Drawings

QUINOLINE OR ISOQUINOLINE SUBSTITUTED P2X7 ANTAGONISTS

CROSS-REFERENCE TO RELATED APPLICATIONS

This application is a national phase of International Application No. PCT/US2009/041249 filed on Apr. 21, 2009, which application claims priority from EP08154909.9 filed on Apr. 22, 2008.

The present invention is related to novel compounds of formula (I) having P2X7 antagonistic properties, pharmaceutical compositions comprising these compounds, chemical processes for preparing these compounds and their use in the treatment or prophylaxis of diseases associated with P2X7 receptor activity in animals, in particular humans.

The P2X7 receptor is a ligand-gated ion channel and is present on a variety of cell types, largely those known to be involved in the inflammatory/immune process, specifically, macrophages, mast cells and lymphocytes (T and B). Activation of the P2X7 receptor by extracellular nucleotides, in particular adenosine triphosphate, leads to the release of interleukin-P (IL-1 P) and giant cell formation (macrophages/microglial cells), degranulation (mast cells) and L-selectin shedding (lymphocytes). P2X7 receptors are also located on antigen-presenting cells (APQ, keratinocytes, salivary acinar cells (parotid cells), hepatocytes, erythrocytes, erythroleukaemic cells, monocytes, fibroblasts, bone marrow cells, neurones, and renal mesangial cells.

The P2X7 receptor is also known to be a pain sensor in the nervous system. Experiments using P2X7 deficient mice demonstrate the role of P2X7 in the development of pain as these mice were protected from the development of both adjuvant-induced inflammatory pain and partial nerve ligation induced neuropathic pain.

In view of the clinical importance of P2X7, the identification of compounds that modulate P2X7 receptor function represents an attractive avenue into the development of new therapeutic agents. Such compounds are provided herein.

The present invention relates to a compound of formula (I)

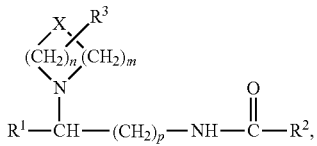

(I)

including any stereochemically isomeric form thereof, wherein n is an integer 1, 2 or 3;
m is an integer 1, 2 or 3;
p is an integer 1 or 2;
$R^3$ is hydrogen, halo, $C_{1-4}$alkyl or $C_{1-4}$alkyloxy;
X represents O, S, $SO_2$, $CR^4R^5$ or $NR^6$;
  wherein $R^4$ and $R^5$ are each independently from another selected from hydrogen, halo, hydroxy, $C_{1-4}$alkyl, $C_{1-4}$alkyloxy, or aryl;
  wherein $R^6$ is hydrogen, phenyl, —CO—$R^7$, or —CO—O—$R^7$, wherein $R^7$ is $C_{1-6}$alkyl or amino;
$R^1$ is a heterocycle selected from pyridinyl or pyrimidinyl, wherein said heterocycle is substituted with one or two substituents each independently from another selected from hydrogen, halo, hydroxy, $C_{1-6}$alkyl, $C_{1-6}$alkyloxy, polyhalo$C_{1-4}$alkyl, phenyl, $C_{3-6}$cycloalkyl, $C_{3-6}$cycloalkyloxy, $C_{3-6}$cycloalkyl$C_{1-4}$alkyloxy, or $NR^8R^9$;
  wherein $R^8$ and $R^9$ are independently from another selected from hydrogen, $C_{1-6}$alkyl, hydroxy$C_{1-6}$alkyl, $C_{3-6}$cycloalkyl, and
  wherein $R^8$ and $R^9$ may be taken together with the nitrogen atom to which they are attached to form a azetidinyl, pyrrolidinyl, piperidinyl, piperazinyl or morpholinyl ring which may be optionally substituted with one or two substituents each independently from another selected from $C_{1-4}$alkyl, $C_{1-4}$alkyloxy, halo, hydroxy, or $C_{1-4}$alkylcarbonyl;
$R^2$ is a heterocycle selected from quinolinyl or isoquinolinyl, wherein said heterocycle is substituted with one or two substituents each independently from another selected from hydrogen, halo, hydroxy, $C_{1-6}$alkyl, $C_{1-6}$alkyloxy, $C_{3-6}$cycloalkyl, $C_{3-6}$cycloalkyloxy, polyhalo$C_{1-4}$alkyl, $NR^{10}R^{11}$, and $OR^{12}$;
  wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, piperidinyl, N-(1,5-dioxa-9-aza-spiro[5.5]undec-9-yl), N-(1,7-diaza-spiro[4.4]non-7-yl), N-(2,6-diaza-spiro[4.5]dec-2-yl), and $C_{1-6}$alkyl substituted with one or two substituents selected from hydroxy, halo, aryl[1], $C_{1-4}$alkyloxy, $C_{3-6}$cycloalkyl, hydroxycarbonyl, $C_{1-4}$alkylsulfonylamino, $C_{3-6}$cycloalkylsulfonylamino, tetrahydrofuranyl, tetrahydropyranyl, pyrrolidinyl, pyridinyl, morpholinyl, amino, mono- or di($C_{1-4}$alkyl)amino, amino substituted with $C_{1-4}$alkyl substituted with hydroxy; and
  wherein $R^{10}$ and $R^{11}$ may be taken together with the nitrogen atom to which they are attached to form a azetidinyl, pyrrolidinyl, piperidinyl, piperazinyl, azepanyl, N-[1,4]-oxazepanyl, morpholinyl, N-(2,6-diaza-spiro[3.3]hept-2-yl), 6-acetyl-2,6-diaza-bicyclo[2.2.2]octane-2-yl, 2-(tetrahydro-furo[3,4-c]pyrrol-5-yl), 2-(2-oxa-5-aza-bicyclo[2.2.1]hept-5-yl), 1,1-dioxo-thiomorpholin-4-yl, 2-(2,6-diaza-bicyclo[2.2.1]hept-2-yl), 1-(1-amino-3-aza-bicyclo[3.1.0]hex-3-yl), N-(3-acetylamino-8-aza-bicyclo[3.2.1]oct-8-yl), N-[1,4]-diazepanyl, 2-(hexahydro-pyrrolo[3,4-c]pyrrol-2-yl), 2-(hexahydro-pyrrolo[3,4-b]pyrrol-1-yl), 2-(hexahydro-pyrrolo[3,4-b]pyrrol-5-yl), 2-(octahydro-pyrrolo[3,4-b]pyridin-6-yl), or 2-(3,6-diaza-bicyclo[3.2.0]hept-3-yl), 1-amino-3-aza-bicyclo[3.1.0]hex-3-yl ring; which may be optionally substituted with one or two substituents each independently from another selected from halo, hydroxy, $C_{1-4}$alkyl, $C_{1-4}$alkyloxy, $C_{1-4}$alkyloxy$C_{1-4}$ alkyl, $C_{3-6}$cycloalkyl, $C_{1-4}$alkylcarbonyl, $C_{1-4}$alkyloxycarbonyl, $C_{1-4}$alkyloxycarbonylamino, $C_{1-6}$alkyl substituted with hydroxy; trifluoromethyl, amino, mono- or di($C_{1-4}$alkyl)amino, amino, mono- or di($C_{1-4}$ alkyl)amino, trifluoromethyl, N-(2-oxo-pyrrolidin-1-yl), 2,4-dihydro-[1,2,4]triazolone-5-yl, $C_{1-4}$alkylcarbonylamino, 2,4-dihydro-[1,2,4]triazolone-4-yl, ($C_{1-4}$ alkylcarbonyl)($C_{1-4}$alkyl)amino, trifluoromethylcarbonylamino, hydroxycarbonyl, methylsulfonylamino, aminocarbonyl;
  wherein $R^{12}$ is azetidinyl, pyrrolidinyl, piperidinyl, or $C_{1-6}$alkyl substituted with amino, $C_{3-6}$cycloalkyl, trifluoromethyl, trifluoroethyl, tetrahydrofuranyl, N-(1-methylpyrrolidinyl), N-(5-oxo-pyrrolidin-2-yl), or pyridinyl;
aryl is phenyl or phenyl substituted with one substituent selected from halo, $C_{1-4}$alkyl, $C_{1-4}$alkyloxy or hydroxy;

aryl$^1$ is phenyl or phenyl substituted with one substituent selected from halo, $C_{1-4}$alkyl, $C_{1-4}$alkyloxy or hydroxy;

or a pharmaceutically acceptable acid addition salt thereof, or a solvate thereof.

As used in the foregoing definitions:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;

$C_{1-6}$alkyl is meant to include $C_{1-4}$alkyl and the higher homologues thereof having 5 or 6 carbon atoms, such as, for example, 2-methylbutyl, pentyl, hexyl and the like;

polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoro-methyl, trifluoromethyl, trifluoroethyl, and the like;

polyhalo$C_{1-6}$alkyl is defined as polyhalosubstituted $C_{1-6}$alkyl, in particular $C_{1-6}$alkyl (as hereinabove defined) substituted with 2 to 6 halogen atoms such as difluoro-methyl, trifluoromethyl, trifluoroethyl, and the like;

$C_{3-6}$cycloalkyl is generic to cyclopropyl, cyclobutyl, cyclopentyl, and cyclohexyl.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

In an embodiment, the present invention concerns compounds of formula (I) wherein n is an integer 1, 2 or 3;
m is an integer 1, 2 or 3;
p is an integer 1 or 2;
$R^3$ is hydrogen, halo, $C_{1-4}$alkyl or $C_{1-4}$alkyloxy;
X represents O, S, $SO_2$, $CR^4R^5$ or $NR^6$;
  wherein $R^4$ and $R^5$ are each independently from another selected from hydrogen, halo, hydroxy, $C_{1-4}$alkyl, $C_{1-4}$alkyloxy, or aryl;
  wherein $R^6$ is hydrogen, phenyl, —CO—$R^7$, or —CO—O—$R^7$, wherein $R^7$ is $C_{1-6}$alkyl or amino;
$R^1$ is a heterocycle selected from pyridinyl or pyrimidinyl, wherein said heterocycle is substituted with one or two substituents each independently from another selected from hydrogen, halo, hydroxy, $C_{1-6}$alkyl, $C_{1-6}$alkyloxy, polyhalo$C_{1-4}$alkyl, phenyl, $C_{3-6}$cycloalkyl, $C_{3-6}$cycloalkyloxy, $C_{3-6}$cycloalkyl$C_{1-4}$alkyloxy, or $NR^8R^9$;
  wherein $R^8$ and $R^9$ are independently from another selected from hydrogen, $C_{1-6}$alkyl, $C_{3-6}$cycloalkyl, and
  wherein $R^8$ and $R^9$ may be taken together with the nitrogen atom to which they are attached to form a pyrrolidinyl, piperidinyl, piperazinyl or morpholinyl ring which may be optionally substituted with one or two substituents each independently from another selected from $C_{1-4}$alkyl, $C_{1-4}$alkyloxy, halo, hydroxy, or $C_{1-4}$alkylcarbonyl;
$R^2$ is a heterocycle selected from quinolinyl or isoquinolinyl, wherein said heterocycle is substituted with one or two substituents each independently from another selected from hydrogen, halo, hydroxy, $C_{1-6}$alkyl, $C_{1-6}$alkyloxy, $C_{3-6}$cycloalkyl, $C_{3-6}$cycloalkyloxy, polyhalo$C_{1-4}$alkyl, and $NR^{10}R^{11}$;
  wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, or $C_{1-6}$alkyl substituted with hydroxy, halo, phenyl, $C_{1-4}$alkyloxy, $C_{3-6}$cycloalkyl, tetrahydrofuranyl, tetrahydropyranyl, or morpholinyl; and
  wherein $R^{10}$ and $R^{11}$ may be taken together with the nitrogen atom to which they are attached to form a azetidinyl, pyrrolidinyl, piperidinyl, piperazinyl, azepanyl, N-[1,4]-oxazepanyl or morpholinyl ring which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino or $C_{1-6}$alkylsubstituted with hydroxy;
aryl is phenyl or phenyl substituted with one substituent selected from halo, $C_{1-4}$alkyl, $C_{1-4}$alkyloxy or hydroxy.

Interesting compounds of formula (I) are those compounds of formula (I) wherein one or more of the following restrictions apply:

a) $R^1$ is a heterocycle selected from pyridinyl or pyrimidinyl wherein said heterocycle is substituted with one substituent selected from hydrogen, halo, hydroxy, $C_{1-6}$alkyl, $C_{1-6}$alkyloxy, polyhalo$C_{1-4}$alkyl or phenyl; or b) $R^1$ is a heterocycle selected from pyridin-3-yl or pyrimidin-5-yl wherein said heterocycle is substituted with one substituent selected from hydrogen, halo, hydroxy, $C_{1-6}$alkyl, $C_{1-6}$alkyloxy or polyhalo$C_{1-4}$alkyl; or c) $R^1$ is a heterocycle selected from pyridin-3-yl or pyrimidin-5-yl wherein said heterocycle is substituted with one substituent selected from hydrogen, halo, hydroxy, methyl, methoxy or trifluoromethyl; or d) $R^2$ is a heterocycle selected from quinolinyl or isoquinolinyl, wherein said heterocycle is substituted with one or two substituents each independently from another selected from hydrogen, halo, hydroxy, $C_{1-6}$alkyl or $C_{1-6}$alkyloxy; or e) $R^2$ is a heterocycle selected from quinolinyl or isoquinolinyl, wherein said heterocycle is substituted with $NR^{10}R^{11}$ wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, or $C_{1-6}$alkyl substituted with hydroxy, halo, phenyl, $C_{1-4}$alkyloxy, $C_{3-6}$cycloalkyl, tetrahydrofuranyl, tetrahydropyranyl, or morpholinyl; or f) $R^2$ is a heterocycle selected from quinolinyl or isoquinolinyl, wherein said heterocycle is substituted with $NR^{10}R^{11}$ wherein $R^{10}$ and $R^{11}$ are taken together with the nitrogen atom to which they are attached to form a azetidinyl, pyrrolidinyl, piperidinyl, piperazinyl, azepanyl, N-[1,4]-oxazepanyl or morpholinyl ring which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino or $C_{1-6}$alkylsubstituted with hydroxy; or g) p is an integer 1; or h) $R^3$ is hydrogen, n is an integer 2, m is an integer 2, and X represents O; or i) $R^3$ is hydrogen, n is an integer 2, m is an integer 2, and X represents $CR^4R^5$ wherein $R^4$ and $R^5$ are each independently from another selected from hydrogen or halo; or j) $R^3$ is hydrogen, n is an integer 2, m is an integer 2, and X represents $NR^6$ wherein $R^6$ is hydrogen, phenyl or —CO—O—$R^7$ wherein $R^7$ is $C_{1-6}$alkyl; or k) $R^1$ is 2-trifluoromethylpyridin-5-yl; or l) $R^1$ is 2-trifluoromethylpyrimidin-5-yl; or m) n is an integer 2, m is an integer 2, and X represents $CR^4R^5$ wherein $R^4$ and $R^5$ are each fluoro; or n) n is an integer 1, m is an integer 3, and X represents $CR^4R^5$ wherein $R^4$ and $R^5$ are each fluoro; or o) $R^3$ is hydrogen, n is an integer 2, m is an integer 3, and X represents O; or p) $R^2$ is quinoline-5-yl substituted or unsubstituted at the 6-position with Cl, F, $OCH_3$, $CH_3$, $CF_3$, with or without an additional substituent at the 2-position.

In an embodiment, the present invention relates to a subset of compounds of formula (I) which are defined as compounds of formula (I-a)

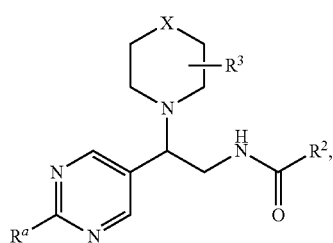

(I-a)

including any stereochemically isomeric form thereof, wherein $R^a$ is hydrogen, halo, hydroxy, $C_{1-6}$alkyl, $C_{1-6}$alkyloxy, polyhalo$C_{1-4}$alkyl, phenyl, $C_{3-6}$cycloalkyl, $C_{3-6}$cycloalkyloxy, $C_{3-6}$cycloalkyl$C_{1-4}$alkyloxy, or $NR^8R^9$;
wherein $R^8$ and $R^9$ are independently from another selected from hydrogen, $C_{1-6}$alkyl, $C_{3-6}$cycloalkyl, and
wherein $R^8$ and $R^9$ may be taken together with the nitrogen atom to which they are attached to form a pyrrolidinyl, piperidinyl, piperazinyl or morpholinyl ring which may be optionally substituted with one or two substituents each independently from another selected from $C_{1-4}$alkyl, $C_{1-4}$alkyloxy, halo, hydroxy, or $C_{1-4}$alkylcarbonyl;

$R^2$ is a heterocycle selected from quinolinyl or isoquinolinyl, wherein said heterocycle is substituted with one or two substituents each independently from another selected from hydrogen, halo, hydroxy, $C_{1-6}$alkyl, $C_{1-6}$alkyloxy, $C_{3-6}$cycloalkyl, $C_{3-6}$cycloalkyloxy, polyhalo$C_{1-4}$alkyl, and $NR^{10}R^{11}$;
wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, or $C_{1-6}$alkyl substituted with hydroxy, halo, phenyl, $C_{1-4}$alkyloxy, $C_{3-6}$cycloalkyl, tetrahydrofuranyl, tetrahydropyranyl, or morpholinyl; and
wherein $R^{10}$ and $R^{11}$ may be taken together with the nitrogen atom to which they are attached to form a azetidinyl, pyrrolidinyl, piperidinyl, piperazinyl, azepanyl, N-[1,4]-oxazepanyl or morpholinyl ring which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino or $C_{1-6}$alkylsubstituted with hydroxy;

$R^3$ is hydrogen, halo, $C_{1-4}$alkyl or $C_{1-4}$alkyloxy;

X represents O or $CR^4R^5$;
wherein $R^4$ and $R^5$ are each independently from another selected from hydrogen, halo, hydroxy, $C_{1-4}$alkyl, $C_{1-4}$alkyloxy, or aryl;

aryl is phenyl or phenyl substituted with one substituent selected from halo, $C_{1-4}$alkyl, $C_{1-4}$alkyloxy or hydroxy;

or a pharmaceutically acceptable acid addition salt thereof, or a solvate thereof.

Compounds of formula (I) can generally be prepared by reacting an intermediate of formula (II) with an intermediate of formula (III), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof.

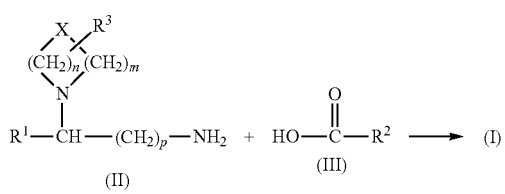

It may be convenient to activate the carboxylic acid of formula (III) by adding an effective amount of a reaction promoter. Non-limiting examples of such reaction promoters include carbonyldiimidazole, N,N'-dicyclohexyl-carbodiimide or 1-(3-dimethylaminopropyl)-3-ethylcarbodiimide, hydroxybenzotriazole, benzotriazolyl-oxytris (dimethylamino)-phosphonium hexafluorophosphate, tetrapyrrolidino-phosphonium hexafluorophosphate, bromotripyrrolidinophosphonium hexafluoro-phosphate, or a functional derivative thereof, such as disclosed by D. Hudson, *J. Org. Chem.* (1988), 53:617.

Compounds of formula (I) can also be prepared by N-acylation an intermediate of formula (II) with an intermediate of formula (IV), wherein W is an appropriate leaving group such as, for example, halo, e.g. fluoro, chloro, bromo, iodo, or in some instances W may also be a sulfonyloxy group, e.g. methanesulfonyloxy, trifluoromethane-sulfonyloxy, benzenesulfonyloxy and the like reactive leaving groups. The reaction can be performed in a reaction-inert solvent such as, for example, acetonitrile, dimethyl acetamide, N-methyl-pyrrolidone or DMF, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

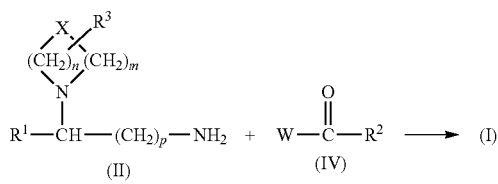

The compounds of formula (I) may further be prepared by converting compounds of formula (I) into each other according to art-known group transformation reactions.

For instance
compounds of formula (I) wherein the heterocycle $R^2$ is substituted with halo can be N-alkylated with $H-NR^{10}R^{11}$ to obtain compounds of formula (I) wherein the heterocycle $R^2$ is substituted with $NR^{10}R^{11}$ using art-known N-alkylation procedures;
compounds of formula (I) wherein the heterocycle $R^2$ is substituted with halo can be converted into the corresponding compounds of formula (I) wherein said halo is replaced by $C_{1-6}$alkyloxy or $C_{3-6}$cycloalkyloxy by treatment with a strong base and an alcohol;
compounds of formula (I) wherein the heterocycle $R^2$ is substituted with a $NR^{10}R^{11}$ substituent bearing a $C_{1-4}$alkyloxycarbonyl group may be converted into their corresponding compounds of formula (I) wherein said $C_{1-4}$alkyloxycarbonyl group is removed by hydrolysis under acid conditions.

Other examples of art-known group transformation reactions to converted compounds of formula (I) into other compounds of formula (I) are hydrolysis of carboxylic esters to the corresponding carboxylic acid or alcohol; hydrolysis of amides to the corresponding carboxylic acids or amines; alcohols may be converted into esters and ethers; primary amines may be converted into secondary or tertiary amines; double bonds may be hydrogenated to the corresponding single bond.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess P2X7 receptor antagonizing properties as demonstrated in the Pharmacological Example D.1.

Therefore the present compounds of formula (I) are useful as a medicine especially in the treatment of a condition or disease mediated by the P2X7 receptor, in particular P2X7 receptor antagonistic activity. Subsequently the present compounds may be used for the manufacture of a medicine for treatment of a condition or a disease mediated by P2X7 receptor activity, in particular P2X7 receptor antagonistic activity.

The present invention also provides the use of a compound of formula (I) or a pharmaceutically acceptable salt thereof for the manufacture of a medicament for the treatment of conditions or diseases selected from P2X7 receptor mediated conditions or diseases.

In an embodiment, the present invention provides a compound of formula (I) for use as a medicine or for use in the treatment of conditions or diseases selected from P2X7 receptor mediated conditions or diseases.

Further, the present invention also provides a method of treatment of a condition mediated by P2X7 receptor activity, in a mammalian subject, which method comprises administering to a mammal in need of such treatment a therapeutically effective amount of a compound of formula (I) or a pharmaceutically acceptable salt thereof.

P2X7 receptor mediated conditions or disorders are e.g. rheumatoid arthritis, osteoarthritis, psoriasis, allergic dermatitis, asthma, hyperresponsiveness of the airway, chronic obstructive pulmonary disease (COPD), bronchitis, septic shock, glomerulonephritis, irritable bowel disease, Crohn's disease, ulcerative colitis, atherosclerosis, growth and metastases of malignant cells, myoblastic leukaemia, diabetes, neurodegenerative disease, Alzheimer's disease, multiple sclerosis, meningitis, osteoporosis, burn injury, ischaemic heart disease, stroke, peripheral vascular disease, varicose veins, glaucoma, bipolar disorder, and neuropathic pain conditions such as diabetic neuropathy, post-herpatic neuralgia, low back pain, chemotherapy-induced neuropathic pain, fibromyalgia and spinal cord injury pain.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the cannabinoid receptors will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible P2X7 receptor antagonistic response.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: 'MeOH' means methanol, 'DCM' means dichloromethane, 'CH$_3$CN' means acetonitrile, 'DIPE' means diisopropyl ether, 'DIPEA' means diisopropylethylamine, 'MgSO$_4$' means magnesium sulphate, 'Na$_2$SO$_4$' means sulfuric acid disodium salt, 'Na$_2$CO$_3$' means carbonic acid disodium salt, 'THF' means tetrahydrofuran, 'EtOH' means ethanol, 'DMF' means N,N-dimethylformamide, 'CF$_3$COOH' means trifluoroacetic acid, 'H$_2$SO$_4$' means sulfuric acid, 'KOAc' means potassium acetate, 'NH$_3$' means ammonia, 'NaBH$_4$' means sodium borohydride, 'NH$_4$Cl' means ammonium chloride, 'NaOH' means sodium hydroxide, and 'NaHCO$_3$' means carbonic acid sodium salt (1:1).

Some compounds have been isolated by resolving a mixture of two enantiomers into its individual enantiomers using chiral column chromatography whereby one of the isolated individual enantiomers is indicated with R* (or S*) and its mirror image indicated with S* (or R*). These compounds indicated with R* or S* are single enantiomers of unknown absolute configuration.

The absolute stereochemical configuration for some of the compounds was determined using vibrational circular dichroism (VCD). A description on the use of VCD for the determination of absolute configuration can be found in Dyatkin A. B. et. al, *Chirality*, 14:215-219 (2002).

A. Synthesis of the Intermediates
Example A.1 a) Preparation of

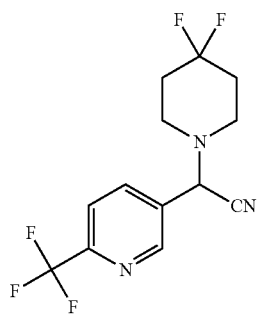

intermediate (1)

4,4-Difluoropiperidine hydrochloric acid salt (0.0286 mol) was dissolved in water (35 ml) and converted into its free base by treatment with a solution of NaHCO$_3$ (2.4 g, 0.0286 mol) in water (10 ml). The mixture was stirred for 30 minutes at room temperature. THF (23 ml) was added at room temperature. 6-(Trifluoromethyl)-3-pyridinecarboxaldehyde (0.0286 mol) and 4-methylbenzene-sulfonic acid (0.030 mol) were added and the mixture was stirred for 30 minutes. A solution of sodium cyanide (0.0286 mol) in water (15 ml) was added slowly and dropwise. The reaction mixture was heated to 70° C., then stirred overnight at 70° C. The mixture was cooled to room temperature, then poured out into a 10% aqueous K$_2$CO$_3$ solution (150 ml). This mixture was extracted with DCM (2×100 ml). The organic layers were combined, washed with a 10% aqueous NaHCO$_3$ solution (3×100 ml), dried (Na$_2$SO$_4$), filtered and the solvent was evaporated, yielding 5.9 g of intermediate (1).

b) Preparation of

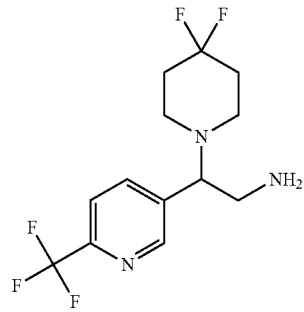

intermediate (2)

A mixture of intermediate (1) (0.045 mol) in NH$_3$/CH$_3$OH was hydrogenated at 14° C. with Raney Nickel as a catalyst in the presence of a thiophene solution (1 ml; 4% in DIPE). After uptake of hydrogen (two equivalents), the catalyst was filtered off and the filtrate was evaporated. The residue was dissolved in DCM. The organic solution was washed with an aqueous 1% Na$_2$CO$_3$ solution. The organic layer was dried (MgSO$_4$), filtered and the solvent was evaporated. The residue was purified on a silica gel tube. The impurities were eluted with DCM/MeOH (98/2) and the product was eluted with DCM/(MeOH/NH$_3$) (90/10). The product fractions were collected and the solvent was evaporated, yielding 12.2 g of intermediate (2).

Using an analogous procedure as described in steps a) and b) intermediate (19) was prepared starting from 6-(trifluoromethyl)-3-pyridinecarboxaldehyde and 4-phenyl-piperidine, intermediate (20) was prepared starting from 6-(trifluoromethyl)-3-pyridinecarboxaldehyde and 4-phenyl-piperazine, and intermediate (22) was prepared starting from 1-methyl-1H-imidazole-2-carboxaldehyde and 4,4-difluoropiperidine hydrochloride.

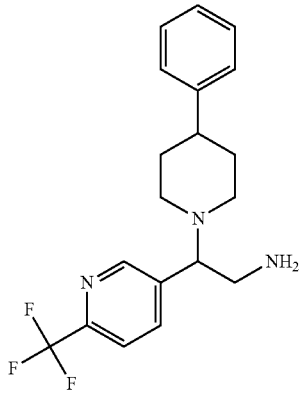

intm. (19)

intm. (20)

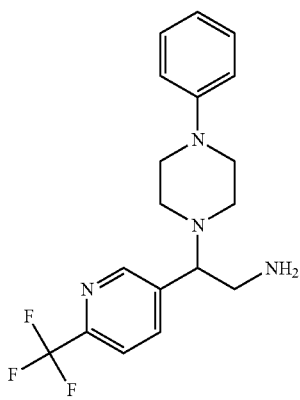

intm. (22)

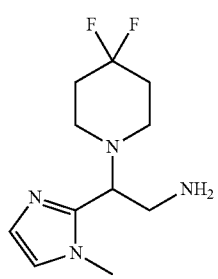

Example A.2 a) Preparation of intermediate (3a)

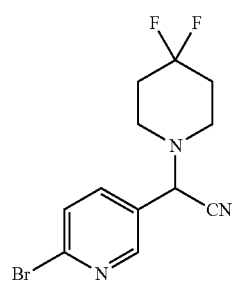

Water (10 ml) and hydrochloric acid (1N, 2 drops) were added to a mixture of 4,4-difluoropiperidine hydrochloride acid salt (0.025 mol) in ethanol (15 ml). 6-Bromo-3-pyridinecarboxaldehyde (0.025 mol) was added portionwise and the mixture was stirred for 30 minutes. Then, the mixture was cooled in an ice-bath. Sodium cyanide (0.025 mol) in water (5 ml) was added dropwise and the mixture was stirred for 1 hour at room temperature. The mixture was stirred overnight at 50° C. The mixture was cooled in an ice-bath while it was stirred. The precipitate was filtered off and washed with water. The precipitate was purified by column chromatography (eluent: DCM/MeOH 99/1). The product fractions were collected and crystallized from DIPE. The precipitate was filtered off and dried, yielding 2.8 g of intermediate (3a)

b) Preparation of intermediate (3b)

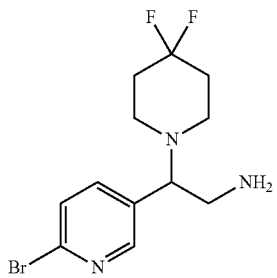

A mixture of intermediate (3a) (0.009 mol) in a solution of ammonia in methanol (150 ml) was hydrogenated at 14° C. with Raney nickel (1 g) as a catalyst in the presence of a thiophene solution (1 ml). After uptake of hydrogen (2 equivalents), the catalyst was filtered off and the filtrate was evaporated. The residue was taken up in DCM and was washed with a 1% $Na_2CO_3$ solution. The organic layer was separated, dried and the solvent was evaporated. The residue was purified by column chromatography over silica gel (eluent: DCM/MeOH 80/20). The product fractions were collected and the solvent was evaporated, yielding 0.320 g of intermediate (3b).

Using an analogous procedure as described in steps a) and b) intermediate (4) was prepared starting from 2-chloro-3-pyridinecarboxaldehyde, intermediate (5) was prepared from 3,3-difluoropyrrolidine hydrochloride and 6-(trifluoromethyl)-pyridine-3-carboxaldehyde, intermediate (6) was prepared from 3,3-difluoroazetidine hydro-chloride and 6-(trifluoromethyl)-pyridine-3-carboxaldehyde, intermediate (7) was prepared from 1-(tert-butyloxycarbonyl)piperazine and 6-(trifluoromethyl)-pyridine-3-carboxaldehyde; intermediate (8) was prepared starting from 3-pyridinecarboxaldehyde, intermediate (9) was prepared from 6-chloro-3-pyridinecarboxaldehyde and 4,4-difluoropiperidine hydrochloride, intermediate (12) was prepared from 2-benzo-furancarboxaldehyde and 4,4-difluoropiperidine hydrochloride.

intm. (4)

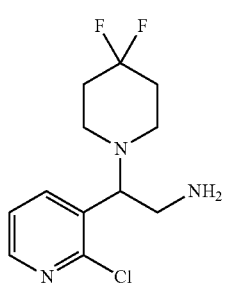

intm. (5)

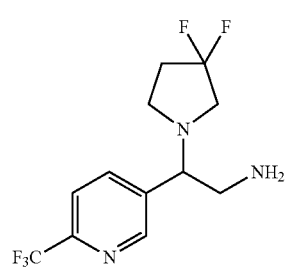

-continued intm. (6)
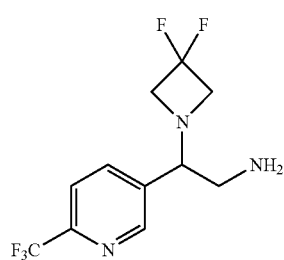

intm. (7)
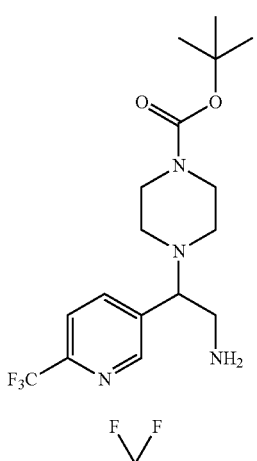

intm. (8)
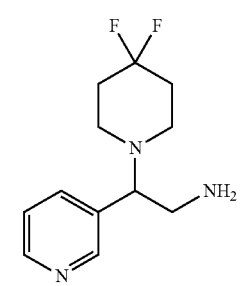

intm. (9)
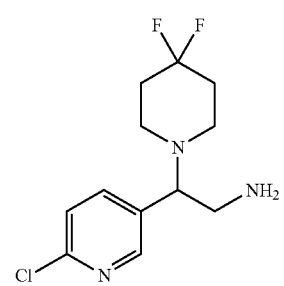

intm. (12)
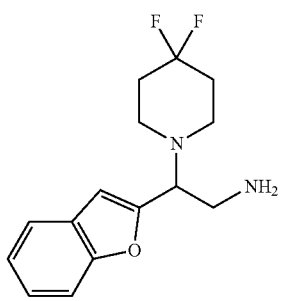

Example A.3 a) Preparation of intermediate (10)

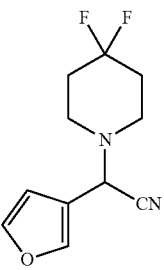

NaHCO$_3$ (0.006 mol) in water was added to a mixture of 4,4-difluoropiperidine hydrochloric acid salt (0.006 mol) in water (5 ml). The reaction mixture was stirred for 30 minutes. Then 3-furancarboxaldehyde (0.006 mol) and 4-methylbenzenesulfonic acid (0.006 mol) in THF (6 ml) were added and the reaction mixture was stirred for 30 minutes. Sodium cyanide (0.0072 mol) in water (3 ml) was added slowly and the reaction mixture was heated at 70° C. for 16 hours. The reaction mixture was cooled and poured into a 10% aqueous NaHCO$_3$ solution. The reaction mixture was extracted with DCM. The organic layer was separated, washed with water, dried with MgSO$_4$, filtered and the solvent was evaporated, yielding 1 g of intermediate (10).

b) Preparation of intermediate (11)

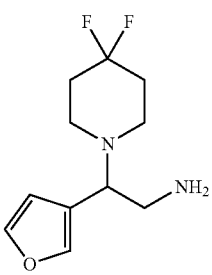

Lithium aluminum tetrahydride (0.012 mol) was added to a mixture of intermediate (10) (0.0044 mol) in THF (10 ml) at 0° C. The reaction mixture was stirred below 5° C. for 3 hours. Water was added to terminate the reaction. The precipitate was filtered off and the filtrate was extracted with DCM. The organic layer was separated, dried with Na$_2$SO$_4$, filtered and the solvent was evaporated, yielding 0.56 g of intermediate (11).

Using an analogous procedure as described in steps a) and b) intermediate (13) was prepared starting from 3-thiophenecarboxaldehyde and 4,4-difluoro-piperidine hydrochloride, intermediate (14) was prepared starting from 5-methyl-2-furancarboxaldehyde and 4,4-difluoro-piperidine hydrochloride, and intermediate (15) was prepared starting from 5-methyl-2-thiophene-carboxaldehyde and 4,4-difluoro-piperidine hydrochloride.

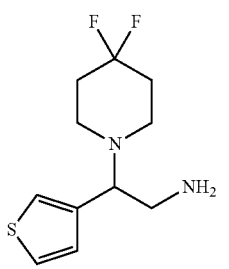

intm. (13)

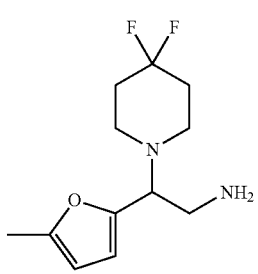

intm. (14)

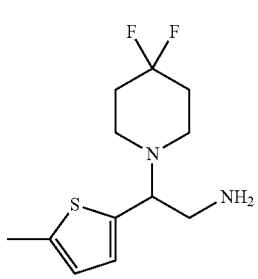

intm. (15)

Example A.4 a) Preparation of

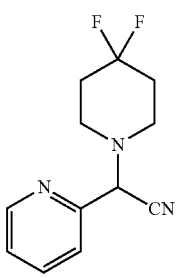

intermediate (16)

Trimethylsilanecarbonitrile (0.006 mol) was added slowly to a mixture of 4,4-difluoro-piperidine hydrochloride (0.006 mol) and 2-pyridinecarboxaldehyde (0.006 mol) in acetic acid (6 ml), while the reaction temperature was kept below 10° C. The reaction mixture was stirred overnight and aqueous ammonia (3 M) was added until the pH turned 10. The reaction mixture was extracted with DCM. The organic layer was separated, dried, filtered and the solvent was evaporated, yielding 1.2 g of intermediate (16).

b) Preparation of

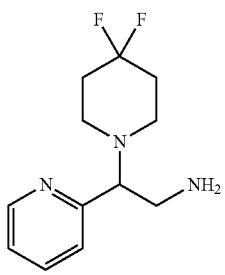

intermediate (17)

A 4% thiophene solution in DIPE (0.06 ml) was added to a mixture of intermediate (16) (0.00166 mol) in $NH_3$/MeOH (12 ml), while the mixture was stirred in an ice bath. Raney Nickel (0.5 g) was added at 0° C. and the reaction mixture was stirred for 16 hours, under hydrogen flow. The catalyst was filtered off and the filtrate was evaporated to dryness, yielding 0.250 g of intermediate (17).

Using an analogous procedure as described in steps a) and b) intermediate (18) was prepared starting from 6-(trifluoromethyl)-3-pyridinecarboxaldehyde and piperidine hydrochloride, intermediate (21) was prepared starting from 6-(trifluoromethyl)-3-pyridinecarboxaldehyde and 4-(4-chlorophenyl)-4-piperidinol, intermediate (23) was prepared starting from 6-(trifluoromethyl)-3-pyridinecarboxaldehyde and morpholine, intermediate (24) was prepared starting from 6-(trifluoromethyl)-3-pyridine-carbox-aldehyde and 1,1-dioxo-1-thio-morpholine, intermediate (25) was prepared starting from 2-(trifluoromethyl)-5-pyrimidinecarboxaldehyde and 4,4-difluoro-piperidine hydrochloride, intermediate (26) was prepared starting from 6-(trifluoromethyl)-3-pyridinecarboxaldehyde and 4-(aminocarbonyl)piperidine, intermediate (27) was prepared starting from 2-(trifluoromethyl)-5-pyrimidinecarboxaldehyde and piperidine, intermediate (28) was prepared starting from 2-(trifluoromethyl)-5-pyrimidine-carboxaldehyde and morpholine, intermediate (31) was prepared starting from 2-(trifluoromethyl)-5-pyrimidinecarboxaldehyde and pyrrolidine, intermediate (32) was prepared starting from 2-(trifluoromethyl)-5-pyrimidinecarboxaldehyde and homopiperidine, intermediate (33) was prepared starting from 2-(trifluoromethyl)-5-pyrimidinecarboxaldehyde and 2-piperazinone, intermediate (34) was prepared starting from 2-(trifluoromethyl)-5-pyrimidinecarboxaldehyde and 3,3-difluoropiperidine hydrochloride, intermediate (35) was prepared starting from 2-(trifluoromethyl)-5-pyrimidinecarboxaldehyde and 3-fluoropiperidine hydrochloride, intermediate (36) was prepared starting from 2-(trifluoromethyl)-5-pyrimidinecarbox-aldehyde and 2-methylmorpholine, intermediate (37) was prepared starting from 2-(trifluoromethyl)-5-pyrimidinecarboxaldehyde and 2-methylpiperidine, intermediate (38) was prepared starting from 2-(trifluoromethyl)-5-pyrimidinecarboxaldehyde and 1,4-oxazepane hydrochloride, intermediate (39) was prepared starting from 2-methyl-5-pyrimidine-carboxaldehyde and 4,4-difluoropiperidine hydrochloride, intermediate (40) was prepared starting from 2-(trifluoromethyl)-5-pyrimidinecarboxaldehyde and 3-methoxypiperidine hydrochloride, intermediate (55) was prepared starting from 2-methyl-5-pyrimidinecarboxaldehyde and morpholine, intermediate (53) was prepared starting from 2-(trifluoromethyl)-5-pyrimidinecarboxaldehyde and 4-fluoropiperidine hydrochloride, and intermediate (54) was prepared starting from 2-methoxy-5-pyrimidine-carboxaldehyde and 4,4-difluoropiperidine hydrochloride.

intm. (18)
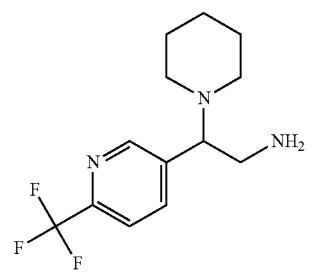
intm. (21)
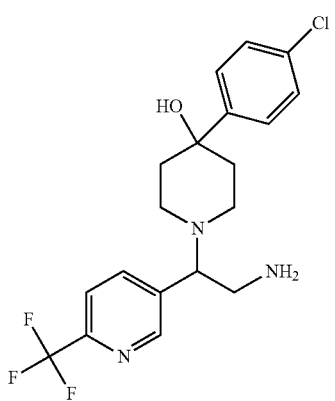
intm. (23)
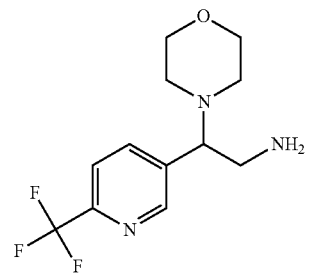
intm. (24)
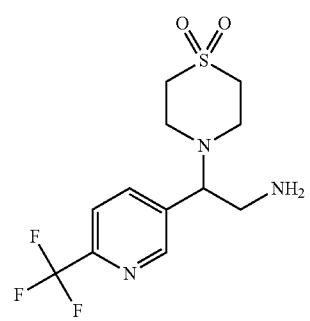
intm. (25)
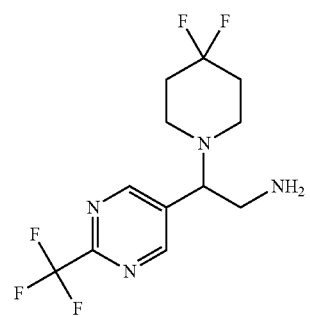
intm. (26)
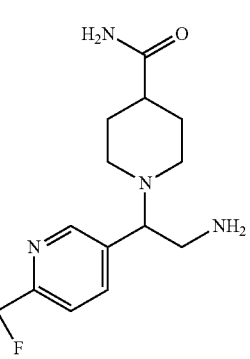
intm. (27)
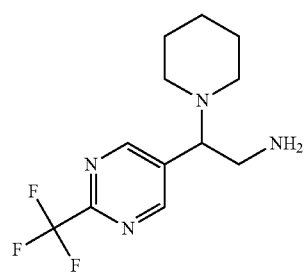
intm. (28)
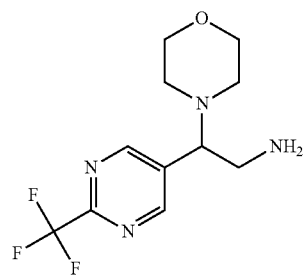
intm. (31)
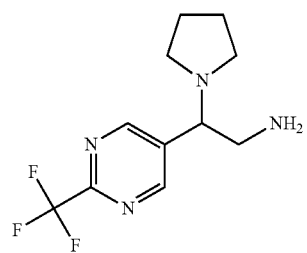
intm. (32)
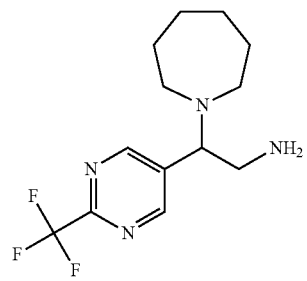

intm. (33)
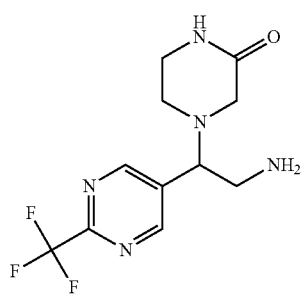
intm. (34)
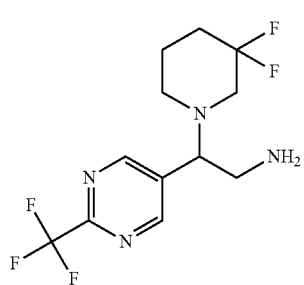
intm. (35)
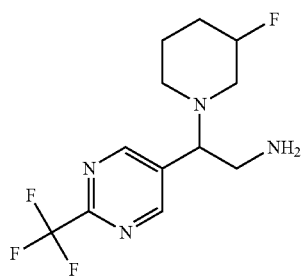
intm. (36)
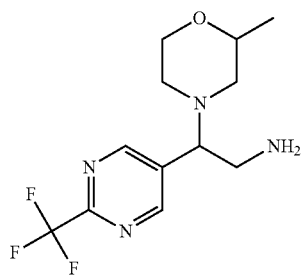
intm. (37)
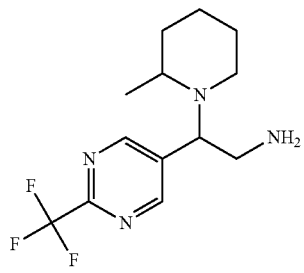
intm. (38)
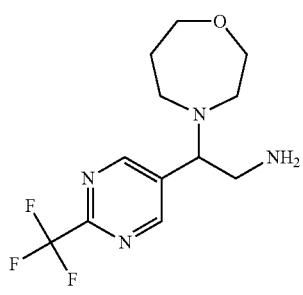
intm. (39)
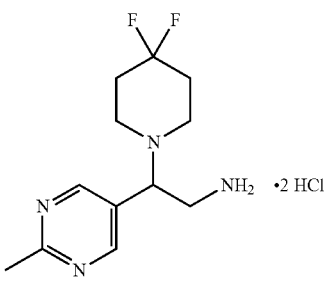
intm. (40)
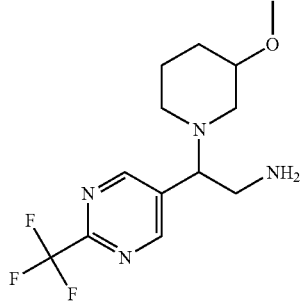
intm. (53)
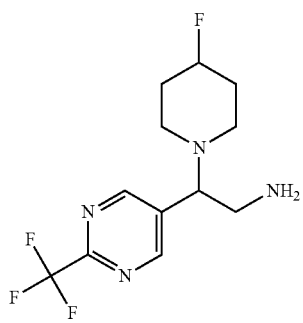
intm. (54)
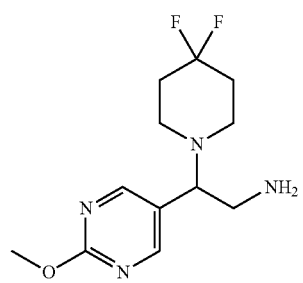

-continued intm. (55)

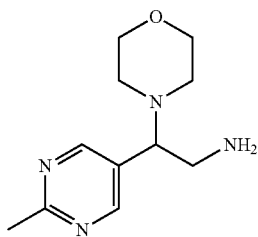

Example A.5 a) Preparation of intermediate (29)

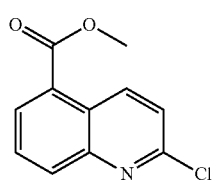

Phosphoryl chloride (10 ml) was added into a mixture of 2-oxy-quinoline-5-carboxylic acid methyl ester (0.03 mol) in 1,2-dichloro-ethane (10 ml). The reaction mixture was stirred at 80° C. overnight. The reaction mixture was quenched with water and extracted with DCM. The organic layer was separated, dried with $Na_2SO_4$, filtered and the solvent was evaporated, yielding 6 g of intermediate (29).

b) Preparation of intermediate (30)

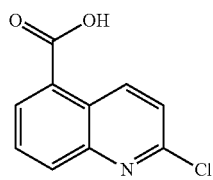

Lithium hydroxide (100 ml) was added into a mixture of intermediate (29) (0.027 mol) in MeOH (50 ml). The reaction mixture was stirred at room temperature for 1 hour. The solvent was evaporated under vacuum and aqueous HCl (2M) was added dropwise into the residue. The precipitate was filtered off and the residue was purified by preparative high-performance liquid chromatography. The product fractions were collected and the solvent was evaporated, yielding intermediate (30).

Example A.6

Preparation of intermediate (41)

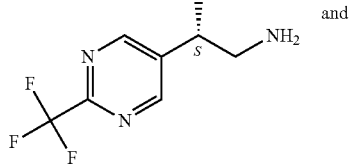

and intermediate (42)

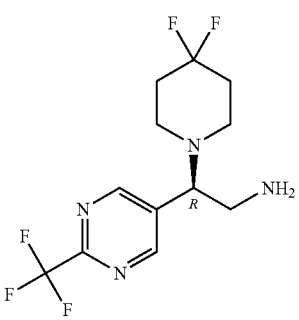

Intermediate (25) (2 g) was separated in its enantiomers with preparative SFC purification. SFC was carried out on a Chiralpak AD-H column (30×250 mm) (Daicel Chemical Industries Ltd): eluent $CO_2$/(methanol containing 0.2% 2-propylamine) 75/25 was hold for 10 minutes; flow rate 50 ml/min; column heater temperature 40° C.; nozzle pressure 100 bar; load: 55 mg/1.5 ml. 2 Peaks were obtained and collected. The first peak was concentrated to dryness and was solidified by drying in the oven under vacuum, yield 0.8 g of intermediate (41). The second peak was concentrated to dryness and was solidified by drying in the oven under vacuum, yielding 0.8 g of intermediate (42).

Example A.7 a) Preparation of intermediate (43)

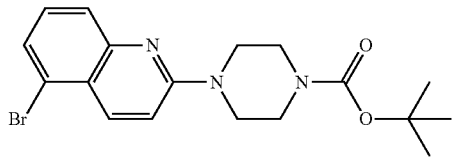

5-Bromo-2-chloro-quinoline (0.02 mol) and 1-(tert-butyloxycarbonyl)piperazine (0.06 mol) in 1-methyl-2-pyrrolidinone (10 ml) were stirred for 2 hours at 100° C. The reaction mixture was poured into 150 ml water, a solid was formed, filtered off, washed and dried. Then the solid was taken up in hot diisopropylether, cooled and filtered off, washed and dried, yielding 4.6 g of intermediate (43).

b) Preparation of

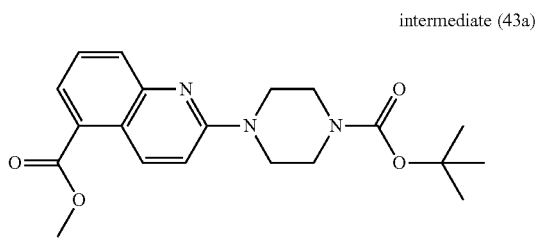

intermediate (43a)

A mixture of intermediate (43) (0.0117 mol), Pd(OAc)$_2$ (0.02 g), 1,3-bis(diphenyl-phosphino)-propane (0.08 g), triethylamine (5 ml) and THF/MeOH (3:1) (80 ml) was reacted under 50 atmosphere CO gas pressure at 125° C. for 16 hours in an autoclave. The reaction mixture was cooled and the solvent evaporated. The residue was taken up in DCM and washed with Brine. The organic layer was dried (MgSO$_4$), filtered and evaporated. The residue was suspended in hot diisopropylether, filtered off, washed and dried, yielding 3.45 g of intermediate (43a).

c) Preparation of

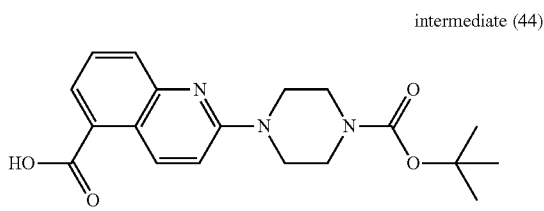

intermediate (44)

Intermediate (43a) (0.0011 mol) was stirred in THF/MeOH (2:1) (3 ml) and water (2 ml). Lithium hydroxide (0.0022 mol) was added at room temperature. The reaction mixture was stirred at room temperature for 4 hours. The organic solvents were removed by evaporation. Water (5 ml) was added and HCl 1N was added dropwise until pH is 3 to 4. A precipitate was formed. The precipitate was filtered off, washed and dried to give a light brown solid, yielding 0.28 g of intermediate (44).

Example A.8 a) Preparation of

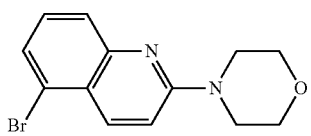

intermediate (45)

5-Bromo-2-chloro-quinoline (0.0220 mol) and morpholine (0.1 mol) were shaken in a closed tube at 100° C. for 2 hours. The reaction mixture was poured into water, a solid was formed, filtered off, washed and dried, yielding 5.9 g of intermediate (45).

b) Preparation of

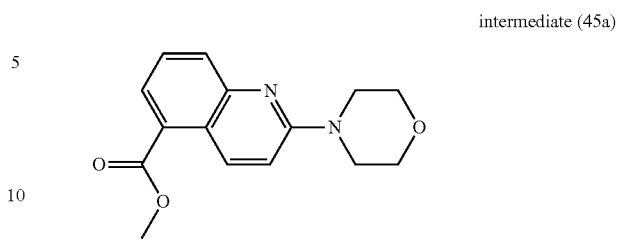

intermediate (45a)

A mixture of intermediate (45) (0.02 mol), Pd(OAc)$_2$ (0.02 g), 1,3-bis(diphenyl-phosphino)-propane (0.08 g), triethylamine (5 ml) and THF/MeOH (3:1) (80 ml) was reacted under 50 atmosphere CO gas pressure at 125° C. for 16 hours in an autoclave. The reaction mixture was cooled and the solvent evaporated. The residue was taken up in DCM and washed with Brine. The organic layer was dried (MgSO$_4$), filtered and evaporated. The residue was suspended in hot diisopropylether, filtered off, washed and dried, yielding 4.45 g of intermediate (45a).

c) Preparation of

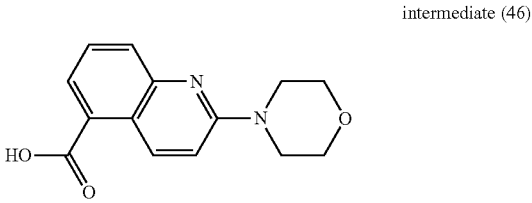

intermediate (46)

Intermediate (45a) (0.016 mol) was stirred in THF/MeOH (2:1) (100 ml) and water (50 ml). Lithium hydroxide (0.032 mol) was added at room temperature. The reaction mixture was stirred at room temperature for 4 hours. The organic solvents were removed by evaporation. Water (50 ml) was added and the impurities were extracted with DCM. The water layer was acidified by adding HCl 1N until pH is 3 to 4. A precipitate was formed. The precipitate was filtered off, washed and dried, yielding 3.12 g of intermediate (46).

Example A.9 a) Preparation of

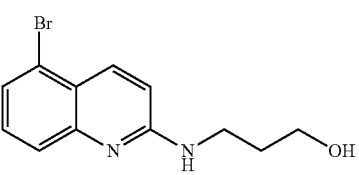

intermediate (47)

5-Bromo-2-chloro-quinoline (0.02 mol) and 3-amino-1-propanol (20 ml) were stirred for 4 hours at 80° C. The reaction mixture was diluted with water and extracted with DCM twice. The combined organic layers were once washed with water, then dried over MgSO$_4$, filtered and evaporated. The residue was crystallised in isopropylether with 2% acetonitrile. The crystals were collected by filtration and dried in vacuum, yielding 2.97 g of intermediate (47).

b) Preparation of

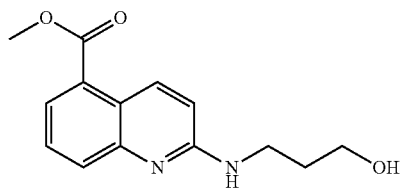

intermediate (48)

A mixture of intermediate (47) (2.9 g), Pd(OAc)$_2$ (0.02 g), 1,3-bis(diphenylphosphino)-propane (0.08 g), triethylamine (5 ml), THF (40 ml) and methanol (10 ml) was reacted under 50 atmosphere CO gas pressure at 125° C. for 16 hours in an autoclave. After reaction, the solvent was evaporated and the residue was diluted with water and extracted with ethyl acetate (3×). The combined organic layers were washed with water (twice), dried over MgSO$_4$, filtered and the solvent was evaporated. The residue was crystallised in isopropylether. The precipitate was filtered and dried in vacuum, yielding 1.25 g of intermediate (48).

c) Preparation of

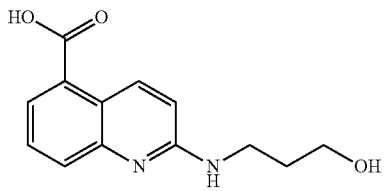

intermediate (49)

Intermediate (48) (0.002 mol) and dioxane (16 ml) were stirred at room temperature. Lithium hydroxide hydrate (0.0025 mol) and water (4 ml) were added dropwise. The reaction mixture was stirred at 50° C. for 4 hours and stirring was continued at room temperature overnight. The reaction mixture was evaporated, redissolved in water and neutralised with 1N HCl. The precipitate was filtered and dried in vacuum, yielding 0.45 g of intermediate (49).

Example A.10 a) Preparation of

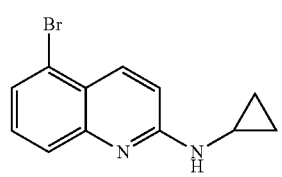

intermediate (50)

5-Bromo-2-chloroquinoline and cyclopropanamine were stirred for 5 days in a closed vessel at 60° C. The reaction mixture was evaporated and the residue was crystallised in CH$_3$CN. The precipitate was filtered and dried in vacuum, yielding 9.3 g (88%) of intermediate (50).

b) Preparation of

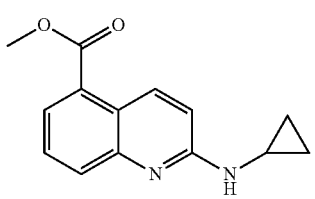

intermediate (51)

Intermediate (50) (36.5 mmol), methanol, palladium diacetate (0.2 mmol), 1,3-bis-(diphenylphosphino)propane (0.4 mmol), triethylamine (10 ml) in THF were stirred under 50 atm CO at 125° C. for 16 hours. The reaction mixture was filtered over dicalite and the filtrate was evaporated. The residue was purified over silica gel (DCM/MeOH 100/0 to 98/2). The corresponding fractions were evaporated. The first residue was triturated in isopropylether, the precipitate filtered and dried in vacuum, yielding 1.95 g of intermediate (51).

c) Preparation of

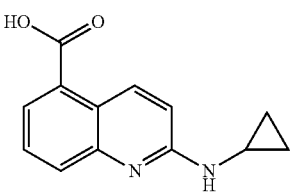

intermediate (52)

Intermediate (51) (8 mmol) and dioxane (40 ml) were stirred at room temperature while lithium hydroxide hydrate (16.1 mmol), dissolved in demineralised water (20 ml) was added dropwise. Stirring was continued overnight at room temperature. The reaction was evaporated and redissolved in 50 ml water. This solution was neutralised with 1N HCl while stirring. After 4 hours stirring the precipitate was filtered and dried in vacuum, yielding 1580 mg of intermediate (52).

Example A.11

Preparation of

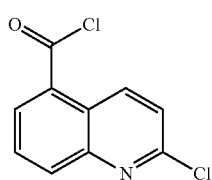

intermediate (56)

Intermediate (30) (3.0 g, 0.013 mol) was suspended in DCM (100 ml; anhydrous). First ethanedioyl dichloride (9.0 g, 0.072 mol) and then DMF (3 drops) were added. The reaction mixture was stirred overnight at room temperature. The solvent was evaporated under reduced pressure, yielding 3.1 g of intermediate (56).

Example A.12 a) Preparation of intermediate (57)

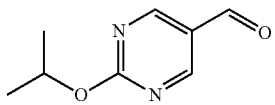

Reaction under nitrogen atmosphere. Sodium (0.00026 mol) was added to ethanol (300 ml) at 0° C. The mixture was stirred at ambient temperature until the solid was dissolved completely. Intermediate (83) (0.0929 mol) was added with stirring until the temperature of the mixture was cooled down to ambient temperature. The trifluoro-methanesulfonate salt of isopropyl imidocarbamate (0.0872 mol) was added with stirring. The reaction mixture was stirred at ambient temperature overnight and the solvent was evaporated in vacuo. The residue was dispersed in water (300 ml). The mixture was extracted with DCM (2×200 ml). The organic layers were combined, washed with a saturated aqueous NaCl solution (200 ml). The separated organic fraction was dried over Na$_2$SO4, filtered and the solvent was evaporated in vacuo. The residue was purified by column chromatography over silica gel (eluent: petroleum ether/ethyl acetate 10/1, v/v). The product fractions were collected and the solvent was evaporated. The residue was dried in vacuo, yielding 6.5 g of intermediate (57).

b) Preparation of intermediate (58)

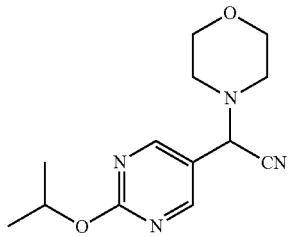

A mixture of intermediate (57) (0.0120 mol), trimethylethynylsilane (0.0240 mol), morpholine (0.0144 mol) and sodium acetate (0.0180 mol) in acetic acid (30 ml) was stirred at ambient temperature overnight. The reaction mixture was concentrated in vacuo. The solvent was evaporated in vacuo. Water (50 ml) was added. The mixture was alkalized with solid NaOH to pH 10. The resulting precipitate was collected by filtration and washed with water (3×50 ml). The precipitate was filtered off and dried in vacuo, yielding 2.5 g of intermediate (58).

c) Preparation of intermediate (59)

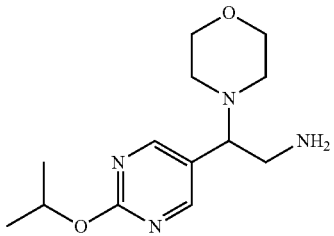

A mixture of crude intermediate (58) (0.0095 mol) dissolved in a mixture of methanol saturated with ammonia (7N, 20 ml) and THF (100 ml) was hydrogenated at ambient temperature under hydrogen atmosphere with Raney nickel (4 g) as a catalyst in the presence of hydrogen overnight. After uptake of hydrogen (2 equivalents), the catalyst was filtered off. The filtrate was evaporated, yielding 2.3 g of intermediate (59).

Example A.13 a) Preparation of intermediate (60)

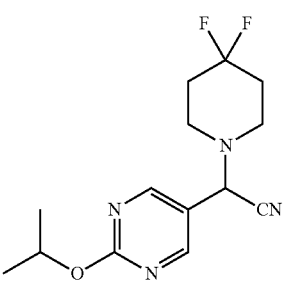

A mixture of intermediate (57) (0.0120 mol), trimethylsilyl cyanide (0.0240 mol), 4,4-difluoropiperidine hydrochloride (0.0144 mol) and sodium acetate (0.0180 mol) in acetic acid (30 ml) was stirred at ambient temperature overnight. The reaction mixture was concentrated in vacuo. The solvent was evaporated in vacuo. Water (50 ml) was added. The mixture was basified with solid NaOH to pH 10. The resulting precipitate was collected by filtration and washed with water (3×50 ml). The precipitate was collected and dried in vacuo, yielding 3.7 g of intermediate (60).

b) Preparation of

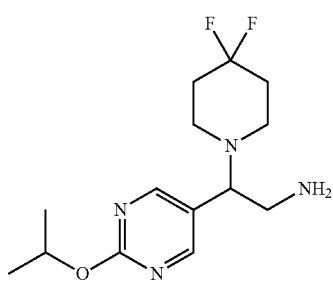

intermediate (61)

A mixture of intermediate (60) (0.0125 mol) dissolved in a mixture of methanol saturated with ammonia (7N, 20 ml) and THF (100 ml) was hydrogenated at ambient temperature under hydrogen atmosphere with Raney nickel (6 g) as a catalyst in the presence of hydrogen overnight. After uptake of hydrogen (2 equivalents), the catalyst was filtered off. The filtrate was evaporated, yielding 3.5 g of intermediate (61).

Example A.14 a) Preparation of

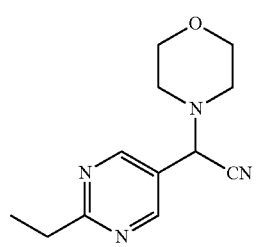

intermediate (62)

A mixture of 2-ethyl-5-pyrimidinecarboxaldehyde (0.0235 mol), morpholine (0.0282 mol), trimethylsilyl cyanide (0.047 mol) and sodium acetate (0.0294 mol) in acetic acid (50 ml) was stirred at room temperature overnight. The reaction mixture was filtered and the solvent was evaporated. The residue was dissolved in water, alkalized with NaHCO$_3$ until pH 8 and extracted twice with ethyl acetate. The organic layers were combined, dried, filtered and the filtrate's solvent was evaporated, yielding 4.8 g of intermediate (62).

b) Preparation of

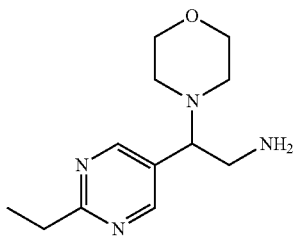

intermediate (63)

A mixture of intermediate (62) (0.0207 mol), Raney nickel (9.6 g) and methanol saturated with ammonia (7N, 10 ml) in methanol (60 ml) was hydrogenated at room temperature overnight. After uptake of hydrogen (2 equivalents), the catalyst was filtered off and the filtrate was evaporated. The crude residue was purified by high-performance liquid chromatography over C18 (eluent: CH$_3$CN/water from 25/75 to 55/45 with 0.1% NH$_3$). The pure fractions were collected and the solvent was evaporated, yielding 2.7 g of intermediate (63).

Example A.15 a) Preparation of

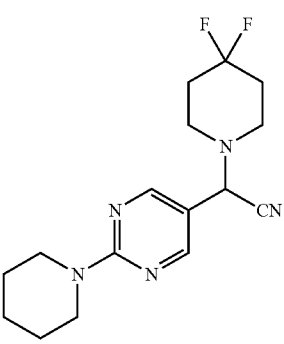

intermediate (64)

A mixture of 2-(1-piperidinyl)-5-pyrimidinecarboxaldehyde (0.00314 mol), trimethylsilyl cyanide (0.00628 mol), 4,4-difluoropiperidine hydrochloride (0.00377 mol) and sodium acetate (0.00408 mol) in acetic acid (15 ml) was stirred at room temperature. The reaction mixture was evaporated under reduced pressure. The residue was stirred in water (20 ml). The aqueous phase was treated with NaHCO$_3$ until pH 8. This mixture was extracted with DCM (3×30 ml). The separated organic layer was dried (Na$_2$SO$_4$), filtered and the solvent was evaporated, yielding 1.0 g of intermediate (64).

b) Preparation of

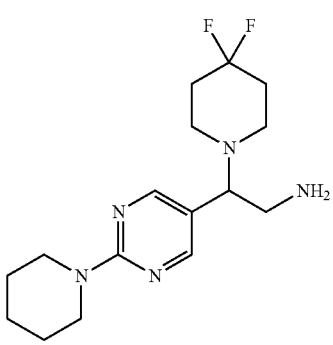

intermediate (65)

A mixture of intermediate (64) (0.00311 mol), Raney nickel (2.0 g) as a catalyst and methanol saturated with ammonia (7N, 5 ml) in ethanol (30 ml) was hydrogenated at room temperature (atmospheric pressure). After uptake of hydrogen (2 equivalents), the catalyst was filtered off and the filtrate was evaporated. The residue was purified by preparative high-performance liquid chromatography over YMC (150×30 mm; C18; eluent: CH$_3$CN/water from 16/84 to 46/54 with 0.1% CF$_3$COOH). The desired fractions were collected and the solvent was evaporated. The residue was dissolved in MeOH and converted into the hydrochloric acid salt by using HCl/1,4-dioxane (40 ml). The precipitate was filtered off and dried by evaporation of remaining solvent, yielding 0.45 g of intermediate (65).

Example A.16 a) Preparation of

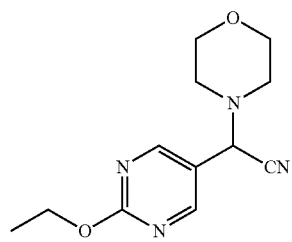

intermediate (66)

A mixture of 2-ethoxy-5-pyrimidinecarboxaldehyde (0.01314 mol), trimethylsilyl cyanide (0.02628 mol), morpholine (0.01445 mol) and sodium acetate (0.01577 mol) in acetic acid (20 ml) was stirred at room temperature. The reaction mixture was evaporated under reduce pressure. Water (30 ml) was added to resulting residue. The aqueous phase was basified with $NaHCO_3$ till pH was 8, extracted with DCM (40 ml, 3 times). The separated organic layer was dried ($Na_2SO_4$), filtered, evaporated, yielding 3.5 g of intermediate (66).

b) Preparation of

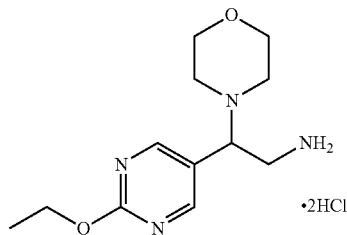

intermediate (67)

·2HCl

A mixture of intermediate (66) (0.01410 mol), Raney nickel (6 g) as a catalyst and methanol saturated with ammonia (7N, 10 ml) in THF (60 ml) was hydrogenated at room temperature (atmospheric pressure). After uptake hydrogen (2 equivalents), the catalyst was filtered off. The residue was evaporated to give 3.4 g crude product. The crude product was purified by preparative high-performance liquid chromatography over YMC (150*30 mm) (C18, eluent: $CH_3CN$/water from 5/95 to 20/80 with 0.1% $CF_3COOH$). The desired fraction was collected and evaporated. The residue was dissolved in methanol and converted into the hydrochloric acid salt by using 1,4-dioxane HCl (40 ml). The residue was evaporated, yielding 2.0 g of intermediate (67).

Example A.17 a) Preparation of

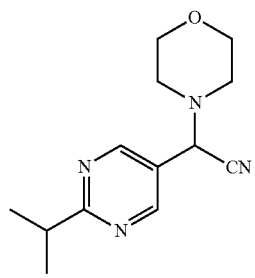

intermediate (68)

A mixture of 2-(1-methylethyl)-5-pyrimidinecarboxaldehyde (0.01332 mol), trimethylsilyl cyanide (0.02664 mol), morpholine (0.01465 mol) and sodium acetate (0.01598 mol) in acetic acid (20 ml) was stirred at room temperature. The reaction mixture was evaporated under reduce pressure. Water (30 ml) was added to the resulting residue. The aqueous phase was basified with $NaHCO_3$ till pH was 8, extracted with DCM (40 ml, 3 times). The separated organic layer was dried ($Na_2SO_4$), filtered, evaporated, yielding 3.3 g of intermediate (68).

b) Preparation of

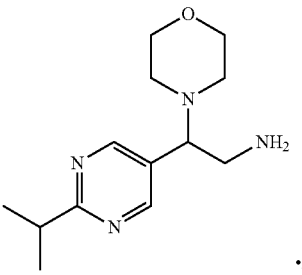

intermediate (69)

·2 HCl

A mixture of intermediate (68) (0.01340 mol), Raney nickel (6 g) as a catalyst and methanol saturated with ammonia (7N) in THF (60 ml) was hydrogenated at room temperature (atmospheric pressure). After uptake of hydrogen (2 equivalents), the catalyst was filtered off. The residue was evaporated to give 3.3 g crude product. The crude product was purified by preparative high-performance liquid chromatography over YMC (150*30 mm) (C18, eluent: $CH_3CN/H_2O$ from 15/85 to 30/70 with 0.1% $CF_3COOH$). The desired fraction was collected and evaporated. The residue was dissolved in methanol and converted into the hydrochloric acid salt by using dioxane HCl (40 ml). The residue was evaporated to give the final product, yielding 2.9 g of intermediate (69).

Example A.18 a) Preparation of

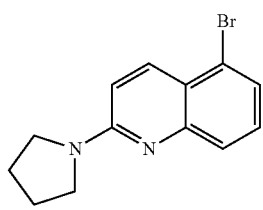

intermediate (70)

Pyrrolidine (0.041237 mol)) was added to chloroquinoline (0.041237 mol)). A vigorous exotherm warmed the reaction solution to boiling point. A reflux condenser was attached, and the solution stirred for 16 hours at 20° C. The bulk of the pyrrolidine was removed by rotary evaporation, and the residue taken up in Na$_2$CO$_3$ (50% aqueous)/DCM. The phases were separated, and the organic layer washed with NaCl (50% saturated). The organic layer was dried (Na$_2$SO$_4$) and the solvent removed. Azeotroped with phenylmethyl, yielding 12 g of intermediate (70).

b) Preparation of

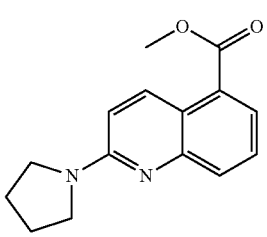

intermediate (71)

A 75-ml stainless steal autoclave was charged under nitrogen atmosphere with intermediate (70) (0.043296 mol), palladium acetate (0.00433 mol, 1.3 bis(diphenyl-phosphino) propane (0.0866 mol) and potassium acetate (0.86593 mol) in MeOH/THF 1/1 (40 ml). The autoclave was closed and pressurized to 50 bar CO and the reaction was carried out for 16 hours at a temperature of 100° C., yielding intermediate (71).

c) Preparation of

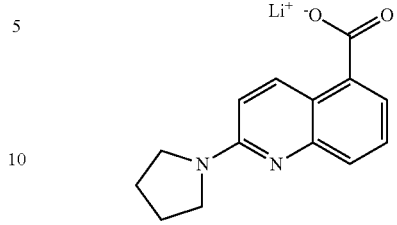

intermediate (72)

Intermediate (71) was converted to intermediate (72) using the methodology of Example A.5.

Example A.19 a) Preparation of

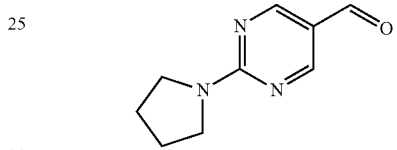

intermediate (73)

2-(Methylthio)pyrimidine-5-carboxaldehyde (0.01193 mol) and pyrrolidine (0.02983 mol) were dissolved in ethanol. The mixture was reacted in a steal-tube at 90° C. overnight. The reaction mixture was evaporated under reduced pressure. The residue was purified by column (silica gel, eluent: petroleum ether/ethyl acetate=20:1). The pure fractions were collected and the solvent was evaporated, yielding 1.56 g of intermediate (73).

Preparation of

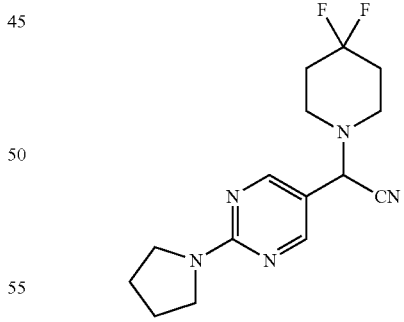

intermediate (74)

A mixture of intermediate (73) (0.0088 mol), trimethylsilyl cyanide (0.1760 mol), 4,4-difluoropiperidine hydrochloride (0.1056 mol) and sodium acetate (0.1144 mol) in acetic acid (20 ml) was stirred at room temperature. The reaction mixture was evaporated under reduced pressure. The residue was added water (20 ml). The aqueous phase was acidified to pH=8 with NaHCO$_3$, extracted with DCM (30 ml—3 times), the separated organic layer was dried (Na$_2$SO4), filtered and evaporated, yielding 2.4 g of intermediate (74).

c) Preparation of

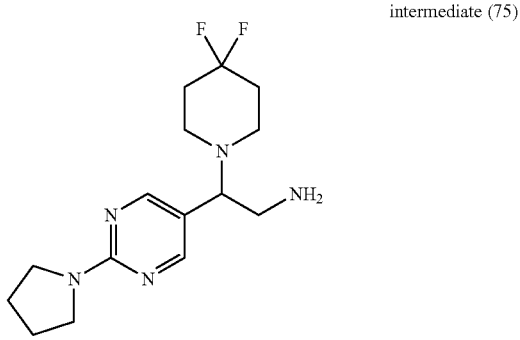

intermediate (75)

A mixture of intermediate (74) (0.0078 mol) and Raney nickel (6 g) as a catalyst in methanol saturated with ammonia (7N, 17 ml) was hydrogenated at room temperature (atmospheric pressure). After uptake of hydrogen (2 equivalents), the catalyst was filtered off and the filtrate was evaporated. The residue was purified by preparative high-performance liquid chromatography over YMC (250*20 mm) (C18, eluent: $CH_3CN$/water from 2/98 to 32/68 with 0.1% $CF_3COOH$). The desired fraction was collected and evaporated. The residue was acidified to pH=5 with HCl/dioxane. The residue was evaporated, yielding 2.4 g of intermediate (75).

Example A.20 a) Preparation of

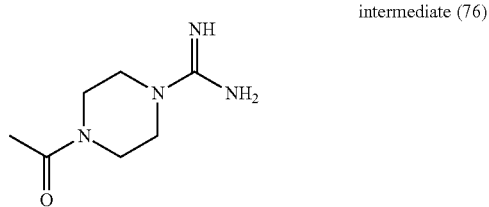

intermediate (76)

A mixture of carbamimidothioic acid, methyl ester, sulfate (2:1) (0.118 mol), 1-acetyl-piperazine (0.094 mol) and NaOH (6 g) in water (100 ml) was stirred at 80° C. for 5 hours. On cooling, enough ethanol (400 ml) was added. The precipitate was filtered off. The filtrate was collected and evaporated under reduced pressure, yielding 15 g of intermediate (76).

b) Preparation of

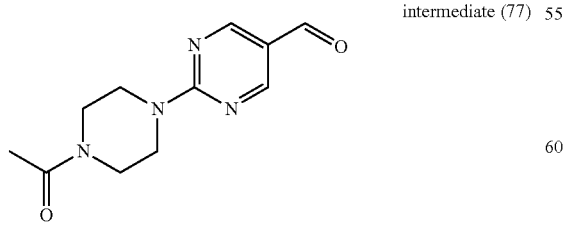

intermediate (77)

Sodium (6 g) was dispersed in ethanol (200 ml). After sodium was completely dissolved, intermediate (76) and intermediate (83) were added. The mixture was stirred at ambient temperature overnight. Solid was filtered off. The filtrate was collected and evaporated under reduced pressure. Then reside was added to DCM (200 ml) and washed with water (200 ml, four times). The resulting organic layer was dried over $Na_2SO_4$ and evaporated. The residue was purified with column chromatography (silica gel, eluent: MeOH/DCM=1/30 v/v). The pure fraction was collected and the solvent was evaporated, yielding 2 g of intermediate (77).

c) Preparation of

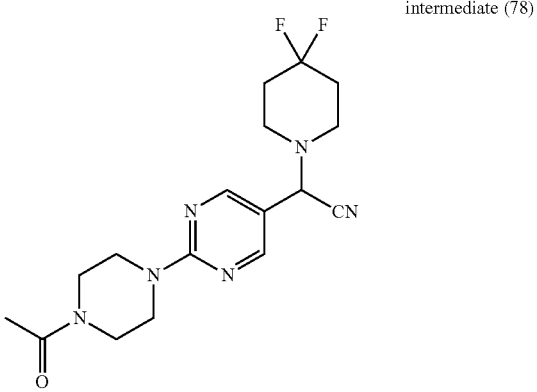

intermediate (78)

A mixture of intermediate (77) (0.0085 mol), 4,4-difluoropiperidine hydrochloride (0.01 mol), trimethylsilyl cyanide (0.017 mol) and sodium acetetate (0.011 mol) in acetic acid (20 ml) was stirred at ambient temperature overnight. Solvent was removed under reduced pressure. Water (50 ml) was added to above residue and basified with $NaHCO_3$ till pH was 8. DCM was added and extracted (50 ml, three times). The organic lay was combined and evaporated under reduced pressure, yielding 3 g of intermediate (78) and was used directly in the next reaction.

d) Preparation of

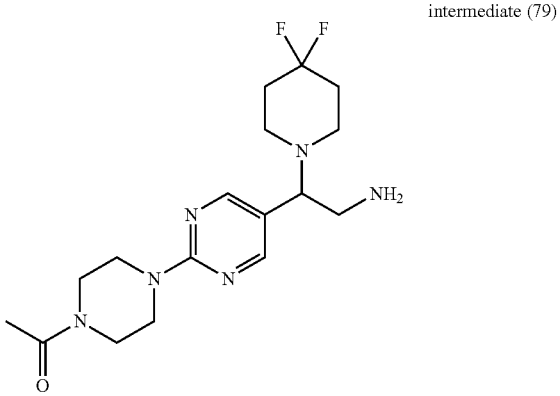

intermediate (79)

A mixture of intermediate (78) (0.0082 mol), Raney nickel (6 g) as a catalyst and methanol saturated with ammonia (7N, 15 ml) in THF (100 ml) was hydrogenated at ambient temperature (atmospheric pressure) overnight. After uptake of hydrogen (2 equivalents), the catalyst was filtered off and filtrate was collected and evaporated under reduced pressure. The residue was purified with high performance liquid chromatography. (eluent: 0.5% $CF_3COOH$ in water/$CH_3CN$ 45/55 v/v). The desired fraction was collected and evaporated under reduced pressure. The residue was dissolved in DCM (50 ml) and converted into the hydrochloric acid salt (1:2) with HCl/dioxane. The solvent was removed under reduced pressure, yielding. 2 g of intermediate (79).

Example A.21 a) Preparation of intermediate (80)

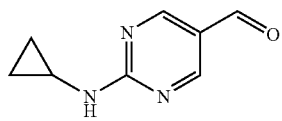

Sodium (2.3 g) was dissolved in ethanol (150 ml). N-cyclopropyl-guanidine, sulfate (2:1) (0.0337 mol) and intermediate (83) (0.0674 mol) were added. The reaction mixture was stirred at room temperature overnight. The mixture was evaporated under reduced pressure. The residue was dissolved in water (50 ml) and extracted with DCM (50 ml, three times). The organic layer was collected and evaporated under reduced pressure. The crude product was purified by column (silica gel, eluent: Petroleum ether/ethyl acetate 3/1). The pure fractions were collected and the solvent was evaporated, yielding 3.6 g of intermediate (80).

b) Preparation of intermediate (81)

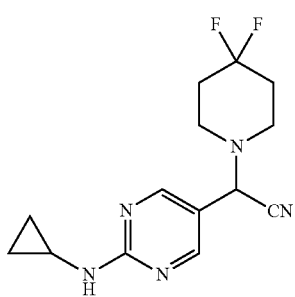

A mixture of intermediate (80) (0.01599 mol), trimethylsilyl cyanide (0.03198 mol), 4,4-difluoropiperidine hydrochloride (0.01759 mol) and sodium acetate (0.01919 mol) in acetic acid (100 ml) was stirred at room temperature. The reaction mixture was evaporated under reduced pressure. Water (60 ml) was added to resulting residue. The aqueous phase was basified with NaHCO₃ till pH was 8, extracted with DCM (50 ml*3), the separated organic layer was dried (Na₂SO₄), filtered, evaporated, yielding 4.4 g of intermediate (81).

c) Preparation of intermediate (82)

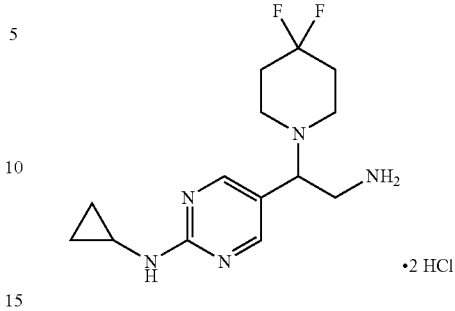

A mixture of intermediate (81) (0.015 mol), Raney nickel (8 g) as a catalyst and methanol saturated with ammonia (7N, 25 ml) in THF (150 ml) was hydrogenated at room temperature (atmospheric pressure). After uptake of hydrogen (2 equivalents), the catalyst was filtered off and the filtrate was evaporated. The residue was purified by preparative high-performance liquid chromatography over YMC (150*30 mm) (C18, eluent: CH3CN/water from 16/84 to 46/54 with 0.1% CF3COOH). The desired fraction was collected and evaporated. The residue was dissolved in MeOH and converted into the hydrochloric acid salt by using 1,4-dioxane HCl (40 ml). The residue was evaporated, yielding 2.0 g (40%) of intermediate (82).

Example A.22 a) Preparation of intermediate (83)

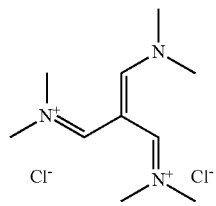

Phosphoric trichloride (2.1 mol) was added slowly into DMF (850 ml) at 0° C. and maintaining the internal temperature between 5 and 10° C. The mixture was stirred for 2 hours. 2-bromo-acetic acid (0.72 mol) was added and the mixture was heated to 90° C. overnight. The solution was cooled to room temperature. The slurry was poured into isopropanol (400 ml) at 0° C. with stirring. Water (30 ml) was added drop wise at 0° C. The slurry was diluted with isopropanol (300 ml) and isopropanyl acetate (300 ml) was added dropwise with stirring. The precipitate was collected by filtration and washed with CH₃CN (300 ml). The residue was dried under reduced pressure, yielding 170 g of intermediate (83).

b) Preparation of intermediate (84)

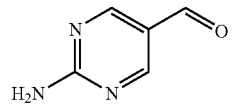

A mixture of intermediate (83) (0.1115 mol), carbonic acid, compd. with guanidine (1:2) (0.0555 mol) and Na₂CO₃

(18 g) in ethanol (200 ml) was refluxed at 80° C. overnight. The reaction mixture was filtrated, dried (Na₂SO₄) and evaporated, yielding 12.2 g of crude intermediate (84).

c) Preparation of

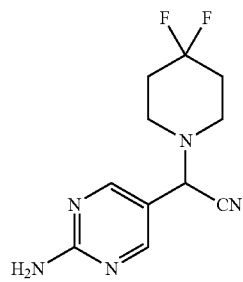

intermediate (85)

A mixture of intermediate (84) (0.02437 mol), trimethylsilyl cyanide (0.04873 mol), 4,4-difluoropiperidine hydrochloride (0.02681 mol) and sodium acetate (0.02924 mol) in acetic acid (80 ml) was stirred at room temperature. The reaction mixture was evaporated under reduced pressure. Water (30 ml) was added to resulting residue. The aqueous phase was basified with NaHCO₃ till pH was 8, extracted with DCM (40 ml, three times), the separated organic layer was dried (Na₂SO₄), filtered, evaporated, yielding 1.86 g of intermediate (85).

d) Preparation of

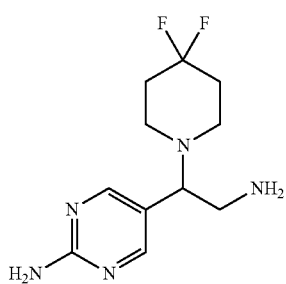

intermediate (86)

A mixture of intermediate (85) (0.00395 mol), Raney nickel (2 g) as a catalyst and methanol saturated with ammonia (7N, 5 ml) in ethanol (30 ml) was hydrogenated at room temperature (atmospheric pressure). After uptake of hydrogen (2 equivalents), the catalyst was filtered off and the filtrate was evaporated. The residue was purified by preparative high-performance liquid chromatography over YMC (250*20 mm) (C18, eluent: CH3CN/water from 8/92 to 18/82 with 0.1% CF3COOH). The desired fraction was collected and evaporated. The residue was acidified to pH=5 with HCl/dioxane. The residue was evaporated, yielding.0.9 g of intermediate (86).

Example A.23 a) Preparation of intermediate (87)

Sodium (2.8 g) was dissolved in ethanol (300 ml). 2-Methylpropionamidine hydrochloride (0.08157 mol) and intermediate (83) (0.08157 mol) were added. The reaction mixture was stirred at room temperature overnight. The mixture was evaporated under reduce pressure. The residue was dissolved in water (50 ml) and extracted with DCM (50 ml, three times). The organic layer was collected and evaporated under reduce pressure. The crude product was purified by column (silica gel, eluent: Petroleum ether/ethyl acetate 10/1 V/V). The pure fractions were collected and the solvent was evaporated, yielding 6.0 g of intermediate (87).

b) Preparation of

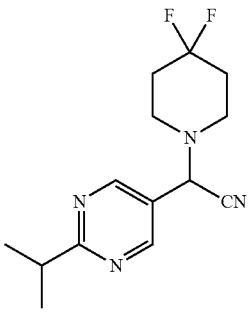

intermediate (88)

A mixture of intermediate (87) (0.01998 mol), trimethylsilyl cyanide (0.03996 mol), 4,4-difluoropiperidine hydrochloride (0.02198 mol) and sodium acetate (0.02398 mol) in acetic acid (30 ml) was stirred at room temperature overnight. The reaction mixture was evaporated under reduce pressure. Water (50 ml) was added to the resulting residue. The aqueous phase was basified with NaHCO₃ till pH was 8 and extracted with DCM (40 ml, three times). The separated organic layer was dried (Na₂SO₄), filtered, evaporated, yielding 5.2 g of intermediate (88).

c) Preparation of

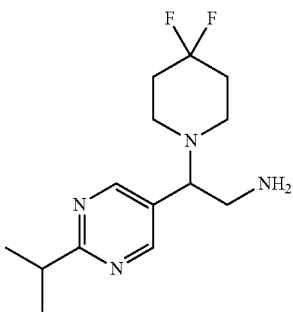

intermediate (89)

A mixture of intermediate (88) (0.01855 mol), Raney nickel (10 g) as a catalyst and methanol saturated with ammo-

Example A.24 a) Preparation of

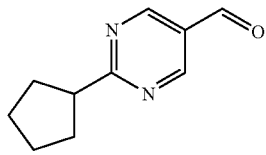

intermediate (90)

Sodium (5.8 g) was dissolved in ethanol (300 ml). Cyclopentanecarboximidamide monohydrochloride (0.16819 mol) and intermediate (83) (0.16819 mol) were added. The reaction mixture was stirred at room temperature overnight. The mixture was evaporated under reduce pressure. The residue was dissolved in water (50 ml) and extracted with DCM (50 ml, three times). The organic layer was collected and evaporated under reduce pressure. The crude product was purified by column (silica gel, eluent: petroleum ether/ethyl acetate 10/1 V/V). The pure fraction was collected and evaporated under reduce pressure, yielding 6.0 g of intermediate (90).

b) Preparation of

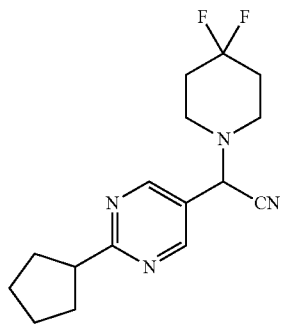

intermediate (91)

A mixture of intermediate (90) (0.01702 mol), trimethylsilyl cyanide (0.03404 mol), 4,4-difluoropiperidine hydrochloride (0.01872 mol) and sodium acetate (0.02042 mol) in acetic acid (30 ml) was stirred at room temperature. The reaction mixture was evaporated under reduce pressure. Water (30 ml) was added to the resulting residue. The aqueous phase was basified with NaHCO₃ till pH was 8, extracted with DCM (40 ml, three times), the separated organic layer was dried (Na₂SO₄), filtered, evaporated, yielding 3.86 g of intermediate (91).

c) Preparation of

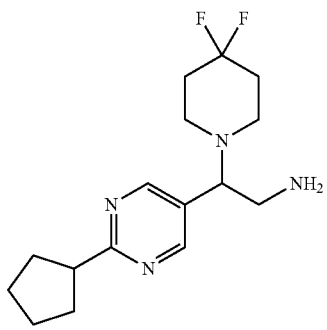

intermediate (92)

A mixture of intermediate (91) (0.0126 mol), Raney nickel (7 g) as a catalyst and methanol saturated with ammonia (7N, 6 ml) in THF (40 ml) was hydrogenated at room temperature (atmospheric pressure). After uptake of hydrogen (2 equivalents), the catalyst was filtered off. The solvent was evaporated, yielding 4.1 g of crude intermediate (92).

Example A.25 a) Preparation of

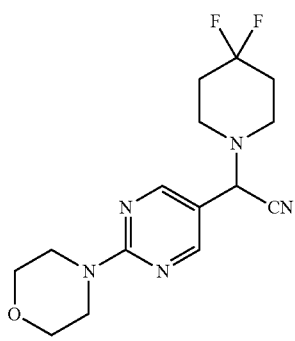

intermediate (93)

A mixture of 2-(4-morpholinyl)-5-pyrimidinecarboxaldehyde (6.6 g), 4,4-difluoro-piperidine hydrochloride (0.0213 mol), trimethylsilyl cyanide (0.0647 mol), and sodium acetate (2.6 g) in acetic acid (120 ml) was stirred at ambient temperature overnight. The reaction mixture was concentrated in vacuum. The residue was dissolved in water (100 ml). The aqueous solution was basified with NaHCO₃ to pH=10. The aqueous was extracted by DCM (200 ml, three times). The separated organic layers was dried over Na₂SO4 and filtered off. The filtrate was concentrated in vacuum, yielding 4.8 g of intermediate (93).

b) Preparation of intermediate (94)

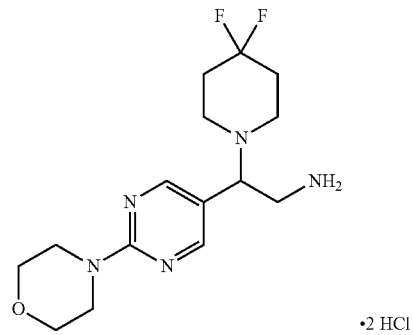

• 2 HCl

A mixture of intermediate (93) (4.8 g) and methanol saturated with ammonia (7N, 40 ml) in ethanol (350 ml) was hydrogenated at ambient temperature under hydrogen atmosphere with Raney nickel (10 g) as a catalyst in the presence of H$_2$ overnight. After uptake of hydrogen (2 equivalents), the catalyst was filtered off. The filtrate was evaporated in vacuum to afford the crude product. The crude product was purified by high-performance liquid chromatography (C18, eluent: CH$_3$CN/water from 10/90 to 40/60 with 0.1% CF$_3$COOH). The fraction was concentrated in vacuum. The residue was dissolved in methanol and converted into the hydrochloric acid salt by HCl in using 1,4-dioxane (150 ml), yielding 2.5 g of intermediate (94).

b) Preparation of intermediate (96)

• 2 HCl

A mixture of intermediate (95) (7.5 g) and methanol saturated with ammonia (7N, 50 ml) in THF (300 ml) was hydrogenated at ambient temperature under hydrogen atmosphere with Raney nickel (10 g) as a catalyst in the presence of hydrogen overnight. After uptake of hydrogen (2 equivalents), the catalyst was filtered off. The filtrate was evaporated.in vacuum to afford the crude product. The crude product was purified by high-performance liquid chromatography (C18, eluent: CH$_3$CN/water from 10/90 to 40/60 with 0.1% CF$_3$COOH). The fraction was concentrated in vacuum. The residue was dissolved in MeOH and converted into the hydrochloric acid salt by using 1,4-dioxane HCl (150 ml), yielding 3.5 g of intermediate (96).

Example A.26

Example A.27 a) Preparation of intermediate (95)

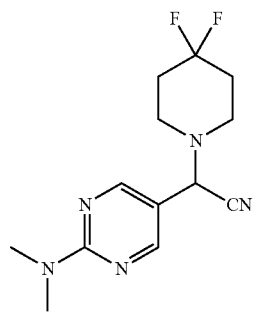

a) Preparation of intermediate (97)

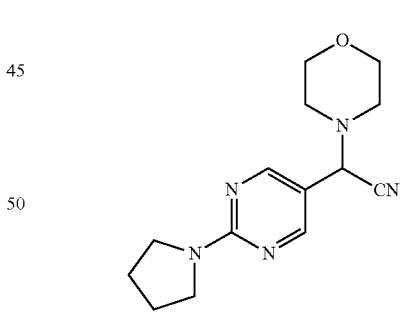

A mixture of 2-(dimethylamino)-5-pyrimidinecarboxaldehyde (0.0331 mol), trimethylsilyl cyanide (0.0662 mol), 4,4-difluoropiperidine hydrochloride (0.0397 mol), and sodium acetate (0.0496 mol) in acetic acid (50 ml) was stirred at ambient temperature overnight. The reaction mixture was concentrated in vacuum. The residue was dissolved in water (300 ml). The aqueous solution was basified with NaHCO$_3$ to pH=10. The aqueous was extracted by DCM (300 ml, three times). The separated organic layers was dried over Na$_2$SO$_4$ and filtered off. The filtrate was concentrated in vacuum, yielding 7.5 g of intermediate (95).

A mixture of 2-(1-pyrrolidinyl)-5-pyrimidinecarboxaldehyde (0.0169 mol), morpholine (0.0203 mol), trimethylsilyl cyanide (0.0508 mol) and sodium acetate (0.15 g) in acetic acid (45 ml) was stirred at ambient temperature overnight. The reaction mixture was concentrated in vacuum. The residue was dissolved in water (100 ml). The aqueous solution was basified with NaHCO$_3$ to pH=10. The aqueous was extracted by DCM (200 ml, three times). The separated organic layers was dried over Na$_2$SO$_4$ and filtered off. The filtrate was concentrated in vacuum, yielding 3.5 g of crude intermediate (97).

b) Preparation of intermediate (98)

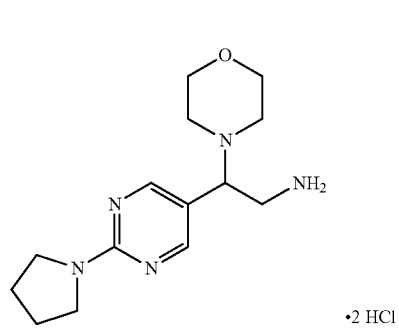

·2 HCl

A mixture of intermediate (97) (3.5 g) and methanol saturated with ammonia (50 ml) in THF (100 ml) and methanol (200 ml) was hydrogenated at ambient temperature under hydrogen atmosphere with Raney nickel (9 g) as a catalyst in the presence of hydrogen overnight. After uptake of hydrogen (2 equivalents), the catalyst was filtered off. The filtrate was evaporated in vacuum to afford the crude product. The crude product was purified by high-performance liquid chromatography (C18, eluent: $CH_3CN$/water from 10/90 to 40/60 with 0.1% $CF_3COOH$). The fraction was concentrated in vacuum. The residue was dissolved in methanol and converted into the hydrochloric acid salt by using HCl in 1,4-dioxane (150 ml), yielding 3 g of intermediate (98).

Example A.28 a) Preparation of intermediate (99)

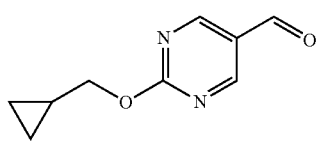

Sodium (8 g) was added to ethanol (300 ml) at 0° C. under nitrogen atmosphere. The mixture was stirred at ambient temperature until the solid was dissolved completely. Intermediate (83) (0.1432 mol) was added with stirring until the temperature of the mixture was cooled down to ambient temperature. Carbamimidic acid, cyclopropylmethyl ester 1,1,1-trifluoro-methanesulfonate (0.0946 mol) was added with stirring. The reaction mixture was stirred at ambient temperature overnight. The solvent was evaporated in vacuum. The residue was dispersed in water (300 ml). The mixture was extracted with DCM (300 ml*2). The combined organic fraction was washed with saturated brine aqueous (200 ml). The separated organic fraction was dried over $Na_2SO_4$ and the solvent was evaporated in vacuum. The residue was purified by column chromatography (silica gel, eluent: petroleum ether/ethyl acetate=10/1, v/v). The pure fraction was collected and the solvent was evaporated in vacuum. The residue was dried in vacuum, yielding 15.0 g of intermediate (99).

b) Preparation of intermediate (100)

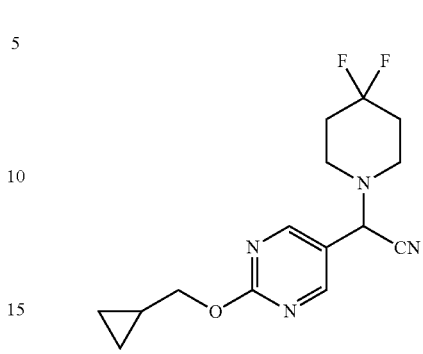

A mixture of intermediate (99) (0.0112 mol), 4,4-difluoropiperidine hydrochloride (0.0135 mol), trimethylsilyl cyanide (0.0224 mol), and sodium acetate (0.0169 mol) in acetic acid (30 ml) was stirred at ambient temperature overnight. The reaction mixture was concentrated in vacuum. The solvent was evaporated in vacuum. Water (50 ml) was added. The mixture was basified with solid NaOH to pH=10. The resulting precipitate was collected by filtration and washed with water (50 ml, three times). The precipitate was collected and dried in vacuum, yielding 3.2 g of intermediate (100).

c) Preparation of intermediate (101)

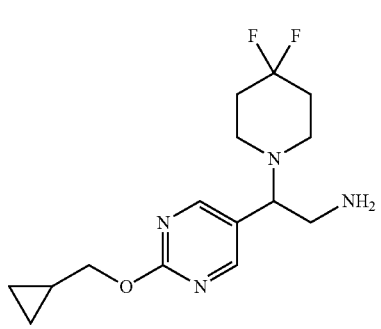

A mixture of intermediate (100) (3.2 g) and methanol saturated with ammonia (7N, 20 ml) in THF (100 ml) was hydrogenated at ambient temperature under hydrogen atmosphere with Raney nickel (6 g) as a catalyst in the presence of hydrogen overnight. After uptake of hydrogen (2 equivalents), the catalyst was filtered off. The filtrate was evaporated in vacuum to afford the crude product, yielding 3.0 g of intermediate (101)

Example A.29 a) Preparation of

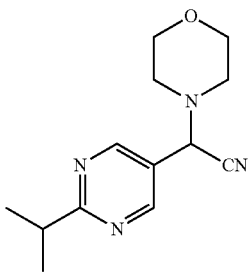

intermediate (102)

A mixture of intermediate (87) (0.01323 mol), trimethylsilyl cyanide (0.02646 mol), morpholine (0.01455 mol) and sodium acetate (0.01588 mol) in acetic acid (20 ml) was stirred at room temperature. The reaction mixture was evaporated under reduce pressure. Water (30 ml) was added to resulting residue. The aqueous phase was basified with NaHCO₃ till pH was 8, extracted with DCM (40 ml, three times). The separated organic layer was dried (Na2SO4), filtered, evaporated, yielding 3.3 g of intermediate (102).

b) Preparation of

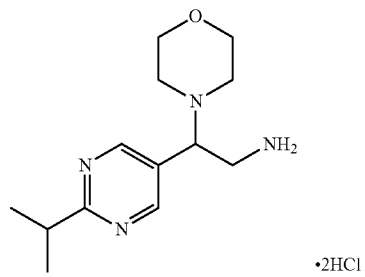

intermediate (103)

·2HCl

A mixture of intermediate (102) (0.01334 mol), Raney nickel (6 g) as a catalyst and methanol saturated with ammonia (7N, 10 ml) in THF (60 ml) was hydrogenated at room temperature (atmospheric pressure). After uptake of hydrogen (2 equivalents), the catalyst was filtered off. The residue was evaporated to give 3.0 g crude product. The crude product was purified by preparative high-performance liquid chromatography over YMC (150*30 mm) (C18, eluent: CH₃CN/water from 15/85 to 25/75 with 0.1% CF₃COOH). The desired fraction was collected and evaporated. The residue was dissolved in MeOH and converted into the hydrochloric acid salt by using 1,4-dioxane HCl (40 ml). The residue was evaporated to give the final product, yielding 1.8 g of intermediate (103).

Example A.30 a) Preparation of

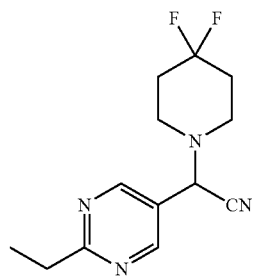

intermediate (104)

A mixture of 2-ethyl-5-pyrimidinecarboxaldehyde (0.0235 mol), 4,4-difluoropiperidine hydrochloride (0.0282 mol), trimethylsilyl cyanide (0.047 mol) and sodium acetate (0.0294 mol) in acetic acid (50 ml) was stirred at room temperature overnight. Then the mixture was filtered and the solvent was evaporated. The residue was dissolved in water, basified with NaHCO₃ to pH=8 and extracted by ethyl acetate twice. The combined organic phase was dried, filtered and concentrated to give the desired product, yielding 5.0 g of intermediate (104).

b) Preparation of

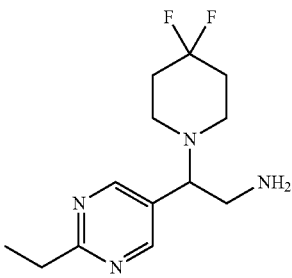

intermediate (105)

A mixture of intermediate (104) (0.0188 mol), Raney nickel (10 g) and methanol saturated with ammonia (7N, 10 ml) in methanol (60 ml) was hydrogenated at room temperature overnight. After uptake of hydrogen (2 equivalents), the catalyst was filtered off and the filtrate was evaporated, yielding 4.4 g of intermediate (105).

Example A.31 a) Preparation of

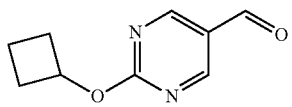

intermediate (106)

Sodium (8.2 g) was added to ethanol (500 ml) at 0° C. under nitrogen atmosphere. The mixture was stirred at ambient temperature until the solid was dissolved completely.

Intermediate (83) (0.2378 mol) was added with stirring until the temperature of the mixture was cooled down to ambient temperature. The trifluoro-methanesulfonate salt of cyclobutyl imidocarbamate (0.1189 mol) was added with stirring. The reaction mixture was stirred at ambient temperature overnight. The solvent was evaporated in vacuum. The residue was dispersed in water (500 ml). The mixture was extracted with DCM (200 ml, 3 times). The combined organic fraction was washed with saturated brine aqueous (200 ml). The separated organic fraction was dried over $Na_2SO_4$ and the solvent was evaporated in vacuum. The residue was purified by column chromatography (silica gel, eluent: petroleum ether/ethyl acetate=10/1). The pure fraction was collected and the solvent was evaporated in vacuum. The product was dried in vacuum to yield the corresponding product as white solid, yielding 16.6 g of intermediate (106).

b) Preparation of intermediate (107)

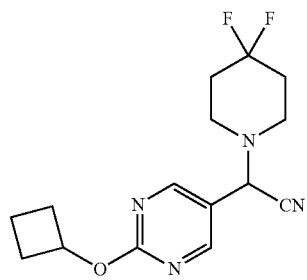

A mixture of intermediate (106) (0.0112 mol), 4,4-difluoropiperidine hydrochloride (0.0127 mol), trimethylsilyl cyanide (0.0224 mol), and sodium acetate (0.0146 mol) in acetic acid (30 ml) was stirred at ambient temperature overnight. The reaction mixture was concentrated in vacuum. The solvent was evaporated in vacuum. Water (50 ml) was added. The mixture was basified with solid NaOH to pH=10. The resulting precipitate was collected by filtration and washed with water (50 ml, three times). The precipitate was collected and dried in vacuum to afford the crude product, yielding 3.0 g of crude intermediate (107).

c) Preparation of intermediate (108)

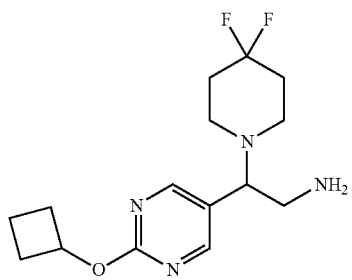

A mixture of intermediate (107) (3 g crude) and methanol saturated with ammonia (7N, 20 ml) in THF (100 ml) was hydrogenated at ambient temperature under hydrogen atmosphere with Raney nickel (10 g) as a catalyst in the presence of hydrogen overnight. After uptake of hydrogen (2 equivalents), the catalyst was filtered off. The filtrate was evaporated in vacuum to afford the crude product, yielding 3.0 g of crude intermediate (108).

Example A.32 a) Preparation of intermediate (200)

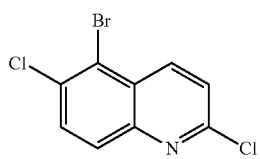

Bromine (5.2 mL, 101 mmol) was added dropwise over a period of 30 min. to 2,6-dichloroquinoline (20 g, 101 mmol) and aluminum chloride (40 g, 303 mmol) at 120° C. The resulting mixture was stirred at 120° C. for 1 hour, cooled to rt and methanol/water (1:1 v:v, 150 mL) was slowly added. The methanol was removed under reduced pressure and the resulting slurry was extracted with DCM. The organic phases were combined, washed with saturated aqueous sodium bicarbonate, dried with $Na_2SO_4$, filtered, concentrated and purified by flash column chromatography (30-100% DCM in hexanes) to provide the desired product (23 g, 83%). $^1$H NMR (500 MHz, $CDCl_3$) δ 8.51 (dd, J=8.9, 0.7, 1H), 7.92 (dd, J=9.0, 0.7, 1H), 7.76 (dd, J=8.9, 4.2, 1H), 7.49 (d, J=8.6, 1H).

a) Preparation of intermediate (201)

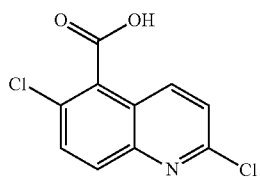

To a solution of intermediate (200) (20.0 g, 72.3 mmol) in THF (200 mL) at 0° C. was added dropwise 2 M isopropylmagnesium chloride in THF (36.5, 72.9 mmol). The reaction mixture was stirred for 30 min. and anhydrous $CO_2$ was gently bubbled through the reaction mixture, which was kept at 0° C., for 60 min. The reaction mixture was poured into water and extracted with EtOAc. The organic phases were combined, dried with $Na_2SO_4$, filtered and concentrated to provide the desired product (13 g, 74%). $^1$H NMR (500 MHz, DMSO) δ 14.40 (s, 1H), 8.29 (dd, J=8.9, 0.7, 1H), 8.07 (dd, J=9.0, 0.7, 1H), 7.94 (d, J=9.0, 1H), 7.74 (d, J=8.9, 1H).

Using an analogous procedure as described in steps a) and b) intermediate (202) was prepared starting from 6-methyl-2-chloroquinoline and intermediate (203) was prepared starting from 6-chloroquinoline.

intm. (202)

intm. (203)

Intm. (202): ¹H NMR (500 MHz, DMSO) δ 13.84 (s, 1H), 8.59 (d, J=8.9, OH), 8.33 (d, J=8.9, 1H), 7.96 (d, J=8.7, 1H), 7.75 (d, J=8.7, 1H), 7.64 (d, J=8.9, 1H).

Intm. (203): ¹H NMR (500 MHz, DMSO) δ 14.24 (s, 1H), 9.01 (dd, J=4.2, 1.5, 1H), 8.24 (dd, J=7.9, 0.7, 1H), 8.13 (d, J=9.0, 1H), 7.87 (d, J=9.0, 1H), 7.69 (dd, J=8.6, 4.2, 1H).

Example A.33 a) Preparation of

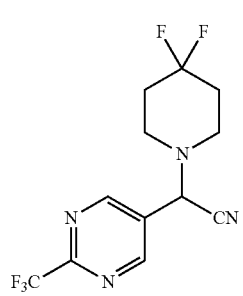

intermediate (204)

To a mixture of 2-trifluoromethyl-pyrimidine-5-carbaldehyde (8.8 g, 0.049 mol), 4,4-difluoropiperidine hydrochloric acid salt (8.3 g, 0.052 mol), and sodium acetate (6.1 g, 0.075 mol) in acetic acid (35 mL) was added trimethylsilylcyanide (13.6 mL, 0.099 mol). The resulting solution was allowed to stir for 12 h at rt. The resulting mixture was concentrated, then neutralized with saturated aqueous sodium bicarbonate to pH 7-8, partitioned between H$_2$O (100 mL), and CH$_2$Cl$_2$ (75 mL). The layers were separated and the aqueous layer was extracted with CH$_2$Cl$_2$ (2×75 mL). The combined organic layers were dried over Na$_2$SO$_4$, filtered, and concentrated. The resulting orange solid was used without purification (6.9 g, 45%). MS (ESI): mass calcd. for C$_{12}$H$_{11}$F$_5$N$_4$, 306.1; m/z found, 305.1 [M−H]. ¹H NMR (CDCl$_3$) δ 9.09 (d, J=7.5, 2H), 5.03 (s, 1H), 2.86-2.63 (m, 4H), 2.21-1.97 (m, 4H).

Using an analogous procedure as described in steps a) intermediate (205-207) were prepared starting from either 2-trifluoromethyl-pyrimidine-5-carbaldehyde or 2-methylsulfanyl-pyrimidine-5-carbaldehyde and 4,4-difluoropiperidine hydrochloride or morpholine, or piperidine respectively.

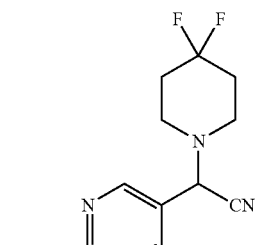

intm. (205)

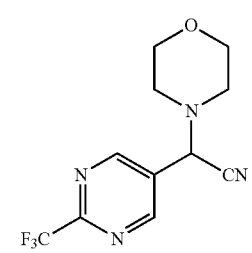

intm. (206)

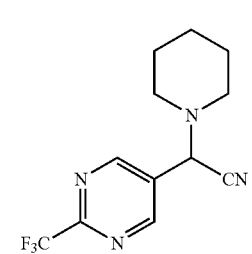

intm. (207)

Example A.34 a) Preparation of

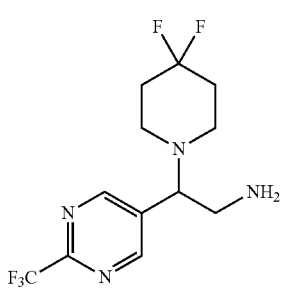

intermediate (208)

A mixture of (4,4-difluoro-piperidin-1-yl)-(2-trifluoromethyl-pyrimidin-5-yl)-acetonitrile (6.0 g, 0.019 mol) and 7N ammonia in MeOH (6 mL) in MeOH (60 mL) was hydrogenated with Raney Nickel as a catalyst at rt. After uptake of hydrogen (two equivalents), the catalyst was filtered off and the filtrate was evaporated. The resulting oil was used without purification (5.9 g, 98%). MS (ESI): mass calcd. for C$_{12}$H$_{15}$F$_5$N$_4$, 310.1; m/z found, 311.2 [M+H]$^+$. ¹H NMR (CD$_3$OD) δ 8.94 (d, J=9.3, 2H), 3.78 (t, J=6.7, 1H), 3.22 (dd, J=13.3, 7.2, 1H), 2.99 (dd, J=13.3, 6.3, 1H), 2.67-2.48 (m, 4H), 2.07-1.94 (m, 4H).

Using an analogous procedure as described in steps a) intermediates (27) and (28) were prepared.

intm. (28)

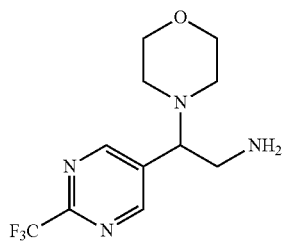

intm. (27)

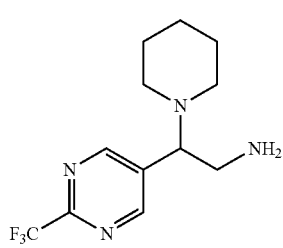

Example A.35 a) Preparation of intermediate (209)

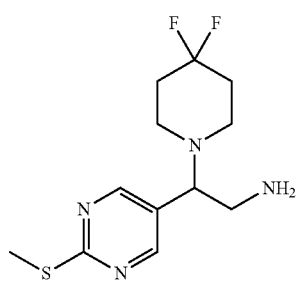

To a solution of (4,4-difluoro-piperidin-1-yl)-(2-methyl-sulfanyl-pyrimidin-5-yl)-acetonitrile (2.6 g, 9.0 mmol) and CH$_2$Cl$_2$ (100 mL) at −60° C. was added diisobutylaluminum hydride (18 mL, 1 M in CH$_2$Cl$_2$) dropwise. After 1 h, the resulting solution was warmed to 0° C. over 3 h and quenched with 30% aqueous Rochelle salt (50 mL). The resulting mixture was stirred vigorously at rt for 1 h. After which time, organic layer separated and the aqueous layer was extracted (CH$_2$Cl$_2$×50 mL). The combined organics were dried over Na$_2$SO$_4$, filtered, and concentrated. The resulting residue was purified on silica gel using CH$_2$Cl$_2$-MeOH (10% NH$_3$ solution) to afford an orange oil (1.2 g, 46%). MS (ESI): mass calcd. for C$_{12}$H$_{18}$F$_2$N$_4$S, 288.1; m/z found, 289.1 [M+H]$^+$. $^1$H NMR (CD$_3$OD) δ 8.50 (s, 2H), 3.66 (dd, J=8.4, 6.0, 1H), 3.24 (dd, J=13.1, 8.4, 1H), 2.93-2.84 (m, 2H), 2.64-2.53 (m, 5H), 2.49-2.38 (m, 2H), 2.05-1.84 (m, 5H).

Example A.36

Preparation of intermediate (210)

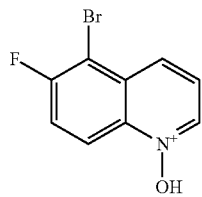

a) 5-Bromo-6-fluoro-1-hydroxy-quinolinium. To a stirred solution of 5-bromo-6-fluoro-quinoline (1.1 g, 4.87 mmol) in DCM (25 mL) was added 3-chloroperoxy-benzoic acid (1.00 g, 5.839 mmol) in portions. The mixture was heated in a 45° C. oil bath for 16 h. The reaction was cooled to r.t. and sodium thiosulfate was added (10 mL) followed by saturated sodium hydrogen carbonate (30 mL). The mixture was extracted with DCM (3×50 mL), the organic layers combined, dried with Na$_2$SO$_4$, filtered and evaporated in vacuo to afford a white solid (986 mg, 84%) which was used without further purification. MS (electrospray): mass calculated for C$_9$H$_6$Br$_F$NO, 241.96; m/z found 243.2, [M+H]$^+$. $^1$H NMR (400 MHz, CDCl$_3$) δ 8.79 (dd, J=9.6, 5.1, 1H), 8.52 (d, J=6.1, 1H), 8.06 (dd, J=8.8, 0.7, 1H), 7.51 (ddd, J=17.7, 9.7, 6.2, 1H), 7.43 (dd, J=8.8, 6.1, 1H).

Preparation of intermediate (211)

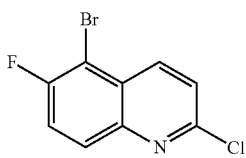

b) 5-Bromo-2-chloro-6-fluoro-quinoline. To a stirred solution of 5-bromo-6-fluoro-1-hydroxy-quinolinium (1.1 g, 4.53 mmol) in DCM (23 mL) was added phosphorous oxychloride (0.82 mL, 9.05 mmol). The mixture was heated in a 45° C. oil bath for 4 h, cooled to r.t. and evaporated to dryness in vacuo. The residue was partitioned between DCM (100 mL) and saturated sodium hydrogen carbonate (100 mL). The organic layer was dried with Na$_2$SO$_4$, filtered, evaporated in vacuo and purified by silica gel chromatography (EtOAc/hexanes) to obtain a pale pink solid (815 mg, 69%). $^1$H NMR (400 MHz, CDCl$_3$) δ 8.49 (d, J=8.9, 1H), 8.01 (dd, J=9.3, 5.0, 1H), 7.60-7.45 (m, 2H).

Preparation of intermediate (212)

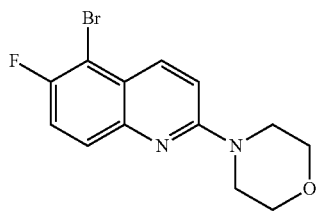

c. 5-Bromo-6-fluoro-2-morpholin-4-yl-quinoline. A solution of 5-bromo-2-chloro-6-fluoro-quinoline (0.20 g, 0.77 mmol) and morpholine (0.27 mg, 3.07 mmol) in NMP (0.8 mL) was heated in a heating block at 120° C. in a sealed microwave vial for 16 h. The reaction was cooled to rt and partitioned between DCM (20 mL) and 10% aqueous $NH_4Cl$ (10 mL). The organic layer was dried with $Na_2SO_4$, filtered and evaporated to give the crude product as a yellow oil (200 mg, 83%) which was used without further purification. MS (electrospray): mass calculated for $C_{13}H_{12}BrFN_2O$, 310.01, m/z found 313.0, [M+H]$^+$. $^1$H NMR (400 MHz, CDCl$_3$) δ 8.25 (dd, J=9.4, 0.6, 1H), 7.70-7.51 (m, 1H), 7.35 (dd, J=9.1, 8.4, 1H), 7.01 (dd, J=23.8, 9.3, 1H), 3.85 (dd, J=6.0, 3.8, 4H), 3.77-3.67 (m, 4H).

Using an analogous procedure as described in step c) intermediate (213) was prepared starting from 5-bromo-2-chloro-6-fluoro-quinoline and 3(R)-hydroxypyrrolidine, intermediate (214) was prepared starting from 5-bromo-2-chloro-6-fluoro-quinoline and ethanolamine, intermediate (215) was prepared starting from 5-bromo-2-chloro-6-fluoro-quinoline and N-methylpiperazine, intermediate (216) was prepared starting from 5-Bromo-1-chloro-isoquinoline and morpholine, intermediate (217) was prepared starting from 5-Bromo-1-chloro-isoquinoline and ethanolamine, and intermediate (218) was prepared starting from 5-bromo-2-chloro-6-methoxy-quinoline and morpholine.

intm. (213)

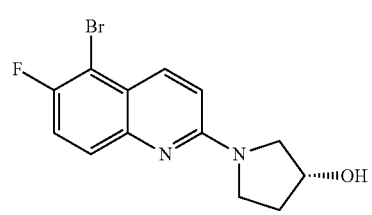

intm. (214)

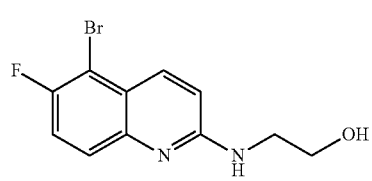

intm. (215)

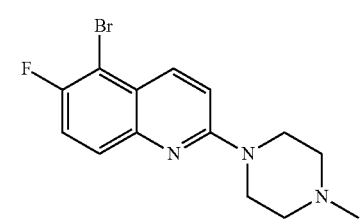

intm. (216)

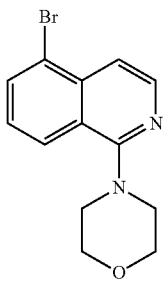

intm. (217)

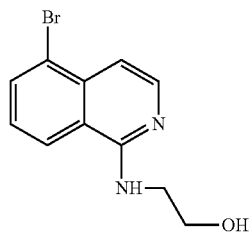

intm. (218)

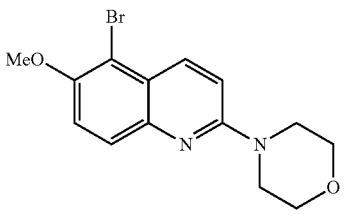

B. Preparation of the Final Compounds

Example B.1

Preparation of compound (1)

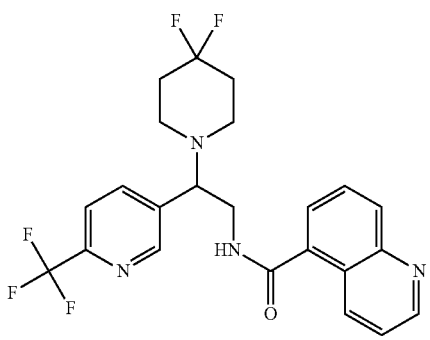

A mixture of intermediate (2) (0.0032 mol), 5-quinolinecarboxylic acid (0.0064 mol), N-cyclohexylcarbodiimide, N'-methyl polystyrene (0.013 mol, supplier Novabiochem product number; 01-64-0211) and 1-hydroxybenzotriazole (HOBT)/1-methyl-2-pyrrolidinone (NMP) (0.0032 mol; 400 mg HOBT in 6 ml NMP) in DCM (60 ml) was stirred for 3 hours at room temperature. (Polystyrylmethyl)trimethylammonium bicarbonate (0.032 mol, supplier Novabiochem product number; 01-64-0419) and methylisocyanate polystyrene (0.0036 mol, supplier Novabiochem product number; 01-64-0169) were added to the reaction mixture and then again stirred for 2 hours at room temperature. The reaction mixture was filtered. The filtrate's solvent was evaporated. The residue was recrystallized from H₂O/CH₃CN. The precipitate was filtered off and dried (vacuum), yielding 0.630 g of compound (1).

Example B.2

Preparation of compound (2)

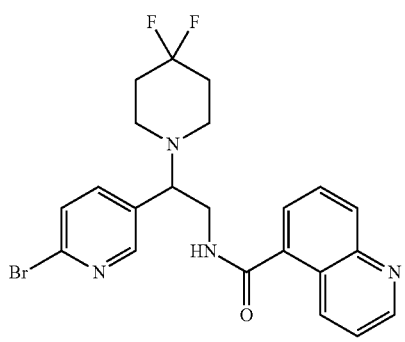

A mixture of intermediate (3b) (0.0003 mol), 5-quinolinecarbonyl chloride, hydrochloride (0.0005 mol) and DIPEA (1 ml) in ethyl acetate (5 ml) was stirred overnight at room temperature. This mixture was washed with a 1% $Na_2CO_3$ solution (10 ml). The organic layer was separated, dried and the solvent was evaporated. The residue was crystallized from CH₃CN, filtered off and dried, yielding 0.100 g of compound (2).

Example B.3

Preparation of compound (8)

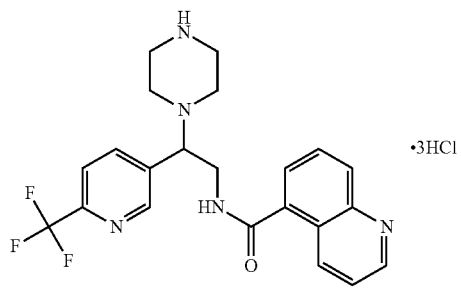

·3HCl

6N HCl in 2-propanol (0.4 ml) was added to a solution of compound (9) (0.0005 mol) in 2-propanol (9 ml) and stirred for 2 hours at 60° C. 6N HCl in 2-propanol was added again and the reaction mixture was stirred for 3 hours at 60° C. 6N HCl in 2-propanol was added again and the reaction mixture was stirred for 30 minutes at 70° C. The solvent was evaporated. The residue was suspended in 2-propanone. The precipitate was filtered off and dried (vacuo), yielding 0.1717 g of compound (8).

Example B.4

Preparation of compound (10)

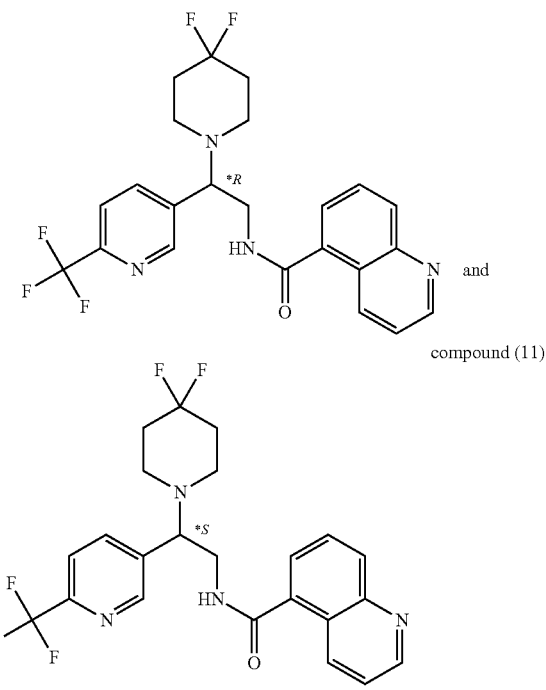

and compound (11)

Compound (1) (0.0004 mol) was separated in its enantiomers with preparative SFC purification. SFC was carried out on a Chiralpak AD-H column (Daicel Chemical Industries Ltd): eluent CO₂/(MeOH containing 0.2% 2-propylamine) 50/50 (isocratic); flow rate 50 ml/min; column heater temperature 40° C.; nozzle pressure 100 bar. Two product fraction groups were collected and their solvent was evaporated. Each residue was suspended in water and the resulting precipitate was filtered off and dried, yielding 0.062 g of compound (10) (R or S) and 0.057 g of compound (11) (R or S).

Example B.5

Preparation of compound (12)

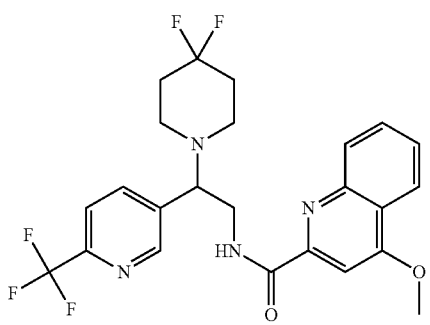

Intermediate (2) (0.0002 mol) was dissolved in DMF (3 ml). 1-Hydroxy-1H-benzotriazole (0.022 g) was added. A solution of 4-methoxy-2-quinolinecarboxylic acid (0.0003 mol) in DMF (1 ml) was added. N-cyclohexylcarbodiimide, N'-methyl polystyrene (0.00064 mol, supplier Novabiochem product number; 01-64-0211) was added. The resultant reaction mixture was shaken for 3 hours at room temperature. (Polystyrylmethyl)trimethylammonium bicarbonate (0.0016 mol, supplier Novabiochem product number; 01-64-0419) and methylisocyanate polystyrene (0.0002 mol, supplier Novabiochem product number; 01-64-0169) were added. The resultant reaction mixture was stirred overnight at room temperature. The scavenger and resin were filtered off and the filtrate's solvent was evaporated. The residue was purified by reversed-phase high-performance liquid chromatography (Shandon Hyperprep® C18 BDS (Base Deactivated Silica) 8 μm, 250 g, I.D. 5 cm). A gradient with a buffer solution and organic solvents was applied. The desired fractions were collected and worked-up, yielding compound (12).

Using an analogous procedure but replacing 4-methoxy-2-quinolinecarboxylic acid with 3-quinolinecarboxylic acid, 2-quinolinecarboxylic acid, 5-isoquinolinecarboxylic acid, 2-propyl-4-quinoline-carboxylic acid, 6-quinolinecarboxylic acid and 3-ethyl-2-methyl-6-quinoline-carboxylic acid respectively yielded compounds (13), (14), (16), (18), (19) and (24).

Example B.6

Prepaparation of compound (7)

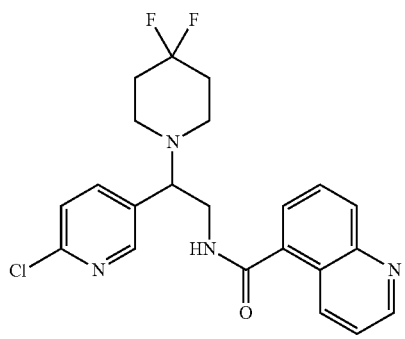

Oxalyl dichloride (0.002 mol) was added to a suspension of 5-quinolinecarboxylic acid (0.001 mol) in DCM (10 mL). DMF (small drop) was added, and the mixture stirred for 16 hours. The solvent was removed. The residue was dissolved in DCM (10 mL), and intermediate (9) (0.001 mol) and triethylamine added in rapid succession at 0° C. Stirring was continued for 4 hours, allowing the temperature to increase to 20° C. HCl (0.001 M, 10 mL) was added, and the phases separated. The organic layer was washed with Na₂CO₃ (aq) (50% saturated), water and brine. The solvent was removed, and the residue was purified by column chromatograpy over silica gel (DCM/CH₃OH 100-97.5%). The pure fractions were collected and the solvent removed. The residue was triturated under DIPE, and then dried at 60° C. in a vacuum oven, yielding 0.26 g of compound (7).

Example B.7

Preparation of compound (15)

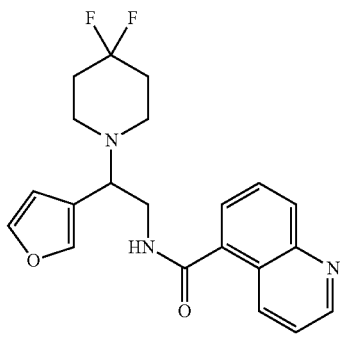

1-Hydroxy-1H-benzotriazole (0.180 g) and N'-(ethylcarbonimidoyl)-N,N-dimethyl-1,3-propanediamine, monohydrochloride (0.120 g) were added to a mixture of intermediate (11) (0.00087 mol) and 5-quinolinecarboxylic acid (0.00087 mol) in DCM (5 ml). The reaction mixture was stirred overnight, was washed with a 10% aqueous NaOH solution and dried with Na₂SO₄. The solvent was evaporated, yielding 0.120 g of compound (15).

Example B.8

Preparation of compound (46)

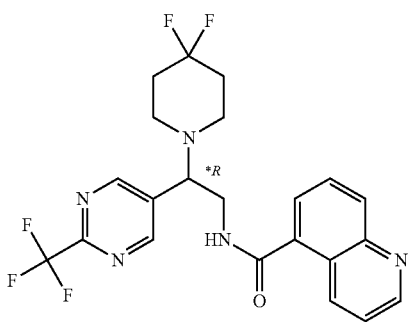

and compound (47)

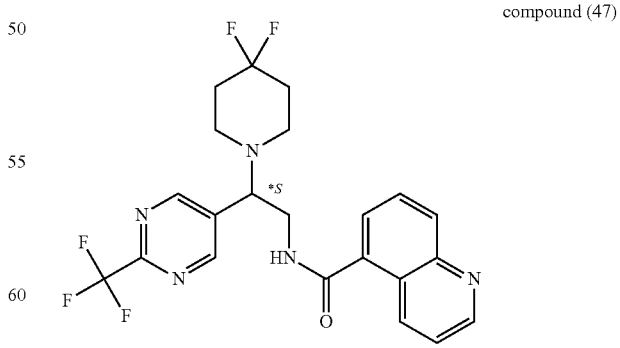

Intermediate (25) (0.0075 mol), 5-quinolinecarboxylic acid (0.0075 mol), 1-[bis-(dimethylamino)methylene]-1H-benzotriazoliumhexafluorophosphate(1-) 3-oxide (1:1) (0.008 mol), DIPEA (3.3 ml) and DMF (75 ml) were stirred during 16 hours in a closed vessel. The reaction mixture was diluted with water (150 ml) and acetonitrile (10 ml) and stirred overnight at room temperature. The precipitate was filtered and dried in vacuum. A part (2.85 g) of the residue (3.383 g, 97%) was purified in its enantiomers by preparative SFC. SFC was carried out on a Chiralpak AD-H column (30×250 mm) (Daicel Chemical Industries Ltd): eluent CO$_2$/ (MeOH containing 0.2% 2-propylamine) 60/40; flow rate 50 ml/min; column heater temperature 40° C.; nozzle pressure 100 bar; load: 76 mg/4 ml. Two Peaks were obtained and collected. The first combined fractions were evaporated and the residue was crystallised from isopropylether/acetonitrile 10/1. The precipitate was filtered off and dried in vacuum, yielding 1.099 g of compound (46). The second combined fractions were evaporated and the residue was crystallised in isopropylether/acetonitrile 10/1. The precipitate was filtered and dried in vacuum, yielding 1.082 g of compound (47).

Example B.9

Preparation of compound (34)

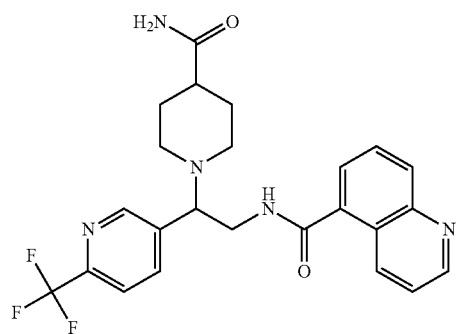

1H-1,2,3-triazolo[4,5-b]pyridinium, 1-[bis(dimethylamino)methylene]-hexafluorophosphate(1-), 3-oxide (0.001422 mol) was added to a mixture of intermediate (26) (0.000948 mol) and 5-quinolinecarboxylic acid (0.001138 mol) and DIPEA (0.001422 mol) in DMF (10 ml), at 0° C. under nitrogen flow. The reaction mixture was stirred and gradually warmed to room temperature, overnight. The solvent was evaporated under vacuum. The residue was purified by preparative high-performance liquid chromatography. The product fractions were collected and the solvent was evaporated, yielding 0.180 g of compound (34).

Example B.10

Preparation of compound (35)

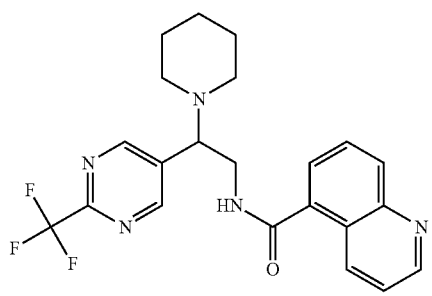

A mixture of intermediate (27) (0.0026 mol), 5-quinolinecarboxylic acid (0.0026 mol), N'-(ethylcarbonimidoyl)-N,N-dimethyl-1,3-propanediamine, monohydrochloride (0.0038 mol), pyridine (0.0077 mol) and DCM (50 ml) was stirred at room temperature for 18 hours. The reaction mixture was poured out in water and K$_2$CO$_3$ (1 g). The organic layer was separated, dried (MgSO$_4$), filtered and evaporated. The residue was purified on a Biotage flash silica column, eluent: DCM/MeOH, gradient 100/0 to 95/5, the pure fractions were collected and evaporated. The residue was crystallized from DIPE, yielding 0.773 g of compound (35).

Example B.11

Preparation of compound (39)

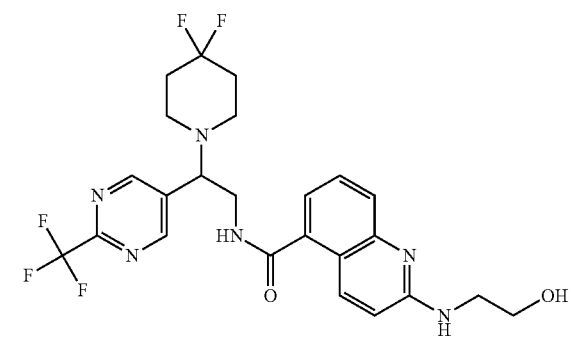

Compound (38) (0.0001 mol) and 2-amino-ethanol (1 ml) were stirred overnight at 80° C. The reaction mixture was diluted with water and three times extracted with ethyl acetate. The combined organic layers were evaporated and purified over a normal phase disposable flash column with DCM/MeOH 95/5. The corresponding fractions were evaporated and the residue was dried in vacuum, yielding 0.026 g of compound (39).

Example B.12

Preparation of compound (41)

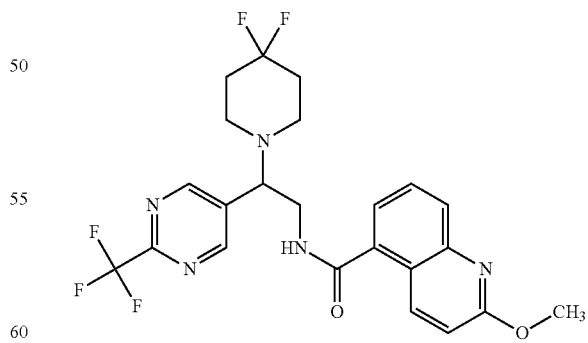

Compound (38) (0.0002 mol) and MeOH (p.a., 2 ml) were stirred at room temperature and NaOCH$_3$ 30% in MeOH (0.1 ml) was added. The reaction mixture was allowed to stir for 20 hours at 60° C., followed by an evaporation. The residue was purified on a normal phase disposable flash column with DCM/MeOH 98/2 as eluent. The corresponding fractions were evaporated, yielding 0.081 g of compound (41).

Example B.13

Preparation of

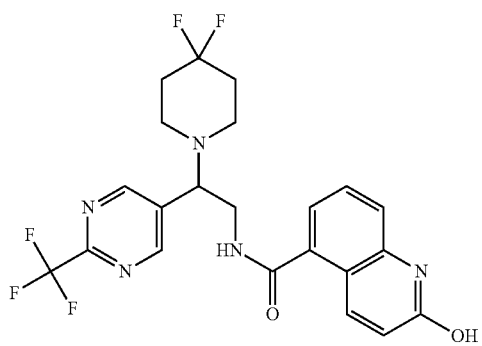

compound (77)

Compound (38) (0.0004 mol), HCl (1M, 1 ml) and acetic acid (1 ml) were stirred at 60° C. for 48 hours. The reaction mixture was diluted with water and acetonitrile. The precipitate was filtered and dried in vacuum, yielding 0.144 g of compound (77).

Example B.14

Preparation of

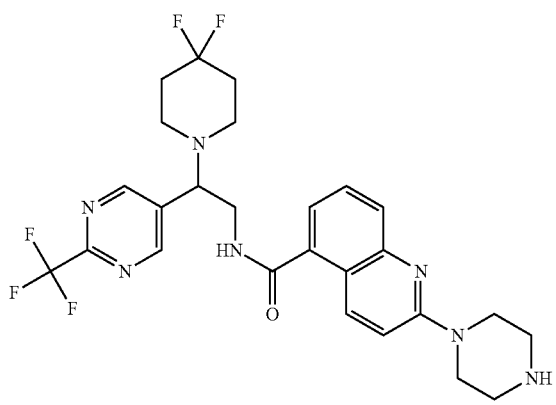

compound (78)

Compound (74) (0.0006 mol) and DCM (6 ml) were stirred at room temperature. A mixture of $CF_3COOH$ (2 ml) in DCM (2 ml) was added dropwise. The reaction mixture was allowed to stir for 16 hours. The reaction mixture was evaporated and the residue dissolved in water. This solution was alkalised with $K_2CO_3$ and two times extracted with DCM. The combined organic layer was dried with $MgSO_4$, filtered and evaporated. The residue was purified over a normal phase disposable flash column with DCM/MeOH-ammonia 98/2 to 95/5. The corresponding fractions were evaporated and triturated in isopropylether. The precipitate was filtered and dried in vacuum, yielding 0.305 g of compound (78).

Example B.15

Preparation of

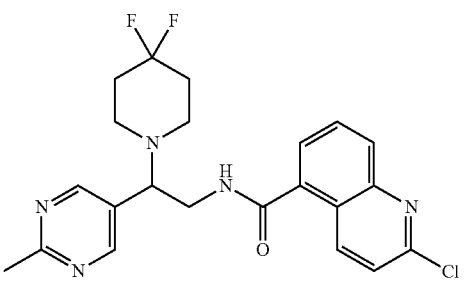

compound (135)

Intermediate (39) (0.0053 mol), intermediate (30) (0.0053 mol), 1-[bis(dimethyl-amino)methylene]-1H-1,2,3-triazolo[4,5-b]pyridinium hexafluorophosphate(1-) 3-oxide (1:1) (HATU) (0.0053 mol), DIPEA (0.016 mol) and DMF 60 ml) were stirred during 20 hours in a closed vessel. The reaction mixture was evaporated, dissolved in DCM and washed with saturated sodium carbonate solution and with water. The organic layer was dried over $MgSO_4$, filtered and evaporated. The residue was crystallised in DIPE with 20% acetonitrile. The filtrate was evaporated, yielding 1.5 g of compound (135).

Example B.16

Preparation of

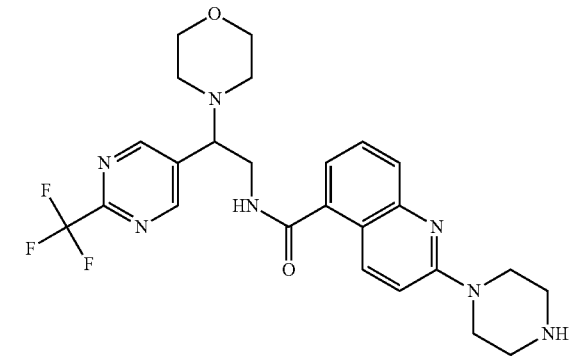

compound (102)

Compound (37) (0.001 mol) and piperazine (0.01 mol) in 1-methyl-2-pyrrolidinone (3 ml) were stirred for 2 hours at 115° C. The reaction mixture was diluted with water and extracted with ethyl acetate. The organic layer was dried ($MgSO_4$), filtered and the solvent was evaporated. The residue was suspended in diisopropylether and a little 2-propanol, the solid was filtered off, washed and dried in vacuum, yielding 0.12 g of compound (102).

Example B.17

Preparation of

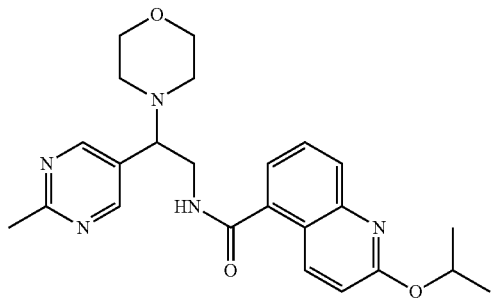

compound (117)

A mixture of sodium hydride (0.0146 mol) and 2-propanol (10 ml) was stirred for 15 minutes. Then a mixture of compound (156) (0.00146 mol) in 2-propanol (5 ml) was added and this mixture was stirred and refluxed at 140° C. for 30 minutes, in a microwave oven. The precipitate was filtered off and the filtrate was evaporated. The residue was purified by high-performance liquid chromatography (eluent: $CH_3CN$/$H_2O$ 75/25 to $CH_3CN$/$H_2O$ 55/45 with 0.1% $CF_3COOH$). The product fractions were collected and the solvent was evaporated, yielding 0.17 g of compound (117).

Example B.18

Preparation of

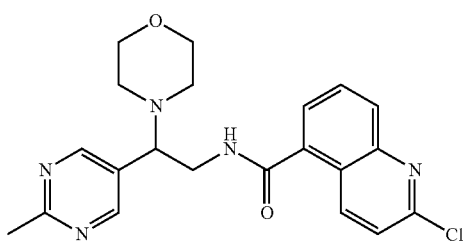

compound (156)

Intermediate (56) (0.014 mol) was suspended in DCM (q.s., anhydrous). A solution of intermediate (55) (0.011 mol) and triethylamine (0.023 mol) in DCM was added to the suspension, stirred at room temperature. The reaction mixture was stirred overnight at room temperature. The solvent was evaporated under reduced pressure. The residue was purified by preparative HPLC (eluent: $CH_3CN$/$H_2O$ from 25/75 to 55/45+0.1% $CF_3COOH$). The product fractions were collected and then dried by lyophilization, yielding 4.0 g (88%) of compound (156).

Example B.19

Preparation of

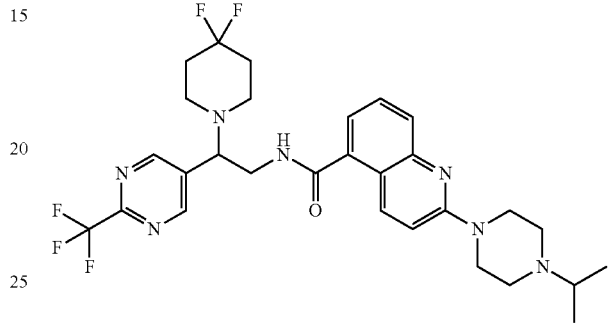

compound (134)

Compound 164 (0.5 mmol), isopropylpiperazine (1 mmol) and dimethylsulfoxide (1 ml) were stirred at 100° C. for 6 hours. The reaction mixture was diluted with 10 ml water and under reflux further dissolved with addition of methanol (about 5 ml). The solution was stirred overnight, the precipitate was filtered and dried in vacuum, yielding 218 mg of compound (134).

Example B.20

Preparation of

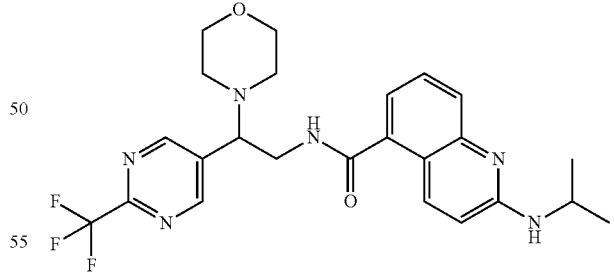

compound (168)

A mixture of compound 37 (0.644 mmol), tris(dibenzylideneacetone)dipalladium (0.022 mmol), 2,2'-bis(diphenylphosphino)-1,1'-binaphthyl (0.033 mmol) and sodium tert-butoxide (2.0812 mmol) in 2-propanamine (5 ml) was stirred at 80° C. overnight. The mixture was filtered and concentrated to give the crude product. The crude product was purified by high-performance liquid chromatography (C18, eluent: $CH_3CN$/water from 22/78 to 42/58 with 0.1% $CF_3COOH$). The pure fractions were collected and the organic solvent was evaporated. The product was obtained by lyophilization, yielding 0.08 g of compound (168).

Example B.21

Preparation of compound (140)

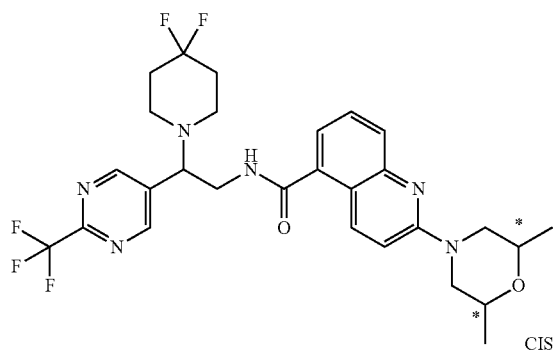

CIS

Compound 164 (0.5 mmol), cis-2,6-dimethylmorpholine (2 mmol) and 2-methoxy-ethanol (2 ml) were stirred at 80° C. for 16 hours. The reaction mixture was evaporated and 300 mg residue was purified by reversed-phase high-performance liquid chromatography (Shandon Hyperprep® C18 BDS (Base Deactivated Silica) 8 µm, 250 g, I.D. 5 cm). A gradient with 2 mobile phases was applied. Phase A: a 0.25% $NH_4HCO_3$ solution in water; phase B: $CH_3CN$). The corresponding fractions were collected and evaporated. The residue was crystallised in isopropylether with 5% $CH_3CN$. The crystals were collected by filtration and dried in vacuum, yielding 120 mg of compound (140).

Example B.22

Preparation of compound (173)

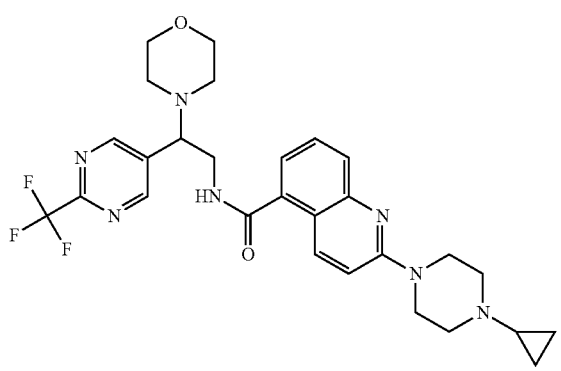

A mixture of compound (37), 1-cyclopropyl-piperazine (0.0027 mol), tris(dibenzylidene-acetone)dipalladium (0.054 mmol), 1,1'-[1,1'-binaphthalene]-2,2'-diylbis[1,1-d]phenyl-phosphine (0.081 mmol) and 2-methyl-propanol, sodium salt (1:1) (0.00162 mol) in THF (5 ml) was stirred at 80° C. for 40 minutes under microwave. The mixture was filtered and concentrated to give the crude product. The crude product was purified by high-performance liquid chromatography (C18, eluent: $CH_3CN$/water from 8/92 to 38/62 with 0.1% $CF_3COOH$). The pure fractions were collected and the organic solvent was evaporated. The aqueous mixture was basified with solid $NaHCO_3$ to pH=8. The aqueous mixture was extracted with DCM (40 ml) twice. The combined organic layers was washed with de-ion water (20 ml). The separated organic fraction was dried over sodium sulfate, filtered off the solid and the solvent was evaporated. The product was obtained by lyophilization, yielding 0.04 g of compound (173).

Example B.23

Preparation of compound (273)

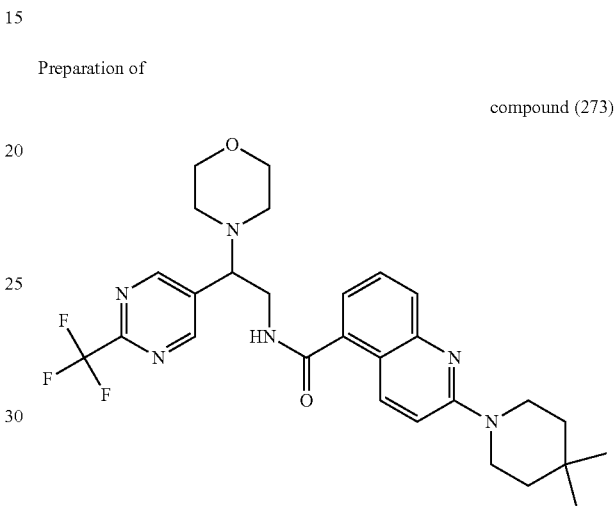

A mixture of compound (316) (0.19 mmol) and 4,4-dimethyl-piperidine (0.98 mmol) was stirred at 60° C. for 3 days. The reaction mixture was concentrated in vacuum. The residue was purified by high-performance liquid chromatography (reverse phase column, eluent: $CH_3CN$/water from 10/90 to 40/60 with 0.1% $CF_3COOH$). The pure fractions were collected and the product was obtained by lyophilization, 25.77 mg of compound (273).

Example B.24

Preparation of compound (316)

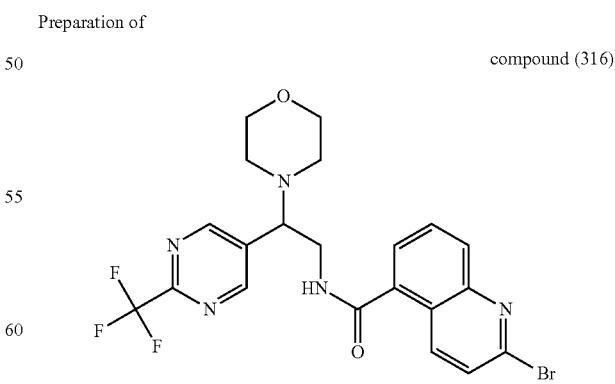

A mixture of compound (37) (0.0043 mol) and phosphoric tribromide (0.0209 mol) was stirred at 100° C. for 5 hours. Ice-water was added into the reaction mixture with stirring. The aqueous solution was acidified by $NaHCO_3$ to pH=10.

The aqueous solution was extracted by DCM (300 ml, three times). The combined organic layers were dried over Na$_2$SO$_4$ and filtered off. The solvent was concentrated in vacuum to afford the product, yielding 2 g of compound (316).

Example B.30 a) Preparation of

Compound (400)

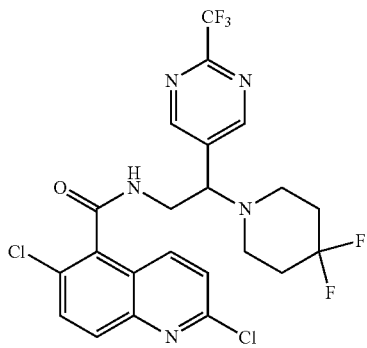

To intermediate (201) (2.4 g, 9.9 mmol) and (benzotriazol-1-yloxy)tris(dimethylamino) phosphonium hexafluorophosphate (4.4 g, 9.9 mmol) in DCM (15 mL), at 0° C. was added triethylamine (5.5 mL, 39 mmol) and the reaction mixture stirred for 20 min. Intermediate 25 (3.1 g, 9.9 mmol) was added and the reaction mixture was slowly warmed to rt and stirred for 12 hours. Water was added and the reaction mixture was extracted with DCM. The organic phases were combined, dried with Na$_2$SO$_4$, filtered, concentrated and purified by flash column chromatography (0-100% EtOAc in hexane) to provide the desired product (4.5 g, 85%).

Using an analogous procedure as described in example B.30 compound (401) was prepared starting from intermediate (202) and compound (402) was prepared starting from intermediate 201 and intermediate (23). Additionally one skilled in the art will recognize that compounds analogous to compound 400 can be made by the coupling of any commercially available quinoline or isoquinoline carboxylate, with the appropriate amine intermediates listed above in examples A1-A43 to afford final products of formula (I).

compound (401)

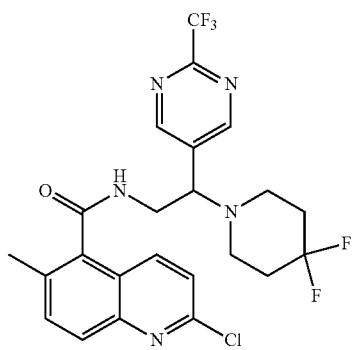

Compound (402)

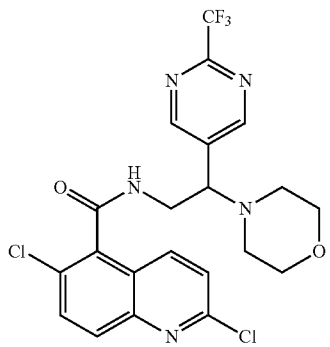

Example B.31 a) Preparation of compound (403)

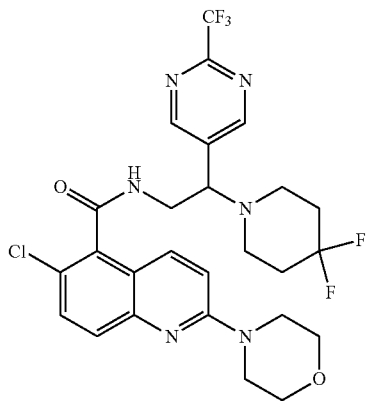

To compound (402) (75 mg, 0.14 mmol) and triethylamine (0.10 mL, 0.56 mmol) in acetonitrile (2 mL) was added morpholine (25 mg, 0.28 mmol). The reaction vessel was sealed and heated to 120° C. for 14 h. The reaction mixture was cooled to rt and purified by HPLC (C18, eluent: CH$_3$CN/water from 10/90 to 100/0 with 0.1% CF$_3$COOH) to provide the desired product (70 mg, 71%). One skilled in the art will realize that certain examples wherein the amine nucleophile contains an additional nucleophilic functionality will require the use of a protecting group such as a Boc group. In these cases a deprotection step may be required to reveal the final compound.

Example B.32 a) Preparation of compound (582)

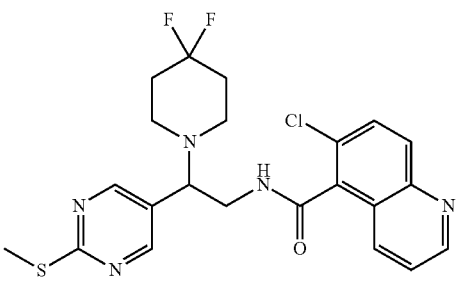

Compound 582, 6-chloro-quinoline-5-carboxylic acid [2-(4,4-difluoro-piperidin-1-yl)-2-(2-methylsulfanyl-pyrimidin-5-yl)-ethyl]-amide was prepared analogous to Example B.30 by coupling 6-chloro-quinoline-5-carboxylic acid and 2-(4,4-difluoro-piperidin-1-yl)-2-(2-methylsulfanyl-pyrimidin-5-yl)-ethylamine.

Example B.33 a) Preparation of compound (583)

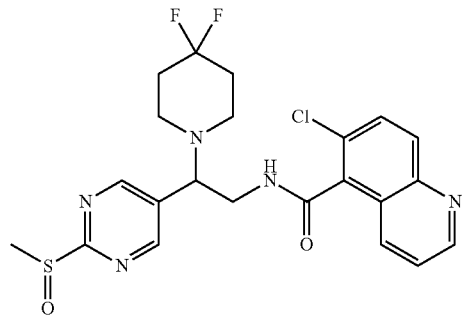

To a solution of 6-chloro-quinoline-5-carboxylic acid [2-(4,4-difluoro-piperidin-1-yl)-2-(2-methylsulfanyl-pyrimidin-5-yl)-ethyl]-amide (400 mg, 0.8 mmol) in $CH_2Cl_2$ (5 mL) and DMF (2 mL) was added 1 M solution of methansulfonic acid in $CH_2Cl_2$ (1.6 mL, 1.6 mmol) at rt. The resulting solution was cooled to −20° C. and 3-chloroperoxybenzoic acid (77% maximum in $H_2O$) (192 mg, 1.1 mmol) was added in a single portion. After 1 h, the solution was allowed to warm to rt over 3 h. The reaction mixture was portioned between aqueous saturated sodium bicarbonate (10 mL). The aqueous layer was extracted with $CH_2Cl_2$ (2×10 mL). The combined organic layers were dried ($MgSO_4$), filtered, and concentrated. The residue was purified directly by silica gel $CH_2Cl_2$-MeOH to afford a white solid (150 mg, 36%). MS (ESI): mass calcd. for $C_{22}H_{22}ClF_2N_5O_2S$, 493.1; m/z found, 494.1 [M+H]$^+$. $^1$H NMR ($CD_3OD$) δ 9.08 (s, 2H), 9.01 (dd, J=4.6, 1.6, 1H), 8.42-8.31 (m, 1H), 8.12 (dd, J=9.1, 0.7, 1H), 7.88 (d, J=9.1, 1H), 7.77 (dd, J=8.6, 4.6, 1H), 4.35 (t, J=7.0, 1H), 4.22 (dd, J=13.8, 6.4, 1H), 4.11 (d, J=13.6, 8.0, 1H), 2.99 (s, J=1.4, 3H), 2.94-2.78 (m, 4H), 2.09 (ddd, J=20.9, 13.2, 6.7, 4H).

Example B.34

Preparation of compound (584)

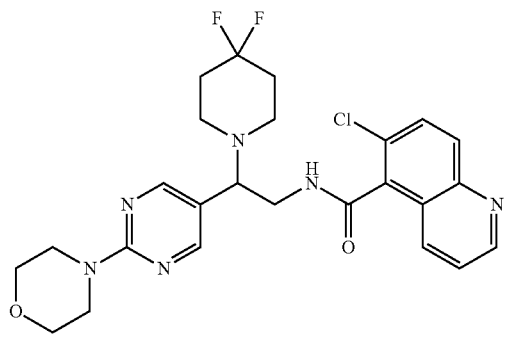

To a solution of 6-chloro-quinoline-5-carboxylic acid [2-(4,4-difluoro-piperidin-1-yl)-2-(2-methanesulfinyl-pyrimidin-5-yl)-ethyl]-amide (20 mg, 0.04 mmol) and $CH_3CN$ (1 mL) was added triethylamine (0.01 mL, 0.08 mmol) followed by morpholine (7 mg, 0.08 mmol) in a sealed tube. The reaction vessel was heated to 90° C. After 12 h, the resulting solution was cooled and purified by preparative reverse-phase HPLC to afford a white solid (17 mg, 66%). MS (ESI): mass calcd. for $C_{25}H_{27}ClF_2N_6O_2$, 516.1; m/z found, 517.2 [M+H]$^+$. $^1$H NMR ($CD_3OD$) δ 8.97 (dd, J=4.5, 1.6, 1H), 8.57 (s, 2H), 8.13-8.07 (m, 2H), 7.83 (d, J=9.1, 1H), 7.65 (dd, J=8.6, 4.5, 1H), 4.70 (dd, J=10.4, 5.4, 1H), 4.36-4.26 (m, 2H), 3.89-3.84 (m, 4H), 3.76-3.72 (m, 4H), 3.56-3.40 (m, 4H), 2.44-2.34 (m, 4H).

Example B.35

Preparation of compound (593)

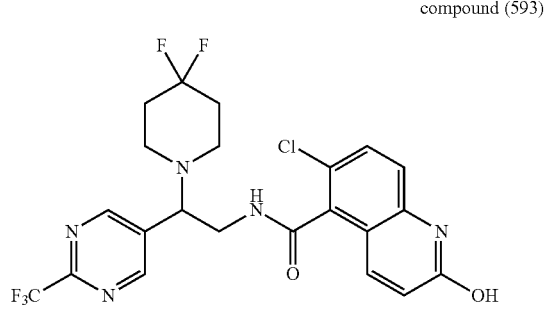

To a solution of 2,6-dichloro-quinoline-5-carboxylic acid [2-(4,4-difluoro-piperidin-1-yl)-2-(2-trifluoromethyl-pyrimidin-5-yl)-ethyl]-amide (100 mg, 0.2 mmol) and 4N HCl in dioxane (3 mL) was added water (7 μL). The resulting mixture was heated to 90° C. After 12 h, the resulting mixture was concentrated and purified by preparative reverse-phase HPLC to afford the title compound as a colorless solid (56 mg, 58%). MS (ESI): mass calcd. for $C_{22}H_{19}ClF_5N_5O_2$, 515.1; m/z found, 516.2 [M+H]$^+$. $^1$H NMR (($CD_3$)$_2$SO) δ 11.96 (s, 1H), 9.13 (s, 2H), 8.79 (t, J=5.8, 1H), 7.55 (m, 2H), 7.31 (d, J=8.9, 1H), 6.53 (d, J=9.8, 1H), 4.25-4.22 (m, 1H), 3.94-3.82 (m, 2H), 2.75-2.54 (m, 4H), 2.06-1.93 (m, 4H).

Example B.36

Preparation of compound (596)

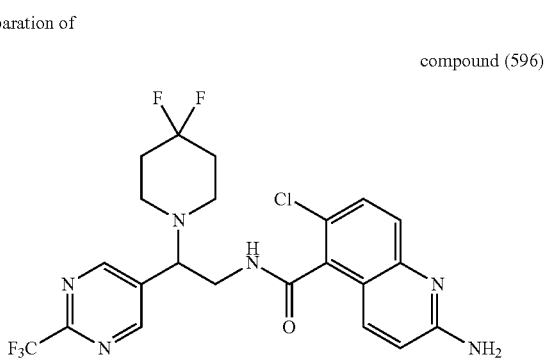

A solution of 2,6-dichloro-quinoline-5-carboxylic acid [2-(4,4-difluoro-piperidin-1-yl)-2-(2-trifluoromethyl-pyrimidin-5-yl)-ethyl]-amide (100 mg, 0.2 mmol) and 7N ammonia in MeOH was heated to 100° C. After 60 h, the resulting mixture was cooled, concentrated, and purified directly by preparative reverse-phase HPLC to afford the title compound as a colorless solid (13 mg, 13%). MS (ESI): mass calcd. for $C_{22}H_{20}ClF_5N_6O$, 514.1; m/z found, 516.2 [M+H]+. $^1$H NMR (CDCl$_3$) δ 8.90 (s, 2H), 7.95 (d, J=9.3, 1H), 7.89 (d, J=9.2, 1H), 7.68 (d, J=9.0, 1H), 6.82 (d, J=9.5, 1H), 6.55-6.47 (m, 1H), 4.08 (d, J=3.7, 3H), 2.70 (d, J=23.7, 4H), 2.07 (d, J=2.3, 4H).

Example B.37

Preparation of compound (598)

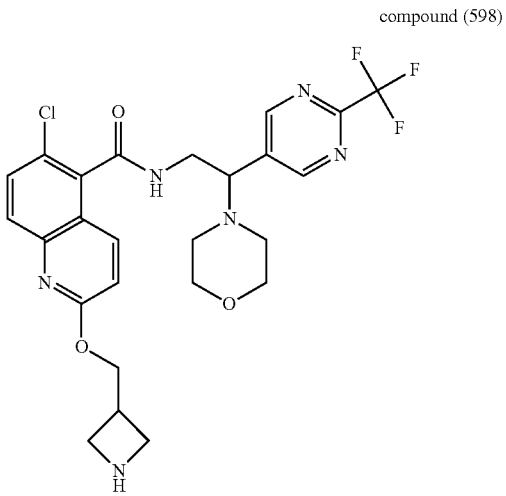

To a mixture of sodium hydride (0.88 mmol) and THF (0.8 mL) was added t-butyl 3-(hydroxymethyl)azetidine-1-carboxylate (0.8 mmol), and the reaction mixture was allowed to stir for 15 min. followed by the addition of compound 402 (0.8 mmol). The mixture was sealed and heated to 120° C. in a heating block for 12 hours. Upon complete consumption of starting material, the reaction mixture was poured over brine (100 mL) and extracted three times with DCM (75 mL). Combined organics were dried with Na$_2$SO$_4$, filtered, and evaporated in vacuo. The resulting residue was dissolved in formic acid (1 mL) and treated with 4 M HCl in dioxane (1 mL). This mixture was allowed to stir for 3 hours, until complete Boc removal was observed. The reaction mixture was then concentrated in vacuo and purified by HPLC (eluent: CH$_3$CN/H$_2$O 10/95 to CH$_3$CN/H$_2$O 95/5 with 0.1% CF$_3$COOH). The product fractions were collected and the solvent was removed by lyophilization yielding 0.009 g of compound as the trifluoroacetate salt. In subsequent examples some alcohols will not have an amine functionality requiring Boc protection. In these cases the acidic Boc deprotection step is deleted.

Example B.38

Preparation of compound (609)

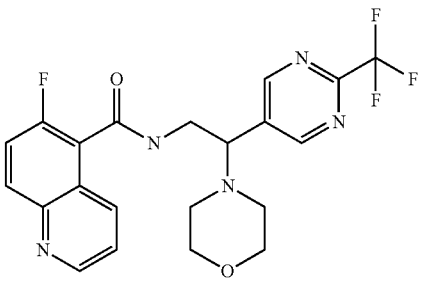

6-Fluoro-quinoline-5-carboxylic acid [2-morpholin-4-yl-2-(2-trifluoromethyl-pyrimidin-5-yl)-ethyl]-amide To a solution of intermediate (28) (0.17 g, 0.62 mmol) in THF (0.9 mL), in a 5 mL microwave vial containing a magnetic stirbar, was added sequentially 5-bromo-6-fluoro-quinoline (0.10 g, 0.44 mmol), 1,8-diazabicyclo(5.4.0)undec-7-ene (0.05 g, 0.30 mmol), trans-di-u-acetobis[2-(di-o-tolyl-phosphine)-benzyl]di-palladium (II) (0.005 g, 0.005 mmol), tri-tert-butylphosphonium tetrafluoroborate (0.004 gg, 0.02 mmol) and molybdenum hexacarbonyl (0.12 mg, 0.44 mmol). The vial was sealed and heated to 150° C. in a microwave reactor. The resulting mixture was diluted with DCM and washed with water. The organic layer was dried with Na$_2$SO$_4$, filtered through celite and evaporated in vacuo and purified by high-performance liquid chromatography (eluent: CH$_3$CN/H$_2$O 10/95 to CH$_3$CN/H$_2$O 95/5 with 0.1% CF$_3$COOH). The product fractions were collected and the solvent was removed by lyophilization (0.05 mg, 25%) to give the title compound as the trifluoroacetate salt.

Tables F-1, F-2, F-3 and F-4 lists the compounds that were prepared according to one of the above Examples.

TABLE F-1

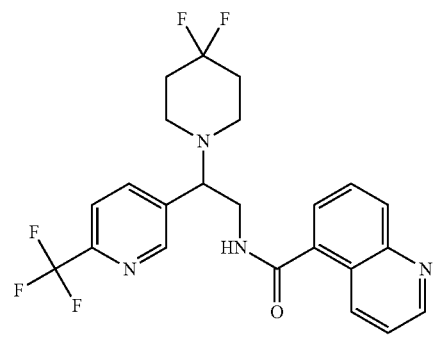

Co. No. 1; Ex. B.1

TABLE F-1-continued
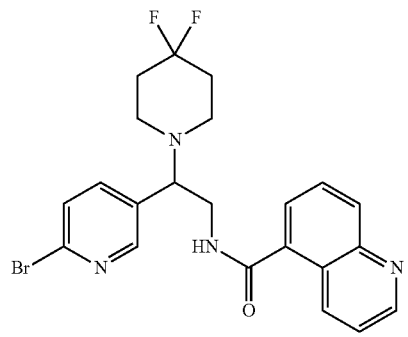
Co. No. 2; Ex. B.2
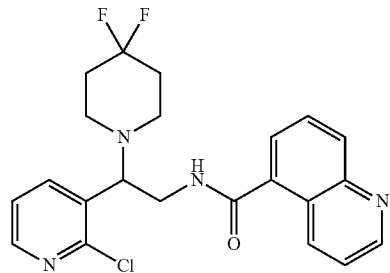
Co. No. 3; Ex. B.2
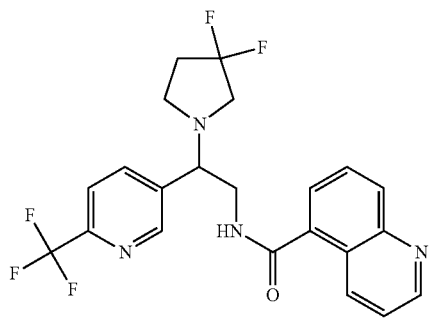
Co. No. 4; Ex. B.1
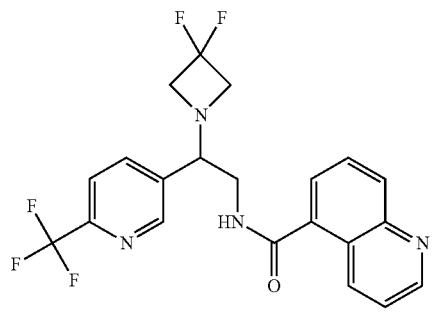
Co. No. 5; Ex. B.2

TABLE F-1-continued
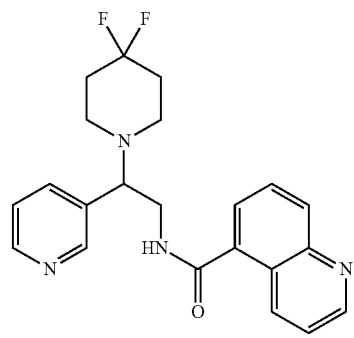
Co. No. 6; Ex. B.2
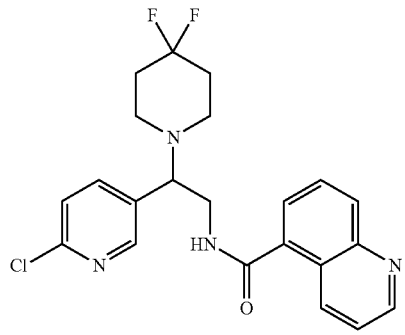
Co. No. 7; Ex. B.6
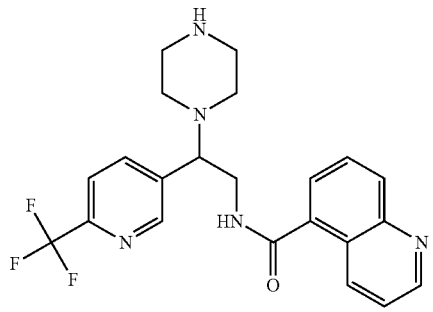
Co. No. 8; Ex. B.3; •3HCl
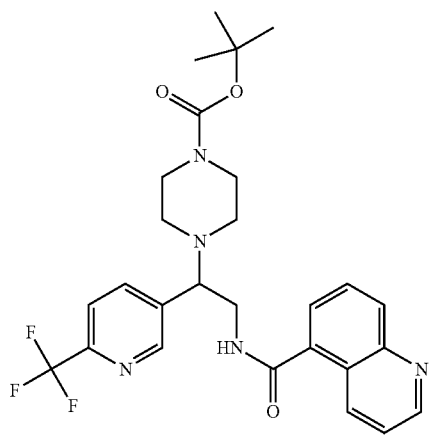
Co. No. 9; Ex. B.1

TABLE F-1-continued
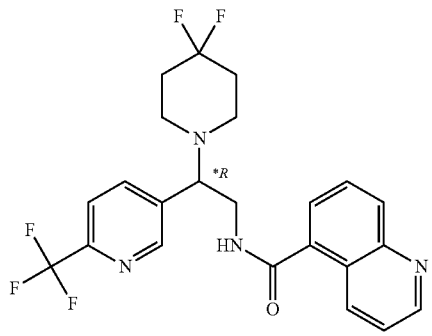
Co. No. 10; Ex. B.4
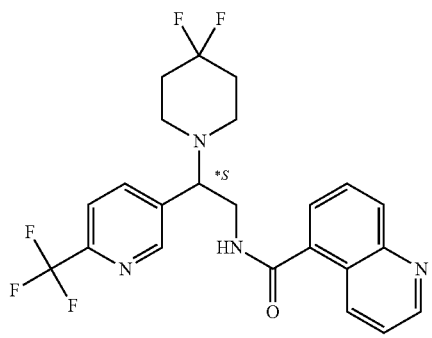
Co. No. 11; Ex. B.4
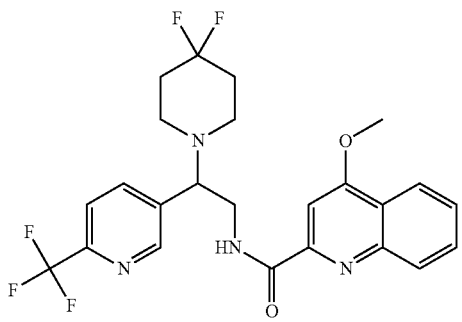
Co. No. 12; Ex. B.5
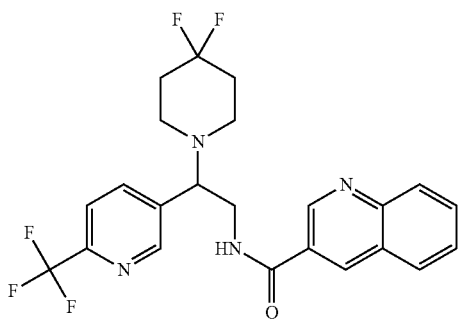
Co. No. 13; Ex. B.5

TABLE F-1-continued
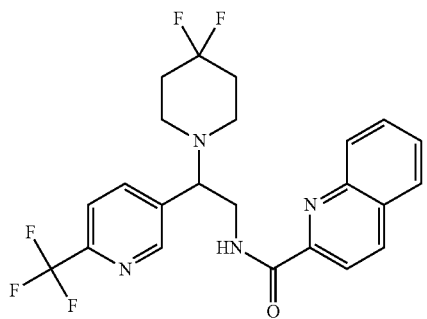
Co. No. 14; Ex. B.5
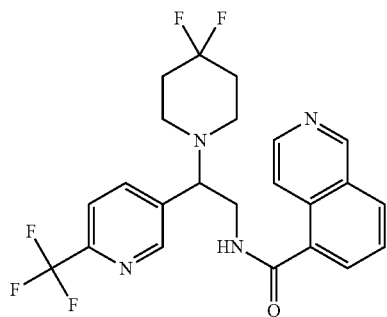
Co. No. 16; Ex. B.5
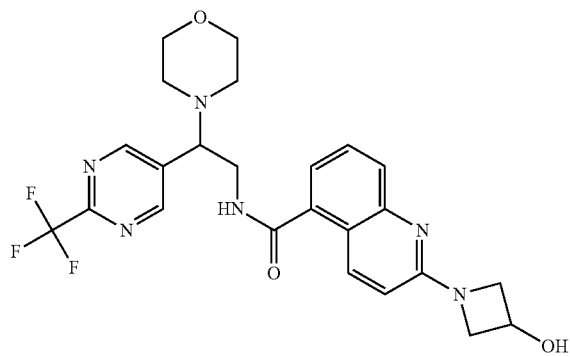
Co. No. 17; Ex. B.16
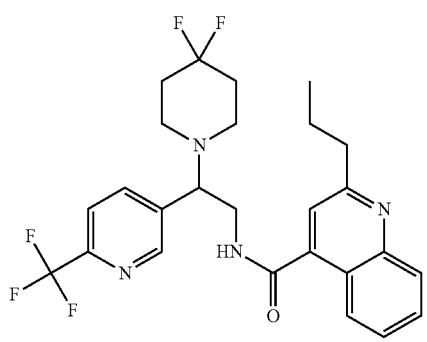
Co. No. 18; Ex. B.5

TABLE F-1-continued
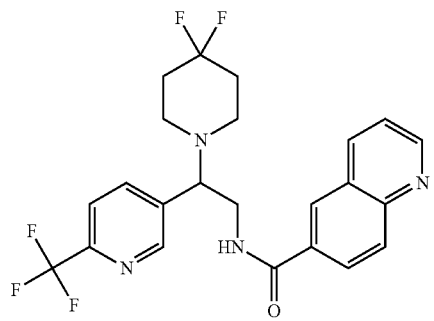
Co. No. 19; Ex. B.5
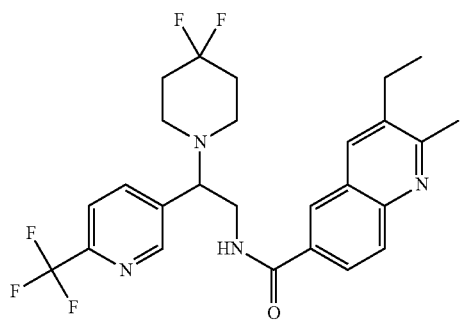
Co. No. 24; Ex. B.5
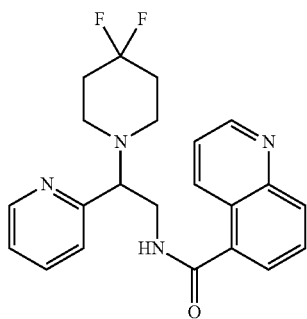
Co. No. 25; Ex. B.7
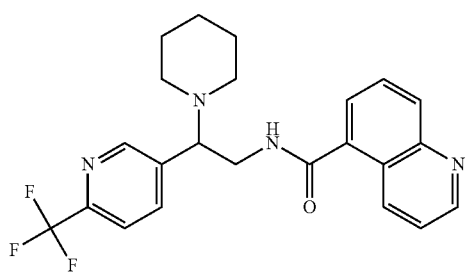
Co. No. 26; Ex. B.7

TABLE F-1-continued
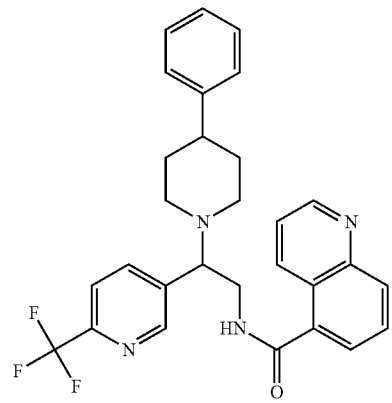
Co. No. 27; Ex. B.7
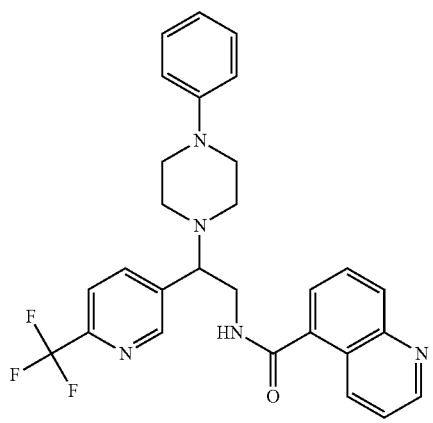
Co. No. 28; Ex. B.7
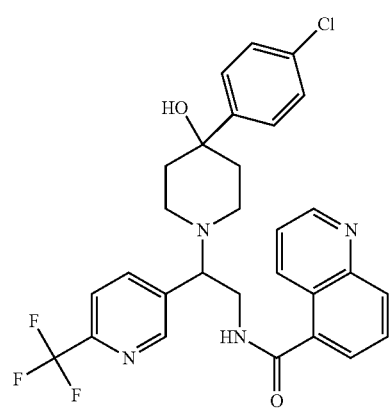
Co. No. 29; Ex. B.7

TABLE F-1-continued
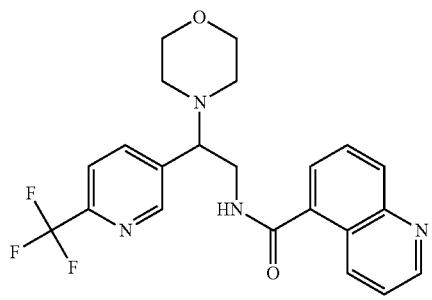
Co. No. 31; Ex. B.7
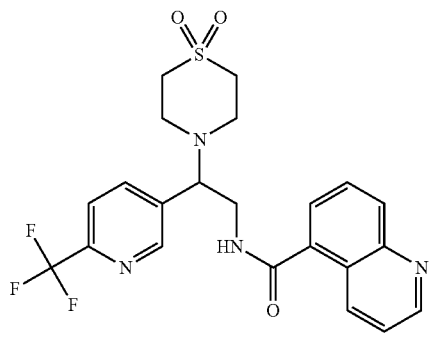
Co. No. 32; Ex. B.9
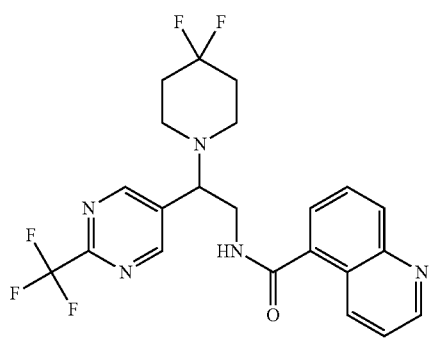
Co. No. 33; Ex. B.10
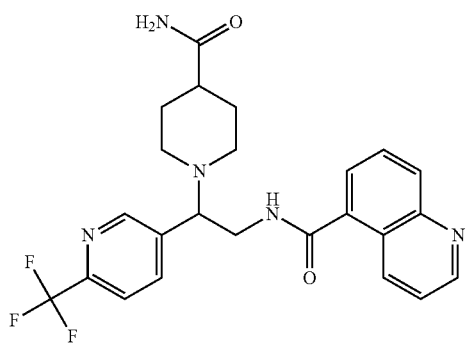
Co. No. 34; Ex. B.9

TABLE F-1-continued
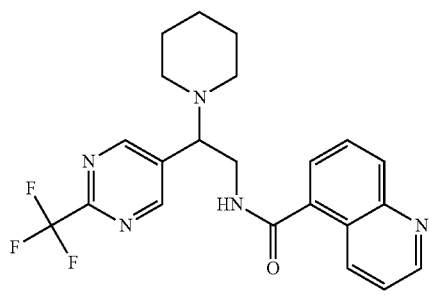
Co. No. 35; Ex. B.10
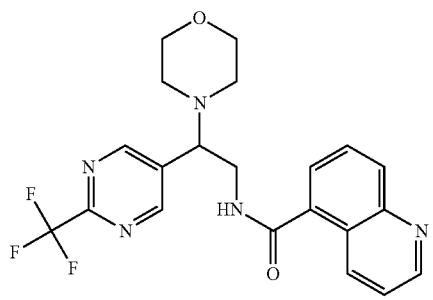
Co. No. 36; Ex. B.10
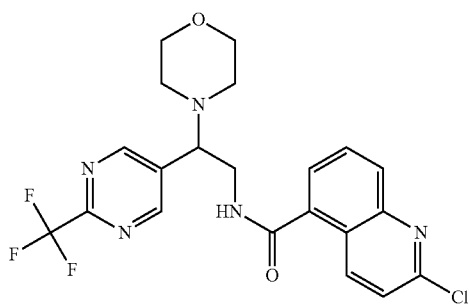
Co. No. 37; Ex. B.10
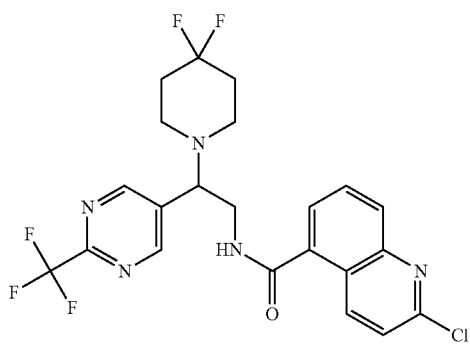
Co. No. 38; Ex. B.9

TABLE F-1-continued
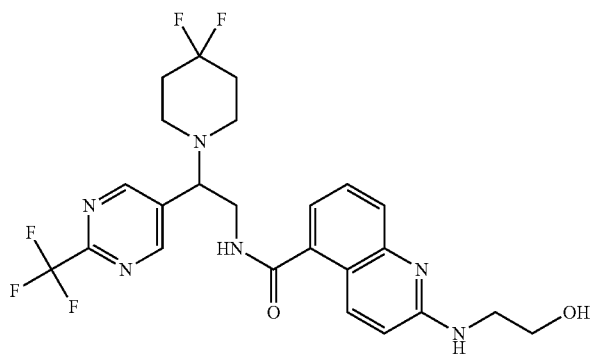
Co. No. 39; Ex. B.11
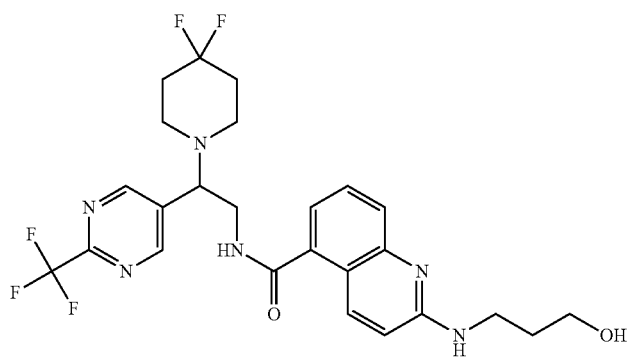
Co. No. 40; Ex. B.11
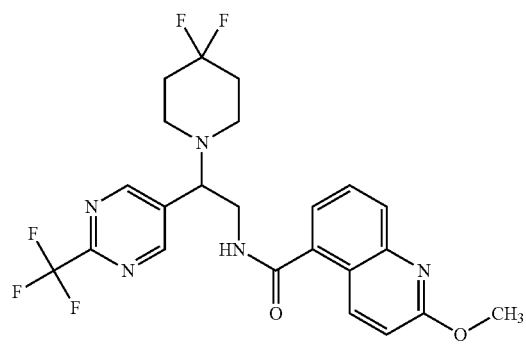
Co. No. 41; Ex. B.12
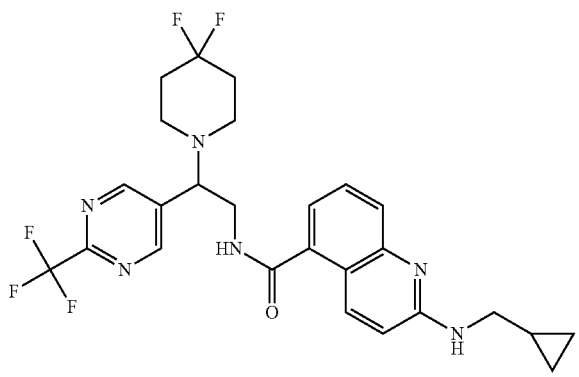
Co. No. 42; Ex. B.11

TABLE F-1-continued
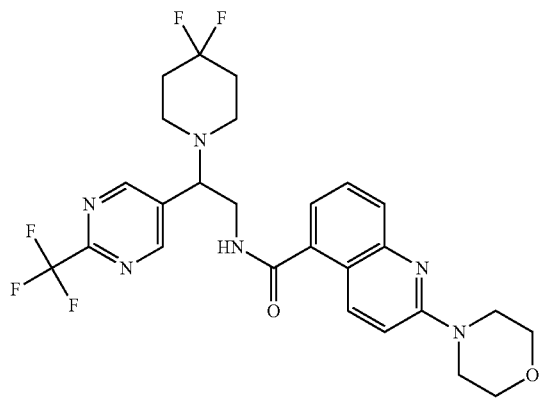
Co. No. 43; Ex. B.11
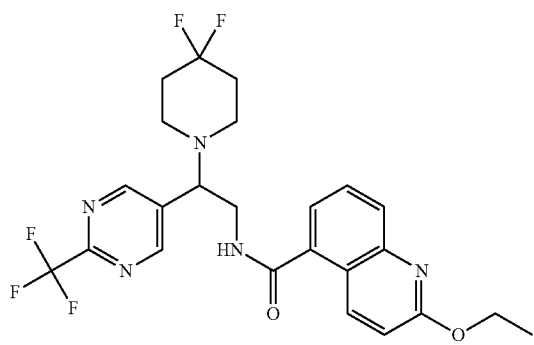
Co. No. 44; Ex. B.12
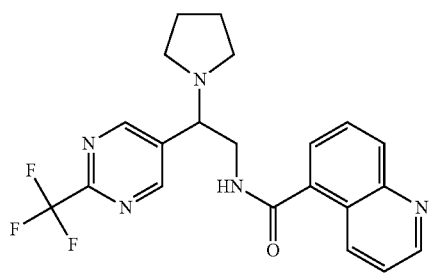
Co. No. 45; Ex. B.9
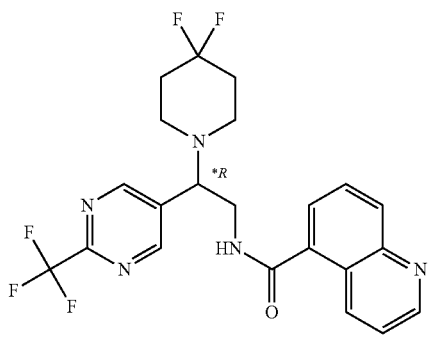
Co. No. 46; Ex. B.8

TABLE F-1-continued
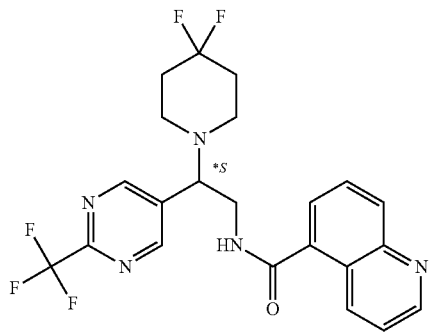
Co. No. 47; Ex. B.8
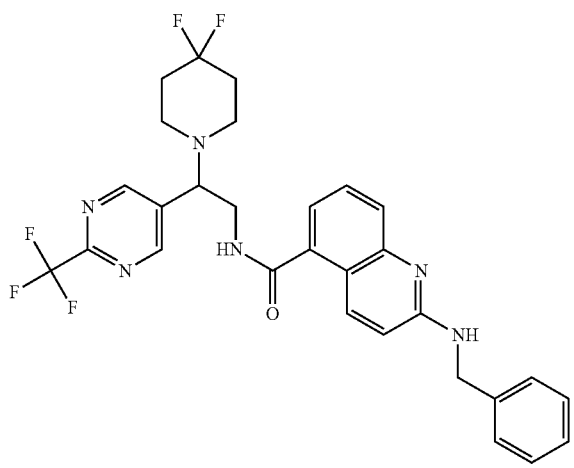
Co. No. 48; Ex. B.11
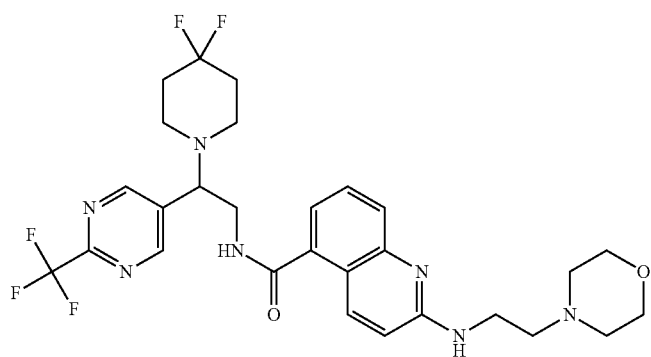
Co. No. 49; Ex. B.11
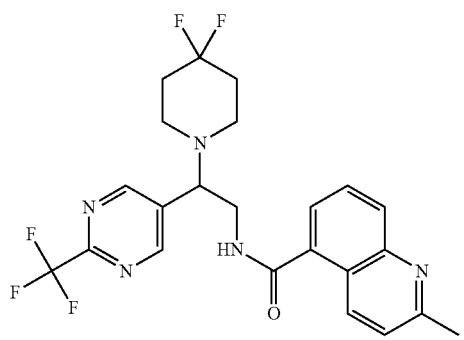
Co. No. 50; Ex. B.9

TABLE F-1-continued
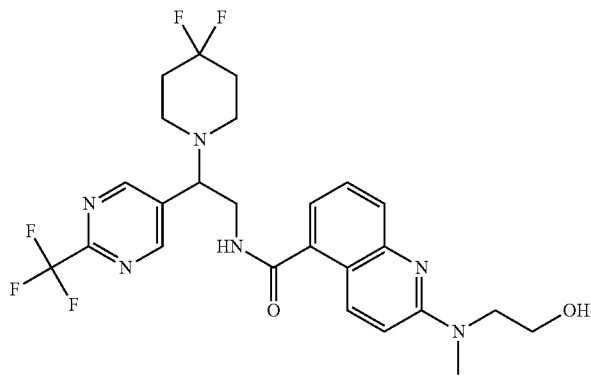
Co. No. 51; Ex. B.11
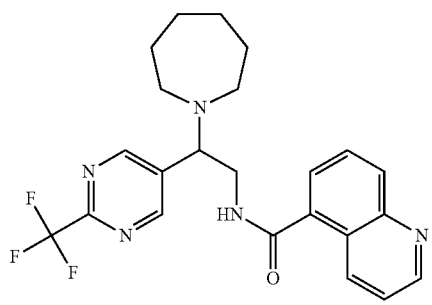
Co. No. 52; Ex. B.9
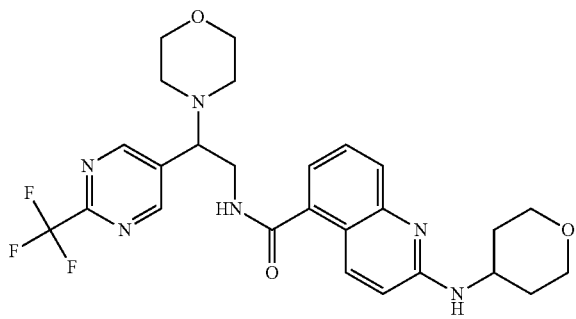
Co. No. 53; Ex. B.11
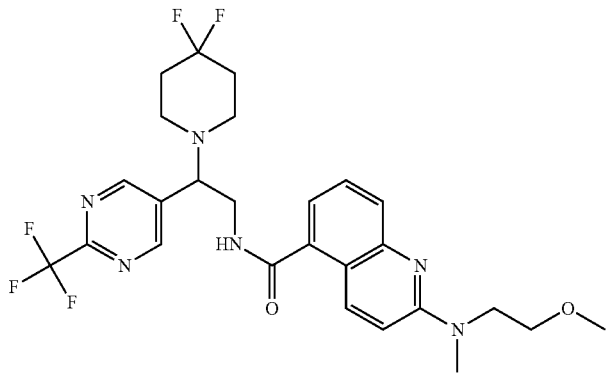
Co. No. 54; Ex. B.11

TABLE F-1-continued
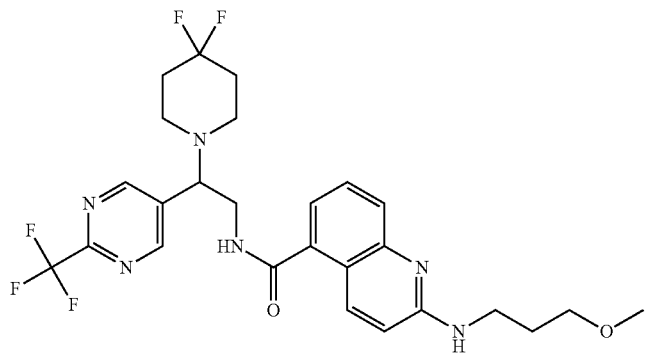
Co. No. 55; Ex. B.11
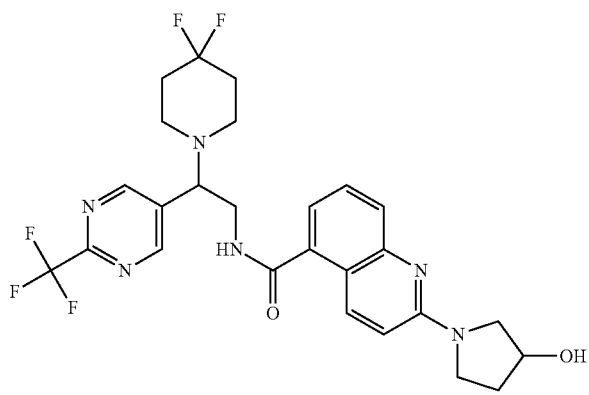
Co. No. 56; Ex. B.11
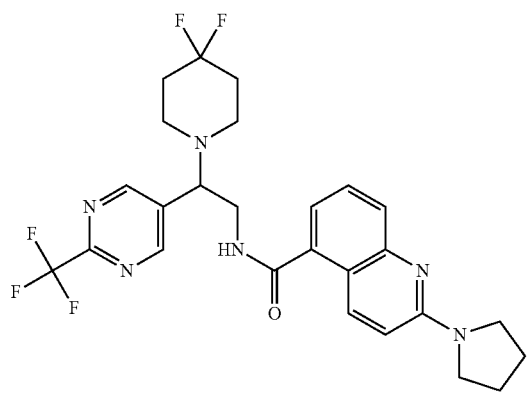
Co. No. 57; Ex. B.11

TABLE F-1-continued
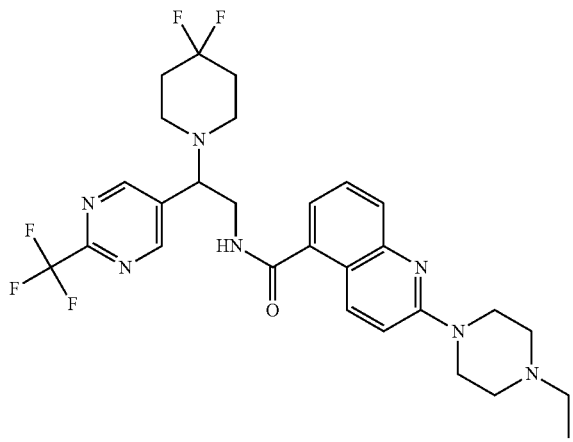
Co. No. 58; Ex. B.11
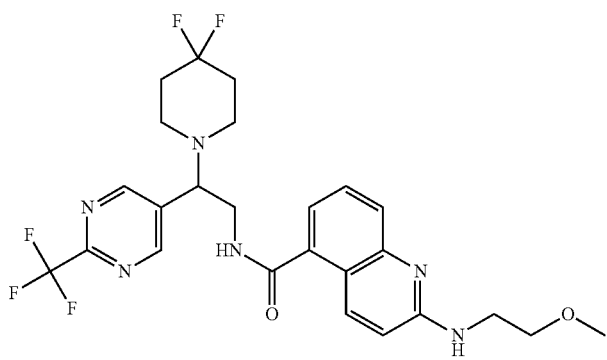
Co. No. 59; Ex. B.11
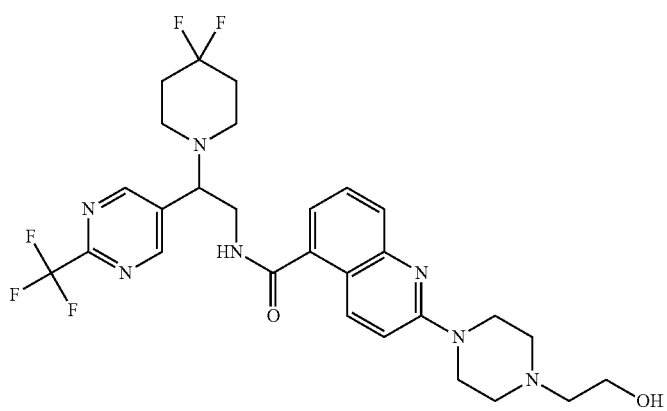
Co. No. 60; Ex. B.11

TABLE F-1-continued
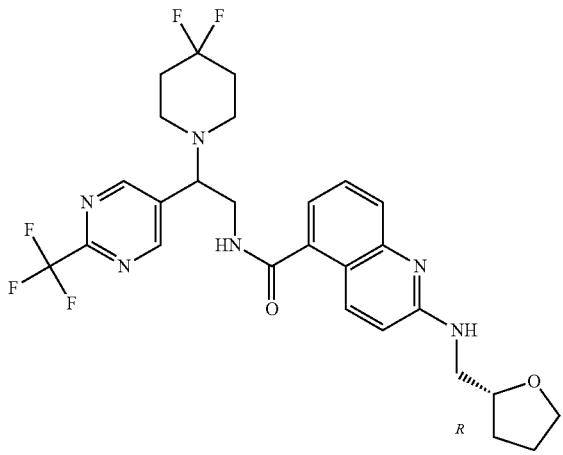
Co. No. 61; Ex. B.11
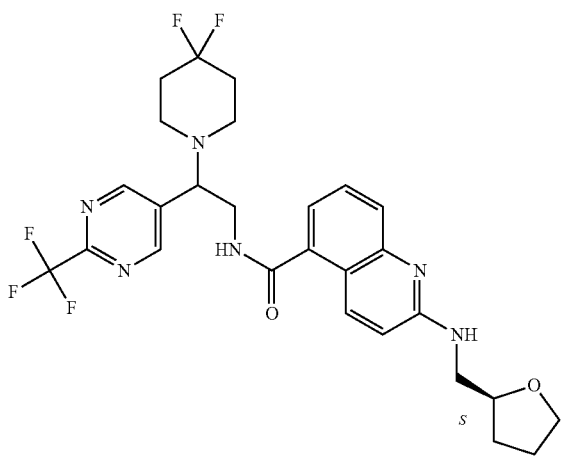
Co. No. 62; Ex. B.11
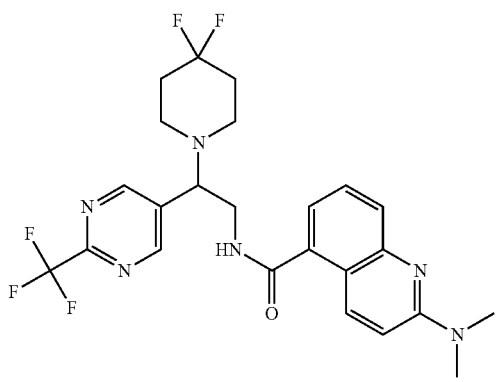
Co. No. 63; Ex. B.11

TABLE F-1-continued
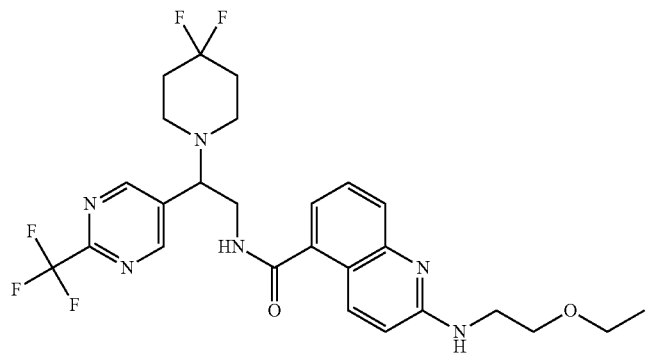
Co. No. 64; Ex. B.11
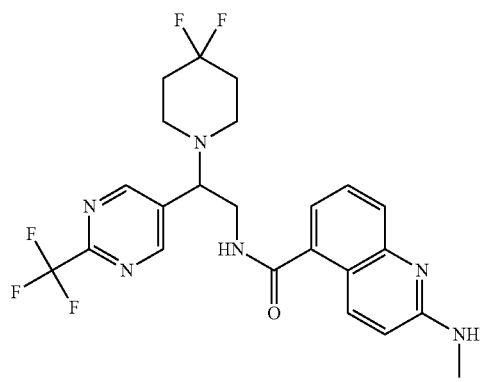
Co. No. 65; Ex. B.11
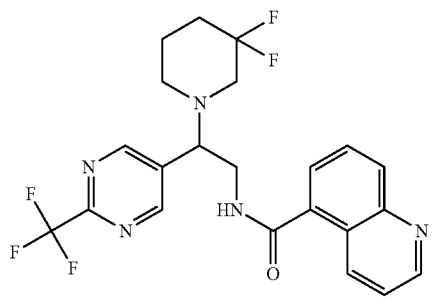
Co. No. 66; Ex. B.9
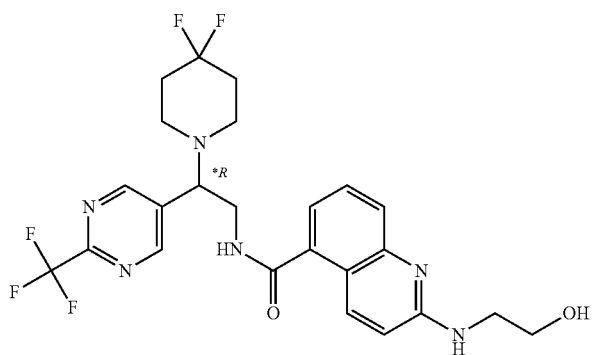
Co. No. 67; Ex. B.4

TABLE F-1-continued
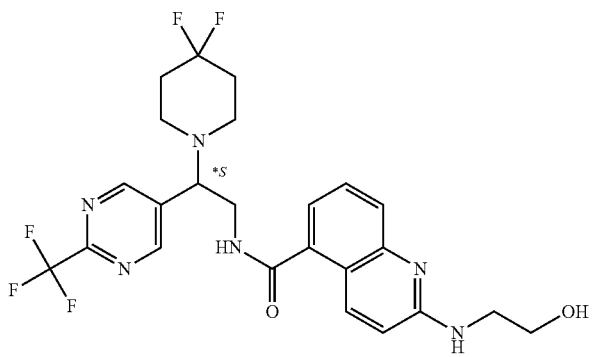
Co. No. 68; Ex. B.4
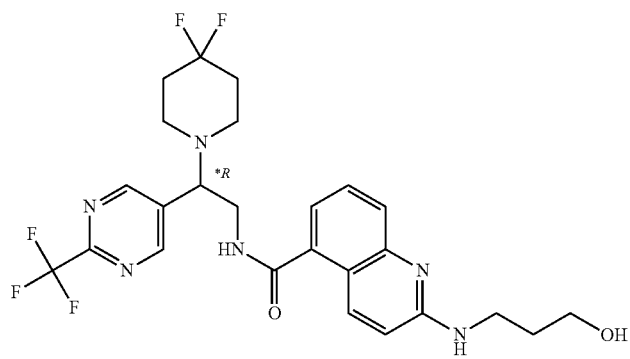
Co. No. 69; Ex. B.4
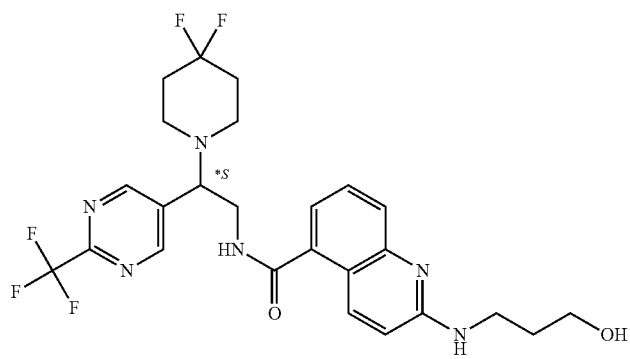
Co. No. 70; Ex. B.4
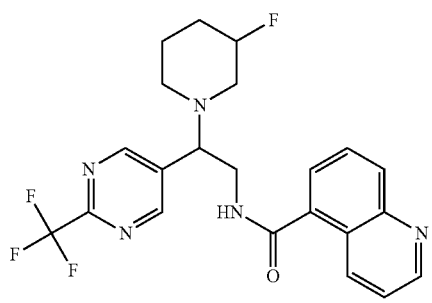
Co. No. 71; Ex. B.9

TABLE F-1-continued
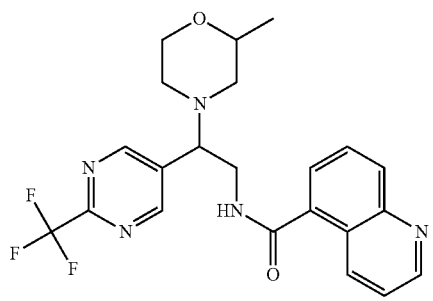
Co. No. 72; Ex. B.9
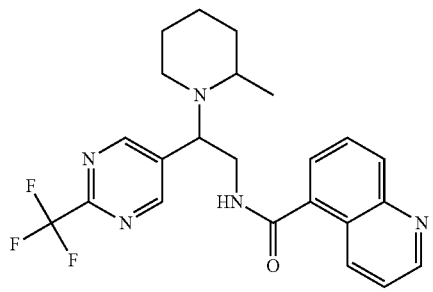
Co. No. 73; Ex. B.9
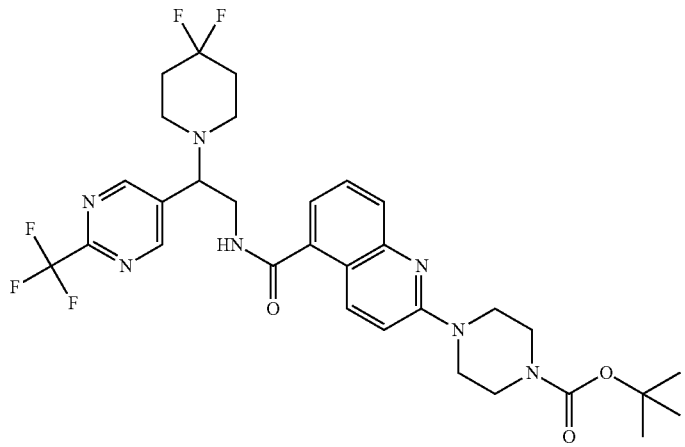
Co. No. 74; Ex. B.11
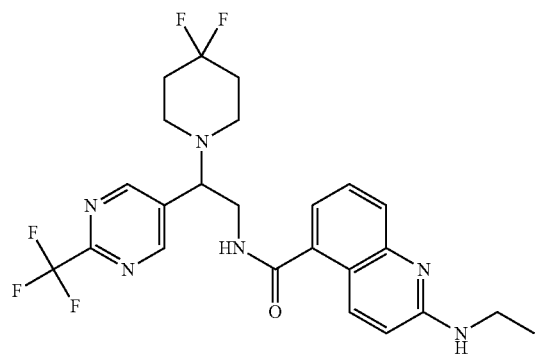
Co. No. 75; Ex. B.11

TABLE F-1-continued
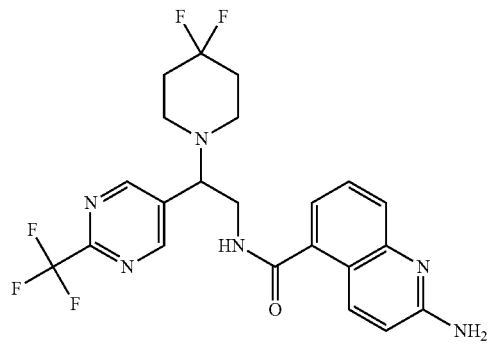
Co. No. 76; Ex. B.11
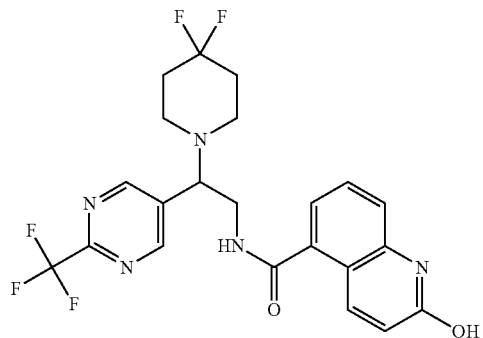
Co. No. 77; Ex. B.13
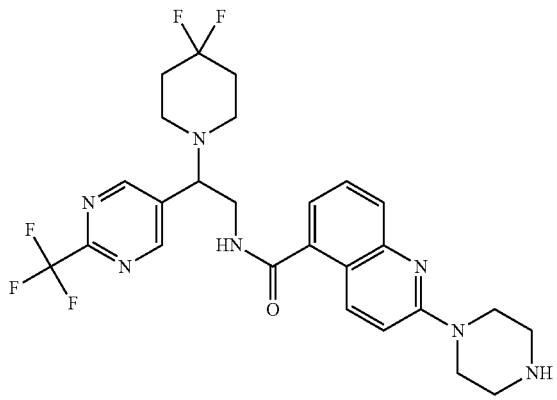
Co. No. 78; Ex. B.14
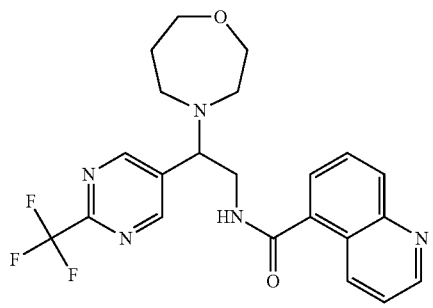
Co. No. 79; Ex. B.9

TABLE F-1-continued
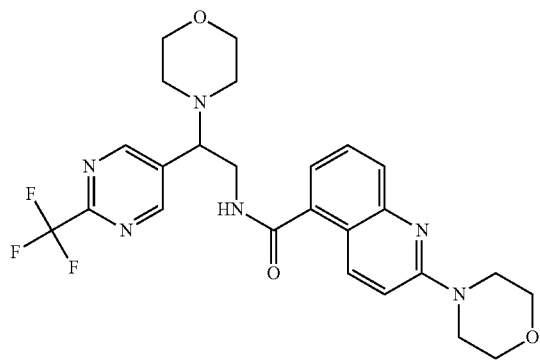
Co. No. 80; Ex. B.11
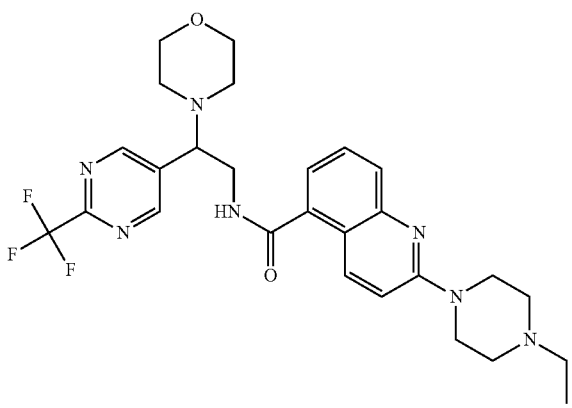
Co. No. 81; Ex. B.11
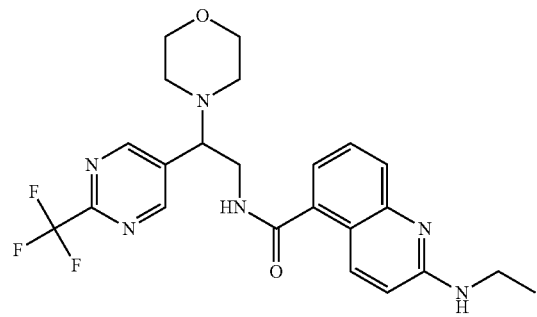
Co. No. 82; Ex. B.11
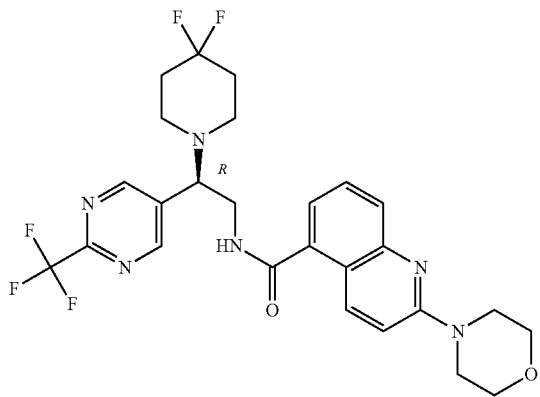
Co. No. 83; Ex. B.4; (R)

TABLE F-1-continued
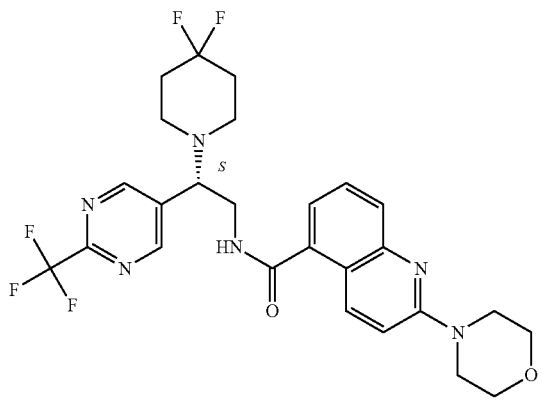
Co. No. 84; Ex. B.4; (S)
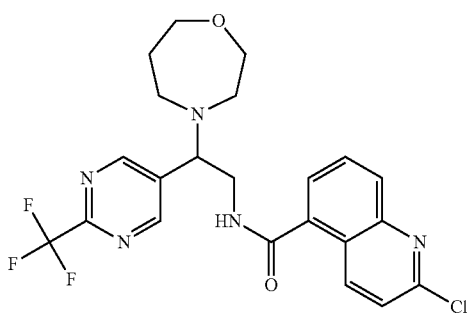
Co. No. 85; Ex. B.9
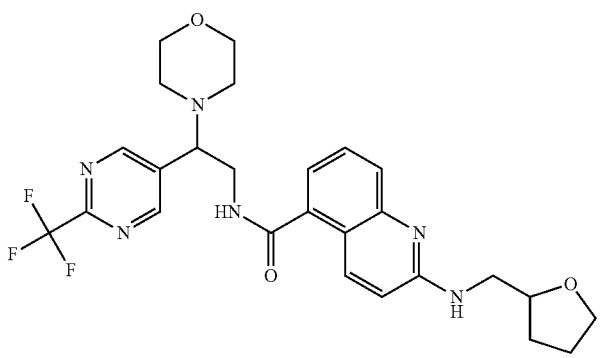
Co. No. 86; Ex. B.11
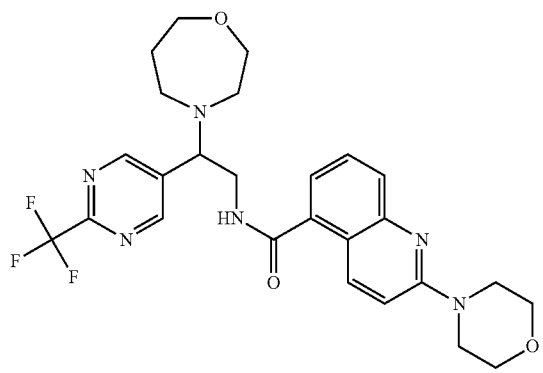
Co. No. 87; Ex. B.11

TABLE F-1-continued
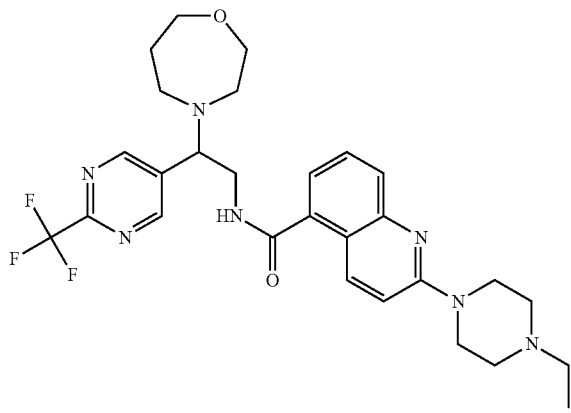
Co. No. 88; Ex. B.11
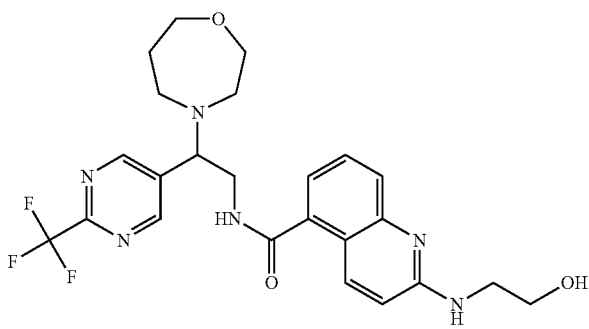
Co. No. 89; Ex. B.11
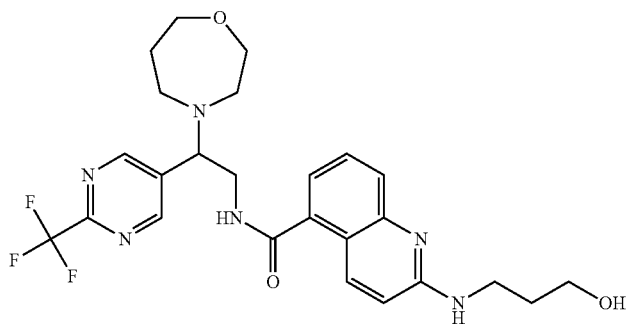
Co. No. 90; Ex. B.11
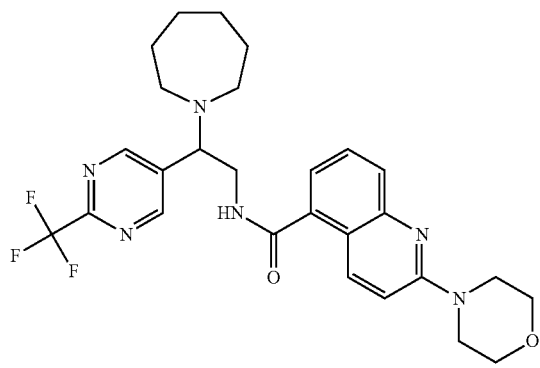
Co. No. 91; Ex. B.11

TABLE F-1-continued
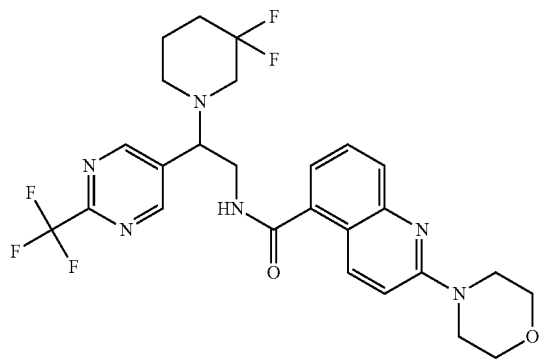
Co. No. 92; Ex. B.11
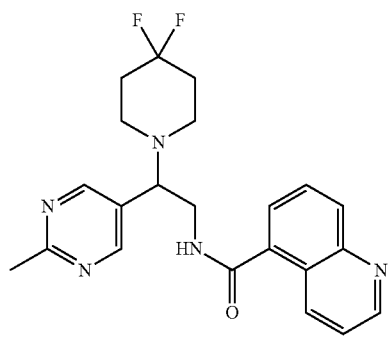
Co. No. 93; Ex. B.9
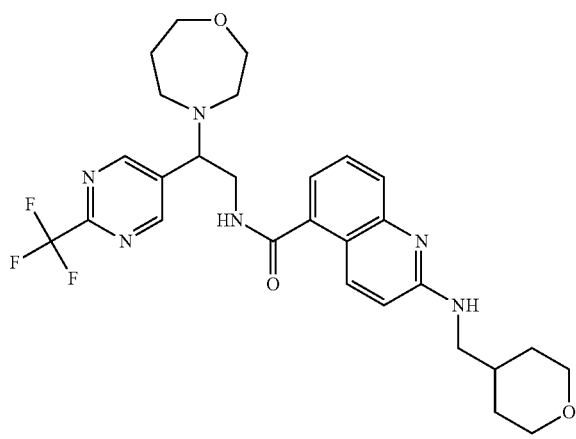
Co. No. 94; Ex. B.11

TABLE F-1-continued
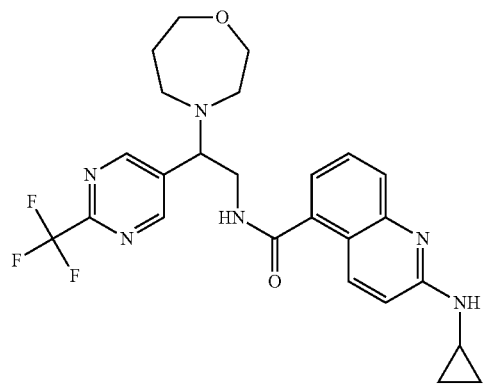
Co. No. 95; Ex. B.11
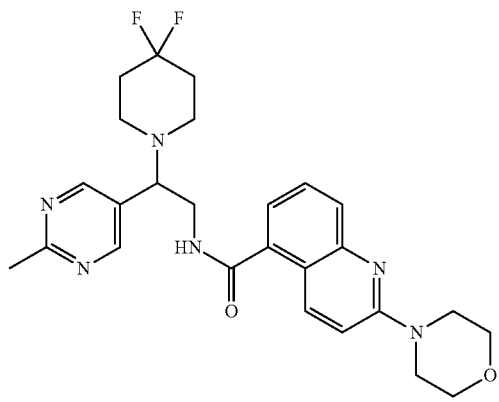
Co. No. 96; Ex. B.11
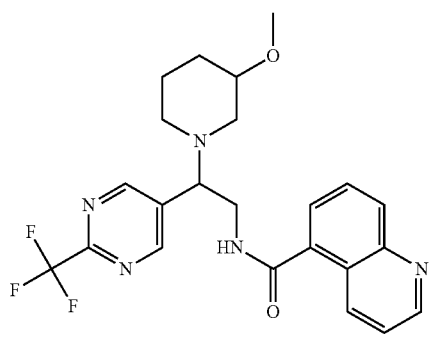
Co. No. 97; Ex. B.2
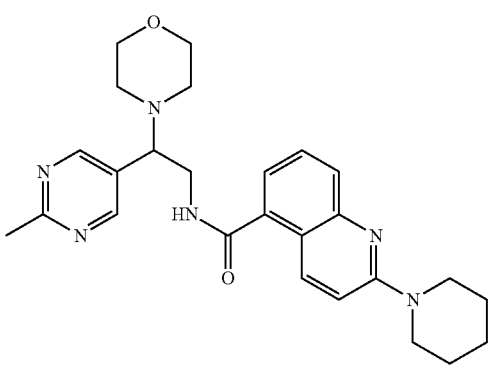
Co. No. 98; Ex. B.11

TABLE F-1-continued
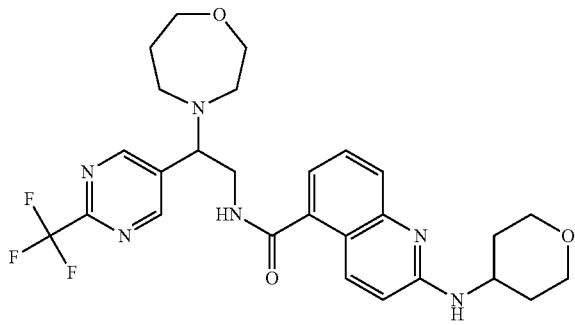
Co. No. 99; Ex. B.11
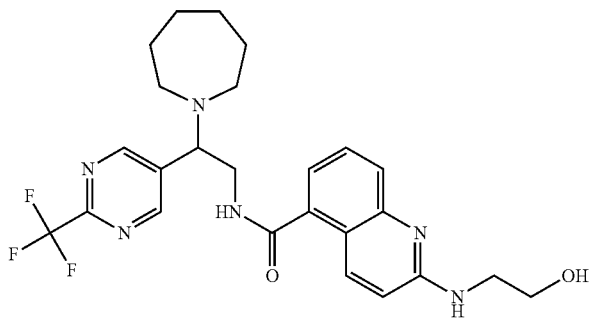
Co. No. 100; Ex. B.11
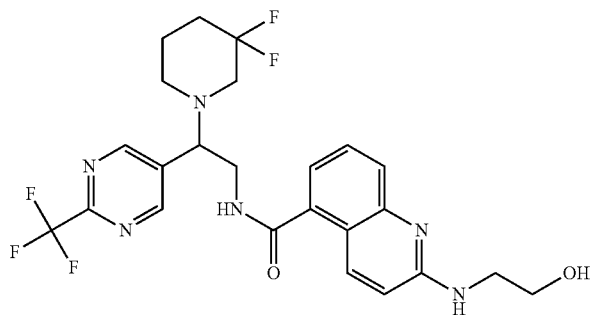
Co. No. 101; Ex. B.11
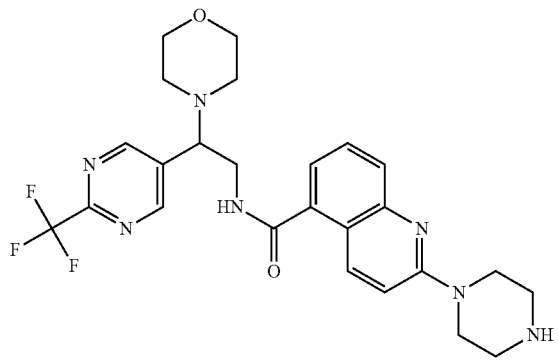
Co. No. 102; Ex. B.16

TABLE F-1-continued
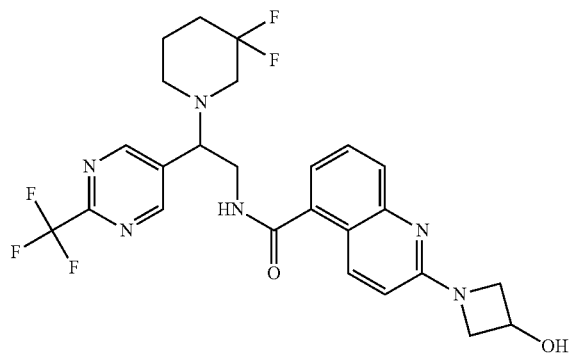
Co. No. 103; Ex. B.16
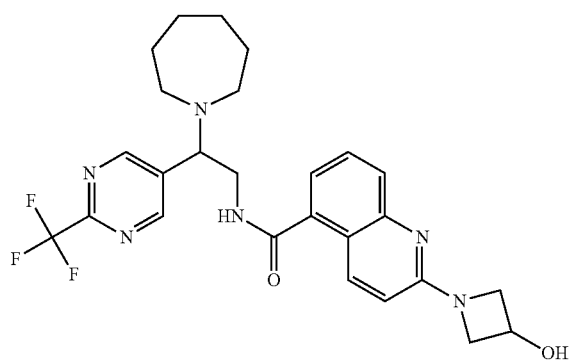
Co. No. 104; Ex. B.16
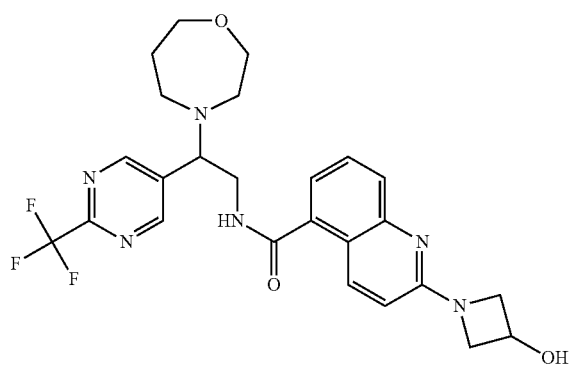
Co. No. 105; Ex. B.16
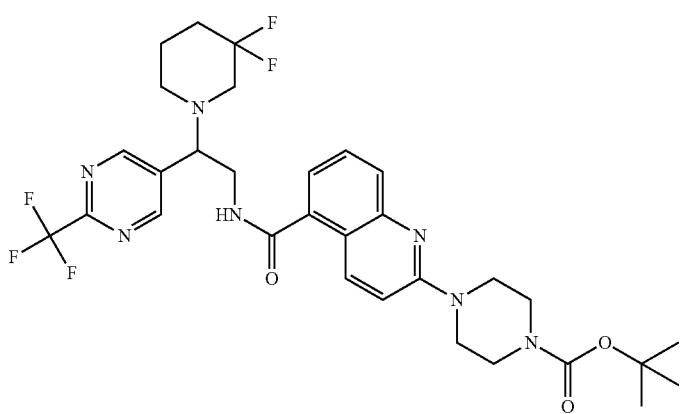
Co. No. 106; Ex. B.16

TABLE F-1-continued
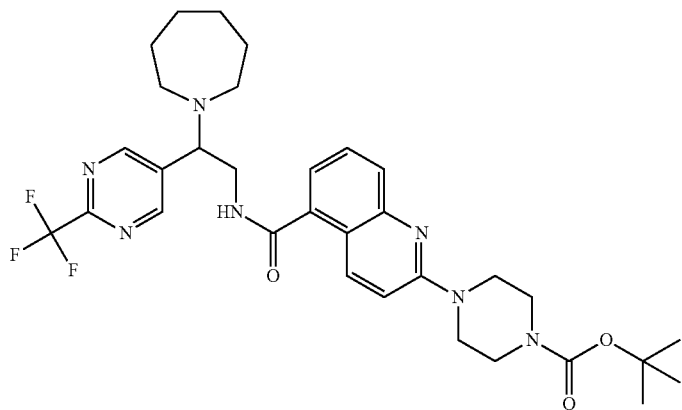
Co. No. 107; Ex. B.16
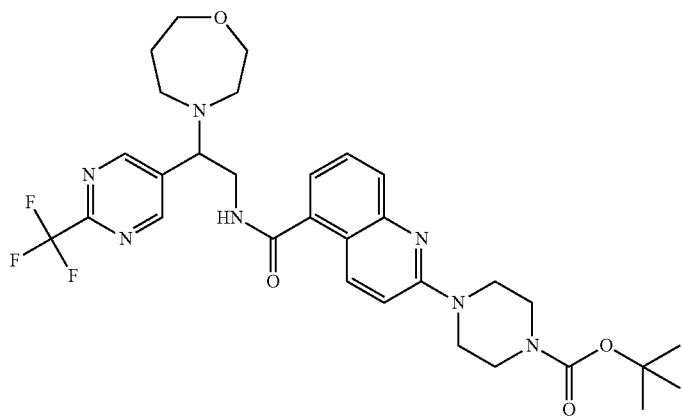
Co. No. 108; Ex. B.16
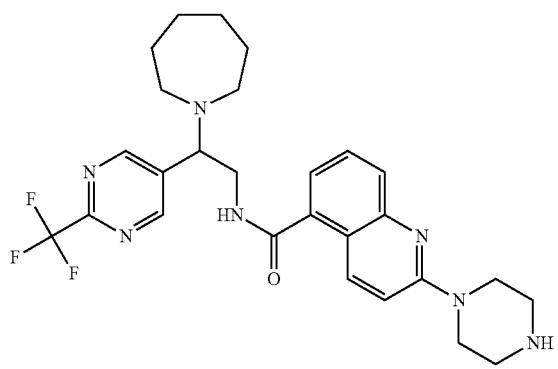
Co. No. 109; Ex. B.14

TABLE F-1-continued
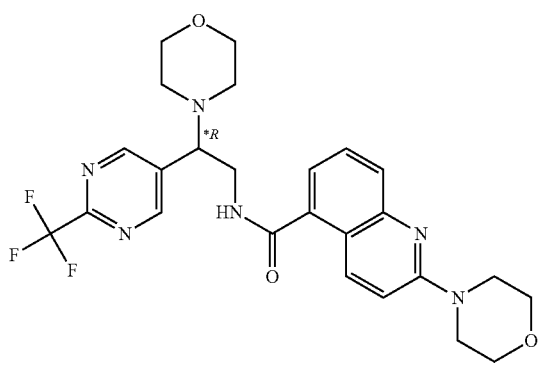
Co. No. 110; Ex. B.4
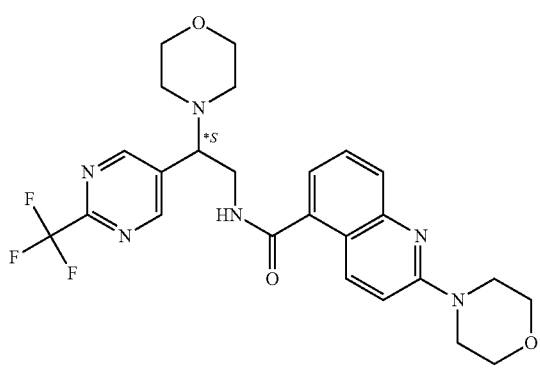
Co. No. 111; Ex. B.4
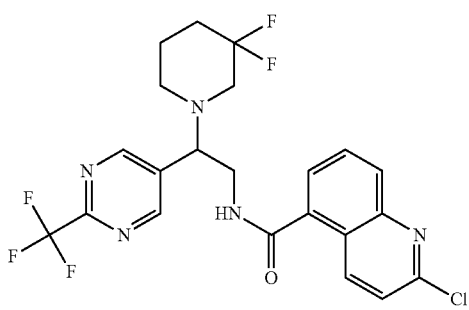
Co. No. 112; Ex. B.9
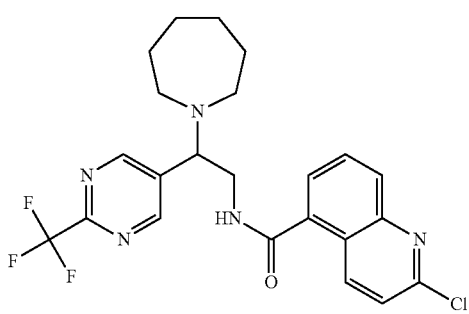
Co. No. 113; Ex. B.9

TABLE F-1-continued
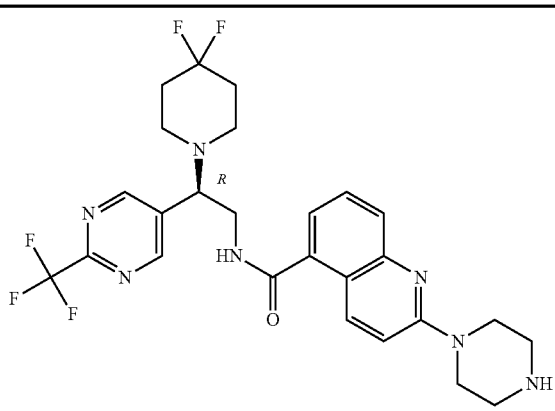
Co. No. 114; Ex. B.4; (R)
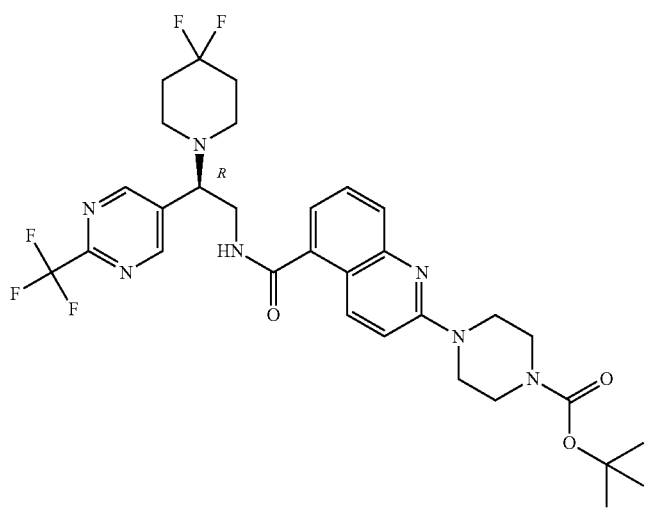
Co. No. 115; Ex. B.9; (R)
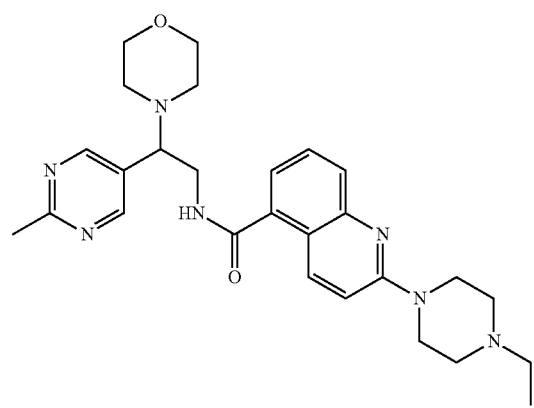
Co. No. 116; Ex. B.11

TABLE F-1-continued
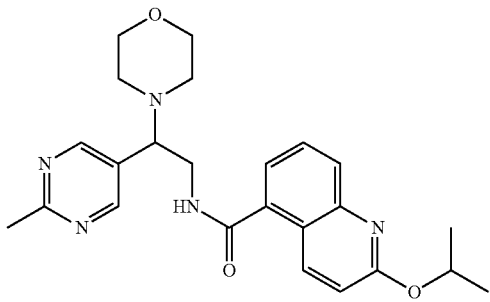
Co. No. 117; Ex. B.17
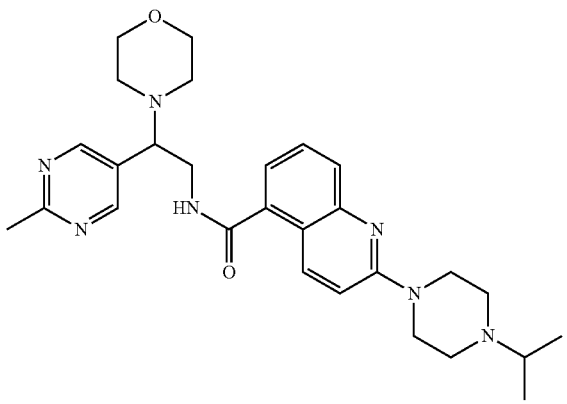
Co. No. 118; Ex. B.11
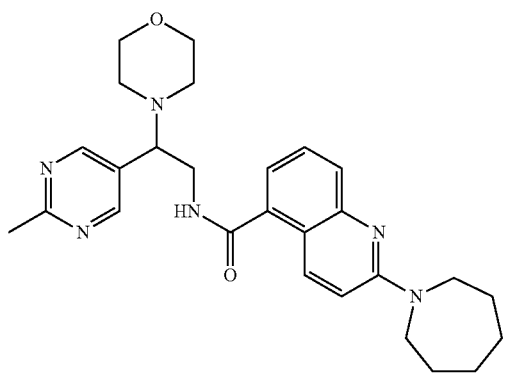
Co. No. 119; Ex. B.11
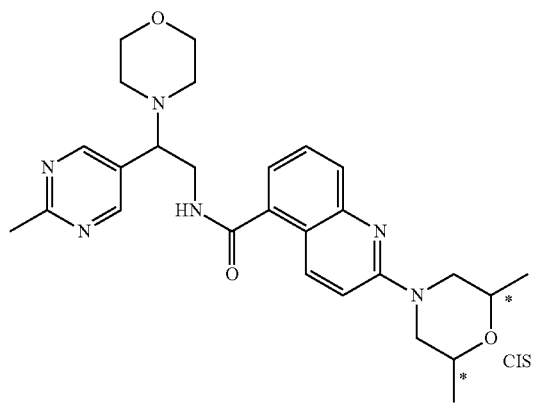
Co. No. 120; Ex. B.11

TABLE F-1-continued
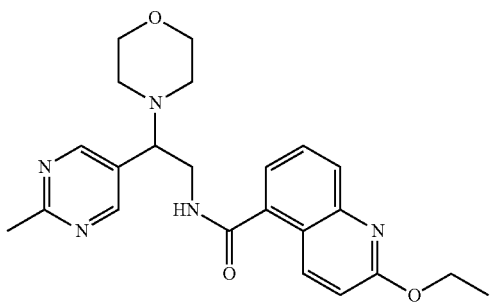
Co. No. 121; Ex. B.17
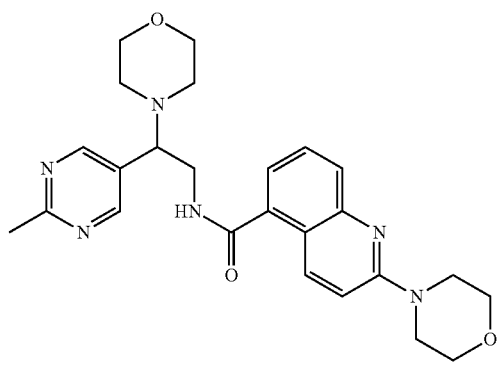
Co. No. 122; Ex. B.11
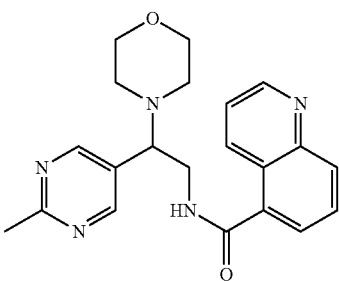
Co. No. 123; Ex. B.18
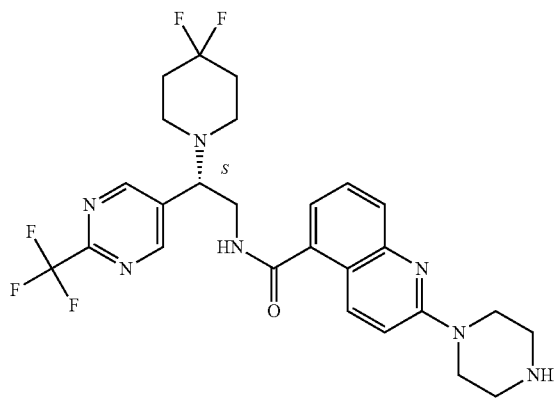
Co. No. 124; Ex. B.4; •HCl; (S)

TABLE F-1-continued
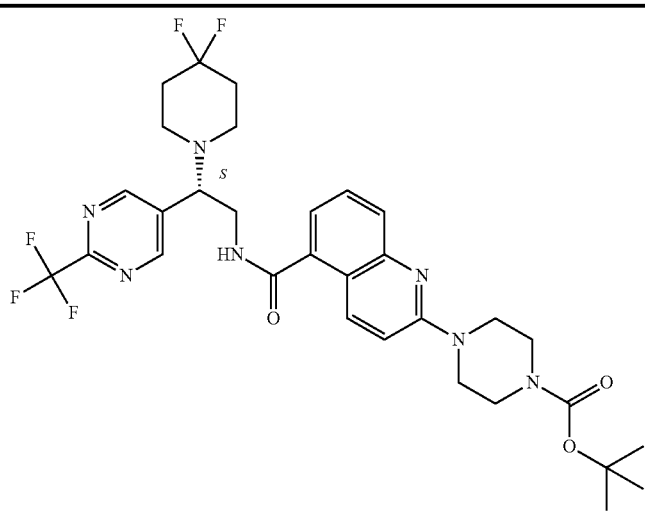
Co. No. 125; Ex. B.9; (S)
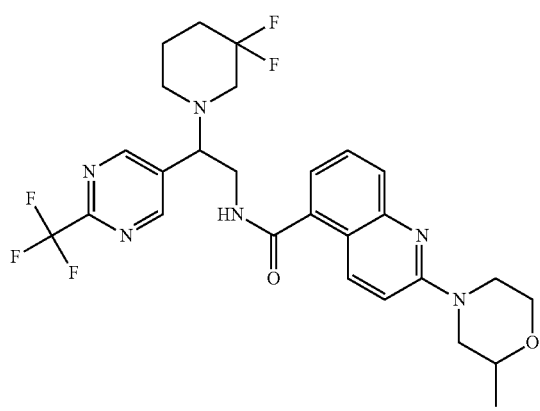
Co. No. 126; Ex. B.16
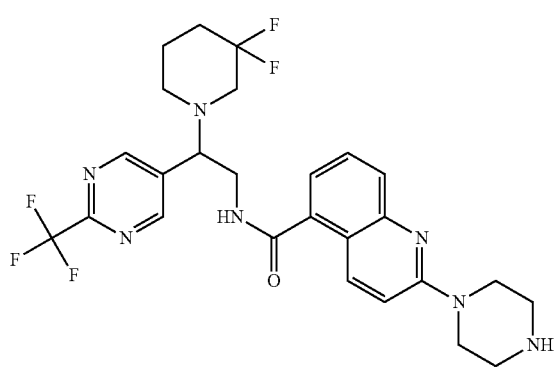
Co. No. 127; Ex. B.14

TABLE F-1-continued
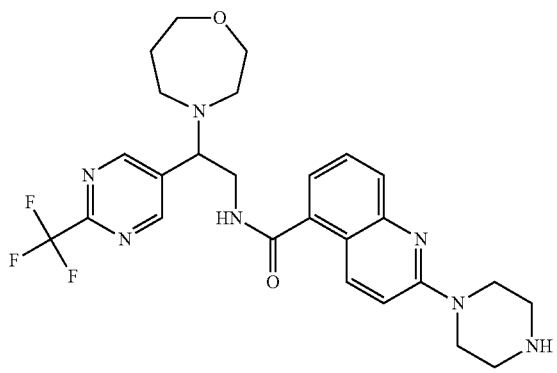
Co. No. 128; Ex. B.14
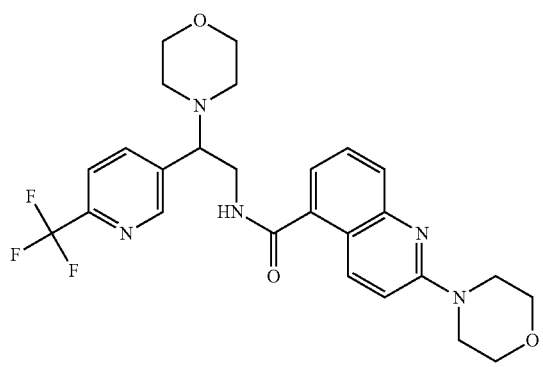
Co. No. 129; Ex. B.9
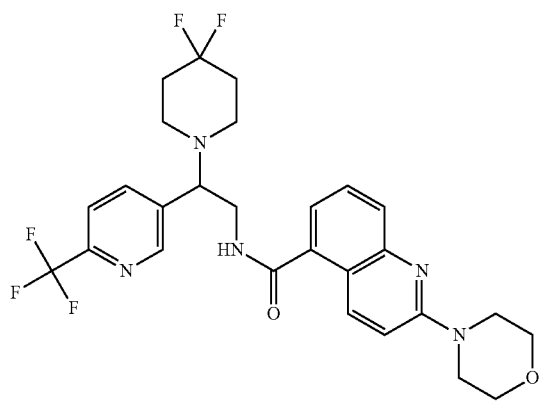
Co. No. 130; Ex. B.9
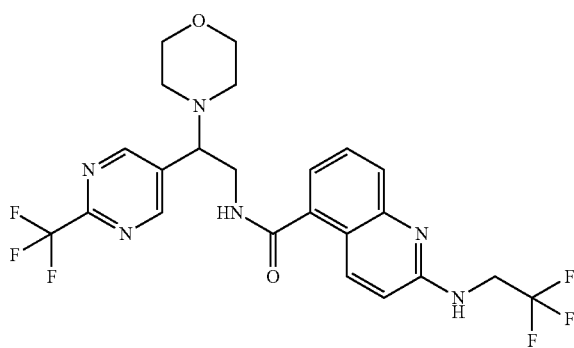
Co. No. 131; Ex. B.11

TABLE F-1-continued
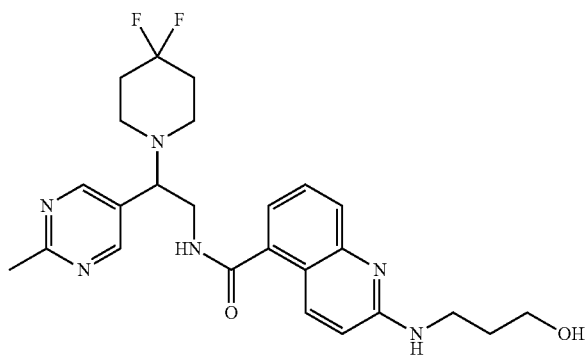
Co. No. 132; Ex. B.9
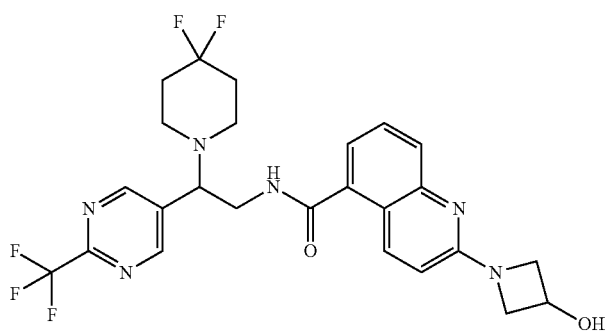
Co. No. 133; Ex. B.21
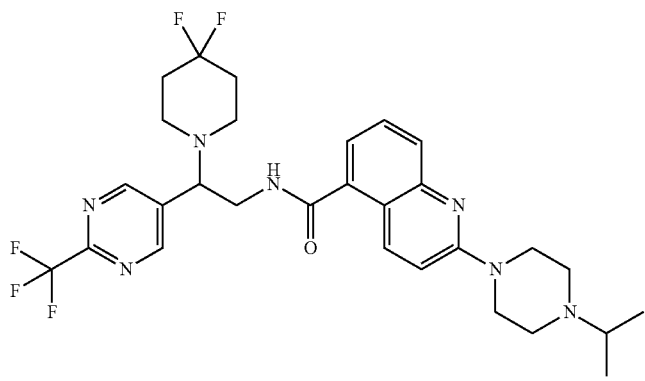
Co. No. 134; Ex. B.19
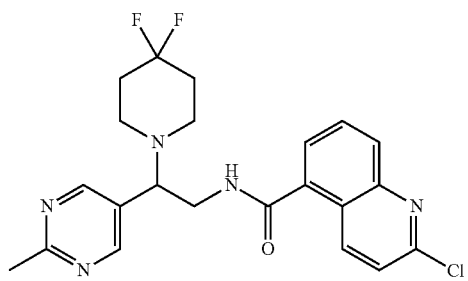
Co. No. 135; Ex. B.15

TABLE F-1-continued
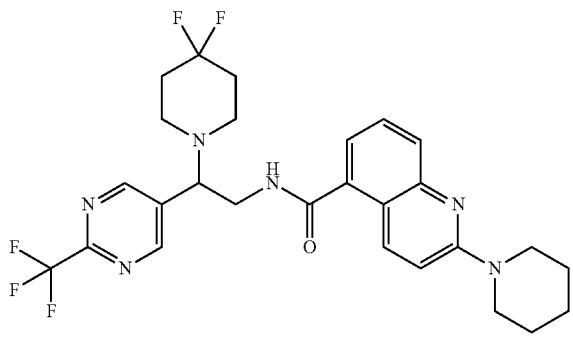
Co. No. 136; Ex. B.19
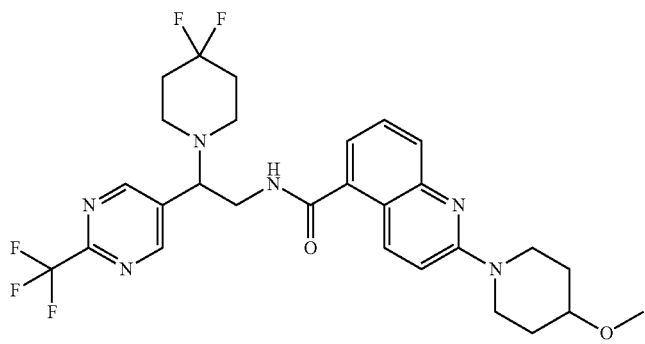
Co. No. 137; Ex. B.19
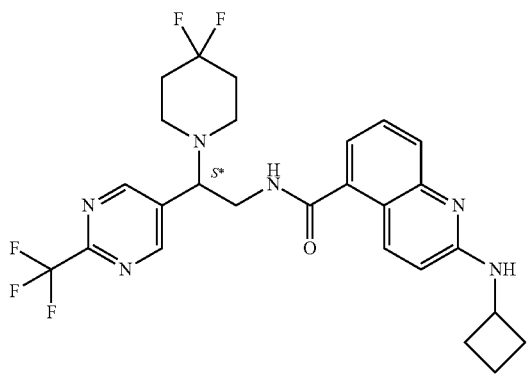
Co. No. 138; Ex. B.16
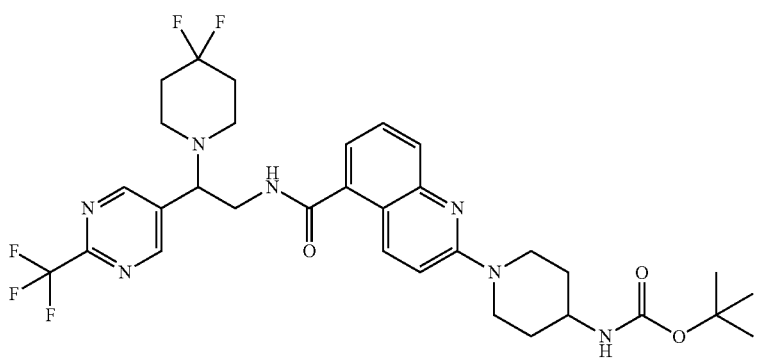
Co. No. 139; Ex. B.19

TABLE F-1-continued
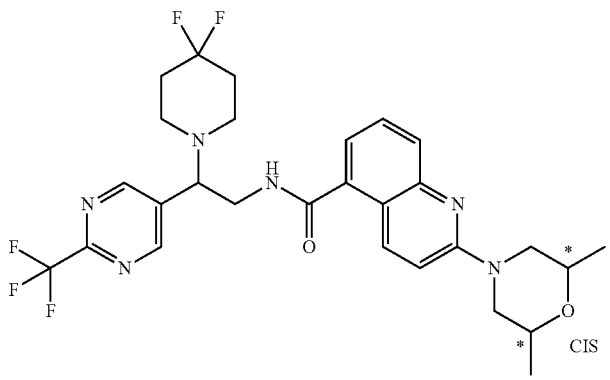
Co. No. 140; Ex. B.21
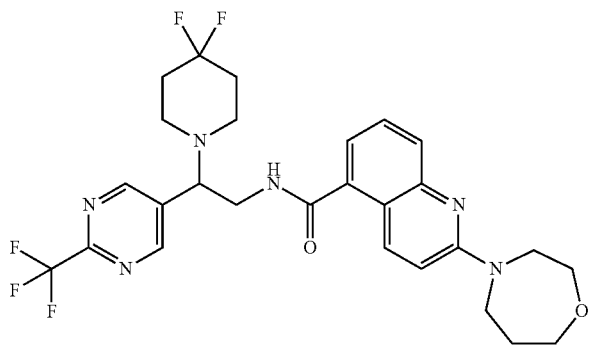
Co. No. 141; Ex. B.21
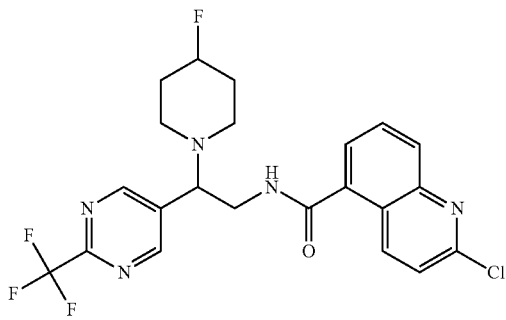
Co. No. 142; Ex. B.15
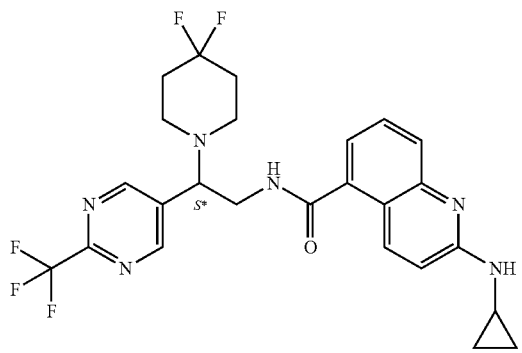
Co. No. 143; Ex. B.19

TABLE F-1-continued
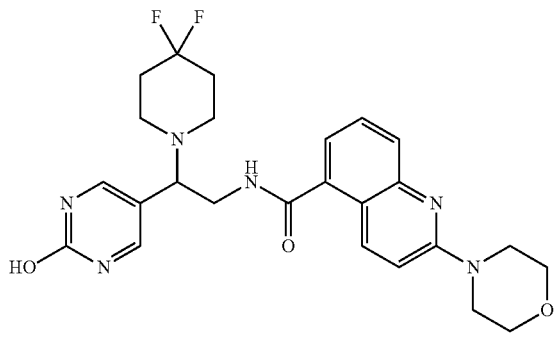
Co. No. 144; Ex. B.11
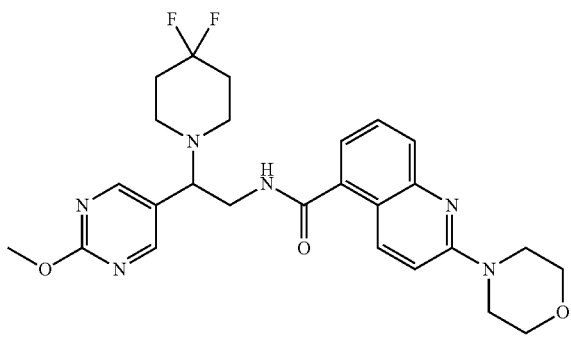
Co. No. 145; Ex. B.11
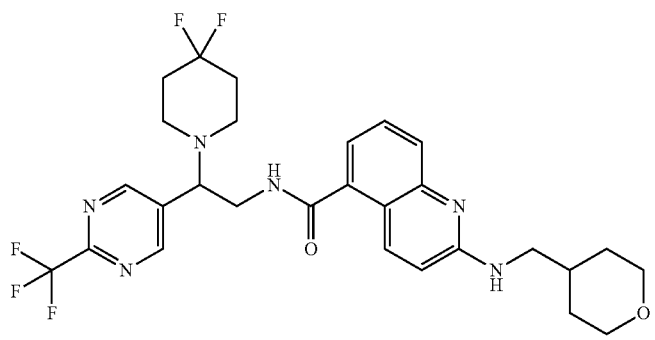
Co. No. 146; Ex. B.19
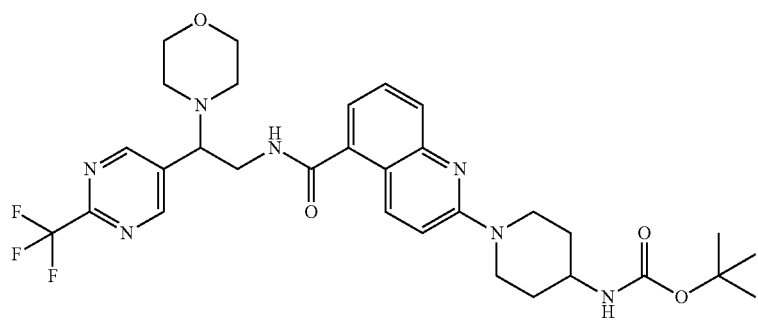
Co. No. 147; Ex. B.11

TABLE F-1-continued
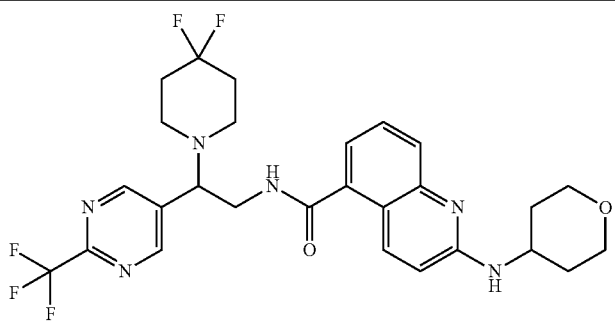
Co. No. 148; Ex. B.19
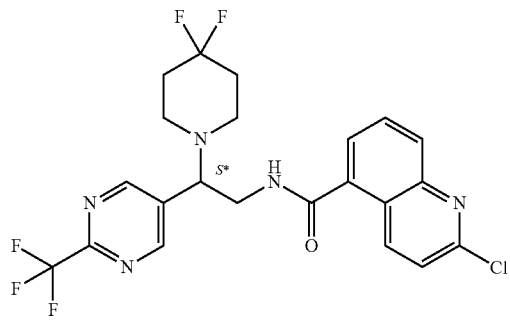
Co. No. 149; Ex. B.15
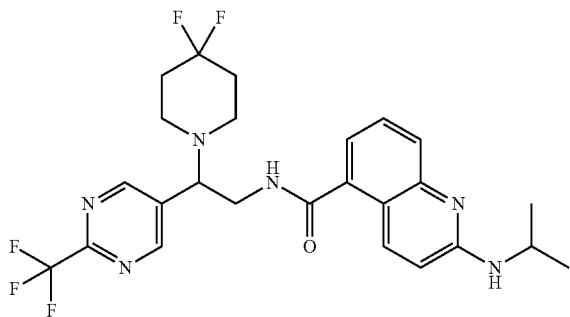
Co. No. 150; Ex. B.19
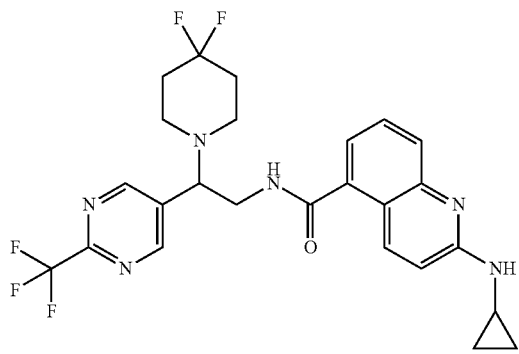
Co. No. 151; Ex. B.9

TABLE F-1-continued
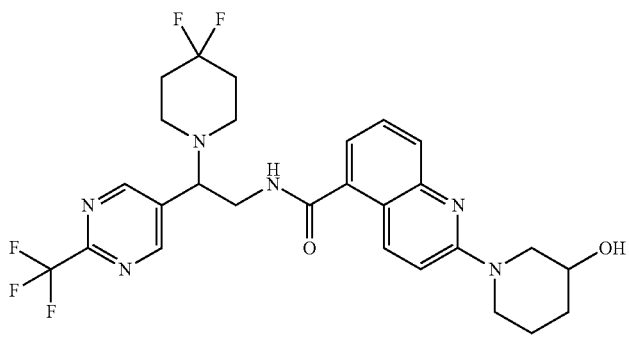
Co. No. 152; Ex. B.19
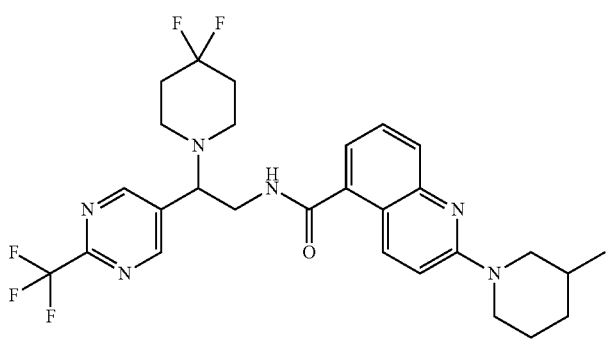
Co. No. 153; Ex. B.19
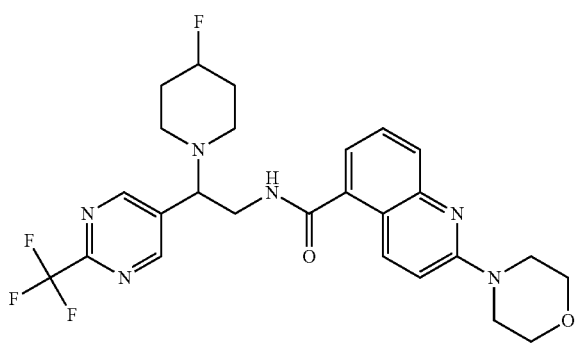
Co. No. 154; Ex. B.11
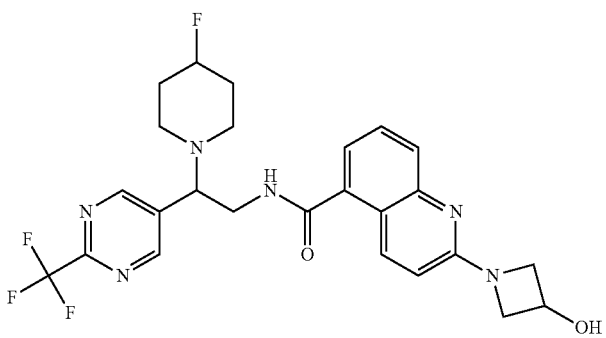
Co. No. 155; Ex. B.16

TABLE F-1-continued
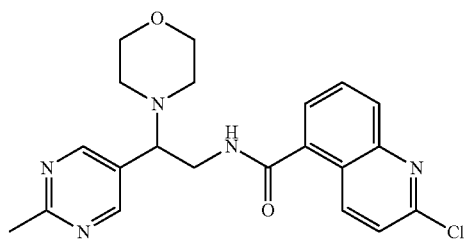
Co. No. 156; Ex. B.18
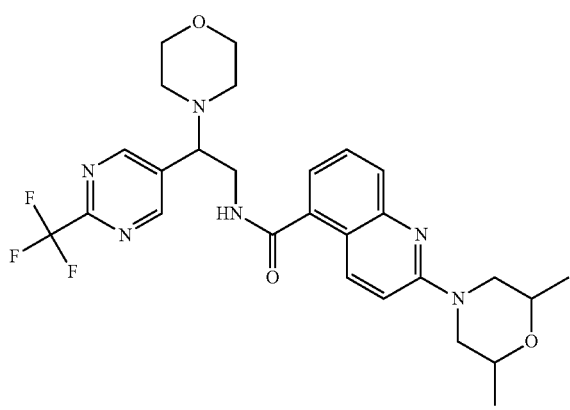
Co. No. 157; Ex. B.11
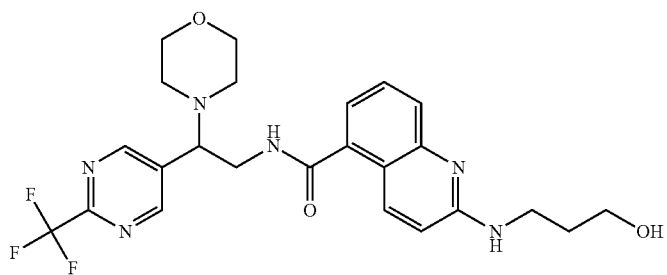
Co. No. 158; Ex. B.11
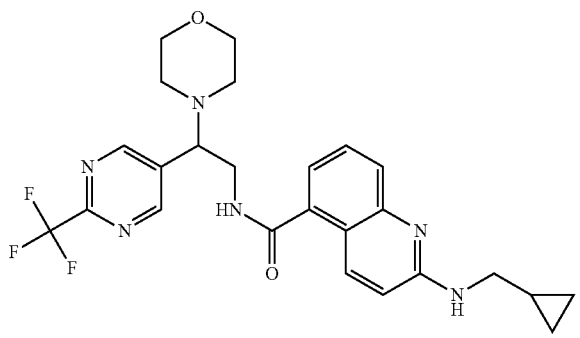
Co. No. 159; Ex. B.11

TABLE F-1-continued
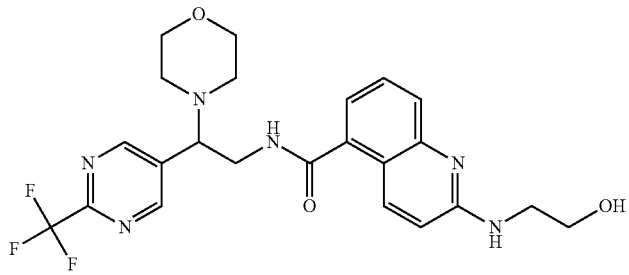
Co. No. 160; Ex. B.11
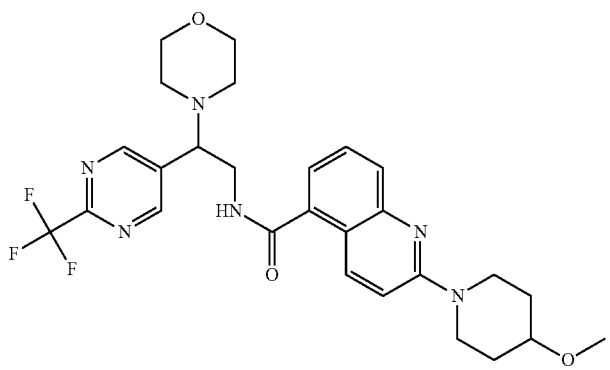
Co. No. 161; Ex. B.11
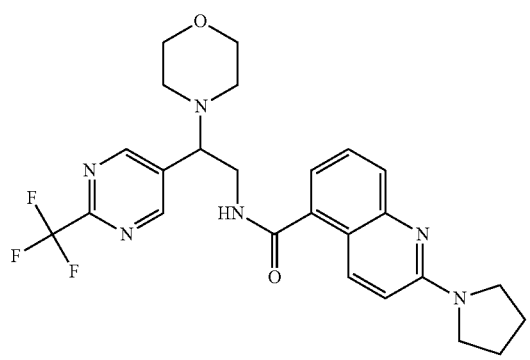
Co. No. 162; Ex. B.11
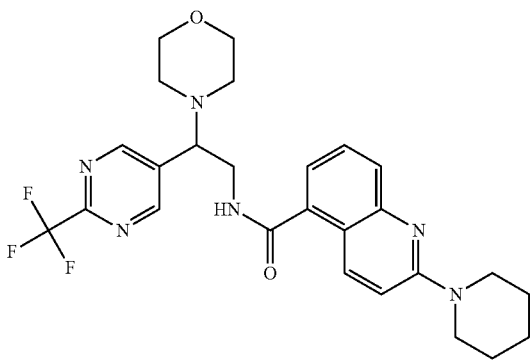
Co. No. 163; Ex. B.11

TABLE F-1-continued
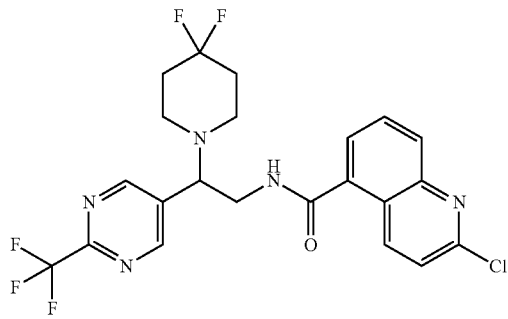
Co. No. 164; Ex. B.15
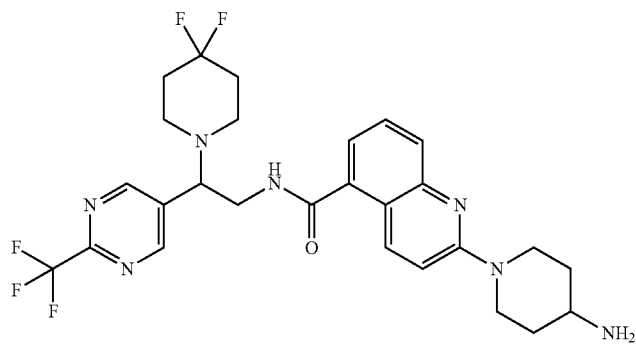
Co. No. 165; Ex. B.14
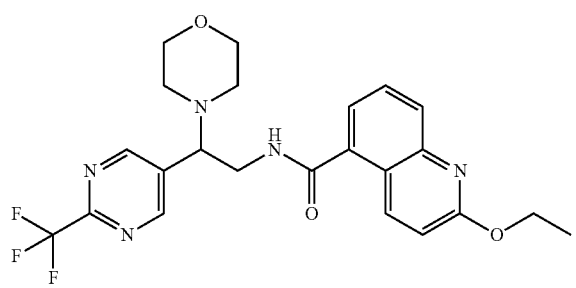
Co. No. 166; Ex. B.17
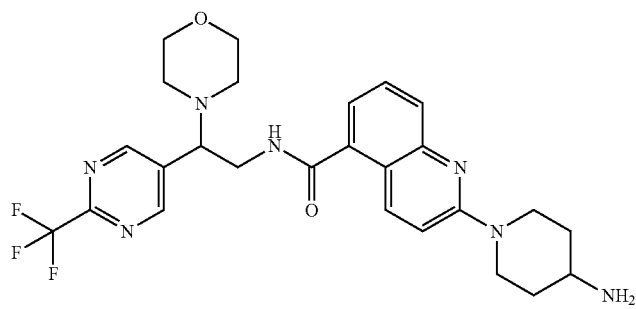
Co. No. 167; Ex. B.14

TABLE F-1-continued
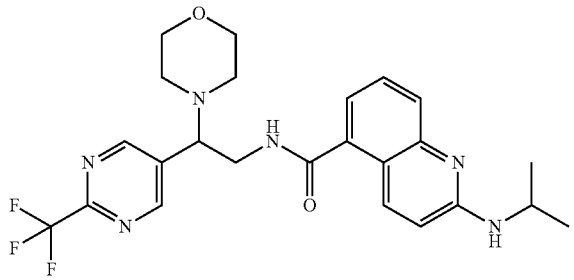
•3 C$_2$HF$_3$O$_2$;
Co. No. 168; Ex. B.20
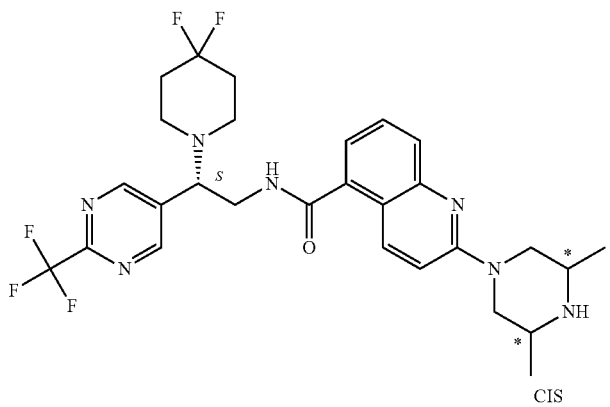
Co. No. 169; Ex. B.21; [(S), (CIS)]
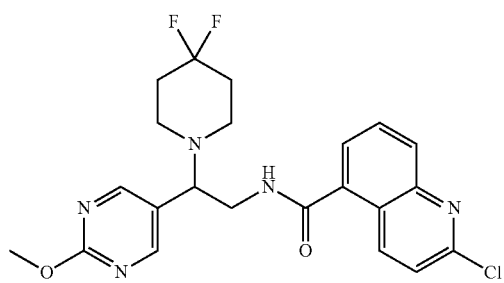
Co. No. 170; Ex. B.5
TABLE F-2
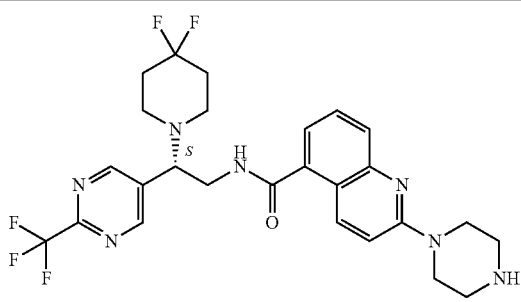
Co. No. 171; Ex. B.4; (S)
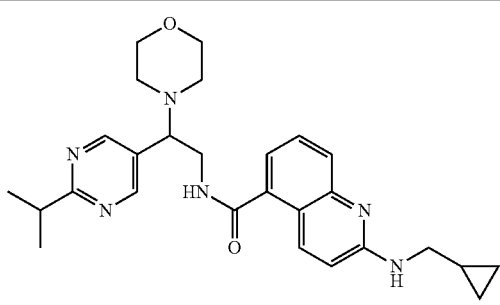 [SMILES: CC(C)c1ncc(C(CNC(=O)c2cccc3nc(NCC4CC4)ccc23)N2CCOCC2)cn1]
Co. No. 244; Ex. B.7

TABLE F-2-continued
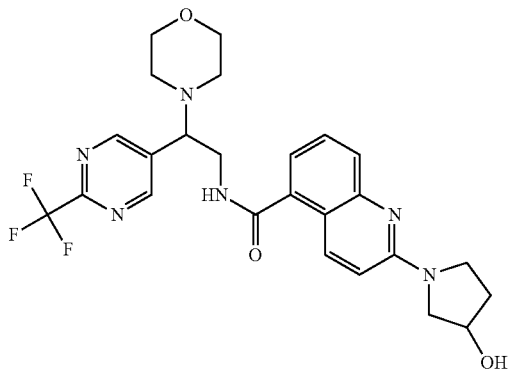 [SMILES: O=C(NCC(c1cnc(C(F)(F)F)nc1)N1CCOCC1)c1cccc2nc(N3CCC(O)C3)ccc12]
Co. No. 172; Ex. B.21
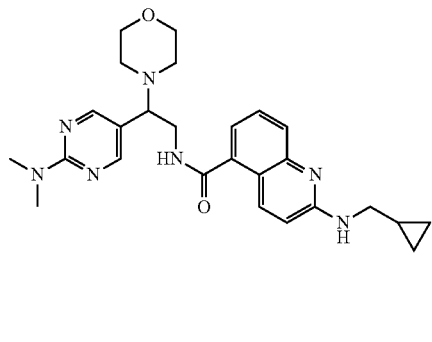
Co. No. 245; Ex. B.7
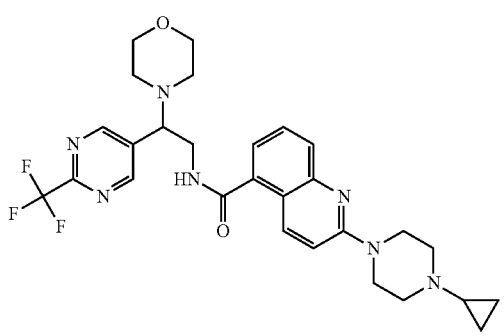 [SMILES: O=C(NCC(c1cnc(C(F)(F)F)nc1)N1CCOCC1)c1cccc2nc(N3CCN(C4CC4)CC3)ccc12]
Co. No. 173; Ex. B.22
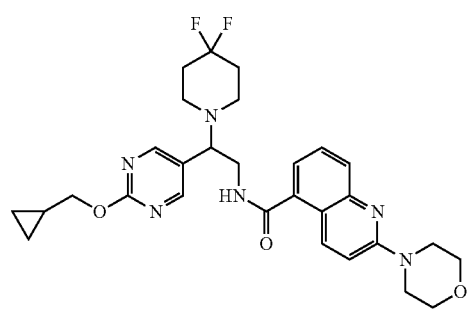 [SMILES: O=C(NCC(c1cnc(OCC2CC2)nc1)N1CCC(F)(F)CC1)c1cccc2nc(N3CCOCC3)ccc12]
Co. No. 246; Ex. B.7
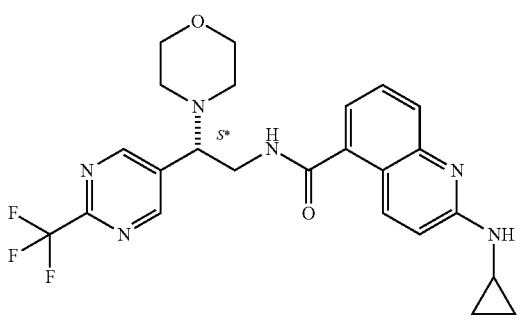
Co. No. 174; Ex. B.9; (S*)
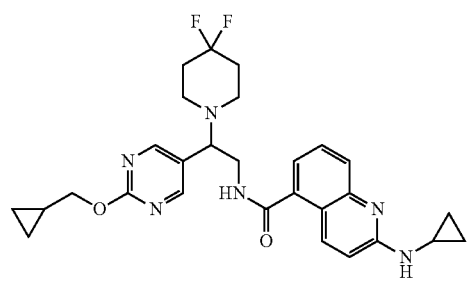 [SMILES: O=C(NCC(c1cnc(OCC2CC2)nc1)N1CCC(F)(F)CC1)c1cccc2nc(NC3CC3)ccc12]
Co. No. 247; Ex. B.7
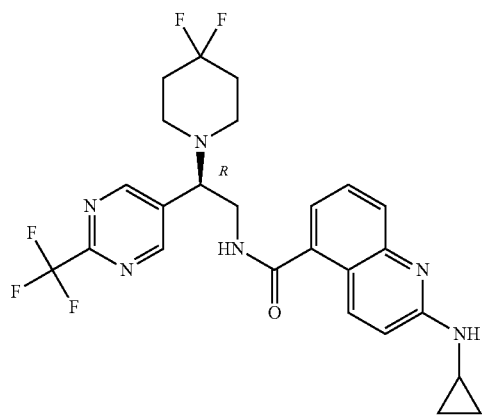
Co. No. 175; Ex. B.9; (R)
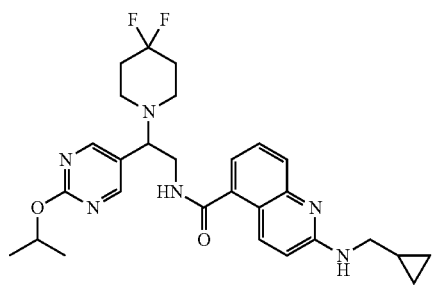 [SMILES: CC(C)Oc1ncc(C(CNC(=O)c2cccc3nc(NCC4CC4)ccc23)N2CCC(F)(F)CC2)cn1]
Co. No. 248; Ex. B.7

TABLE F-2-continued
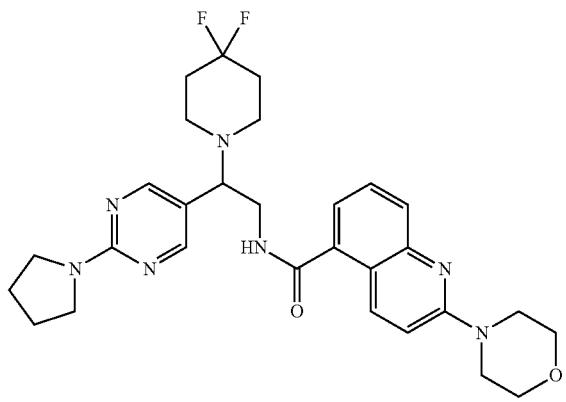 [SMILES: O=C(NCC(c1cnc(N2CCCC2)nc1)N1CCC(F)(F)CC1)c1cccc2nc(N3CCOCC3)ccc12]
Co. No. 176; Ex. B.11
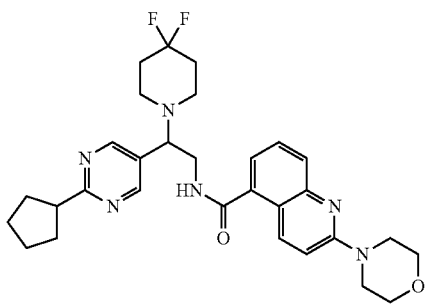 [SMILES: O=C(NCC(c1cnc(C2CCCC2)nc1)N1CCC(F)(F)CC1)c1cccc2nc(N3CCOCC3)ccc12]
Co. No. 249; Ex. B.7
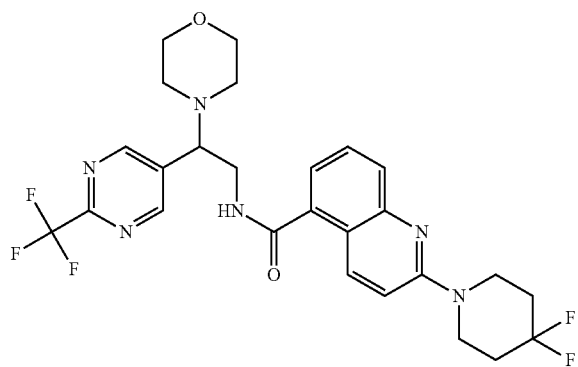 [SMILES: O=C(NCC(c1cnc(C(F)(F)F)nc1)N1CCOCC1)c1cccc2nc(N3CCC(F)(F)CC3)ccc12]
Co. No. 177; Ex. B.21
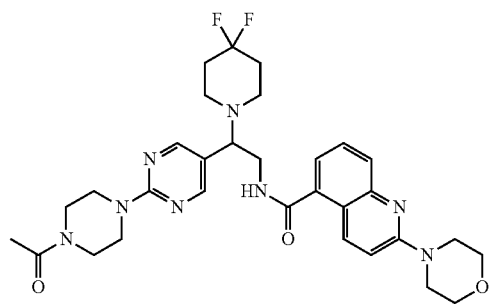 [SMILES: CC(=O)N1CCN(c2ncc(C(CNC(=O)c3cccc4nc(N5CCOCC5)ccc34)N3CCC(F)(F)CC3)cn2)CC1]
Co. No. 250; Ex. B.7
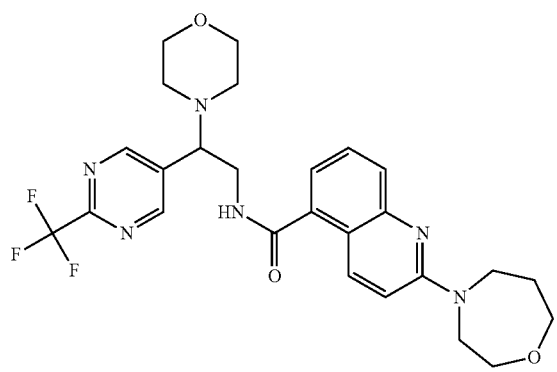 [SMILES: O=C(NCC(c1cnc(C(F)(F)F)nc1)N1CCOCC1)c1cccc2nc(N3CCCOCC3)ccc12]
Co. No. 178; Ex. B.21
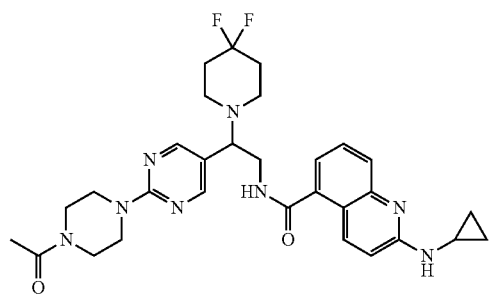 [SMILES: CC(=O)N1CCN(c2ncc(C(CNC(=O)c3cccc4nc(NC5CC5)ccc34)N3CCC(F)(F)CC3)cn2)CC1]
Co. No. 251; Ex. B.7

TABLE F-2-continued
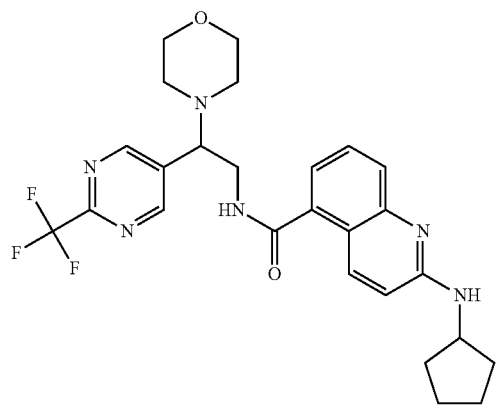 [SMILES: O=C(NCC(c1cnc(C(F)(F)F)nc1)N1CCOCC1)c1cccc2nc(NC3CCCC3)ccc12]
Co. No. 179; Ex. B.11; •C₂HF₃O₂
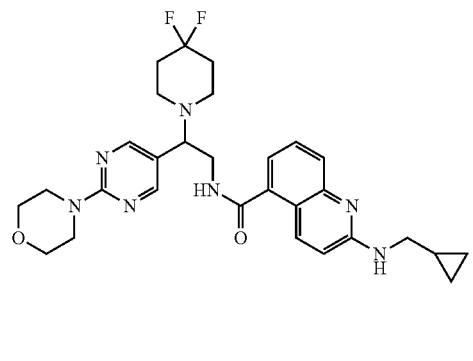 [SMILES: O=C(NCC(c1cnc(N2CCOCC2)nc1)N1CCC(F)(F)CC1)c1cccc2nc(NCC3CC3)ccc12]
Co. No. 252; Ex. B.7
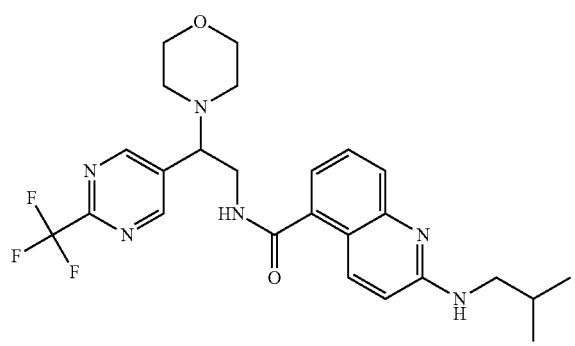 [SMILES: CC(C)CNc1ccc2c(C(=O)NCC(c3cnc(C(F)(F)F)nc3)N3CCOCC3)cccc2n1]
Co. No. 180; Ex. B.11; •C₂HF₃O₂
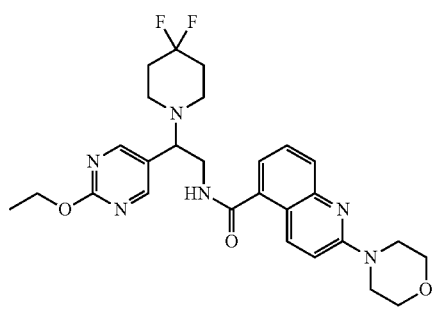 [SMILES: CCOc1ncc(C(CNC(=O)c2cccc3nc(N4CCOCC4)ccc23)N2CCC(F)(F)CC2)cn1]
Co. No. 253; Ex. B.7
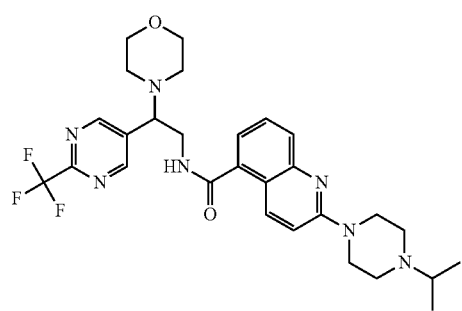 [SMILES: CC(C)N1CCN(c2ccc3c(C(=O)NCC(c4cnc(C(F)(F)F)nc4)N4CCOCC4)cccc3n2)CC1]
Co. No. 181; Ex. B.11
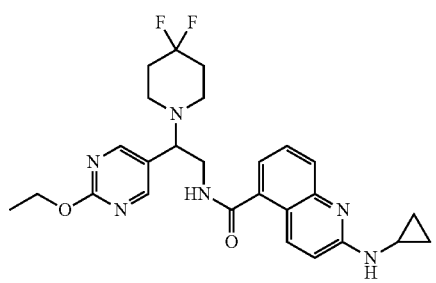 [SMILES: CCOc1ncc(C(CNC(=O)c2cccc3nc(NC4CC4)ccc23)N2CCC(F)(F)CC2)cn1]
Co. No. 254; Ex. B.7
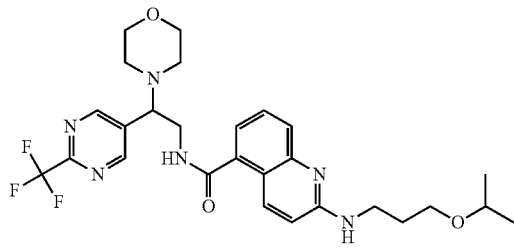 [SMILES: CC(C)OCCCNc1ccc2c(C(=O)NCC(c3cnc(C(F)(F)F)nc3)N3CCOCC3)cccc2n1]
Co. No. 182; Ex. B.11
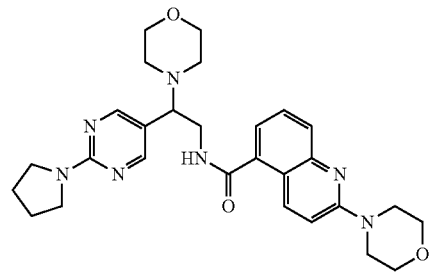 [SMILES: O=C(NCC(c1cnc(N2CCCC2)nc1)N1CCOCC1)c1cccc2nc(N3CCOCC3)ccc12]
Co. No. 255; Ex. B.7

TABLE F-2-continued
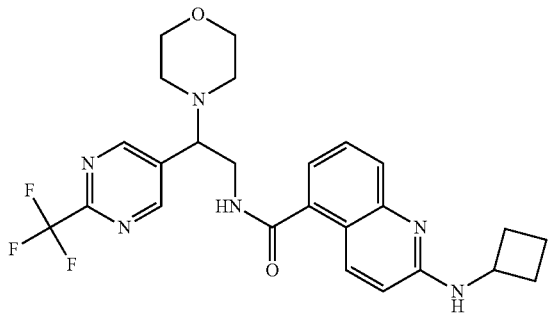 [SMILES: O=C(NCC(c1cnc(C(F)(F)F)nc1)N1CCOCC1)c1cccc2nc(NC3CCC3)ccc12]
Co. No. 183; Ex. B.11
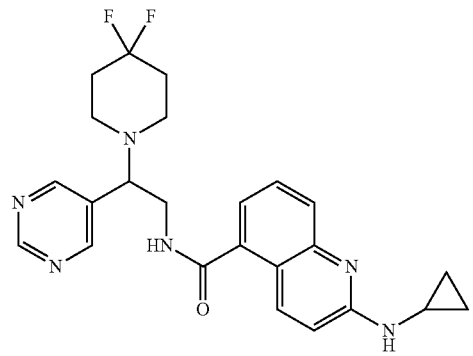 [SMILES: O=C(NCC(c1cncnc1)N1CCC(F)(F)CC1)c1cccc2nc(NC3CC3)ccc12]
Co. No. 256; Ex. B.7
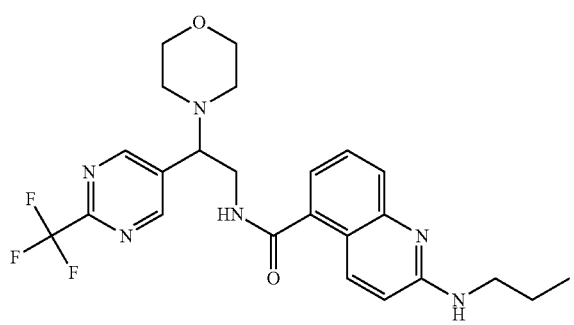 [SMILES: CCCNc1ccc2c(C(=O)NCC(c3cnc(C(F)(F)F)nc3)N3CCOCC3)cccc2n1]
Co. No. 184; Ex. B.11; •C$_2$HF$_3$O$_2$
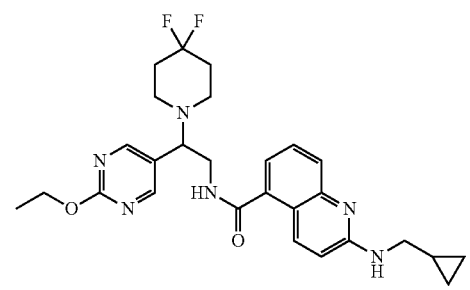 [SMILES: CCOc1ncc(C(CNC(=O)c2cccc3nc(NCC4CC4)ccc23)N2CCC(F)(F)CC2)cn1]
Co. No. 257; Ex. B.7
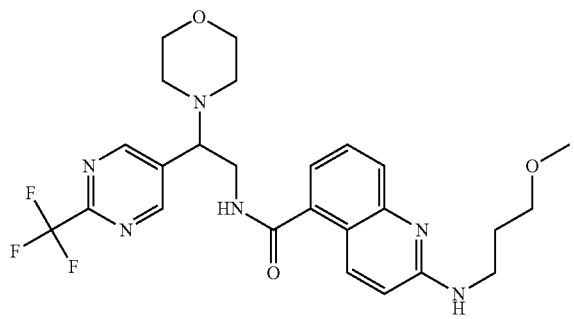 [SMILES: COCCCNc1ccc2c(C(=O)NCC(c3cnc(C(F)(F)F)nc3)N3CCOCC3)cccc2n1]
Co. No. 185; Ex. B.11
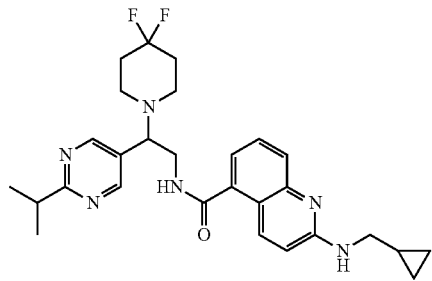
Co. No. 258; Ex. B.7
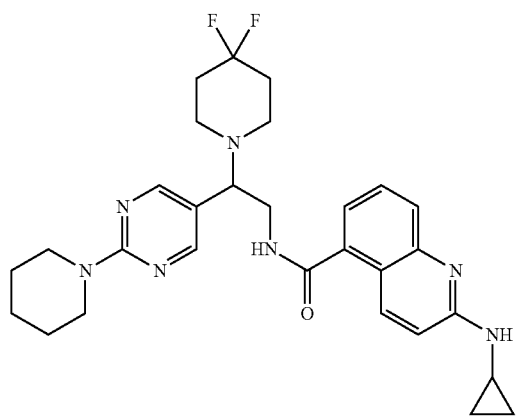 [SMILES: O=C(NCC(c1cnc(N2CCCCC2)nc1)N1CCC(F)(F)CC1)c1cccc2nc(NC3CC3)ccc12]
Co. No. 186; Ex. B.7
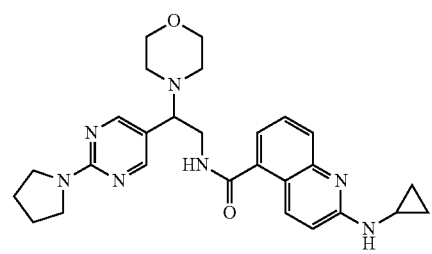 [SMILES: O=C(NCC(c1cnc(N2CCCC2)nc1)N1CCOCC1)c1cccc2nc(NC3CC3)ccc12]
Co. No. 259; Ex. B.7

TABLE F-2-continued
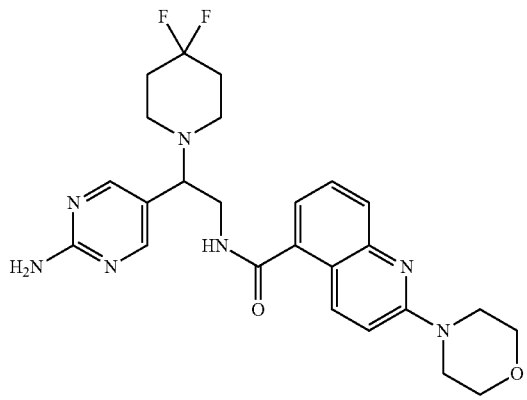 [SMILES: Nc1ncc(C(CNC(=O)c2cccc3nc(N4CCOCC4)ccc23)N2CCC(F)(F)CC2)cn1]
Co. No. 187; Ex. B.7
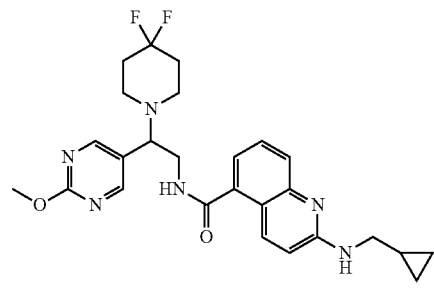 [SMILES: COc1ncc(C(CNC(=O)c2cccc3nc(NCC4CC4)ccc23)N2CCC(F)(F)CC2)cn1]
Co. No. 260; Ex. B.7
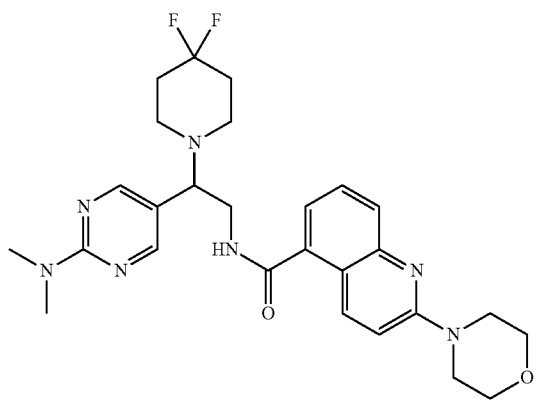
Co. No. 188; Ex. B.7
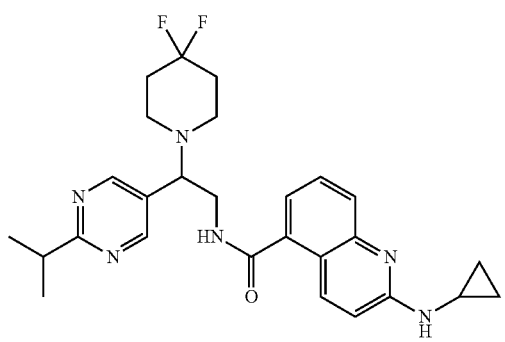 [SMILES: CC(C)c1ncc(C(CNC(=O)c2cccc3nc(NC4CC4)ccc23)N2CCC(F)(F)CC2)cn1]
Co. No. 261; Ex. B.7
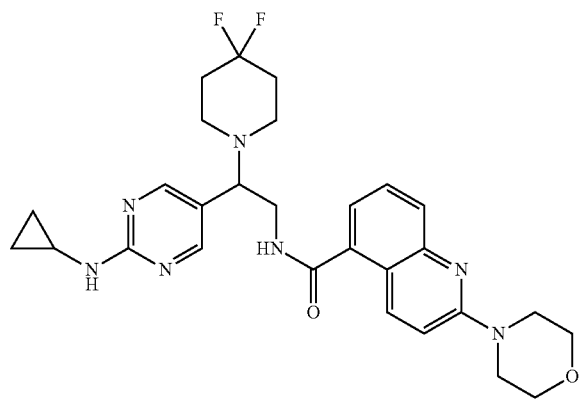 [SMILES: O=C(NCC(c1cnc(NC2CC2)nc1)N1CCC(F)(F)CC1)c1cccc2nc(N3CCOCC3)ccc12]
Co. No. 189; Ex. B.7
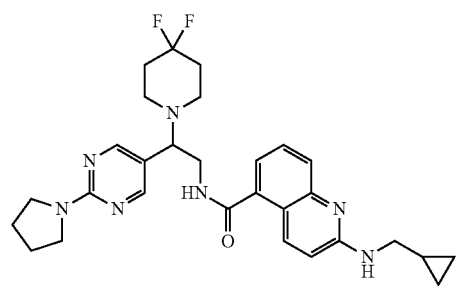 [SMILES: O=C(NCC(c1cnc(N2CCCC2)nc1)N1CCC(F)(F)CC1)c1cccc2nc(NCC3CC3)ccc12]
Co. No. 262; Ex. B.7

TABLE F-2-continued
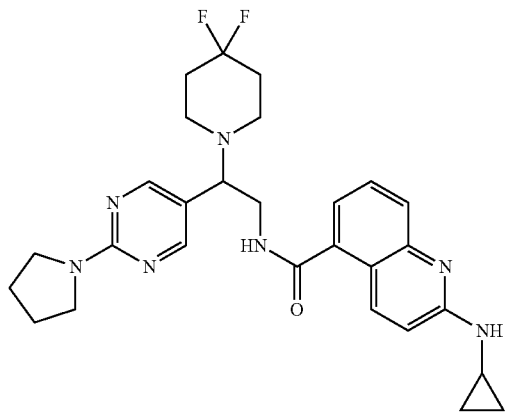 [SMILES: O=C(NCC(c1cnc(N2CCCC2)nc1)N1CCC(F)(F)CC1)c1cccc2nc(NC3CC3)ccc12]
Co. No. 190; Ex. B.7
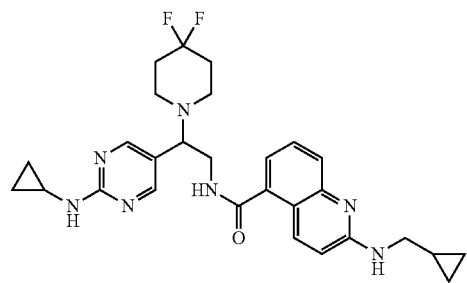 [SMILES: O=C(NCC(c1cnc(NC2CC2)nc1)N1CCC(F)(F)CC1)c1cccc2nc(NCC3CC3)ccc12]
Co. No. 263; Ex. B.7
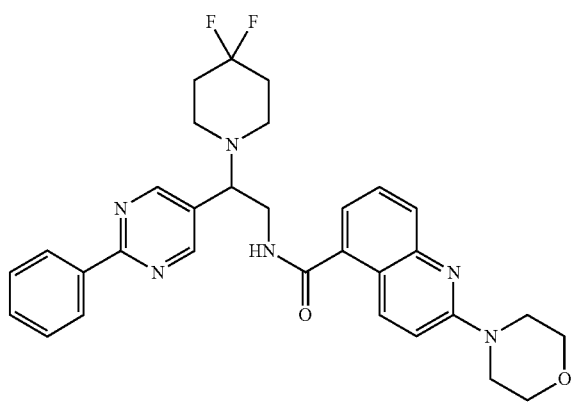 [SMILES: O=C(NCC(c1cnc(-c2ccccc2)nc1)N1CCC(F)(F)CC1)c1cccc2nc(N3CCOCC3)ccc12]
Co. No. 191; Ex. B.7
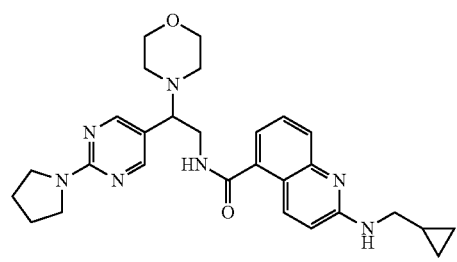 [SMILES: O=C(NCC(c1cnc(N2CCCC2)nc1)N1CCOCC1)c1cccc2nc(NCC3CC3)ccc12]
Co. No. 264; Ex. B.7
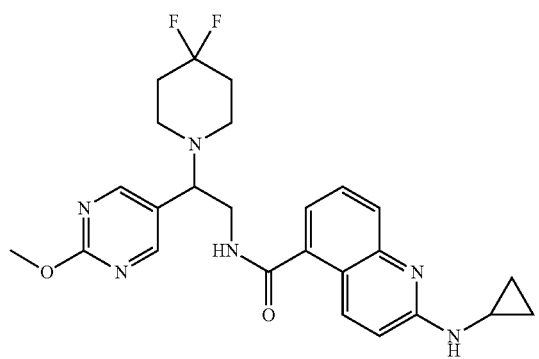
Co. No. 192; Ex. B.7; •C$_2$HF$_3$O$_2$
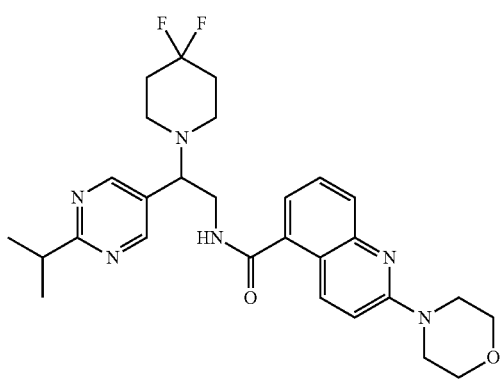
Co. No. 265; Ex. B.7

TABLE F-2-continued
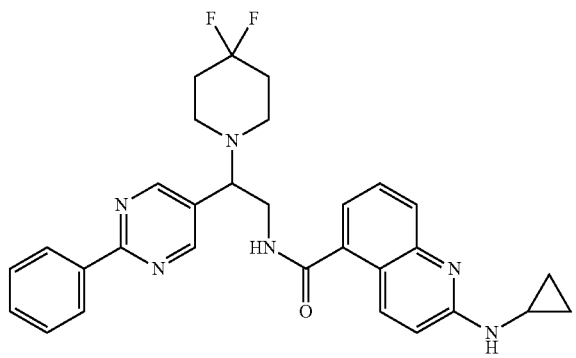 [SMILES: O=C(NCC(c1cnc(-c2ccccc2)nc1)N1CCC(F)(F)CC1)c1cccc2nc(NC3CC3)ccc12]
Co. No. 193; Ex. B.7
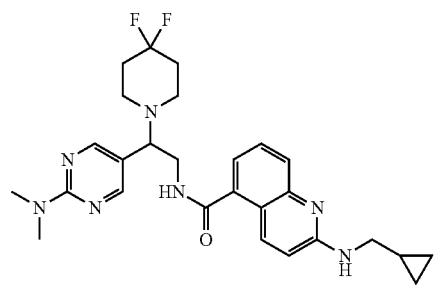
Co. No. 266; Ex. B.7
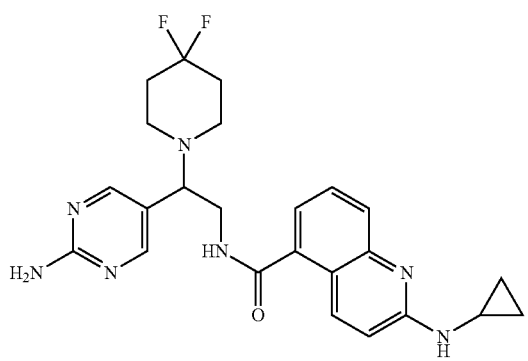 [SMILES: Nc1ncc(C(CNC(=O)c2cccc3nc(NC4CC4)ccc23)N2CCC(F)(F)CC2)cn1]
Co. No. 194; Ex. B.7
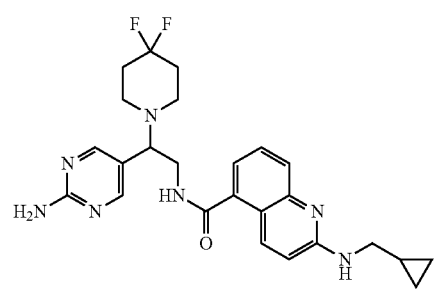 [SMILES: Nc1ncc(C(CNC(=O)c2cccc3nc(NCC4CC4)ccc23)N2CCC(F)(F)CC2)cn1]
Co. No. 267; Ex. B.7
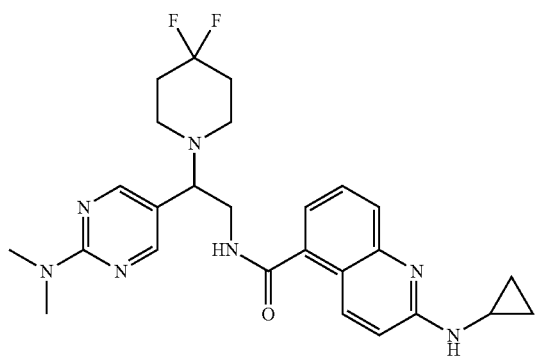 [SMILES: CN(C)c1ncc(C(CNC(=O)c2cccc3nc(NC4CC4)ccc23)N2CCC(F)(F)CC2)cn1]
Co. No. 195; Ex. B.7
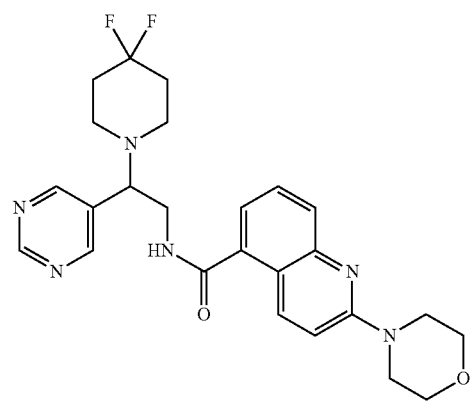 [SMILES: O=C(NCC(c1cncnc1)N1CCC(F)(F)CC1)c1cccc2nc(N3CCOCC3)ccc12]
Co. No. 268; Ex. B.7
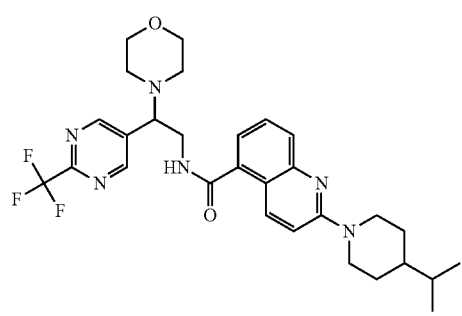 [SMILES: CC(C)C1CCN(c2ccc3c(C(=O)NCC(c4cnc(C(F)(F)F)nc4)N4CCOCC4)cccc3n2)CC1]
Co. No. 196; Ex. B.11; •C$_2$HF$_3$O$_2$
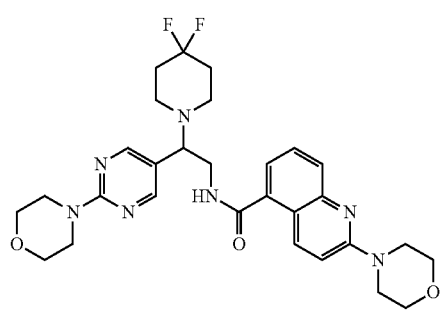 [SMILES: O=C(NCC(c1cnc(N2CCOCC2)nc1)N1CCC(F)(F)CC1)c1cccc2nc(N3CCOCC3)ccc12]
Co. No. 269; Ex. B.7

TABLE F-2-continued
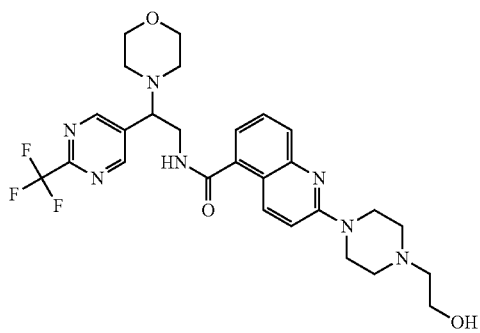 [SMILES: O=C(NCC(c1cnc(C(F)(F)F)nc1)N1CCOCC1)c1cccc2nc(N3CCN(CCO)CC3)ccc12]
Co. No. 197; Ex. B.11
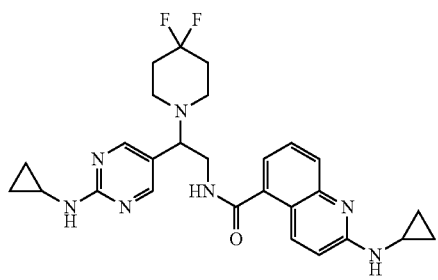 [SMILES: O=C(NCC(c1cnc(NC2CC2)nc1)N1CCC(F)(F)CC1)c1cccc2nc(NC3CC3)ccc12]
Co. No. 270; Ex. B.7
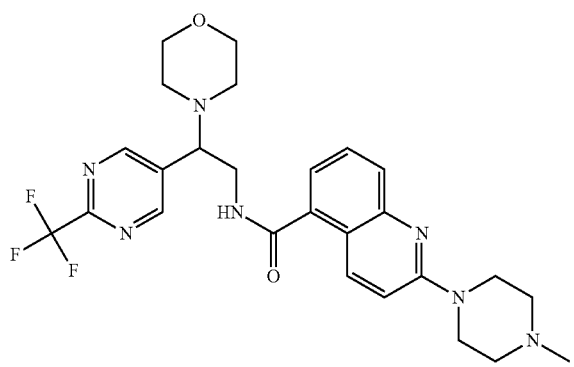 [SMILES: CN1CCN(c2ccc3c(C(=O)NCC(c4cnc(C(F)(F)F)nc4)N4CCOCC4)cccc3n2)CC1]
Co. No. 198; Ex. B.11; •C₂HF₃O₂
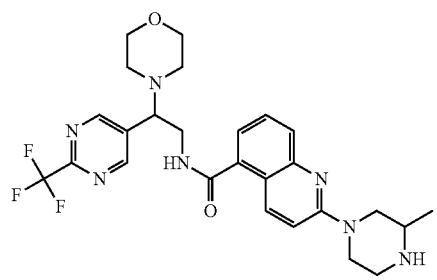 [SMILES: CC1CN(c2ccc3c(C(=O)NCC(c4cnc(C(F)(F)F)nc4)N4CCOCC4)cccc3n2)CCN1]
Co. No. 271; Ex. B.14
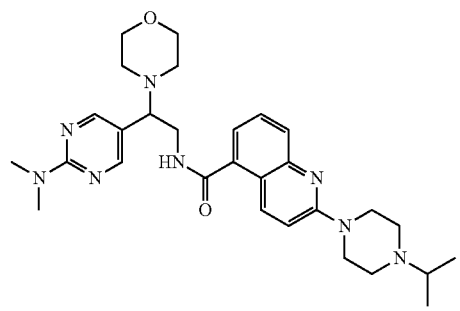
Co. No. 199; Ex. B.7; •C₂HF₃O₂
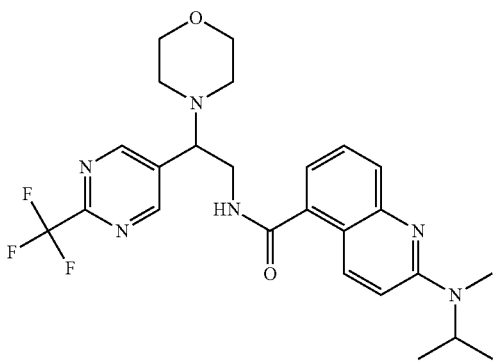 [SMILES: CC(C)N(C)c1ccc2c(C(=O)NCC(c3cnc(C(F)(F)F)nc3)N3CCOCC3)cccc2n1]
Co. No. 272; Ex. B.11
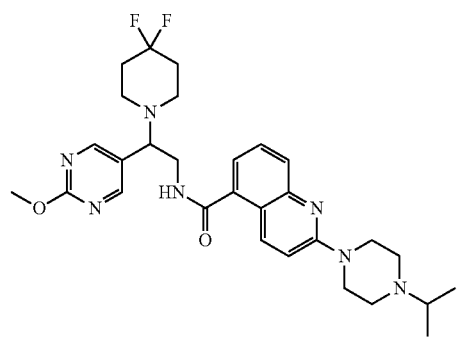 [SMILES: COc1ncc(C(CNC(=O)c2cccc3nc(N4CCN(C(C)C)CC4)ccc23)N2CCC(F)(F)CC2)cn1]
Co. No. 200; Ex. B.7; •C₂HF₃O₂
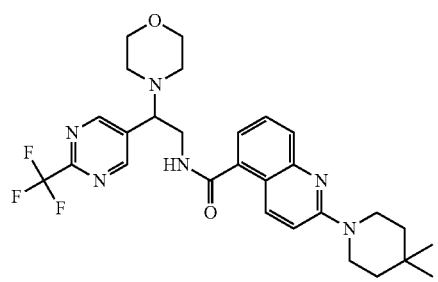 [SMILES: CC1(C)CCN(c2ccc3c(C(=O)NCC(c4cnc(C(F)(F)F)nc4)N4CCOCC4)cccc3n2)CC1]
Co. No. 273; Ex. B.23

TABLE F-2-continued
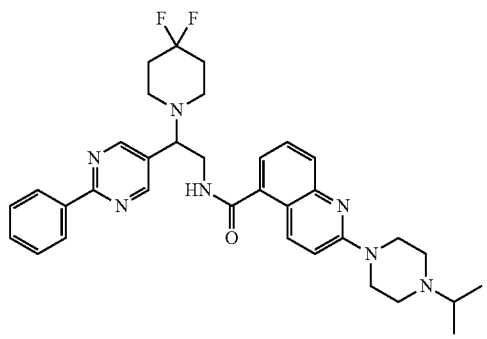 [SMILES: CC(C)N1CCN(c2ccc3c(C(=O)NCC(c4cnc(-c5ccccc5)nc4)N4CCC(F)(F)CC4)cccc3n2)CC1]
Co. No. 201; Ex. B.7; •C₂HF₃O₂
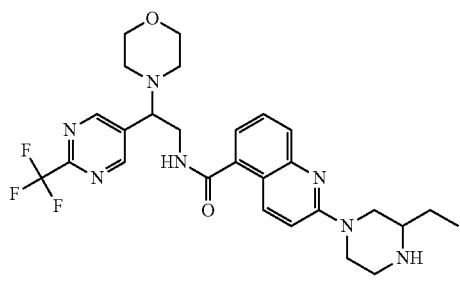 [SMILES: CCC1CN(c2ccc3c(C(=O)NCC(c4cnc(C(F)(F)F)nc4)N4CCOCC4)cccc3n2)CCN1]
Co. No. 274; Ex. B.14
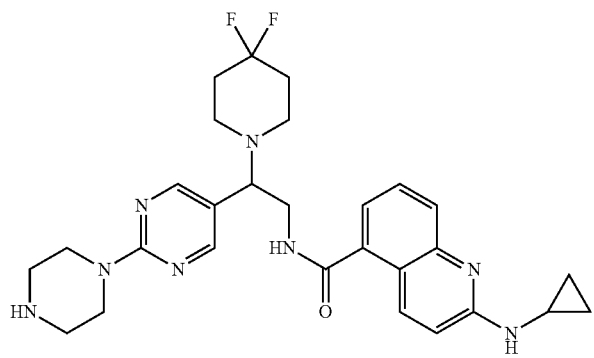 [SMILES: O=C(NCC(c1cnc(N2CCNCC2)nc1)N1CCC(F)(F)CC1)c1cccc2nc(NC3CC3)ccc12]
Co. No. 202; Ex. B.14; •C₂HF₃O₂
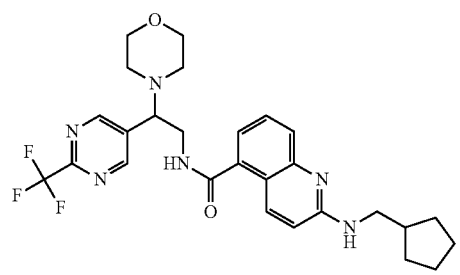 [SMILES: O=C(NCC(c1cnc(C(F)(F)F)nc1)N1CCOCC1)c1cccc2nc(NCC3CCCC3)ccc12]
Co. No. 275; Ex. B.23
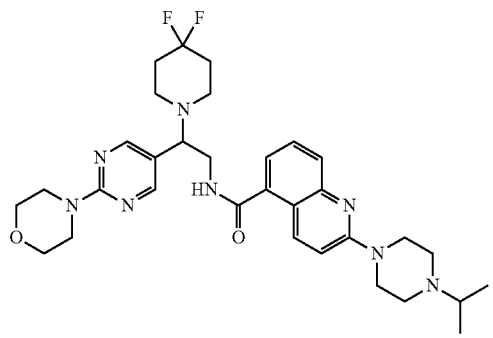 [SMILES: CC(C)N1CCN(c2ccc3c(C(=O)NCC(c4cnc(N5CCOCC5)nc4)N4CCC(F)(F)CC4)cccc3n2)CC1]
Co. No. 203; Ex. B.7; •C₂HF₃O₂
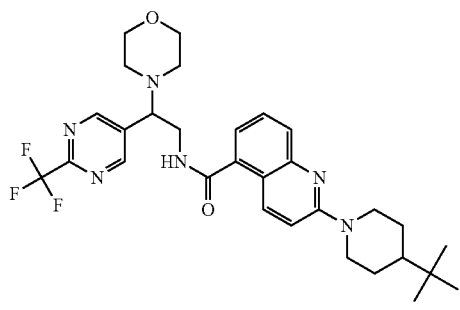 [SMILES: CC(C)(C)C1CCN(c2ccc3c(C(=O)NCC(c4cnc(C(F)(F)F)nc4)N4CCOCC4)cccc3n2)CC1]
Co. No. 276; Ex. B.23
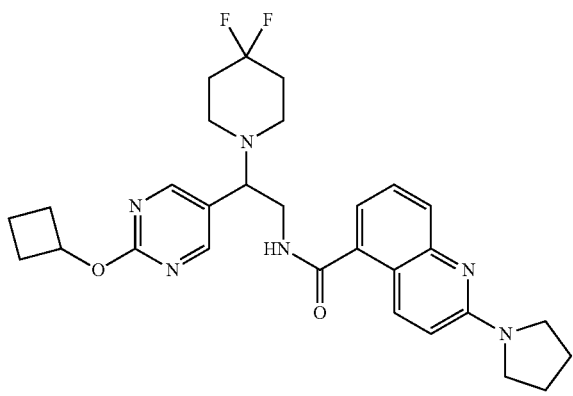 [SMILES: O=C(NCC(c1cnc(OC2CCC2)nc1)N1CCC(F)(F)CC1)c1cccc2nc(N3CCCC3)ccc12]
Co. No. 204; Ex. B.18; •C₂HF₃O₂
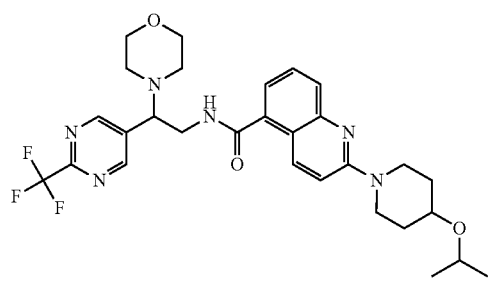 [SMILES: CC(C)OC1CCN(c2ccc3c(C(=O)NCC(c4cnc(C(F)(F)F)nc4)N4CCOCC4)cccc3n2)CC1]
Co. No. 277; Ex. B.23

TABLE F-2-continued
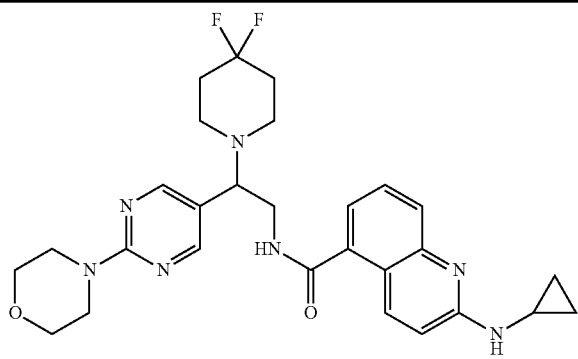
Co. No. 205; Ex. B.7; •C₂HF₃O₂
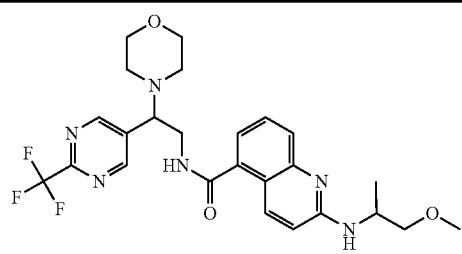
Co. No. 278; Ex. B.11
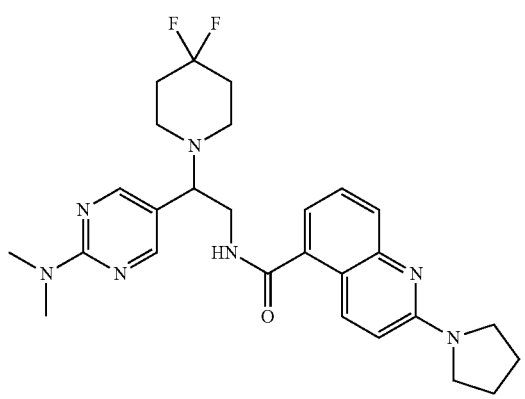
Co. No. 206; Ex. B.18; •C₂HF₃O₂
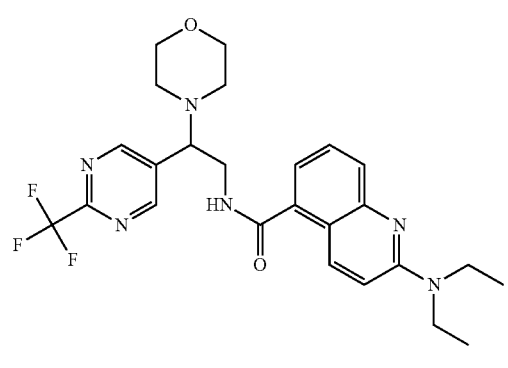 [SMILES: CCN(CC)c1ccc2c(C(=O)NCC(c3cnc(C(F)(F)F)nc3)N3CCOCC3)cccc2n1]
Co. No. 279; Ex. B.11
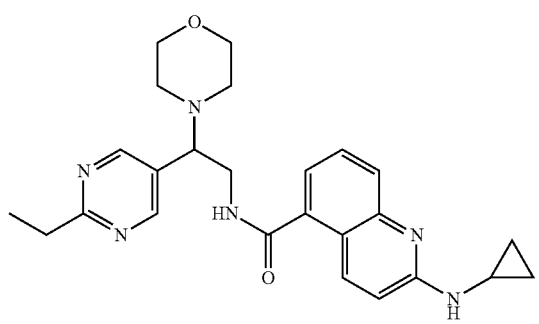 [SMILES: CCc1ncc(C(CNC(=O)c2cccc3nc(NC4CC4)ccc23)N2CCOCC2)cn1]
Co. No. 207; Ex. B.7; •C₂HF₃O₂
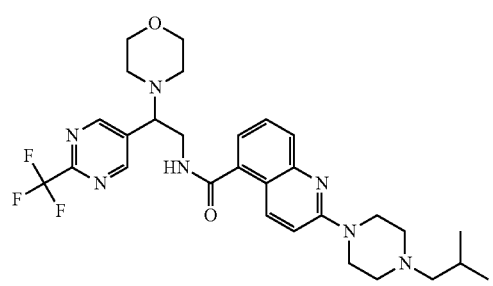 [SMILES: CC(C)CN1CCN(c2ccc3c(C(=O)NCC(c4cnc(C(F)(F)F)nc4)N4CCOCC4)cccc3n2)CC1]
Co. No. 280; Ex. B.11
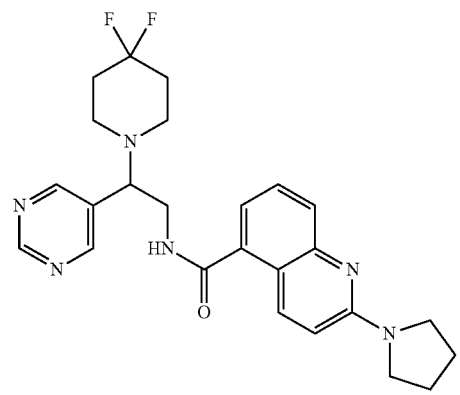 [SMILES: O=C(NCC(c1cncnc1)N1CCC(F)(F)CC1)c1cccc2nc(N3CCCC3)ccc12]
Co. No. 208; Ex. B.18; •C₂HF₃O₂
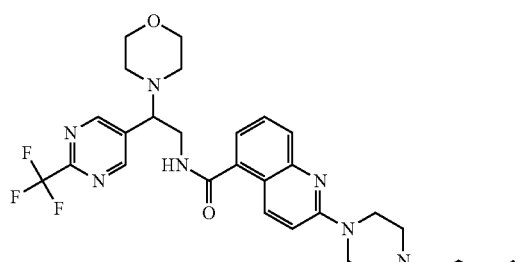
Co. No. 281; Ex. B.11

TABLE F-2-continued
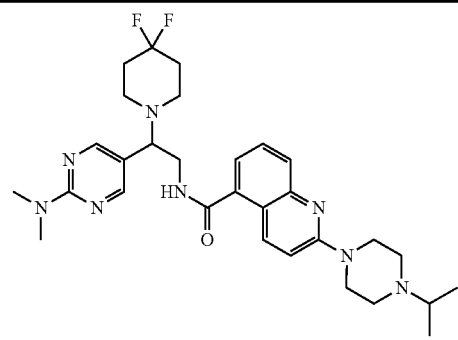
Co. No. 209; Ex. B.7; •C₂HF₃O₂
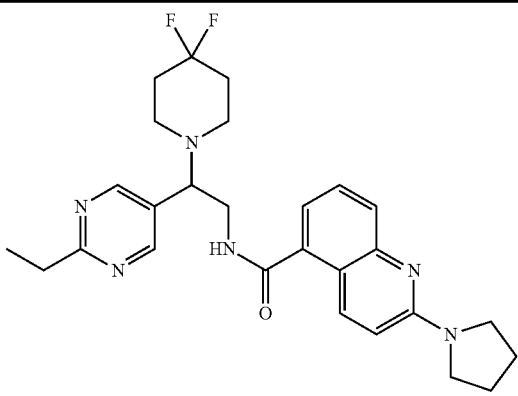
Co. No. 282; Ex. B.18; •C₂HF₃O₂
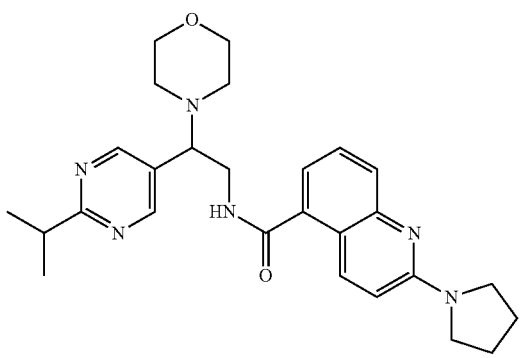 [SMILES: CC(C)c1ncc(C(CNC(=O)c2cccc3nc(N4CCCC4)ccc23)N2CCOCC2)cn1]
Co. No. 210; Ex. B.18; •C₂HF₃O₂
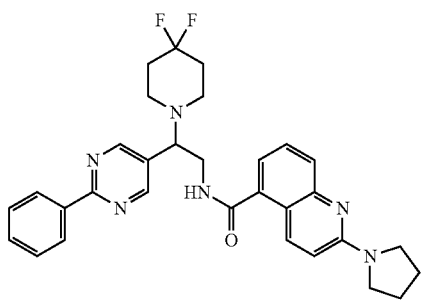 [SMILES: O=C(NCC(c1cnc(-c2ccccc2)nc1)N1CCC(F)(F)CC1)c1cccc2nc(N3CCCC3)ccc12]
Co. No. 283; Ex. B.18; •C₂HF₃O₂
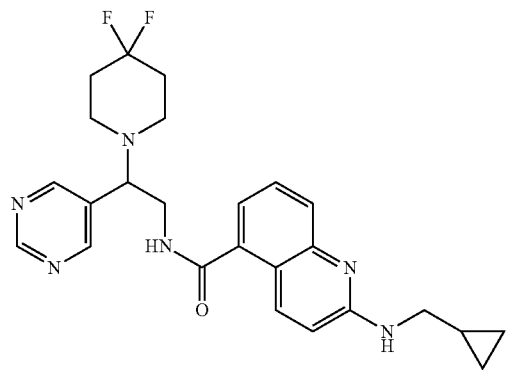 [SMILES: O=C(NCC(c1cncnc1)N1CCC(F)(F)CC1)c1cccc2nc(NCC3CC3)ccc12]
Co. No. 211; Ex. B.7
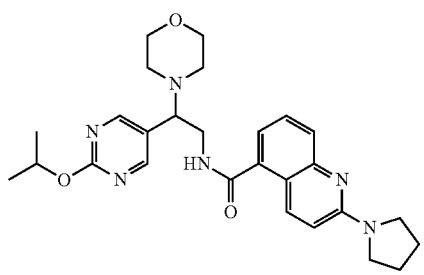 [SMILES: CC(C)Oc1ncc(C(CNC(=O)c2cccc3nc(N4CCCC4)ccc23)N2CCOCC2)cn1]
Co. No. 284; Ex. B.18; •C₂HF₃O₂
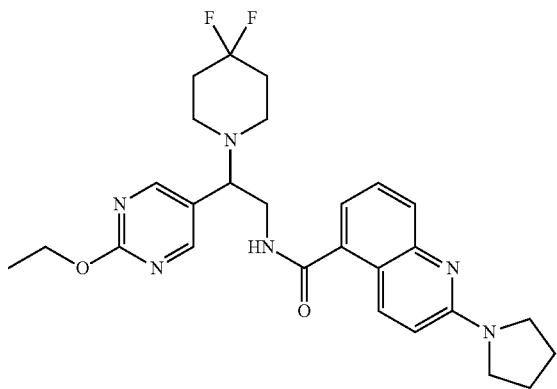 [SMILES: CCOc1ncc(C(CNC(=O)c2cccc3nc(N4CCCC4)ccc23)N2CCC(F)(F)CC2)cn1]
Co. No. 212; Ex. B.18; •C₂HF₃O₂
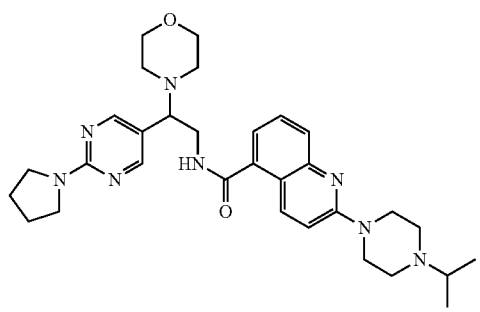 [SMILES: CC(C)N1CCN(c2ccc3c(C(=O)NCC(c4cnc(N5CCCC5)nc4)N4CCOCC4)cccc3n2)CC1]
Co. No. 285; Ex. B.9; •C₂HF₃O₂

TABLE F-2-continued
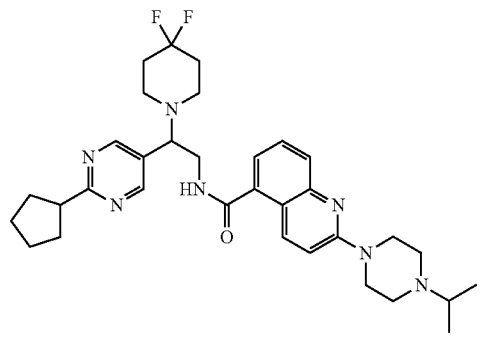
Co. No. 213; Ex. B.7; •C₂HF₃O₂
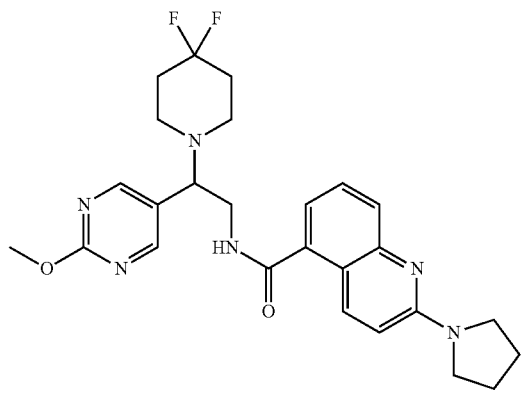 [SMILES: COc1ncc(C(CNC(=O)c2cccc3nc(N4CCCC4)ccc23)N2CCC(F)(F)CC2)cn1]
Co. No. 286; Ex. B.18; •C₂HF₃O₂
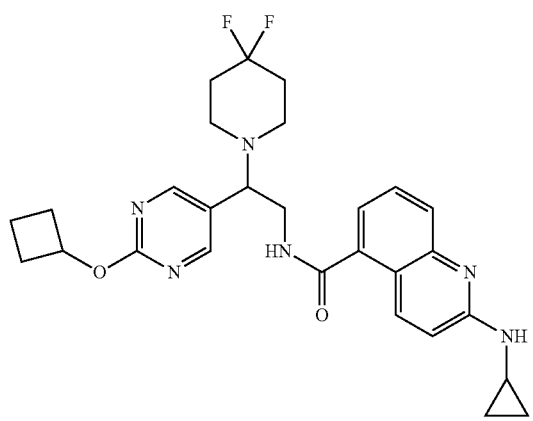 [SMILES: O=C(NCC(c1cnc(OC2CCC2)nc1)N1CCC(F)(F)CC1)c1cccc2nc(NC3CC3)ccc12]
Co. No. 214; Ex. B.7
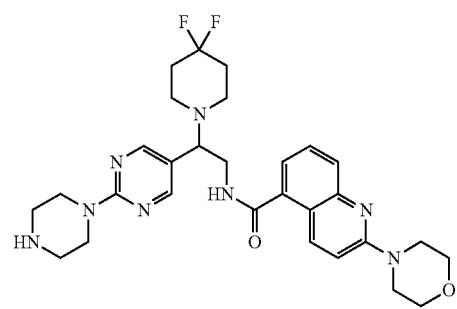 [SMILES: O=C(NCC(c1cnc(N2CCNCC2)nc1)N1CCC(F)(F)CC1)c1cccc2nc(N3CCOCC3)ccc12]
Co. No. 287; Ex. B.14
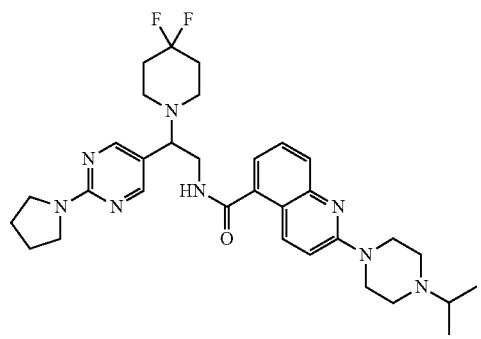 [SMILES: CC(C)N1CCN(c2ccc3c(C(=O)NCC(c4cnc(N5CCCC5)nc4)N4CCC(F)(F)CC4)cccc3n2)CC1]
Co. No. 215; Ex. B.7; •C₂HF₃O₂
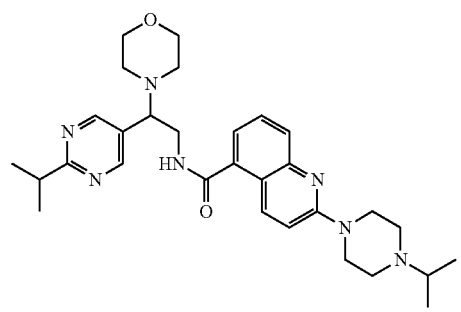
Co. No. 288; Ex. B.7

TABLE F-2-continued
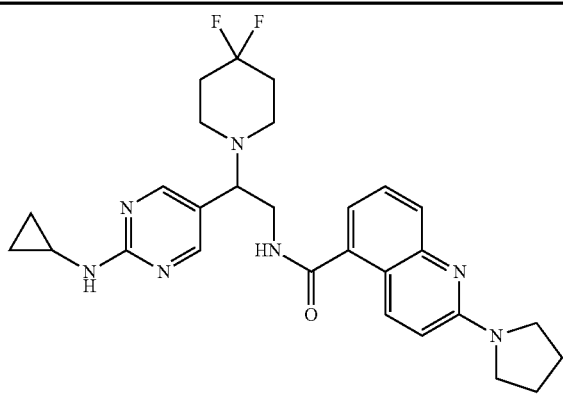
Co. No. 216; Ex. B.18; •C₂HF₃O₂
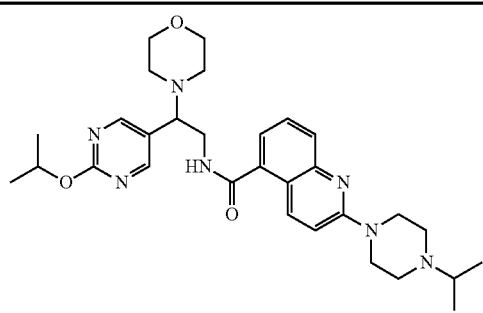
Co. No. 289; Ex. B.7
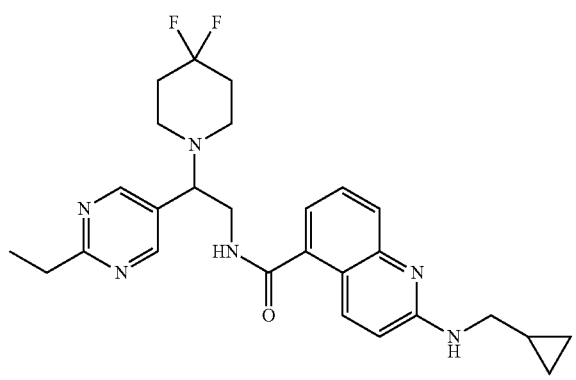 [SMILES: CCc1ncc(C(CNC(=O)c2cccc3nc(NCC4CC4)ccc23)N2CCC(F)(F)CC2)cn1]
Co. No. 217; Ex. B.7; •C₂HF₃O₂
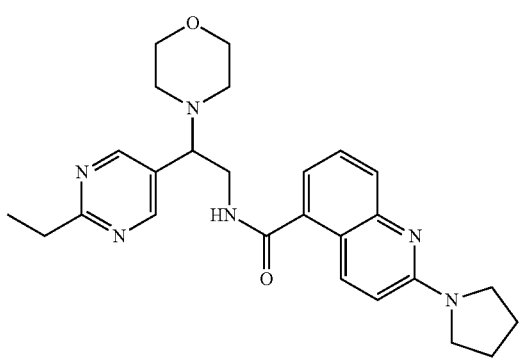 [SMILES: CCc1ncc(C(CNC(=O)c2cccc3nc(N4CCCC4)ccc23)N2CCOCC2)cn1]
Co. No. 290; Ex. B.18; •C₂HF₃O₂
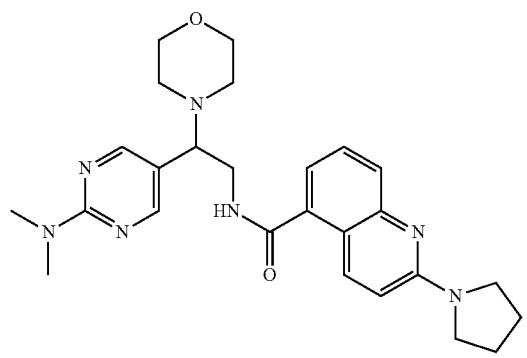 [SMILES: CN(C)c1ncc(C(CNC(=O)c2cccc3nc(N4CCCC4)ccc23)N2CCOCC2)cn1]
Co. No. 218; Ex. B.18; •C₂HF₃O₂
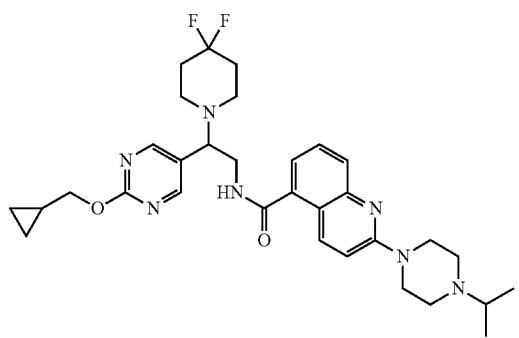 [SMILES: CC(C)N1CCN(c2ccc3c(C(=O)NCC(c4cnc(OCC5CC5)nc4)N4CCC(F)(F)CC4)cccc3n2)CC1]
Co. No. 291; Ex. B.7
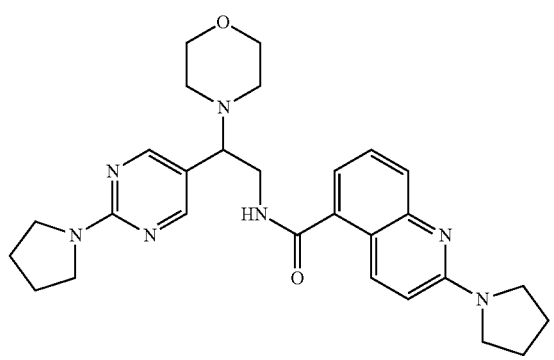 [SMILES: O=C(NCC(c1cnc(N2CCCC2)nc1)N1CCOCC1)c1cccc2nc(N3CCCC3)ccc12]
Co. No. 219; Ex. B.18; •C₂HF₃O₂
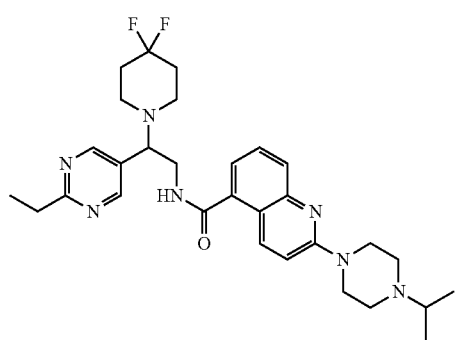 [SMILES: CCc1ncc(C(CNC(=O)c2cccc3nc(N4CCN(C(C)C)CC4)ccc23)N2CCC(F)(F)CC2)cn1]
Co. No. 292; Ex. B.7

TABLE F-2-continued
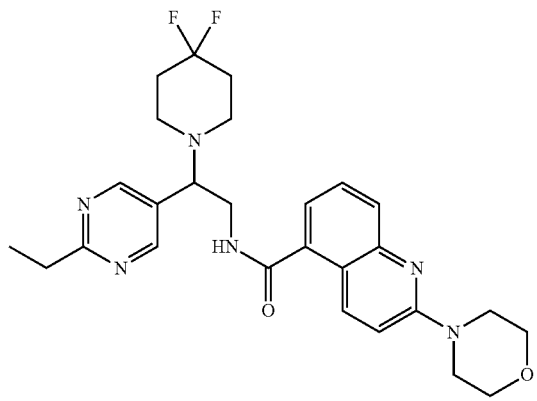 [SMILES: CCc1ncc(C(CNC(=O)c2cccc3nc(N4CCOCC4)ccc23)N2CCC(F)(F)CC2)cn1]
Co. No. 220; Ex. B.7; •C₂HF₃O₂
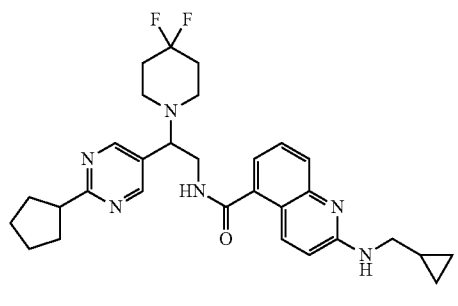 [SMILES: O=C(NCC(c1cnc(C2CCCC2)nc1)N1CCC(F)(F)CC1)c1cccc2nc(NCC3CC3)ccc12]
Co. No. 293; Ex. B.9
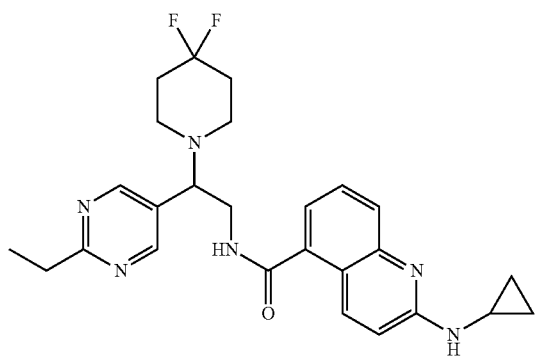 [SMILES: CCc1ncc(C(CNC(=O)c2cccc3nc(NC4CC4)ccc23)N2CCC(F)(F)CC2)cn1]
Co. No. 221; Ex. B.7; •C₂HF₃O₂
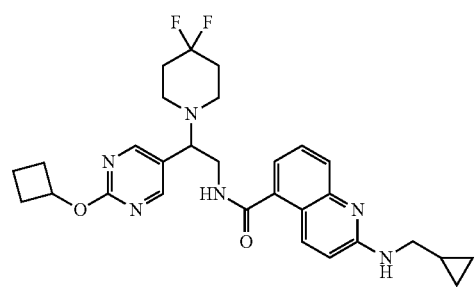 [SMILES: O=C(NCC(c1cnc(OC2CCC2)nc1)N1CCC(F)(F)CC1)c1cccc2nc(NCC3CC3)ccc12]
Co. No. 294; Ex. B.9
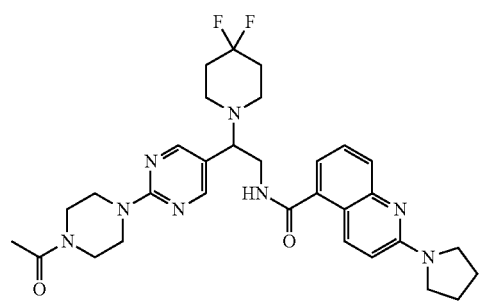 [SMILES: CC(=O)N1CCN(c2ncc(C(CNC(=O)c3cccc4nc(N5CCCC5)ccc34)N3CCC(F)(F)CC3)cn2)CC1]
Co. No. 222; Ex. B.18; •C₂HF₃O₂
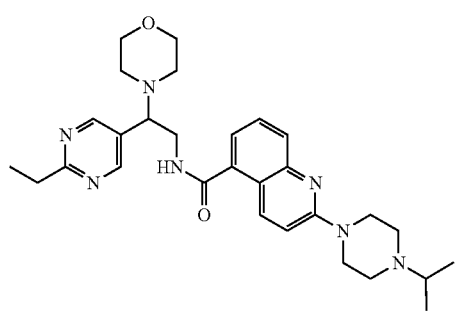 [SMILES: CCc1ncc(C(CNC(=O)c2cccc3nc(N4CCN(C(C)C)CC4)ccc23)N2CCOCC2)cn1]
Co. No. 295; Ex. B.7
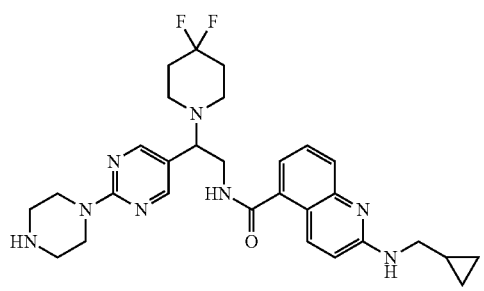 [SMILES: O=C(NCC(c1cnc(N2CCNCC2)nc1)N1CCC(F)(F)CC1)c1cccc2nc(NCC3CC3)ccc12]
Co. No. 223; Ex. B.14
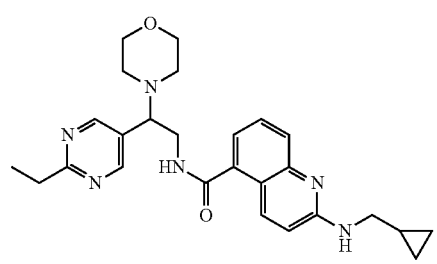 [SMILES: CCc1ncc(C(CNC(=O)c2cccc3nc(NCC4CC4)ccc23)N2CCOCC2)cn1]
Co. No. 296; Ex. B.9; •C₂HF₃O₂

TABLE F-2-continued
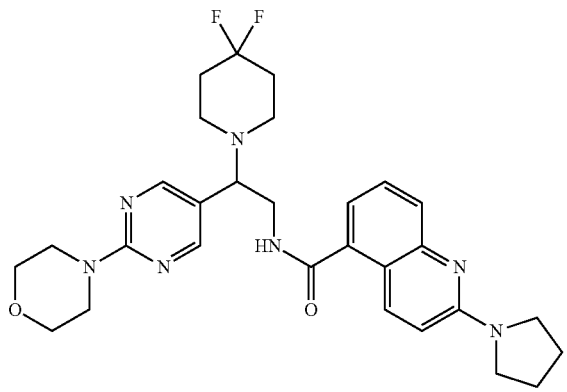 [SMILES: O=C(NCC(c1cnc(N2CCOCC2)nc1)N1CCC(F)(F)CC1)c1cccc2nc(N3CCCC3)ccc12]
Co. No. 224; Ex. B.18; •C₂HF₃O₂
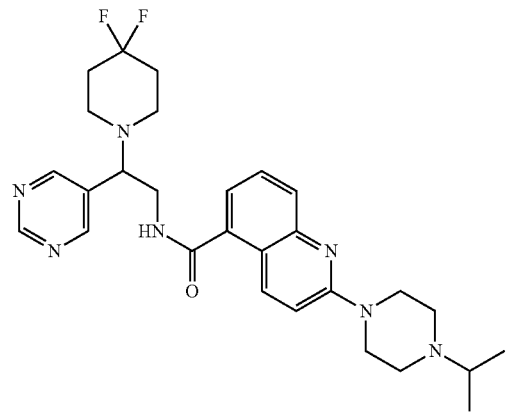 [SMILES: CC(C)N1CCN(c2ccc3c(C(=O)NCC(c4cncnc4)N4CCC(F)(F)CC4)cccc3n2)CC1]
Co. No. 297; Ex. B.7
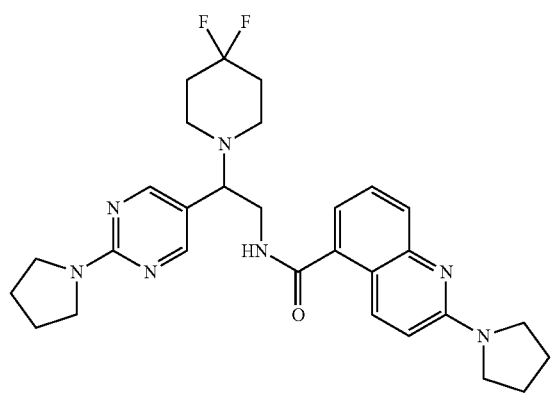 [SMILES: O=C(NCC(c1cnc(N2CCCC2)nc1)N1CCC(F)(F)CC1)c1cccc2nc(N3CCCC3)ccc12]
Co. No. 225; Ex. B.18; •C₂HF₃O₂
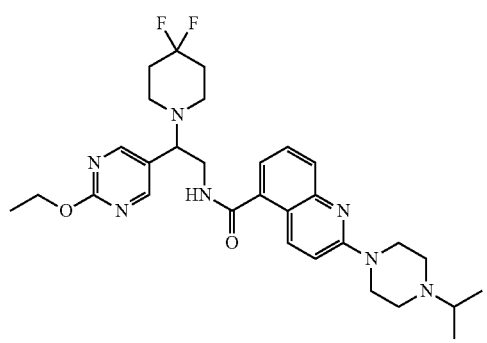 [SMILES: CCOc1ncc(C(CNC(=O)c2cccc3nc(N4CCN(C(C)C)CC4)ccc23)N2CCC(F)(F)CC2)cn1]
Co. No. 298; Ex. B.7
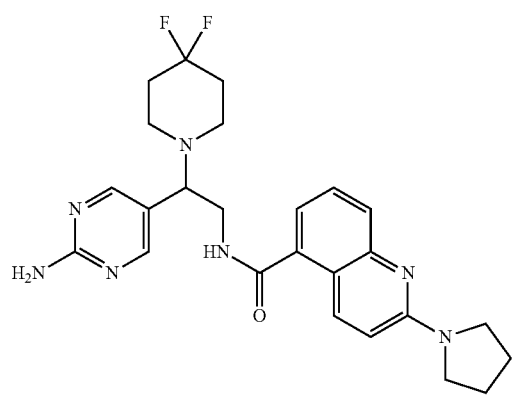 [SMILES: Nc1ncc(C(CNC(=O)c2cccc3nc(N4CCCC4)ccc23)N2CCC(F)(F)CC2)cn1]
Co. No. 226; Ex. B.18; •C₂HF₃O₂
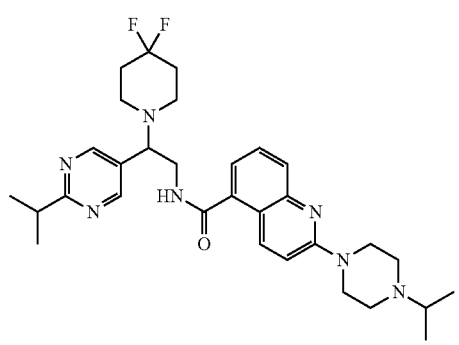
Co. No. 299; Ex. B.7

TABLE F-2-continued
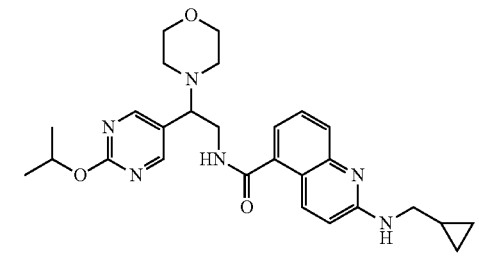 [SMILES: CC(C)Oc1ncc(C(CNC(=O)c2cccc3nc(NCC4CC4)ccc23)N2CCOCC2)cn1]
Co. No. 227; Ex. B.7
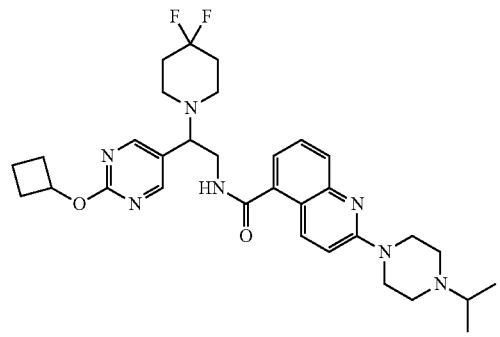 [SMILES: CC(C)N1CCN(c2ccc3c(C(=O)NCC(c4cnc(OC5CCC5)nc4)N4CCC(F)(F)CC4)cccc3n2)CC1]
Co. No. 300; Ex. B.7
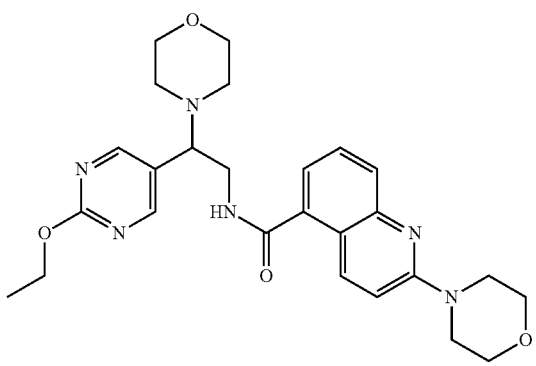 [SMILES: CCOc1ncc(C(CNC(=O)c2cccc3nc(N4CCOCC4)ccc23)N2CCOCC2)cn1]
Co. No. 228; Ex. B.7
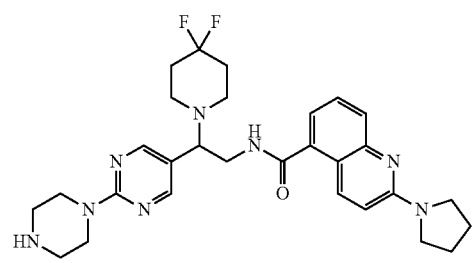 [SMILES: O=C(NCC(c1cnc(N2CCNCC2)nc1)N1CCC(F)(F)CC1)c1cccc2nc(N3CCCC3)ccc12]
Co. No. 301; Ex. B.14; •C$_2$HF$_3$O$_2$
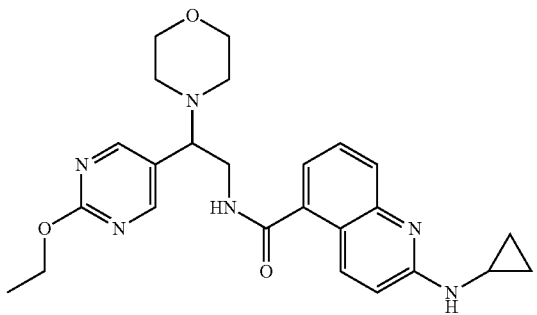 [SMILES: CCOc1ncc(C(CNC(=O)c2cccc3nc(NC4CC4)ccc23)N2CCOCC2)cn1]
Co. No. 229; Ex. B.7
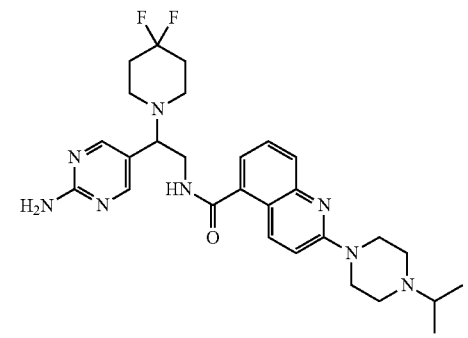 [SMILES: CC(C)N1CCN(c2ccc3c(C(=O)NCC(c4cnc(N)nc4)N4CCC(F)(F)CC4)cccc3n2)CC1]
Co. No. 302; Ex. B.7; •C$_2$HF$_3$O$_2$
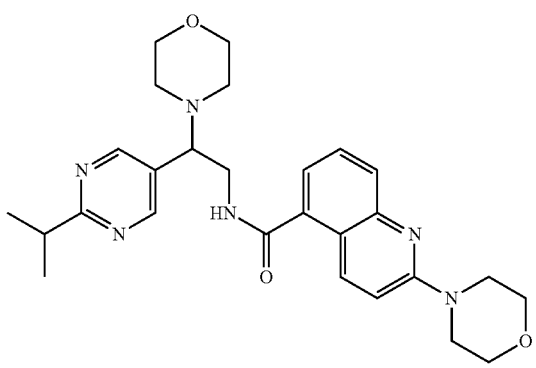
Co. No. 230; Ex. B.7
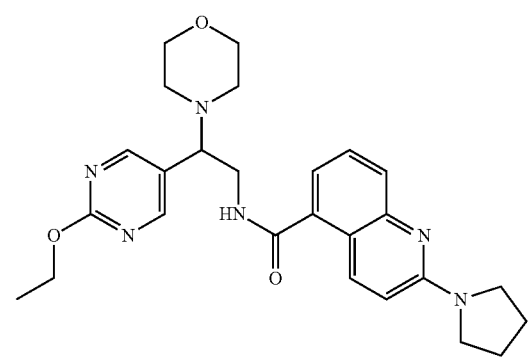 [SMILES: CCOc1ncc(C(CNC(=O)c2cccc3nc(N4CCCC4)ccc23)N2CCOCC2)cn1]
Co. No. 303; Ex. B.18

TABLE F-2-continued
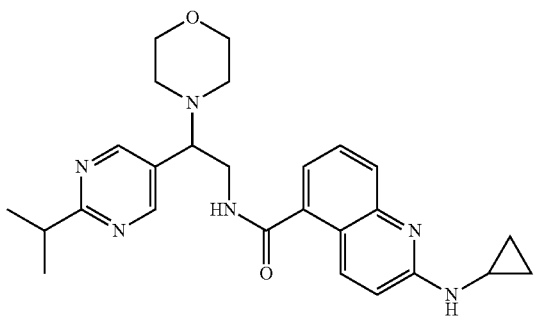
Co. No. 231; Ex. B.7
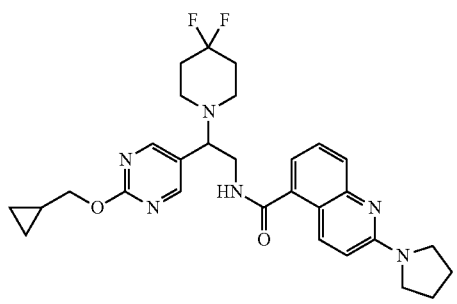 [SMILES: O=C(NCC(c1cnc(OCC2CC2)nc1)N1CCC(F)(F)CC1)c1cccc2nc(N3CCCC3)ccc12]
Co. No. 304; Ex. B.18
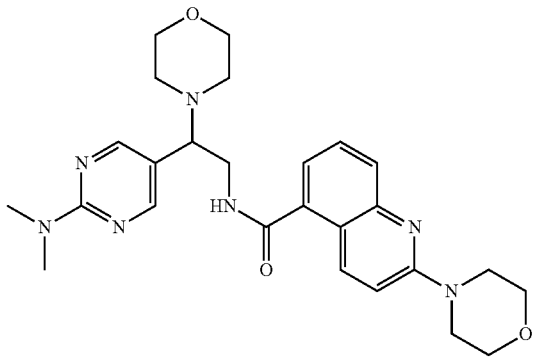
Co. No. 232; Ex. B.7
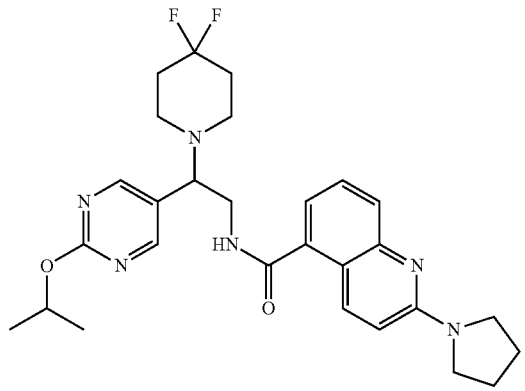 [SMILES: CC(C)Oc1ncc(C(CNC(=O)c2cccc3nc(N4CCCC4)ccc23)N2CCC(F)(F)CC2)cn1]
Co. No. 305; Ex. B.18
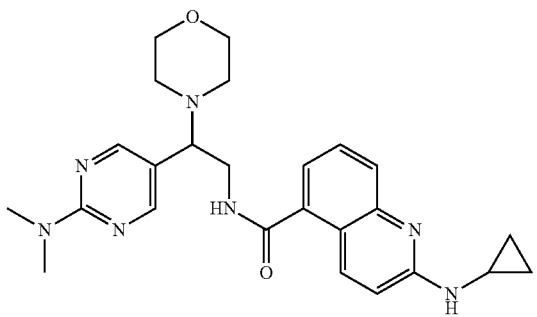 [SMILES: CN(C)c1ncc(C(CNC(=O)c2cccc3nc(NC4CC4)ccc23)N2CCOCC2)cn1]
Co. No. 233; Ex. B.7
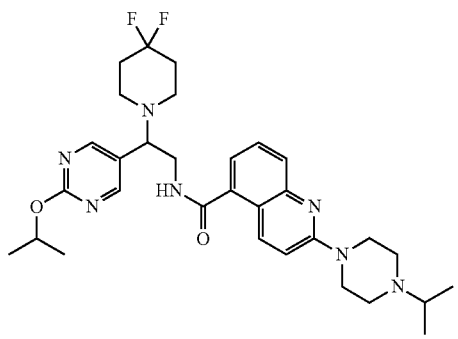 [SMILES: CC(C)Oc1ncc(C(CNC(=O)c2cccc3nc(N4CCN(C(C)C)CC4)ccc23)N2CCC(F)(F)CC2)cn1]
Co. No. 306; Ex. B.7
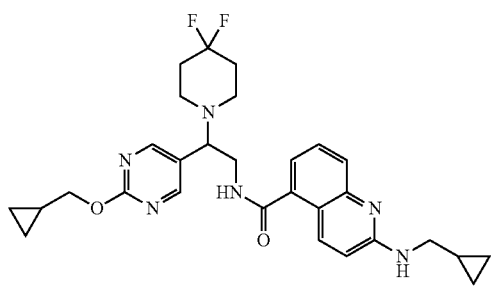 [SMILES: O=C(NCC(c1cnc(OCC2CC2)nc1)N1CCC(F)(F)CC1)c1cccc2nc(NCC3CC3)ccc12]
Co. No. 234; Ex. B.7
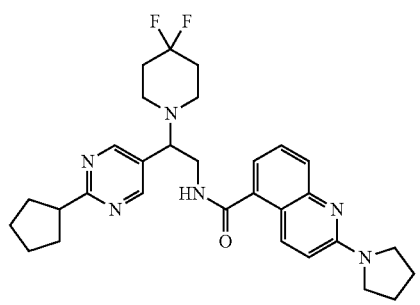 [SMILES: O=C(NCC(c1cnc(C2CCCC2)nc1)N1CCC(F)(F)CC1)c1cccc2nc(N3CCCC3)ccc12]
Co. No. 307; Ex. B.18

TABLE F-2-continued
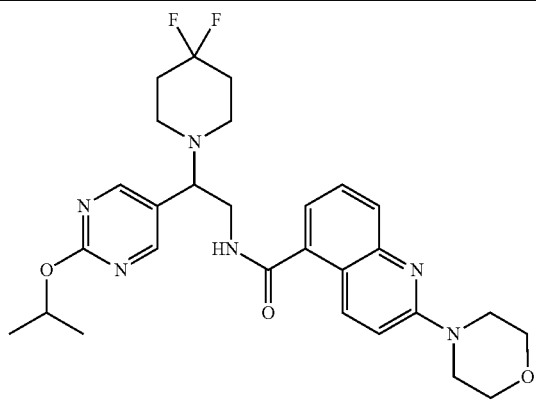
Co. No. 235; Ex. B.7
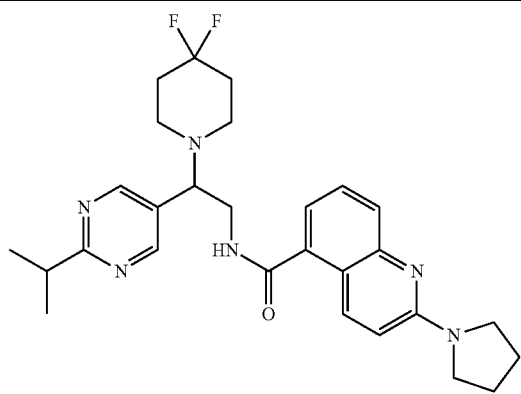
Co. No. 308; Ex. B.18
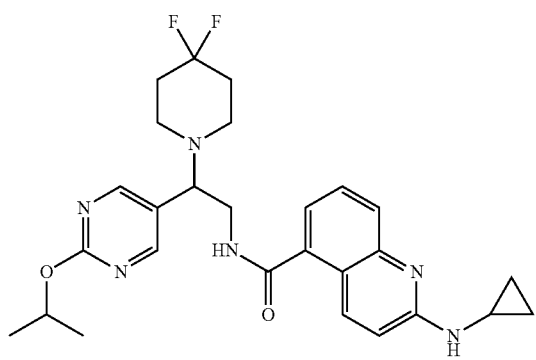 [SMILES: CC(C)Oc1ncc(C(CNC(=O)c2cccc3nc(NC4CC4)ccc23)N2CCC(F)(F)CC2)cn1]
Co. No. 236; Ex. B.7
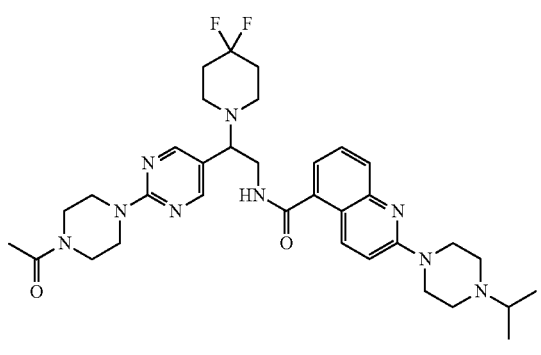 [SMILES: CC(=O)N1CCN(c2ncc(C(CNC(=O)c3cccc4nc(N5CCN(C(C)C)CC5)ccc34)N3CCC(F)(F)CC3)cn2)CC1]
Co. No. 309; Ex. B.7
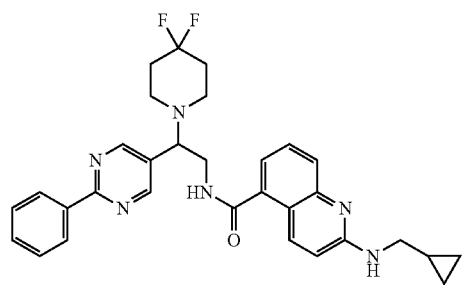 [SMILES: O=C(NCC(c1cnc(-c2ccccc2)nc1)N1CCC(F)(F)CC1)c1cccc2nc(NCC3CC3)ccc12]
Co. No. 237; Ex. B.7
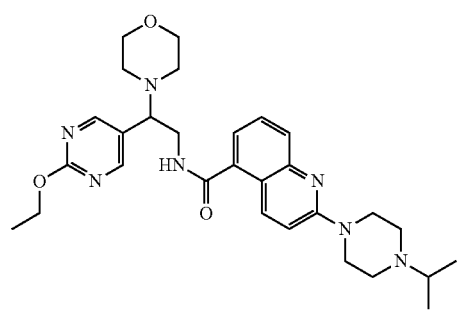 [SMILES: CCOc1ncc(C(CNC(=O)c2cccc3nc(N4CCN(C(C)C)CC4)ccc23)N2CCOCC2)cn1]
Co. No. 310; Ex. B.7
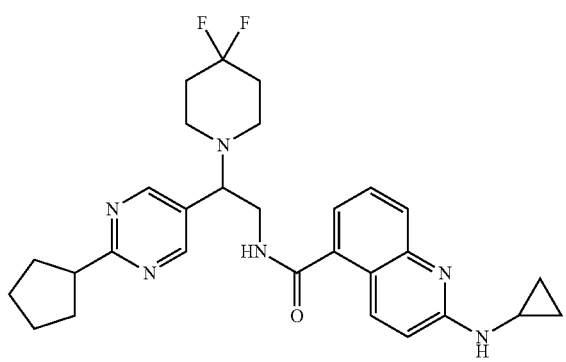 [SMILES: O=C(NCC(c1cnc(C2CCCC2)nc1)N1CCC(F)(F)CC1)c1cccc2nc(NC3CC3)ccc12]
Co. No. 238; Ex. B.7
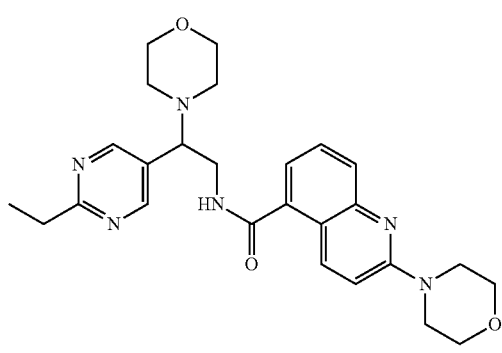 [SMILES: CCc1ncc(C(CNC(=O)c2cccc3nc(N4CCOCC4)ccc23)N2CCOCC2)cn1]
Co. No. 311; Ex. B.7

TABLE F-2-continued
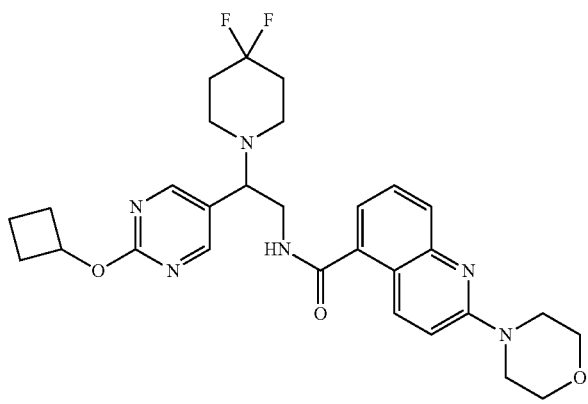 [SMILES: O=C(NCC(c1cnc(OC2CCC2)nc1)N1CCC(F)(F)CC1)c1cccc2nc(N3CCOCC3)ccc12]
Co. No. 239; Ex. B.7
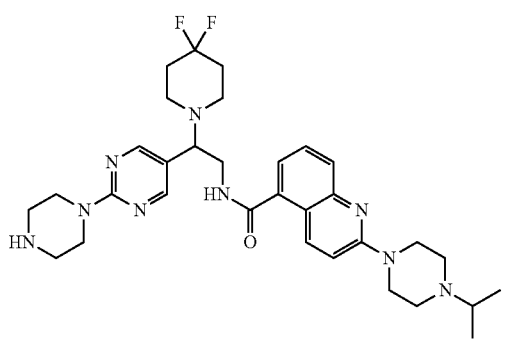 [SMILES: CC(C)N1CCN(c2ccc3c(C(=O)NCC(c4cnc(N5CCNCC5)nc4)N4CCC(F)(F)CC4)cccc3n2)CC1]
Co. No. 312; Ex. B.14
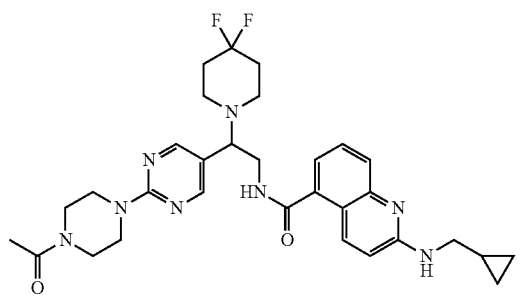 [SMILES: CC(=O)N1CCN(c2ncc(C(CNC(=O)c3cccc4nc(NCC5CC5)ccc34)N3CCC(F)(F)CC3)cn2)CC1]
Co. No. 240; Ex. B.7
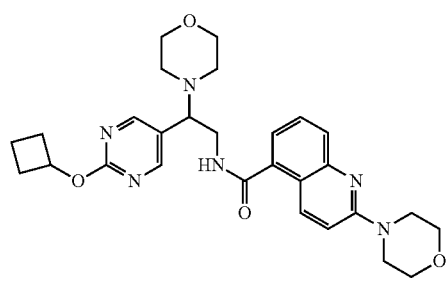 [SMILES: O=C(NCC(c1cnc(OC2CCC2)nc1)N1CCOCC1)c1cccc2nc(N3CCOCC3)ccc12]
Co. No. 313; Ex. B.7
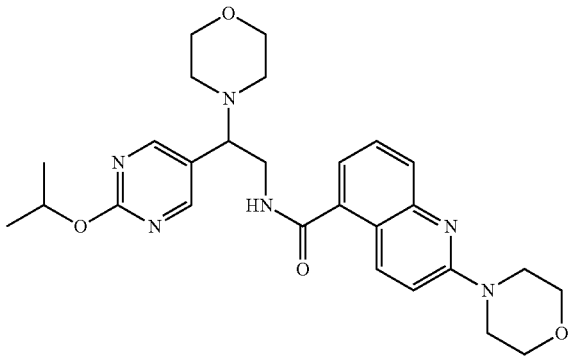 [SMILES: CC(C)Oc1ncc(C(CNC(=O)c2cccc3nc(N4CCOCC4)ccc23)N2CCOCC2)cn1]
Co. No. 241; Ex. B.7
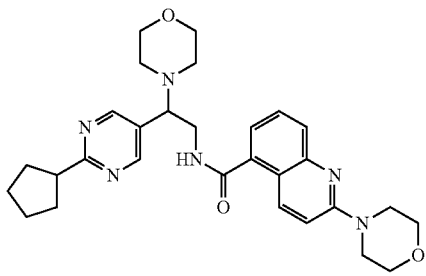 [SMILES: O=C(NCC(c1cnc(C2CCCC2)nc1)N1CCOCC1)c1cccc2nc(N3CCOCC3)ccc12]
Co. No. 314; Ex. B.7
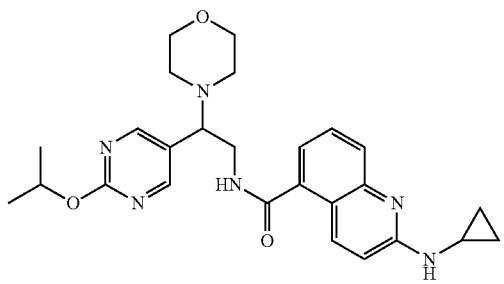 [SMILES: CC(C)Oc1ncc(C(CNC(=O)c2cccc3nc(NC4CC4)ccc23)N2CCOCC2)cn1]
Co. No. 242; Ex. B.7
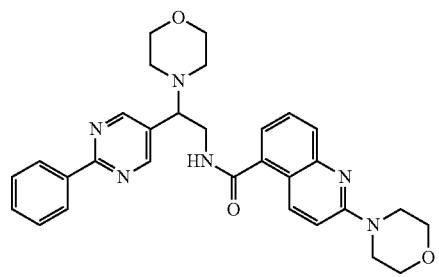 [SMILES: O=C(NCC(c1cnc(-c2ccccc2)nc1)N1CCOCC1)c1cccc2nc(N3CCOCC3)ccc12]
Co. No. 315; Ex. B.7

TABLE F-2-continued
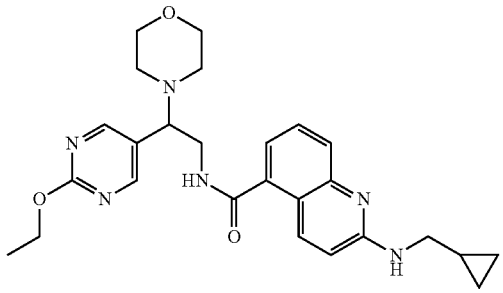 [SMILES: CCOc1ncc(C(CNC(=O)c2cccc3nc(NCC4CC4)ccc23)N2CCOCC2)cn1]
Co. No. 243; Ex. B.7
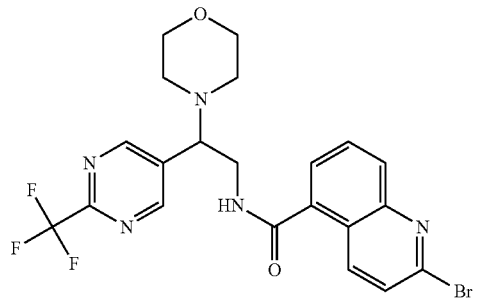 [SMILES: O=C(NCC(c1cnc(C(F)(F)F)nc1)N1CCOCC1)c1cccc2nc(Br)ccc12]
Co. No. 316; Ex. B.24
*C₂HF₃O₂: stands for the trifluoroacetate salt
TABLE F-3
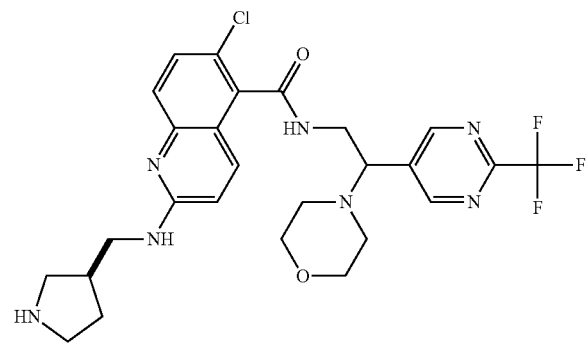
Co. No. 404; Ex. B.31; CF₃CO₂H
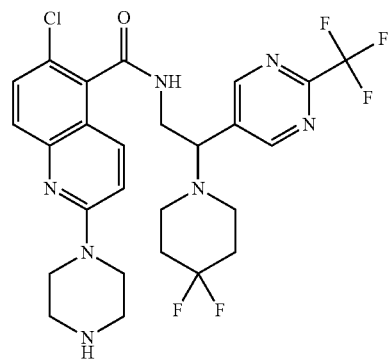 [SMILES: O=C(NCC(c1cnc(C(F)(F)F)nc1)N1CCC(F)(F)CC1)c1c(Cl)ccc2nc(N3CCNCC3)ccc12]
Co. No. 485; B.31; CF₃CO₂H
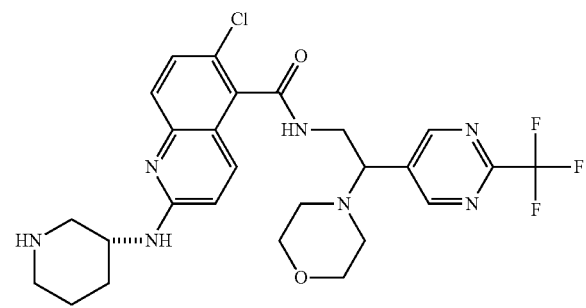 [SMILES: O=C(NCC(c1cnc(C(F)(F)F)nc1)N1CCOCC1)c1c(Cl)ccc2nc(N[C@@H]3CCCNC3)ccc12]
Co. No. 405; Ex. B.31; CF₃CO₂H
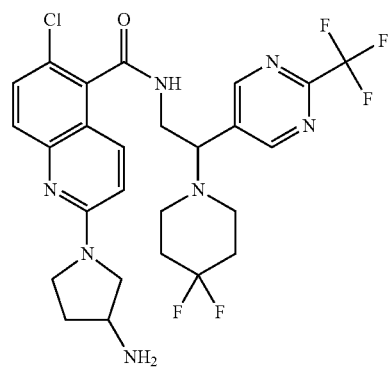 [SMILES: NC1CCN(c2ccc3c(C(=O)NCC(c4cnc(C(F)(F)F)nc4)N4CCC(F)(F)CC4)c(Cl)ccc3n2)C1]
Co. No. 486; B.31; CF₃CO₂H TABLE F-3-continued
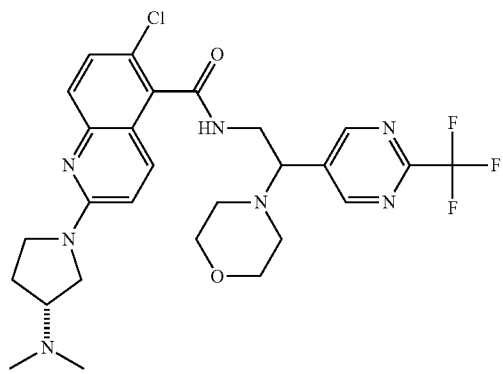 [SMILES: CN(C)[C@@H]1CCN(c2ccc3c(C(=O)NCC(c4cnc(C(F)(F)F)nc4)N4CCOCC4)c(Cl)ccc3n2)C1]
Co. No. 406; Ex. B.31; CF₃CO₂H
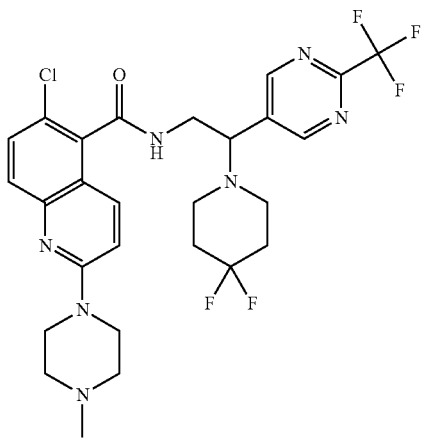 [SMILES: CN1CCN(c2ccc3c(C(=O)NCC(c4cnc(C(F)(F)F)nc4)N4CCC(F)(F)CC4)c(Cl)ccc3n2)CC1]
Co. No. 487; B.31; CF₃CO₂H
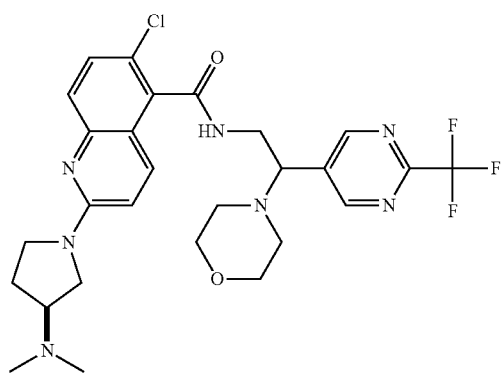 [SMILES: CN(C)[C@H]1CCN(c2ccc3c(C(=O)NCC(c4cnc(C(F)(F)F)nc4)N4CCOCC4)c(Cl)ccc3n2)C1]
Co. No. 407; Ex. B.31; CF₃CO₂H
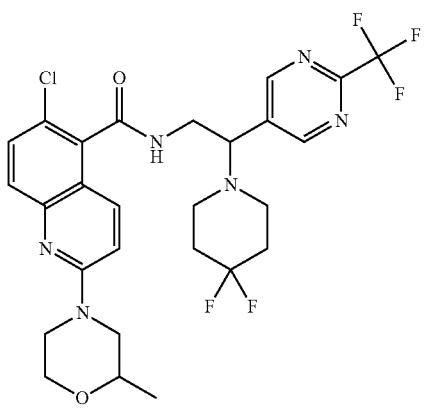 [SMILES: CC1CN(c2ccc3c(C(=O)NCC(c4cnc(C(F)(F)F)nc4)N4CCC(F)(F)CC4)c(Cl)ccc3n2)CCO1]
Co. No. 488; B.31; CF₃CO₂H
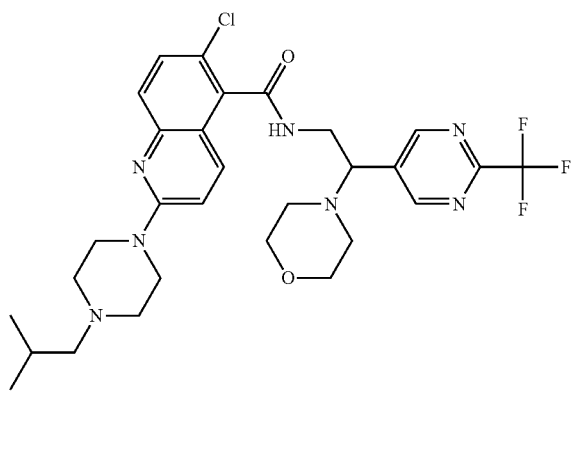 [SMILES: CC(C)CN1CCN(c2ccc3c(C(=O)NCC(c4cnc(C(F)(F)F)nc4)N4CCOCC4)c(Cl)ccc3n2)CC1]
Co. No. 408; Ex. B.31; CF₃CO₂H
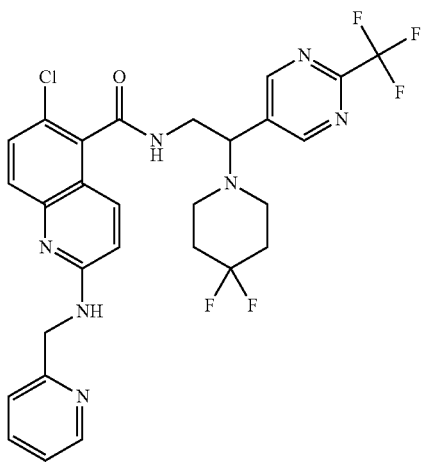 [SMILES: O=C(NCC(c1cnc(C(F)(F)F)nc1)N1CCC(F)(F)CC1)c1c(Cl)ccc2nc(NCc3ccccn3)ccc12]
Co. No. 489; B.31; CF₃CO₂H TABLE F-3-continued
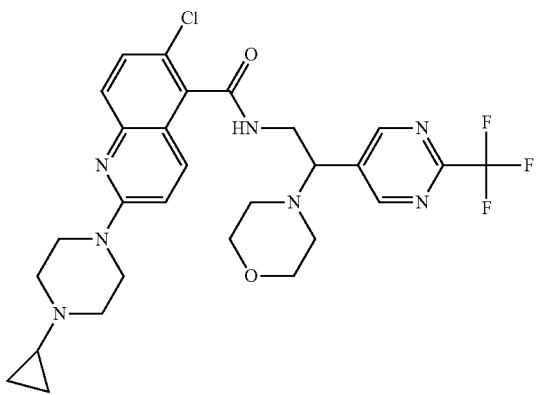 [SMILES: O=C(NCC(c1cnc(C(F)(F)F)nc1)N1CCOCC1)c1c(Cl)ccc2nc(N3CCN(C4CC4)CC3)ccc12]
Co. No. 409; Ex. B.31; CF₃CO₂H
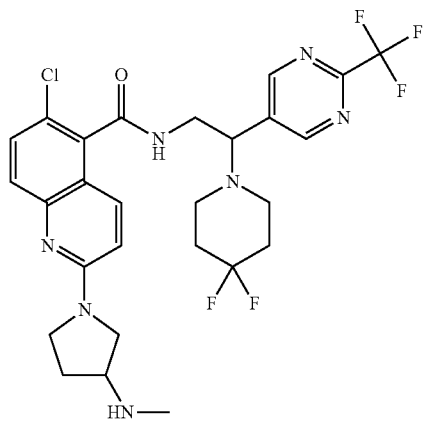 [SMILES: CNC1CCN(c2ccc3c(C(=O)NCC(c4cnc(C(F)(F)F)nc4)N4CCC(F)(F)CC4)c(Cl)ccc3n2)C1]
Co. No. 490; B.31; CF₃CO₂H
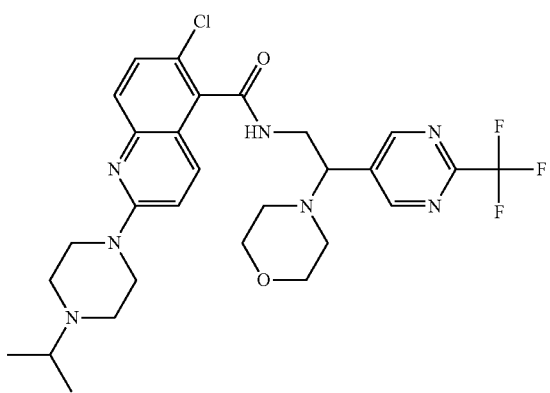 [SMILES: CC(C)N1CCN(c2ccc3c(C(=O)NCC(c4cnc(C(F)(F)F)nc4)N4CCOCC4)c(Cl)ccc3n2)CC1]
Co. No. 410; Ex. B.31; CF₃CO₂H
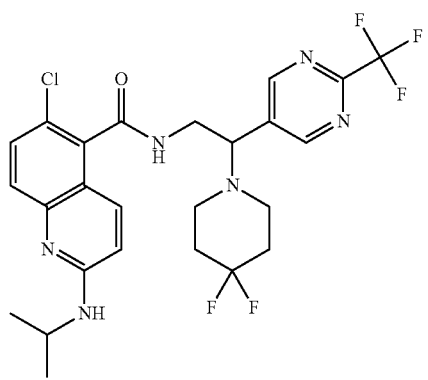 [SMILES: CC(C)Nc1ccc2c(C(=O)NCC(c3cnc(C(F)(F)F)nc3)N3CCC(F)(F)CC3)c(Cl)ccc2n1]
Co. No. 491; B.31; CF₃CO₂H
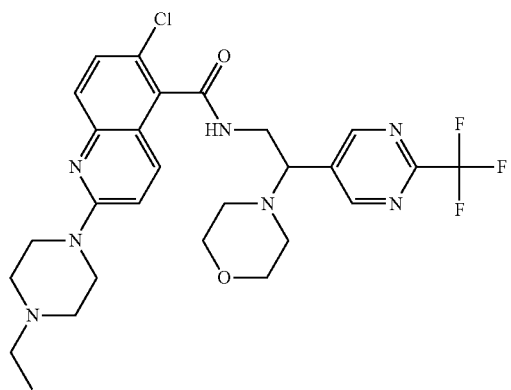 [SMILES: CCN1CCN(c2ccc3c(C(=O)NCC(c4cnc(C(F)(F)F)nc4)N4CCOCC4)c(Cl)ccc3n2)CC1]
Co. No. 411; Ex. B.31; CF₃CO₂H
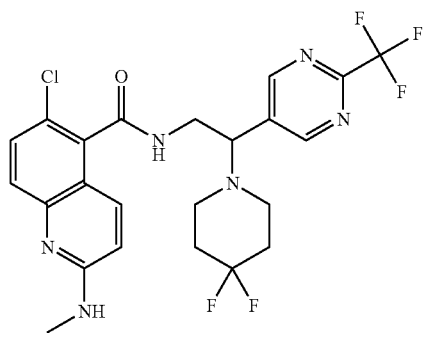 [SMILES: CNc1ccc2c(C(=O)NCC(c3cnc(C(F)(F)F)nc3)N3CCC(F)(F)CC3)c(Cl)ccc2n1]
Co. No. 492; B.31; CF₃CO₂H TABLE F-3-continued
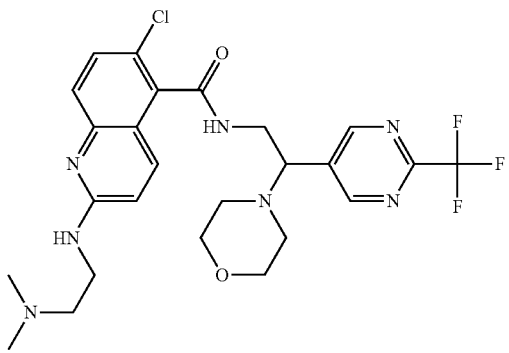 [SMILES: CN(C)CCNc1ccc2c(C(=O)NCC(c3cnc(C(F)(F)F)nc3)N3CCOCC3)c(Cl)ccc2n1]
Co. No. 412; Ex. B.31; CF3CO2H
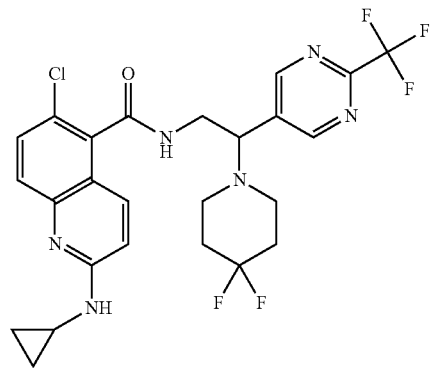 [SMILES: O=C(NCC(c1cnc(C(F)(F)F)nc1)N1CCC(F)(F)CC1)c1c(Cl)ccc2nc(NC3CC3)ccc12]
Co. No. 493; B.31
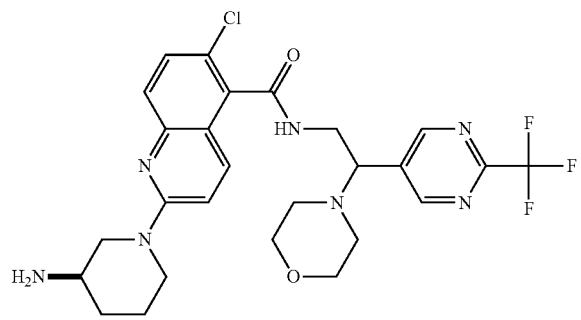 [SMILES: N[C@@H]1CCCN(c2ccc3c(C(=O)NCC(c4cnc(C(F)(F)F)nc4)N4CCOCC4)c(Cl)ccc3n2)C1]
Co. No. 413; Ex. B.31; CF3CO2H
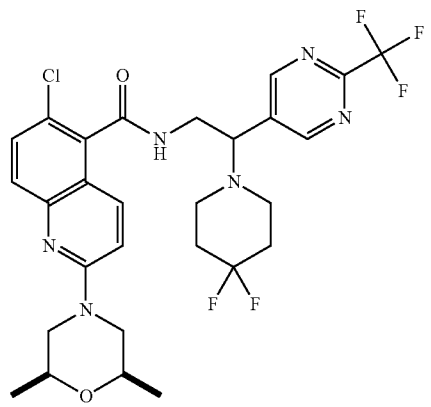 [SMILES: C[C@@H]1CN(c2ccc3c(C(=O)NCC(c4cnc(C(F)(F)F)nc4)N4CCC(F)(F)CC4)c(Cl)ccc3n2)C[C@H](C)O1]
Co. No. 494; B.31; CF3CO2H
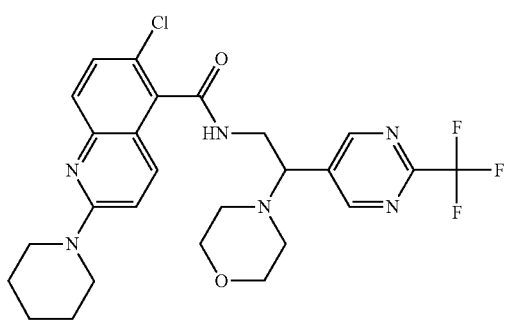 [SMILES: O=C(NCC(c1cnc(C(F)(F)F)nc1)N1CCOCC1)c1c(Cl)ccc2nc(N3CCCCC3)ccc12]
Co. No. 414; Ex. B.31; CF3CO2H
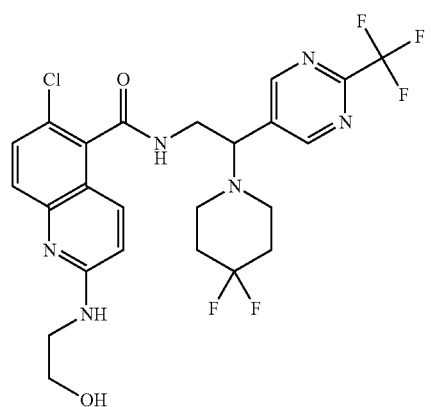 [SMILES: O=C(NCC(c1cnc(C(F)(F)F)nc1)N1CCC(F)(F)CC1)c1c(Cl)ccc2nc(NCCO)ccc12]
Co. No. 495; B.31

TABLE F-3-continued
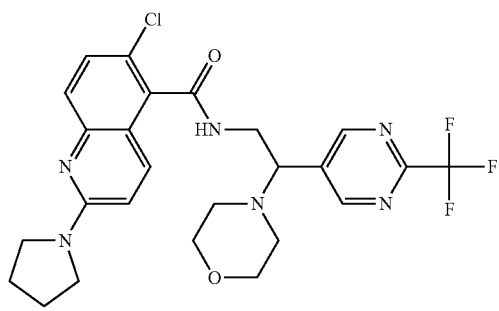 [SMILES: O=C(NCC(c1cnc(C(F)(F)F)nc1)N1CCOCC1)c1c(Cl)ccc2nc(N3CCCC3)ccc12]
Co. No. 415; Ex. B.31; CF₃CO₂H
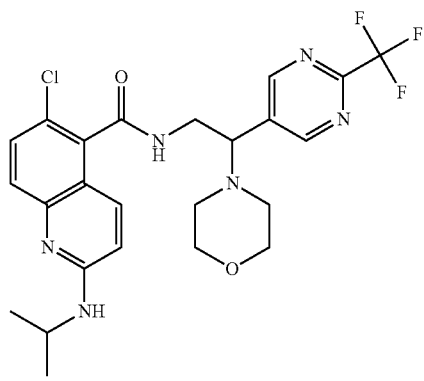 [SMILES: CC(C)Nc1ccc2c(C(=O)NCC(c3cnc(C(F)(F)F)nc3)N3CCOCC3)c(Cl)ccc2n1]
Co. No. 496; B.31; CF₃CO₂H
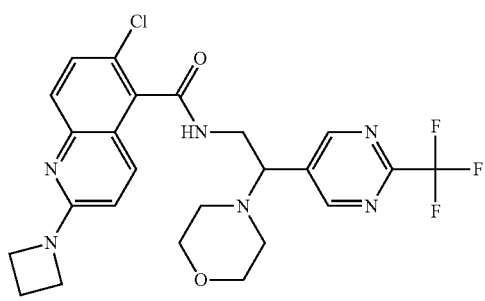 [SMILES: O=C(NCC(c1cnc(C(F)(F)F)nc1)N1CCOCC1)c1c(Cl)ccc2nc(N3CCC3)ccc12]
Co. No. 416; Ex. B.31; CF₃CO₂H
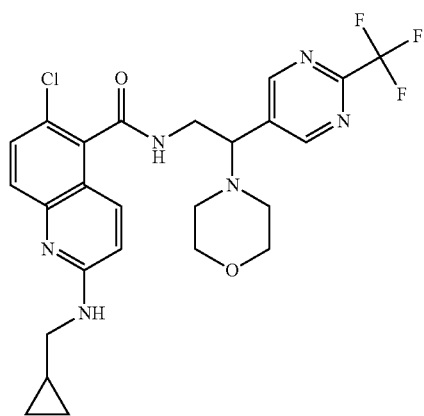 [SMILES: O=C(NCC(c1cnc(C(F)(F)F)nc1)N1CCOCC1)c1c(Cl)ccc2nc(NCC3CC3)ccc12]
Co. No. 497; B.31; CF₃CO₂H
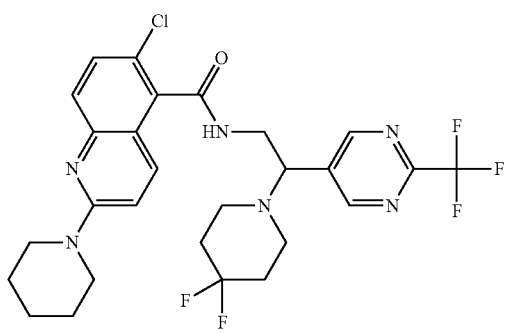 [SMILES: O=C(NCC(c1cnc(C(F)(F)F)nc1)N1CCC(F)(F)CC1)c1c(Cl)ccc2nc(N3CCCCC3)ccc12]
Co. No. 417; Ex. B.31; CF₃CO₂H
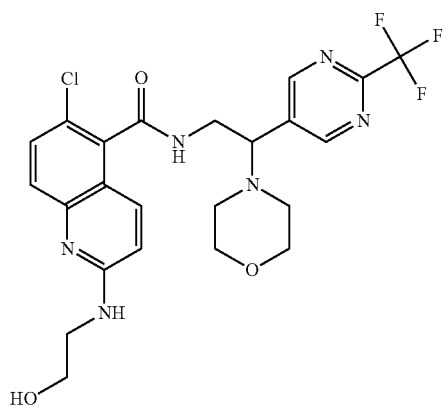 [SMILES: O=C(NCC(c1cnc(C(F)(F)F)nc1)N1CCOCC1)c1c(Cl)ccc2nc(NCCO)ccc12]
Co. No. 498; B.31

TABLE F-3-continued
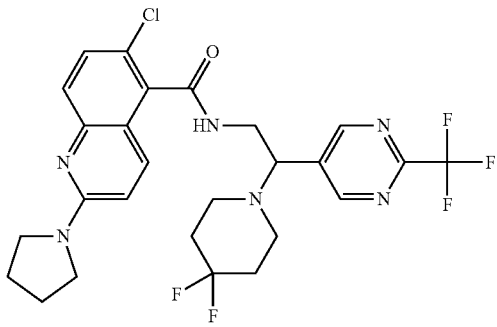 [SMILES: O=C(NCC(c1cnc(C(F)(F)F)nc1)N1CCC(F)(F)CC1)c1c(Cl)ccc2nc(N3CCCC3)ccc12]
Co. No. 418; Ex. B.31; CF$_3$CO$_2$H
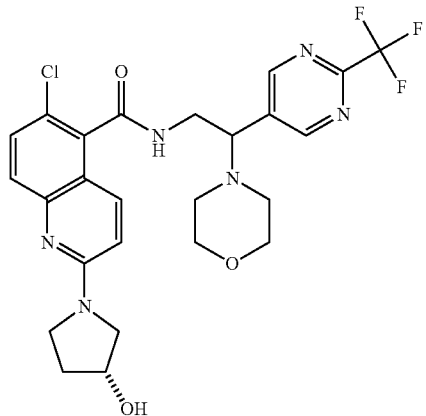 [SMILES: O=C(NCC(c1cnc(C(F)(F)F)nc1)N1CCOCC1)c1c(Cl)ccc2nc(N3CC[C@@H](O)C3)ccc12]
Co. No. 499; B.31
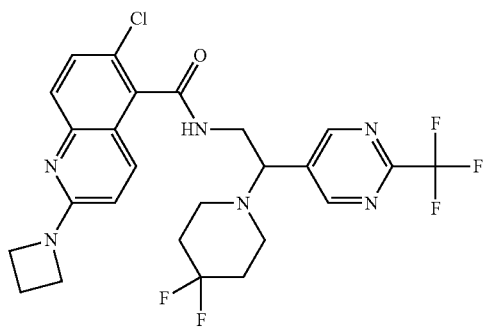 [SMILES: O=C(NCC(c1cnc(C(F)(F)F)nc1)N1CCC(F)(F)CC1)c1c(Cl)ccc2nc(N3CCC3)ccc12]
Co. No. 419; Ex. B.31; CF$_3$CO$_2$H
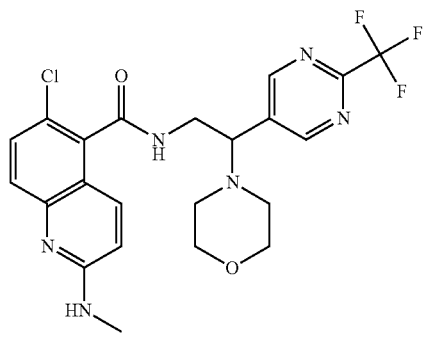 [SMILES: CNc1ccc2c(C(=O)NCC(c3cnc(C(F)(F)F)nc3)N3CCOCC3)c(Cl)ccc2n1]
Co. No. 500; B.31; CF$_3$CO$_2$H
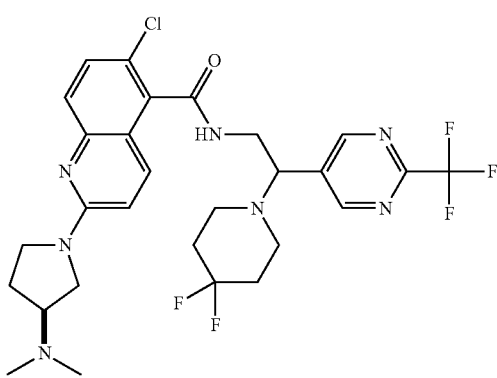 [SMILES: CN(C)[C@H]1CCN(c2ccc3c(C(=O)NCC(c4cnc(C(F)(F)F)nc4)N4CCC(F)(F)CC4)c(Cl)ccc3n2)C1]
Co. No. 420; Ex. B.31; CF$_3$CO$_2$H
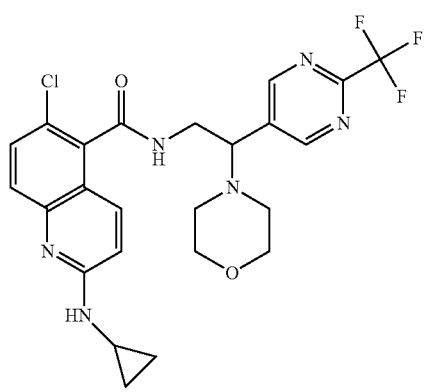 [SMILES: O=C(NCC(c1cnc(C(F)(F)F)nc1)N1CCOCC1)c1c(Cl)ccc2nc(NC3CC3)ccc12]
Co. No. 501; B.31; CF$_3$CO$_2$H TABLE F-3-continued
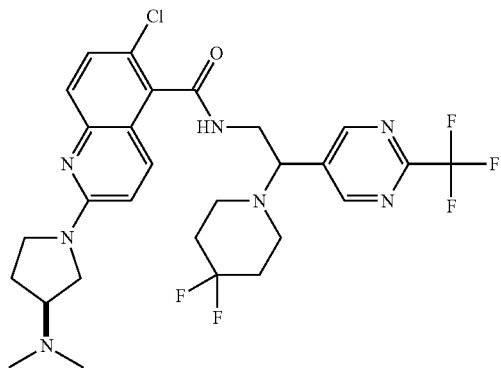 [SMILES: CN(C)[C@H]1CCN(c2ccc3c(C(=O)NCC(c4cnc(C(F)(F)F)nc4)N4CCC(F)(F)CC4)c(Cl)ccc3n2)C1]
Co. No. 421; Ex. B.31; CF$_3$CO$_2$H
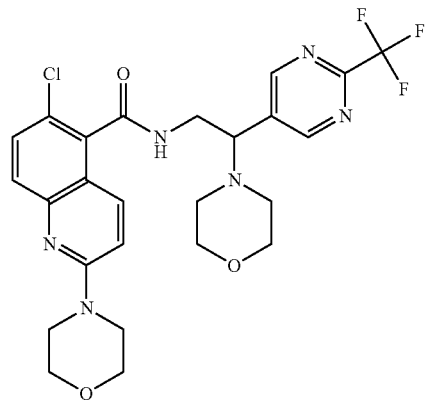 [SMILES: O=C(NCC(c1cnc(C(F)(F)F)nc1)N1CCOCC1)c1c(Cl)ccc2nc(N3CCOCC3)ccc12]
Co. No. 502; B.31
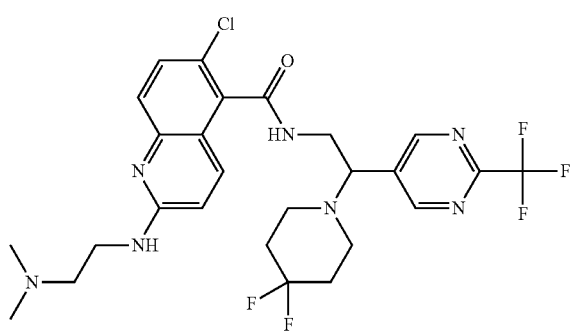 [SMILES: CN(C)CCNc1ccc2c(C(=O)NCC(c3cnc(C(F)(F)F)nc3)N3CCC(F)(F)CC3)c(Cl)ccc2n1]
Co. No. 422; Ex. B.31; CF$_3$CO$_2$H
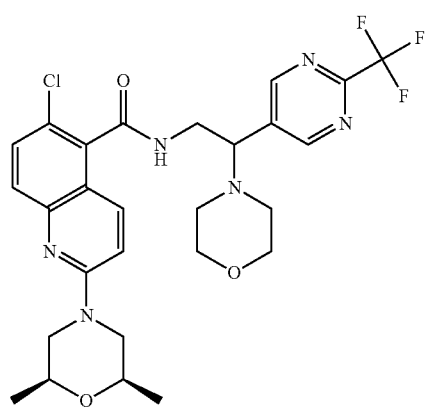 [SMILES: C[C@@H]1CN(c2ccc3c(C(=O)NCC(c4cnc(C(F)(F)F)nc4)N4CCOCC4)c(Cl)ccc3n2)C[C@H](C)O1]
Co. No. 503; B.31; CF$_3$CO$_2$H
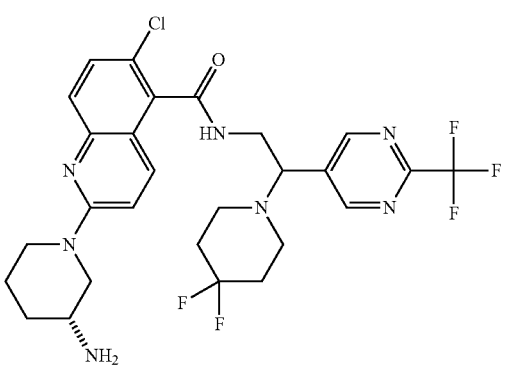 [SMILES: N[C@@H]1CCCN(c2ccc3c(C(=O)NCC(c4cnc(C(F)(F)F)nc4)N4CCC(F)(F)CC4)c(Cl)ccc3n2)C1]
Co. No. 423; Ex. B.31; CF$_3$CO$_2$H
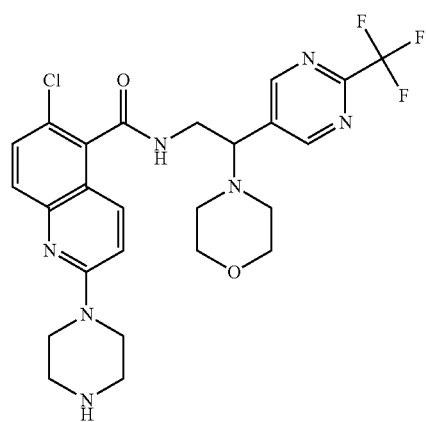 [SMILES: O=C(NCC(c1cnc(C(F)(F)F)nc1)N1CCOCC1)c1c(Cl)ccc2nc(N3CCNCC3)ccc12]
Co. No. 504; B.31; CF$_3$CO$_2$H TABLE F-3-continued
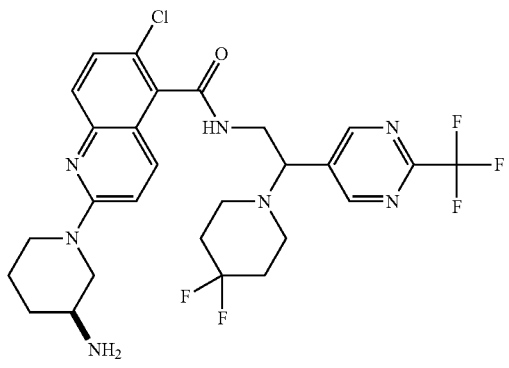 [SMILES: N[C@H]1CCCN(c2ccc3c(C(=O)NCC(c4cnc(C(F)(F)F)nc4)N4CCC(F)(F)CC4)c(Cl)ccc3n2)C1]
Co. No. 424; Ex. B.31; CF$_3$CO$_2$H
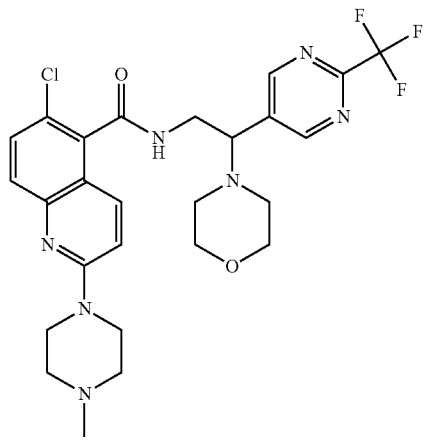 [SMILES: CN1CCN(c2ccc3c(C(=O)NCC(c4cnc(C(F)(F)F)nc4)N4CCOCC4)c(Cl)ccc3n2)CC1]
Co. No. 505; B.31; CF$_3$CO$_2$H
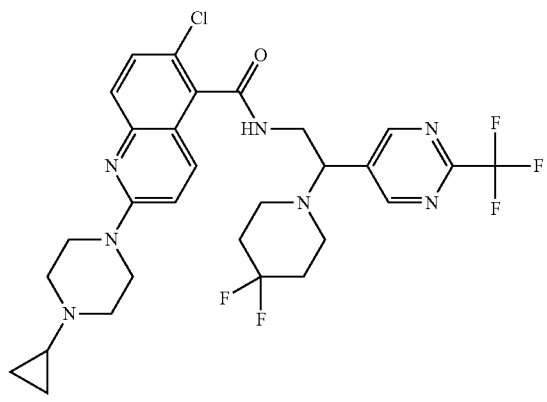 [SMILES: O=C(NCC(c1cnc(C(F)(F)F)nc1)N1CCC(F)(F)CC1)c1c(Cl)ccc2nc(N3CCN(C4CC4)CC3)ccc12]
Co. No. 425; Ex. B.31; CF$_3$CO$_2$H
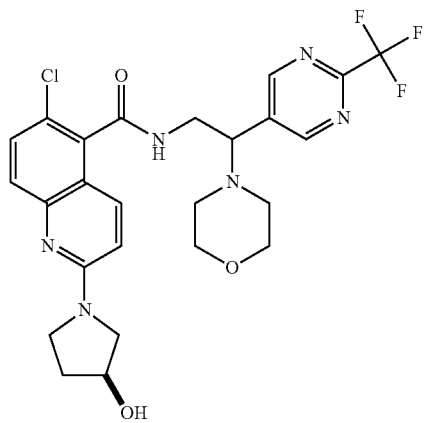 [SMILES: O=C(NCC(c1cnc(C(F)(F)F)nc1)N1CCOCC1)c1c(Cl)ccc2nc(N3CC[C@H](O)C3)ccc12]
Co. No. 506; B.31; CF$_3$CO$_2$H
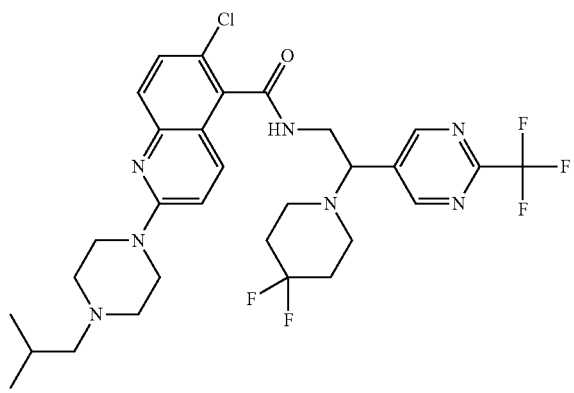 [SMILES: CC(C)CN1CCN(c2ccc3c(C(=O)NCC(c4cnc(C(F)(F)F)nc4)N4CCC(F)(F)CC4)c(Cl)ccc3n2)CC1]
Co. No. 426; Ex. B.31; CF$_3$CO$_2$H
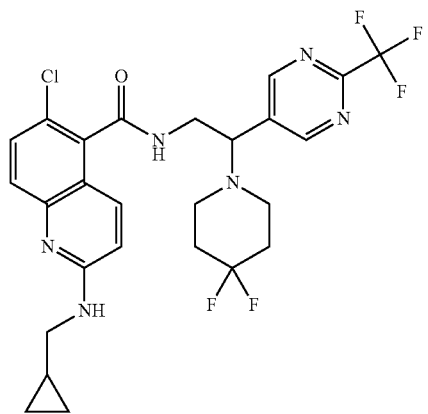 [SMILES: O=C(NCC(c1cnc(C(F)(F)F)nc1)N1CCC(F)(F)CC1)c1c(Cl)ccc2nc(NCC3CC3)ccc12]
Co. No. 507; B.31; CF$_3$CO$_2$H TABLE F-3-continued
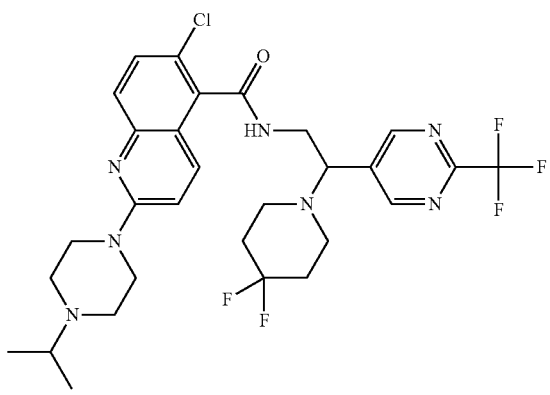 [SMILES: CC(C)N1CCN(c2ccc3c(C(=O)NCC(c4cnc(C(F)(F)F)nc4)N4CCC(F)(F)CC4)c(Cl)ccc3n2)CC1]
Co. No. 427; Ex. B.31; CF₃CO₂H
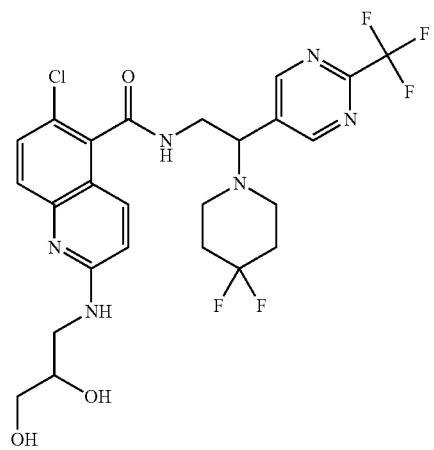 [SMILES: O=C(NCC(c1cnc(C(F)(F)F)nc1)N1CCC(F)(F)CC1)c1c(Cl)ccc2nc(NCC(O)CO)ccc12]
Co. No. 508; B.31; CF₃CO₂H
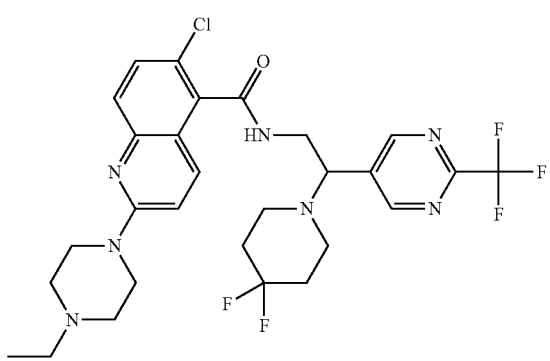 [SMILES: CCN1CCN(c2ccc3c(C(=O)NCC(c4cnc(C(F)(F)F)nc4)N4CCC(F)(F)CC4)c(Cl)ccc3n2)CC1]
Co. No. 428; Ex. B.31; CF₃CO₂H
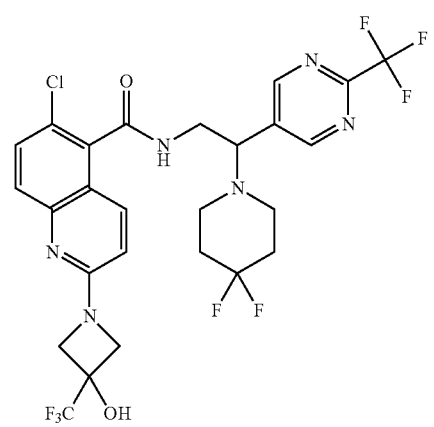 [SMILES: O=C(NCC(c1cnc(C(F)(F)F)nc1)N1CCC(F)(F)CC1)c1c(Cl)ccc2nc(N3CC(O)(C(F)(F)F)C3)ccc12]
Co. No. 509; Ex. B.31; CF₃CO₂H
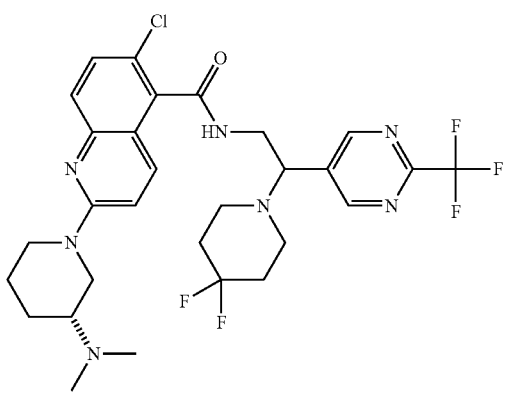 [SMILES: CN(C)[C@@H]1CCCN(c2ccc3c(C(=O)NCC(c4cnc(C(F)(F)F)nc4)N4CCC(F)(F)CC4)c(Cl)ccc3n2)C1]
Co. No. 429; Ex. B.31; CF₃CO₂H
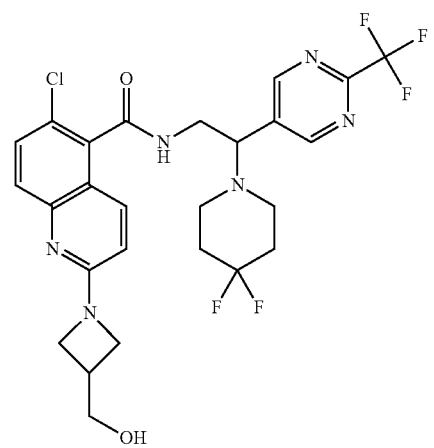 [SMILES: O=C(NCC(c1cnc(C(F)(F)F)nc1)N1CCC(F)(F)CC1)c1c(Cl)ccc2nc(N3CC(CO)C3)ccc12]
Co. No. 510; Ex. B.31; CF₃CO₂H TABLE F-3-continued
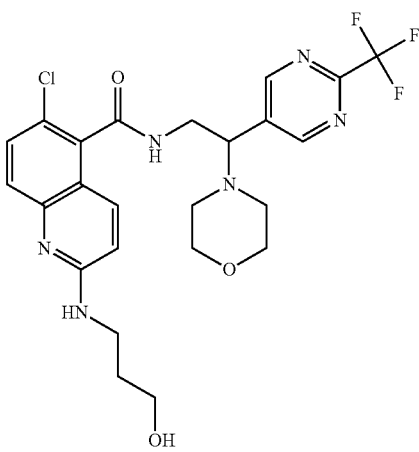 [SMILES: O=C(NCC(c1cnc(C(F)(F)F)nc1)N1CCOCC1)c1c(Cl)ccc2nc(NCCCO)ccc12]
Co. No. 430; Ex. B.31; CF₃CO₂H
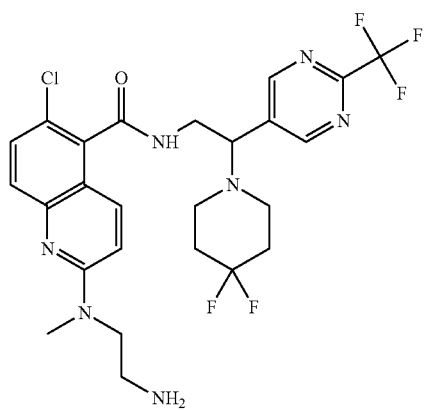 [SMILES: CN(CCN)c1ccc2c(C(=O)NCC(c3cnc(C(F)(F)F)nc3)N3CCC(F)(F)CC3)c(Cl)ccc2n1]
Co. No. 511; Ex. B.31; CF₃CO₂H
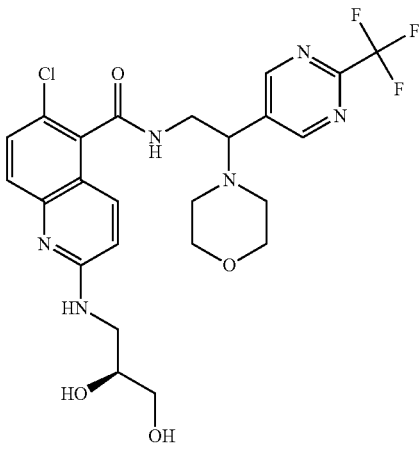 [SMILES: O=C(NCC(c1cnc(C(F)(F)F)nc1)N1CCOCC1)c1c(Cl)ccc2nc(NC[C@H](O)CO)ccc12]
Co. No. 431; Ex. B.31; CF₃CO₂H
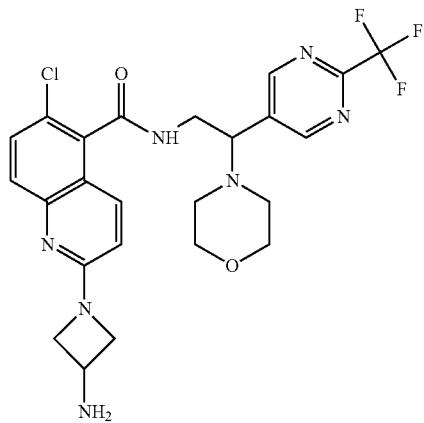 [SMILES: NC1CN(c2ccc3c(C(=O)NCC(c4cnc(C(F)(F)F)nc4)N4CCOCC4)c(Cl)ccc3n2)C1]
Co. No. 512; Ex. B.31
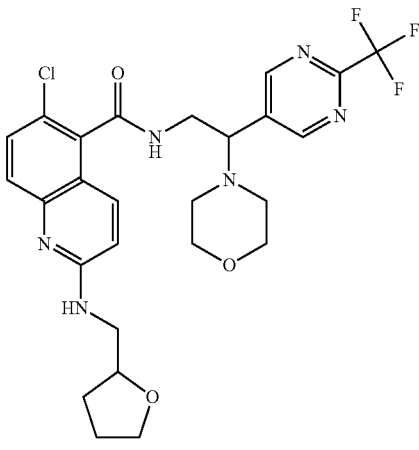 [SMILES: O=C(NCC(c1cnc(C(F)(F)F)nc1)N1CCOCC1)c1c(Cl)ccc2nc(NCC3CCCO3)ccc12]
Co. No. 432; Ex. B.31; CF₃CO₂H
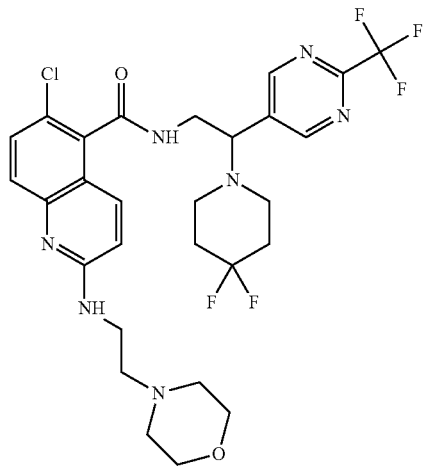 [SMILES: O=C(NCC(c1cnc(C(F)(F)F)nc1)N1CCC(F)(F)CC1)c1c(Cl)ccc2nc(NCCN3CCOCC3)ccc12]
Co. No. 513; Ex. B.31; CF₃CO₂H TABLE F-3-continued
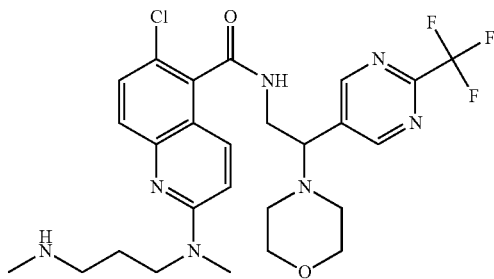 [SMILES: CNCCCN(C)c1ccc2c(C(=O)NCC(c3cnc(C(F)(F)F)nc3)N3CCOCC3)c(Cl)ccc2n1]
Co. No. 433; Ex. B.31; CF₃CO₂H
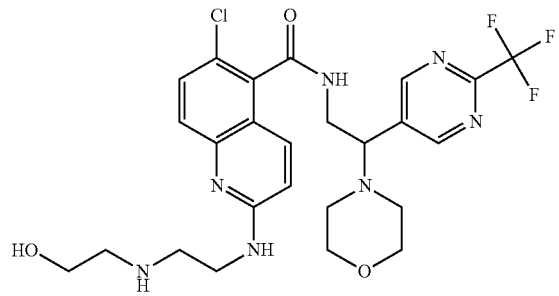 [SMILES: O=C(NCC(c1cnc(C(F)(F)F)nc1)N1CCOCC1)c1c(Cl)ccc2nc(NCCNCCO)ccc12]
Co. No. 514; Ex. B.31
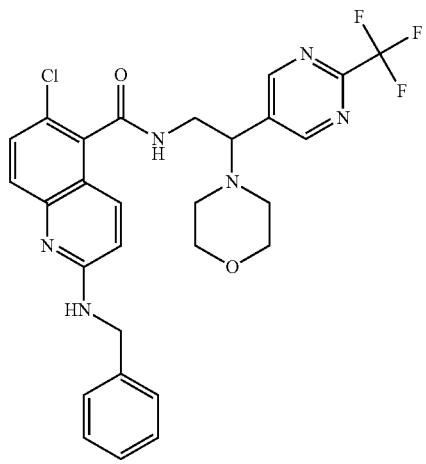 [SMILES: O=C(NCC(c1cnc(C(F)(F)F)nc1)N1CCOCC1)c1c(Cl)ccc2nc(NCc3ccccc3)ccc12]
Co. No. 434; Ex. B.31
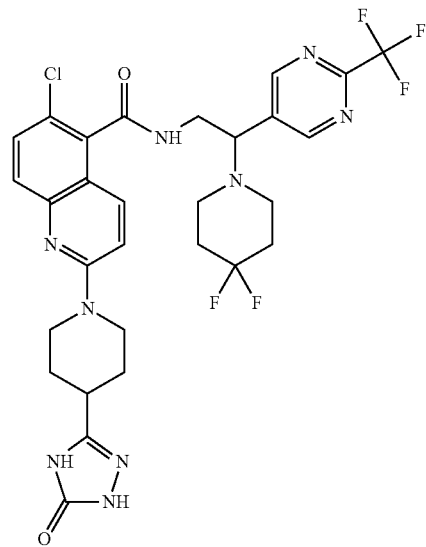 [SMILES: O=C(NCC(c1cnc(C(F)(F)F)nc1)N1CCC(F)(F)CC1)c1c(Cl)ccc2nc(N3CCC(c4n[nH]c(=O)[nH]4)CC3)ccc12]
Co. No. 515; Ex. B.31; CF₃CO₂H
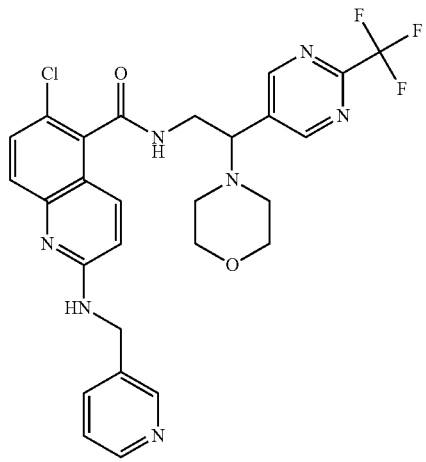 [SMILES: O=C(NCC(c1cnc(C(F)(F)F)nc1)N1CCOCC1)c1c(Cl)ccc2nc(NCc3cccnc3)ccc12]
Co. No. 435; Ex. B.31; CF₃CO₂H
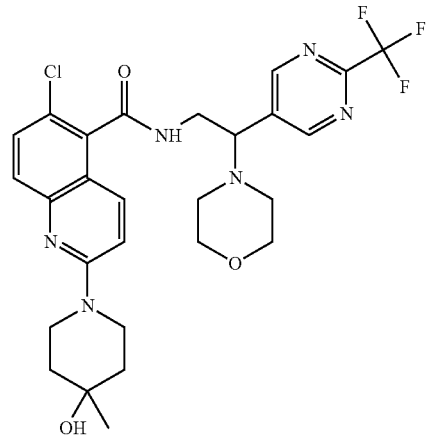 [SMILES: CC1(O)CCN(c2ccc3c(C(=O)NCC(c4cnc(C(F)(F)F)nc4)N4CCOCC4)c(Cl)ccc3n2)CC1]
Co. No. 516; Ex. B.31

TABLE F-3-continued
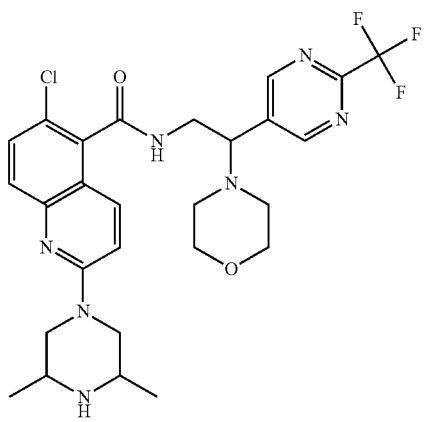 [SMILES: CC1CN(c2ccc3c(C(=O)NCC(c4cnc(C(F)(F)F)nc4)N4CCOCC4)c(Cl)ccc3n2)CC(C)N1]
Co. No. 436; Ex. B.31; CF₃CO₂H
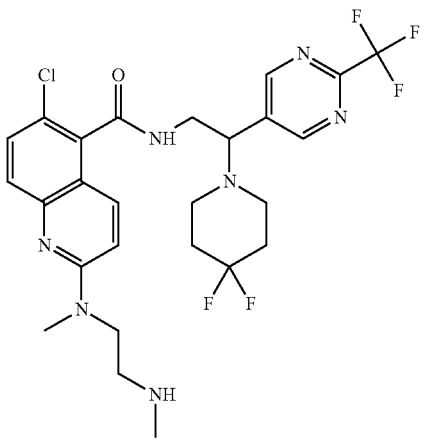 [SMILES: CNCCN(C)c1ccc2c(C(=O)NCC(c3cnc(C(F)(F)F)nc3)N3CCC(F)(F)CC3)c(Cl)ccc2n1]
Co. No. 517; Ex. B.31; CF₃CO₂H
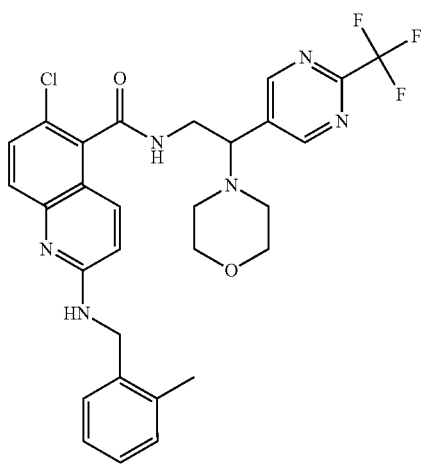 [SMILES: Cc1ccccc1CNc1ccc2c(C(=O)NCC(c3cnc(C(F)(F)F)nc3)N3CCOCC3)c(Cl)ccc2n1]
Co. No. 437; Ex. B.31; CF₃CO₂H
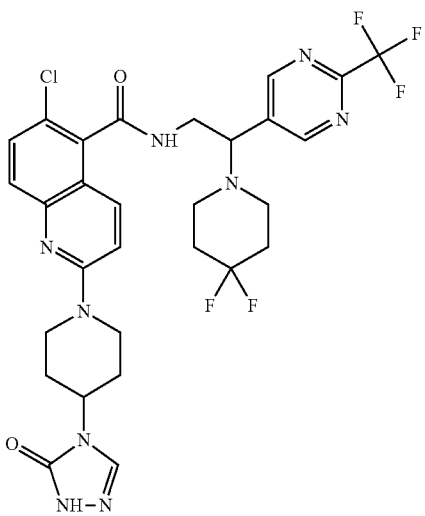 [SMILES: O=C(NCC(c1cnc(C(F)(F)F)nc1)N1CCC(F)(F)CC1)c1c(Cl)ccc2nc(N3CCC(n4cn[nH]c4=O)CC3)ccc12]
Co. No. 518; Ex. B.31; CF₃CO₂H
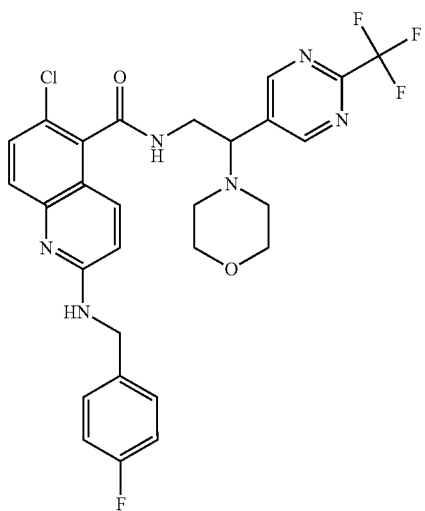 [SMILES: O=C(NCC(c1cnc(C(F)(F)F)nc1)N1CCOCC1)c1c(Cl)ccc2nc(NCc3ccc(F)cc3)ccc12]
Co. No. 438; Ex. B.31
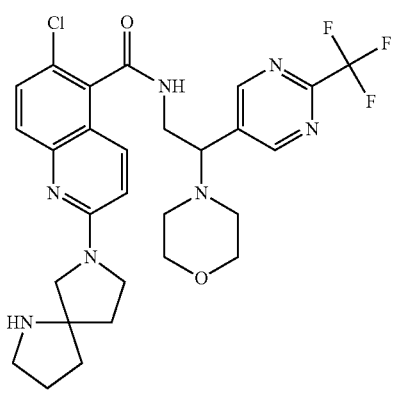 [SMILES: O=C(NCC(c1cnc(C(F)(F)F)nc1)N1CCOCC1)c1c(Cl)ccc2nc(N3CCC4(CCCN4)C3)ccc12]
Co. No. 519; Ex. B.31

TABLE F-3-continued
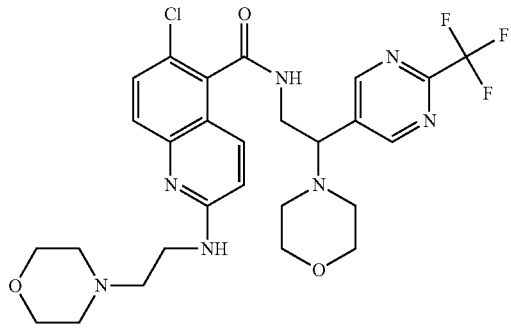 [SMILES: O=C(NCC(c1cnc(C(F)(F)F)nc1)N1CCOCC1)c1c(Cl)ccc2nc(NCCN3CCOCC3)ccc12]
Co. No. 439; Ex. B.31; CF₃CO₂H
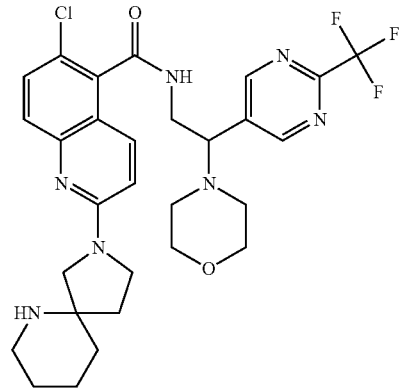 [SMILES: O=C(NCC(c1cnc(C(F)(F)F)nc1)N1CCOCC1)c1c(Cl)ccc2nc(N3CCC4(CCCCN4)C3)ccc12]
Co. No. 520; Ex. B.31
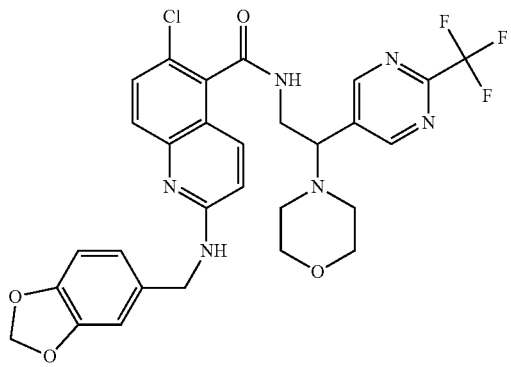 [SMILES: O=C(NCC(c1cnc(C(F)(F)F)nc1)N1CCOCC1)c1c(Cl)ccc2nc(NCc3ccc4c(c3)OCO4)ccc12]
Co. No. 440; Ex. B.31; CF₃CO₂H
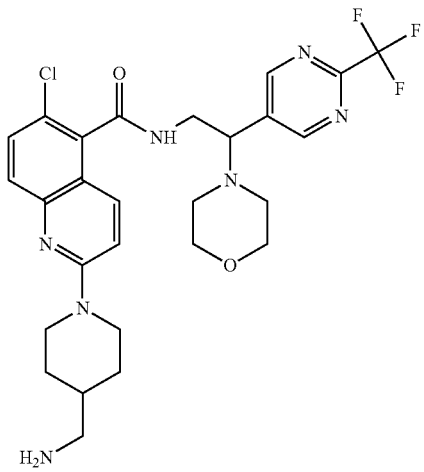 [SMILES: NCC1CCN(c2ccc3c(C(=O)NCC(c4cnc(C(F)(F)F)nc4)N4CCOCC4)c(Cl)ccc3n2)CC1]
Co. No. 521; Ex. B.31
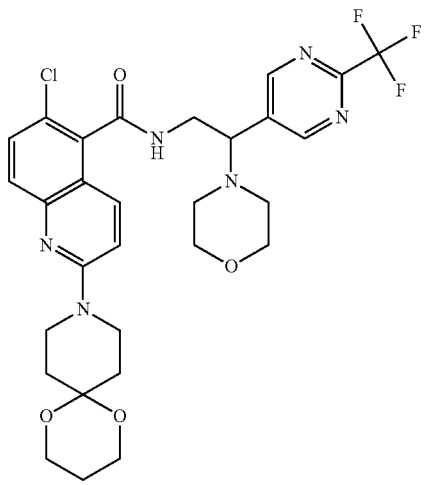 [SMILES: O=C(NCC(c1cnc(C(F)(F)F)nc1)N1CCOCC1)c1c(Cl)ccc2nc(N3CCC4(CC3)OCCCO4)ccc12]
Co. No. 441; Ex. B.31; CF₃CO₂H
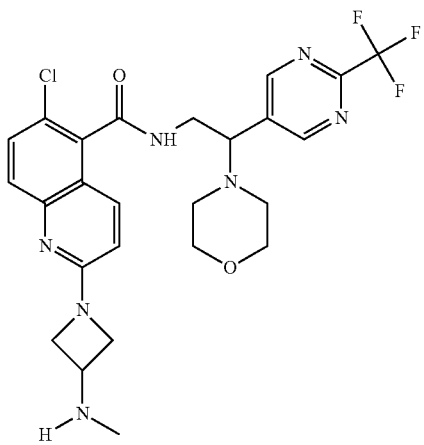 [SMILES: CNC1CN(c2ccc3c(C(=O)NCC(c4cnc(C(F)(F)F)nc4)N4CCOCC4)c(Cl)ccc3n2)C1]
Co. No. 522; Ex. B.31

TABLE F-3-continued
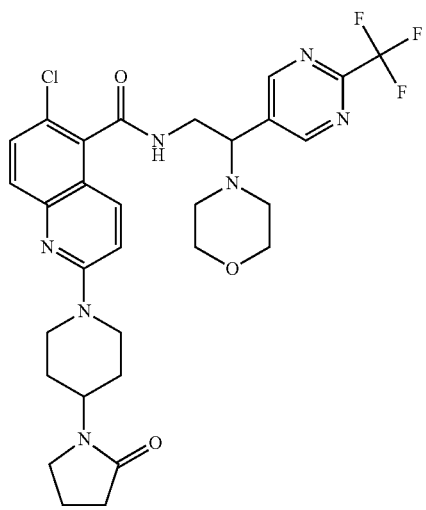 [SMILES: O=C(NCC(c1cnc(C(F)(F)F)nc1)N1CCOCC1)c1c(Cl)ccc2nc(N3CCC(N4CCCC4=O)CC3)ccc12]
Co. No. 442; Ex. B.31; CF₃CO₂H
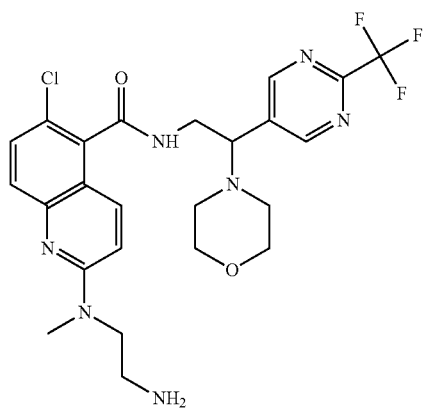 [SMILES: CN(CCN)c1ccc2c(C(=O)NCC(c3cnc(C(F)(F)F)nc3)N3CCOCC3)c(Cl)ccc2n1]
Co. No. 523; Ex. B.31
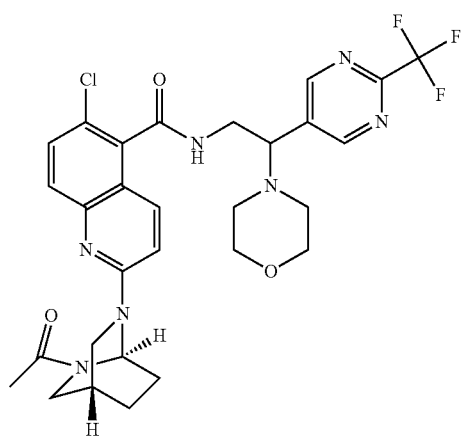 [SMILES: CC(=O)N1C[C@H]2CC[C@@H]1N(c1ccc3c(C(=O)NCC(c4cnc(C(F)(F)F)nc4)N4CCOCC4)c(Cl)ccc3n1)C2]
Co. No. 443; Ex. B.31; CF₃CO₂H
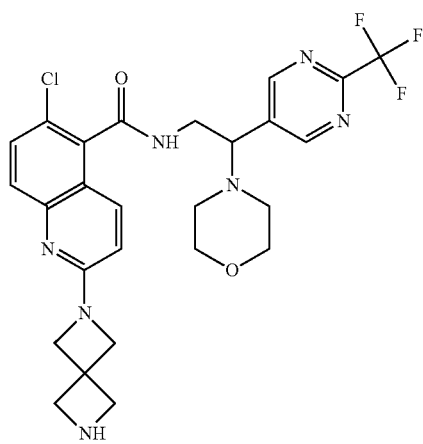 [SMILES: O=C(NCC(c1cnc(C(F)(F)F)nc1)N1CCOCC1)c1c(Cl)ccc2nc(N3CC4(CNC4)C3)ccc12]
Co. No. 524; Ex. B.31
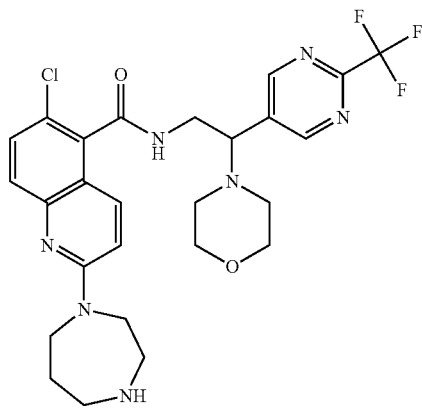 [SMILES: O=C(NCC(c1cnc(C(F)(F)F)nc1)N1CCOCC1)c1c(Cl)ccc2nc(N3CCCNCC3)ccc12]
Co. No. 444; Ex. B.31; CF₃CO₂H
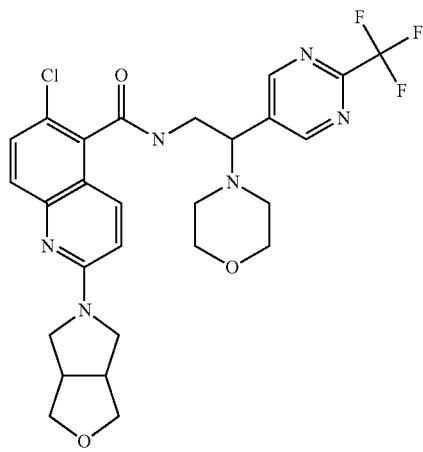 [SMILES: O=C(NCC(c1cnc(C(F)(F)F)nc1)N1CCOCC1)c1c(Cl)ccc2nc(N3CC4COCC4C3)ccc12]
Co. No. 525; Ex. B.31

TABLE F-3-continued
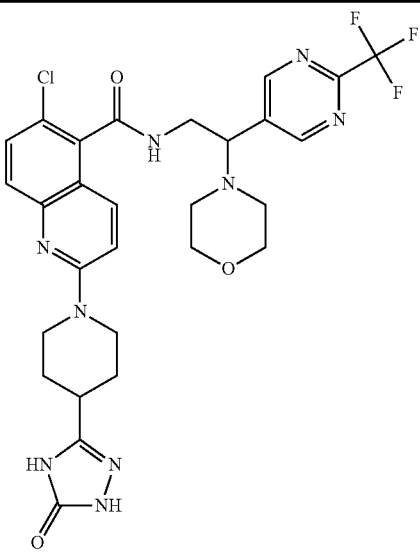
Co. No. 445; Ex. B.31
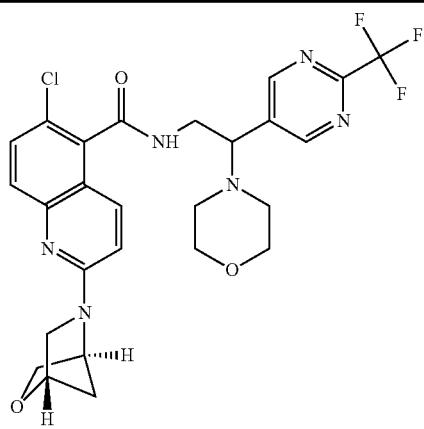
Co. No. 526; Ex. B.31
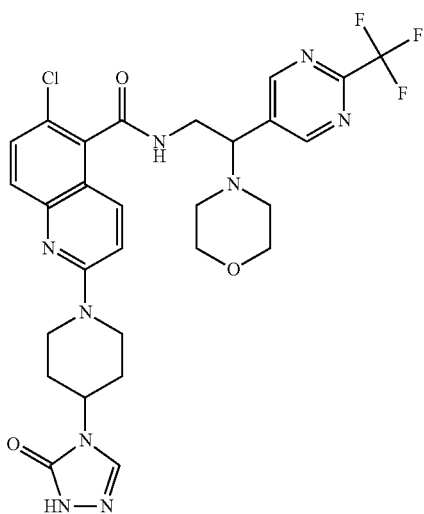 [SMILES: O=C(NCC(c1cnc(C(F)(F)F)nc1)N1CCOCC1)c1c(Cl)ccc2nc(N3CCC(n4cn[nH]c4=O)CC3)ccc12]
Co. No. 446; Ex. B.31; CF$_3$CO$_2$H
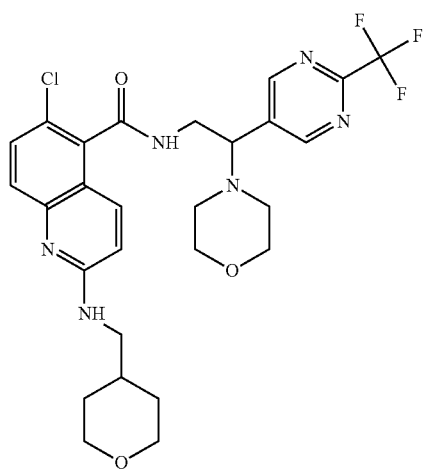 [SMILES: O=C(NCC(c1cnc(C(F)(F)F)nc1)N1CCOCC1)c1c(Cl)ccc2nc(NCC3CCOCC3)ccc12]
Co. No. 527; Ex. B.31
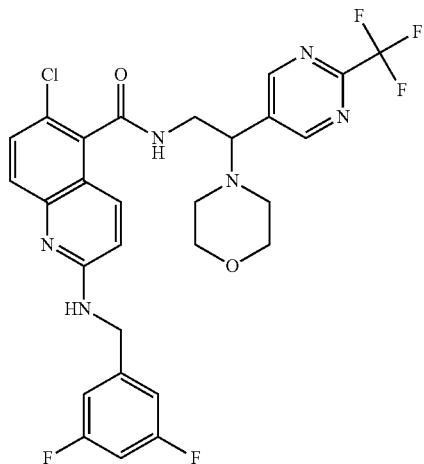 [SMILES: O=C(NCC(c1cnc(C(F)(F)F)nc1)N1CCOCC1)c1c(Cl)ccc2nc(NCc3cc(F)cc(F)c3)ccc12]
Co. No. 447; Ex. B.31; CF$_3$CO$_2$H
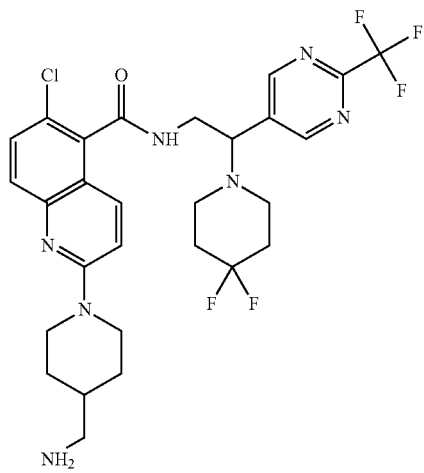 [SMILES: NCC1CCN(c2ccc3c(C(=O)NCC(c4cnc(C(F)(F)F)nc4)N4CCC(F)(F)CC4)c(Cl)ccc3n2)CC1]
Co. No. 528; Ex. B.31; CF$_3$CO$_2$H TABLE F-3-continued
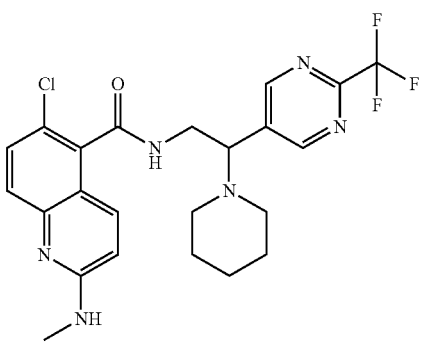 [SMILES: CNc1ccc2c(C(=O)NCC(c3cnc(C(F)(F)F)nc3)N3CCCCC3)c(Cl)ccc2n1]
Co. No. 448; Ex. B.31; CF₃CO₂H
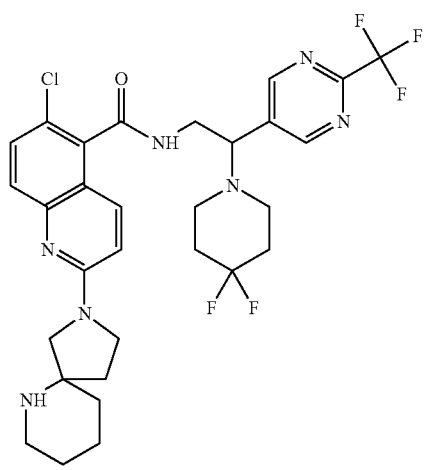 [SMILES: O=C(NCC(c1cnc(C(F)(F)F)nc1)N1CCC(F)(F)CC1)c1c(Cl)ccc2nc(N3CCC4(CCCCN4)C3)ccc12]
Co. No. 529; Ex. B.31; CF₃CO₂H
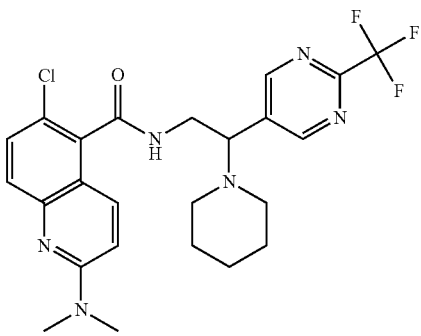 [SMILES: CN(C)c1ccc2c(C(=O)NCC(c3cnc(C(F)(F)F)nc3)N3CCCCC3)c(Cl)ccc2n1]
Co. No. 449; Ex. B.31; CF₃CO₂H
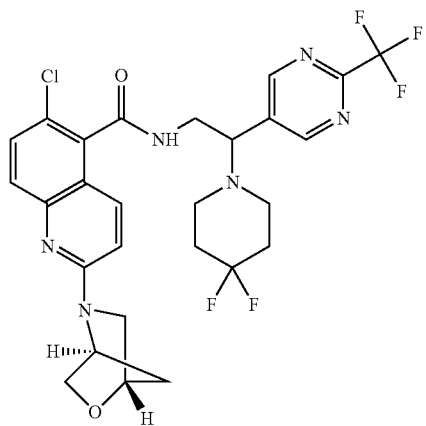 [SMILES: O=C(NCC(c1cnc(C(F)(F)F)nc1)N1CCC(F)(F)CC1)c1c(Cl)ccc2nc(N3C[C@@H]4C[C@H]3CO4)ccc12]
Co. No. 530; Ex. B.31
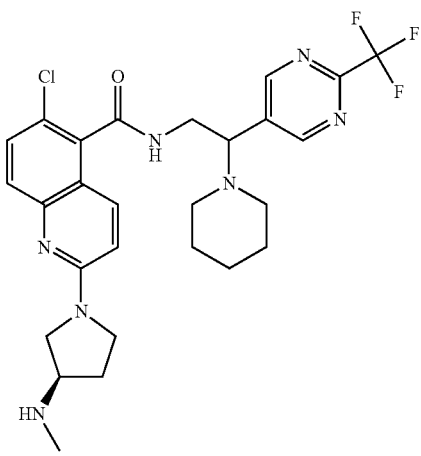 [SMILES: CN[C@@H]1CCN(c2ccc3c(C(=O)NCC(c4cnc(C(F)(F)F)nc4)N4CCCCC4)c(Cl)ccc3n2)C1]
Co. No. 450; Ex. B.31; CF₃CO₂H
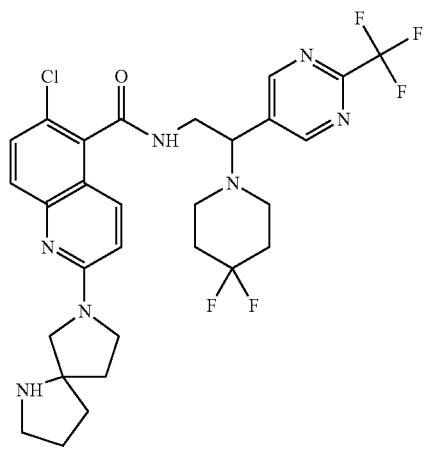 [SMILES: O=C(NCC(c1cnc(C(F)(F)F)nc1)N1CCC(F)(F)CC1)c1c(Cl)ccc2nc(N3CCC4(CCCN4)C3)ccc12]
Co. No. 531; Ex. B.31; CF₃CO₂H TABLE F-3-continued
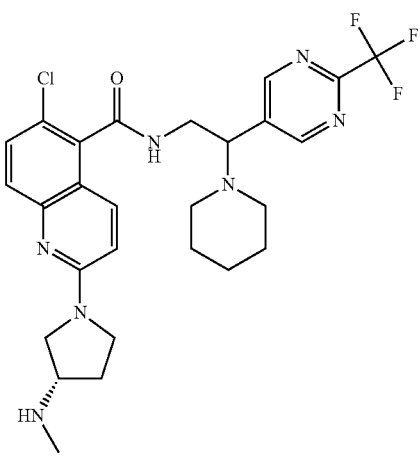 [SMILES: CN[C@H]1CCN(c2ccc3c(C(=O)NCC(c4cnc(C(F)(F)F)nc4)N4CCCCC4)c(Cl)ccc3n2)C1]
Co. No. 451; Ex. B.31; CF$_3$CO$_2$H
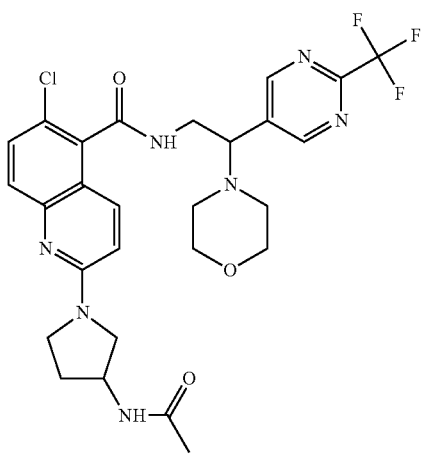 [SMILES: CC(=O)NC1CCN(c2ccc3c(C(=O)NCC(c4cnc(C(F)(F)F)nc4)N4CCOCC4)c(Cl)ccc3n2)C1]
Co. No. 532; Ex. B.31; CF$_3$CO$_2$H
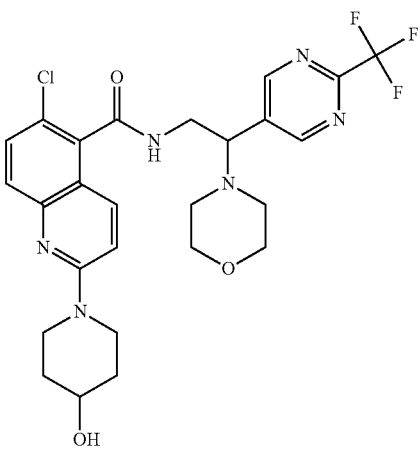 [SMILES: O=C(NCC(c1cnc(C(F)(F)F)nc1)N1CCOCC1)c1c(Cl)ccc2nc(N3CCC(O)CC3)ccc12]
Co. No. 452; Ex. B.31; CF$_3$CO$_2$H
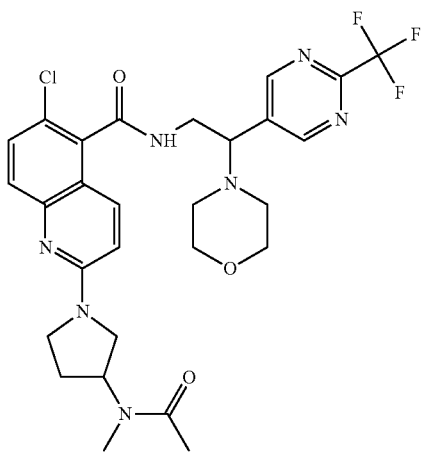 [SMILES: CC(=O)N(C)C1CCN(c2ccc3c(C(=O)NCC(c4cnc(C(F)(F)F)nc4)N4CCOCC4)c(Cl)ccc3n2)C1]
Co. No. 533; Ex. B.31; CF$_3$CO$_2$H
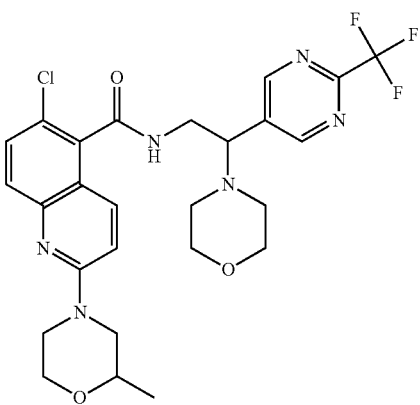 [SMILES: CC1CN(c2ccc3c(C(=O)NCC(c4cnc(C(F)(F)F)nc4)N4CCOCC4)c(Cl)ccc3n2)CCO1]
Co. No. 453; Ex. B.31; CF$_3$CO$_2$H
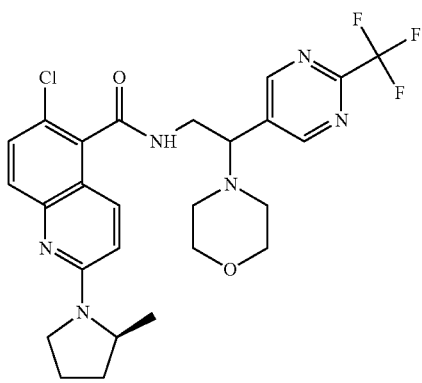 [SMILES: C[C@H]1CCCN1c1ccc2c(C(=O)NCC(c3cnc(C(F)(F)F)nc3)N3CCOCC3)c(Cl)ccc2n1]
Co. No. 534; Ex. B.31

TABLE F-3-continued
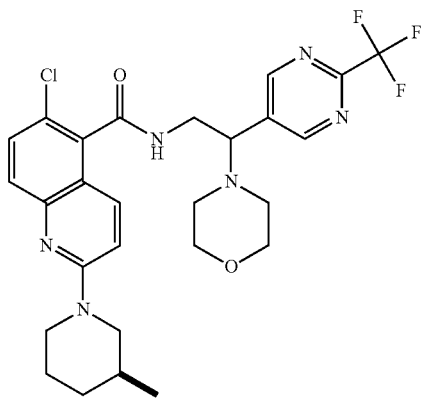 [SMILES: C[C@H]1CCCN(c2ccc3c(C(=O)NCC(c4cnc(C(F)(F)F)nc4)N4CCOCC4)c(Cl)ccc3n2)C1]
Co. No. 454; Ex. B.31; CF₃CO₂H
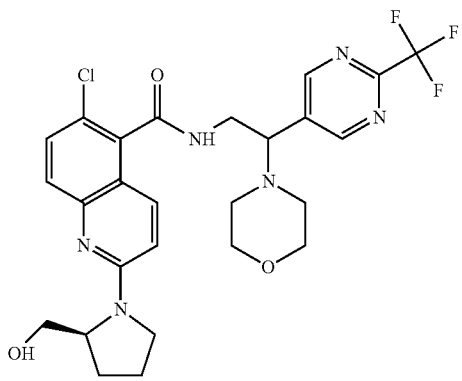 [SMILES: O=C(NCC(c1cnc(C(F)(F)F)nc1)N1CCOCC1)c1c(Cl)ccc2nc(N3CCC[C@H]3CO)ccc12]
Co. No. 535; Ex. B.31; CF₃CO₂H
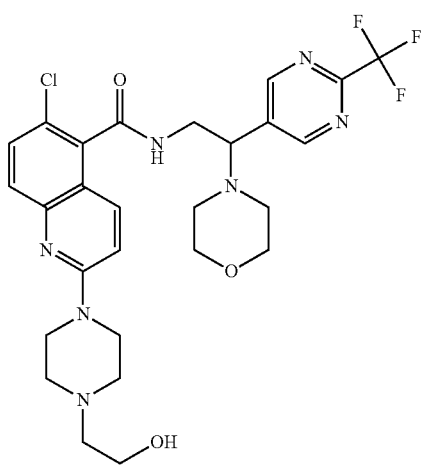 [SMILES: O=C(NCC(c1cnc(C(F)(F)F)nc1)N1CCOCC1)c1c(Cl)ccc2nc(N3CCN(CCO)CC3)ccc12]
Co. No. 455; Ex. B.31; CF₃CO₂H
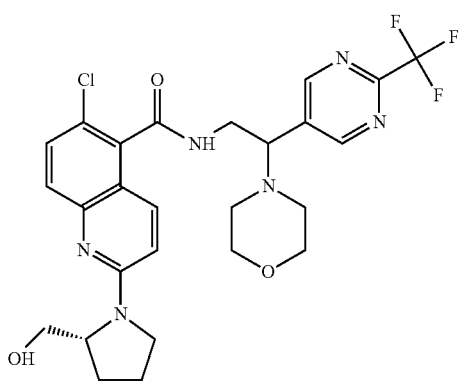 [SMILES: O=C(NCC(c1cnc(C(F)(F)F)nc1)N1CCOCC1)c1c(Cl)ccc2nc(N3CCC[C@@H]3CO)ccc12]
Co. No. 536; Ex. B.31; CF₃CO₂H
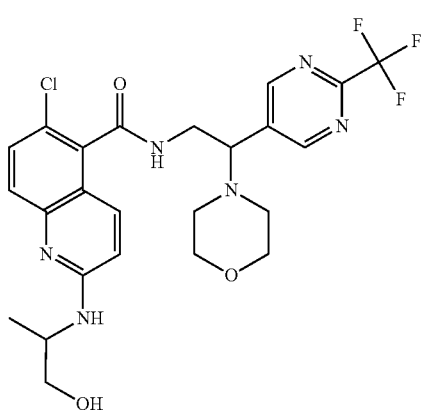 [SMILES: CC(CO)Nc1ccc2c(C(=O)NCC(c3cnc(C(F)(F)F)nc3)N3CCOCC3)c(Cl)ccc2n1]
Co. No. 456; Ex. B.31; CF₃CO₂H
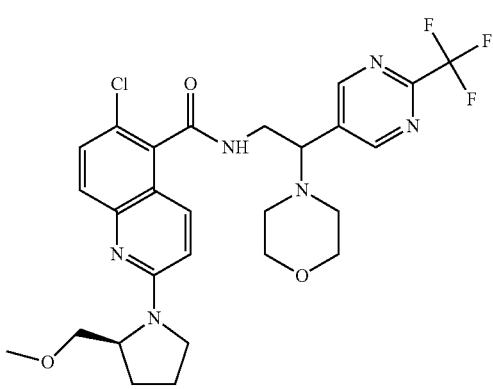 [SMILES: COC[C@@H]1CCCN1c1ccc2c(C(=O)NCC(c3cnc(C(F)(F)F)nc3)N3CCOCC3)c(Cl)ccc2n1]
Co. No. 537; Ex. B.31; CF₃CO₂H TABLE F-3-continued
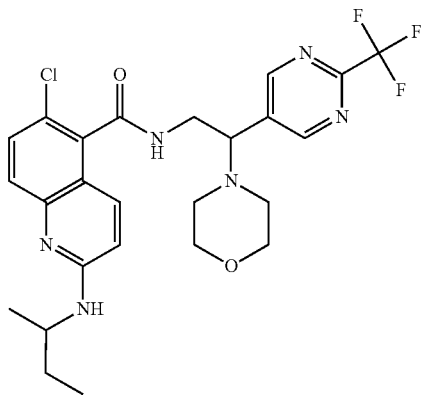 [SMILES: CCC(C)Nc1ccc2c(C(=O)NCC(c3cnc(C(F)(F)F)nc3)N3CCOCC3)c(Cl)ccc2n1]
Co. No. 457; Ex. B.31; CF$_3$CO$_2$H
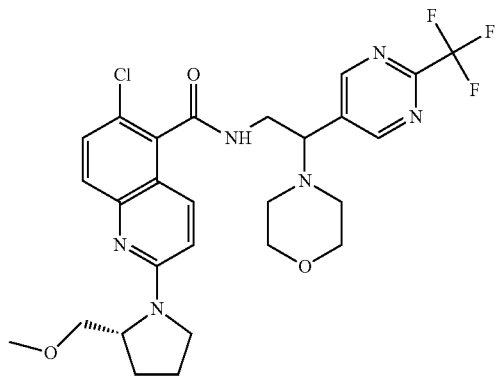 [SMILES: COC[C@H]1CCCN1c1ccc2c(C(=O)NCC(c3cnc(C(F)(F)F)nc3)N3CCOCC3)c(Cl)ccc2n1]
Co. No. 538; Ex. B.31; CF$_3$CO$_2$H
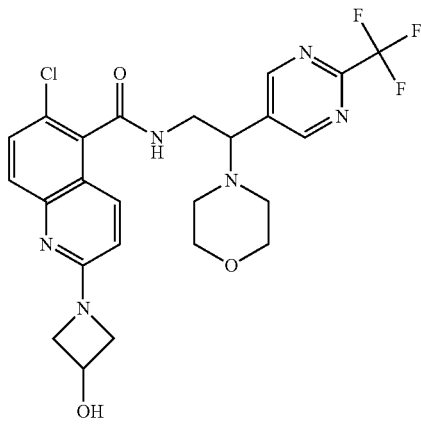 [SMILES: O=C(NCC(c1cnc(C(F)(F)F)nc1)N1CCOCC1)c1c(Cl)ccc2nc(N3CC(O)C3)ccc12]
Co. No. 458; Ex. B.31; CF$_3$CO$_2$H
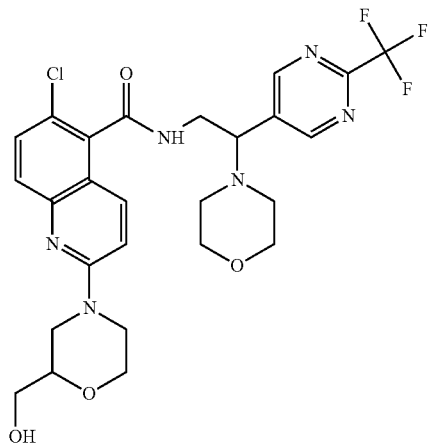 [SMILES: O=C(NCC(c1cnc(C(F)(F)F)nc1)N1CCOCC1)c1c(Cl)ccc2nc(N3CCOC(CO)C3)ccc12]
Co. No. 539; Ex. B.31; CF$_3$CO$_2$H
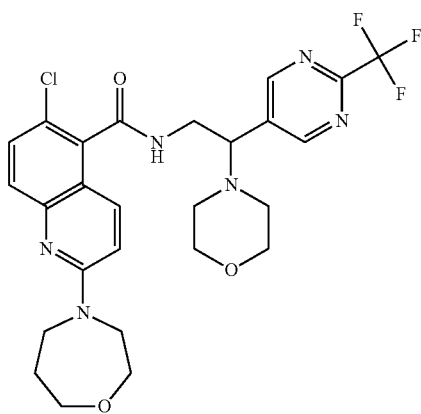 [SMILES: O=C(NCC(c1cnc(C(F)(F)F)nc1)N1CCOCC1)c1c(Cl)ccc2nc(N3CCCOCC3)ccc12]
Co. No. 459; Ex. B.31; CF$_3$CO$_2$H
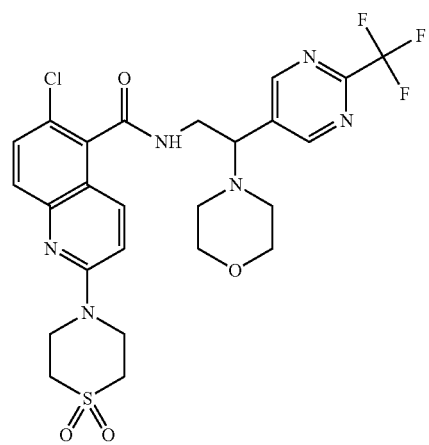 [SMILES: O=C(NCC(c1cnc(C(F)(F)F)nc1)N1CCOCC1)c1c(Cl)ccc2nc(N3CCS(=O)(=O)CC3)ccc12]
Co. No. 540; Ex. B.31

TABLE F-3-continued
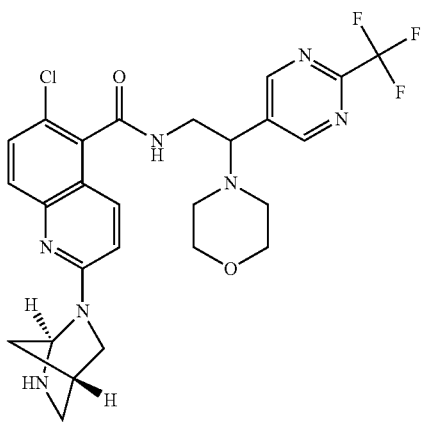 [SMILES: O=C(NCC(c1cnc(C(F)(F)F)nc1)N1CCOCC1)c1c(Cl)ccc2nc(N3C[C@@H]4CN[C@H]3C4)ccc12]
Co. No. 460; Ex. B.31; CF₃CO₂H
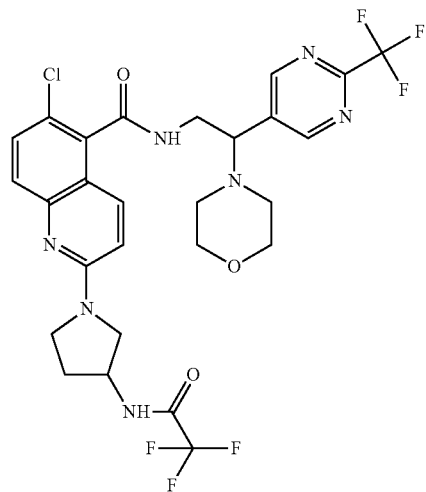 [SMILES: O=C(NCC(c1cnc(C(F)(F)F)nc1)N1CCOCC1)c1c(Cl)ccc2nc(N3CCC(NC(=O)C(F)(F)F)C3)ccc12]
Co. No. 541; Ex. B.31; CF₃CO₂H
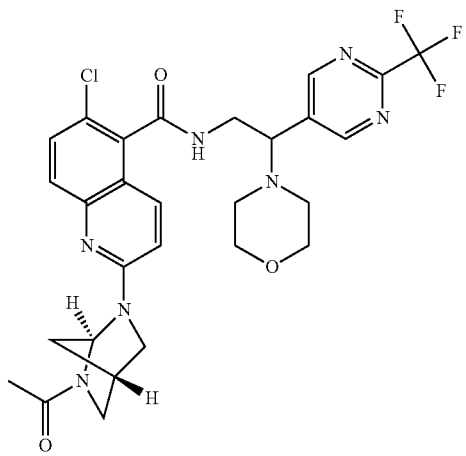 [SMILES: CC(=O)N1C[C@@H]2C[C@H]1N(c1ccc3c(C(=O)NCC(c4cnc(C(F)(F)F)nc4)N4CCOCC4)c(Cl)ccc3n1)C2]
Co. No. 461; Ex. B.31; CF₃CO₂H
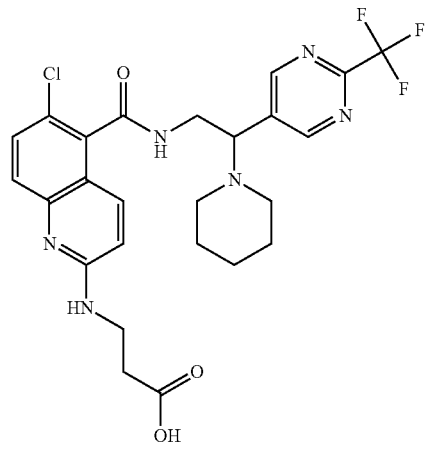 [SMILES: O=C(O)CCNc1ccc2c(C(=O)NCC(c3cnc(C(F)(F)F)nc3)N3CCCCC3)c(Cl)ccc2n1]
Co. No. 542; Ex. B.31; CF₃CO₂H
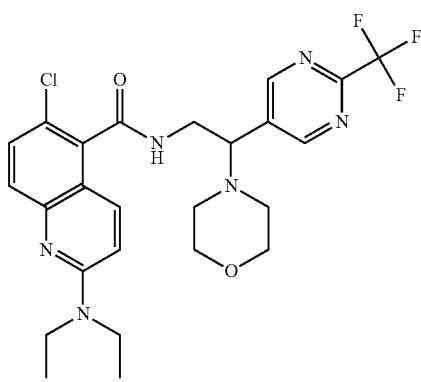 [SMILES: CCN(CC)c1ccc2c(C(=O)NCC(c3cnc(C(F)(F)F)nc3)N3CCOCC3)c(Cl)ccc2n1]
Co. No. 462; Ex. B.31; CF₃CO₂H
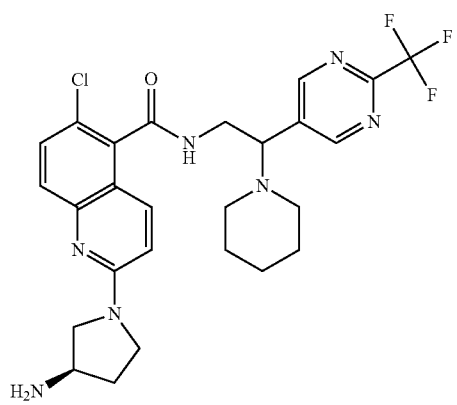
Co. No. 543; Ex. B.31; CF₃CO₂H TABLE F-3-continued
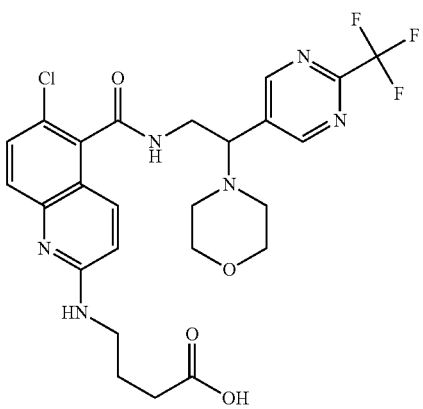 [SMILES: O=C(O)CCCNc1ccc2c(C(=O)NCC(c3cnc(C(F)(F)F)nc3)N3CCOCC3)c(Cl)ccc2n1]
Co. No. 463; Ex. B.31; CF$_3$CO$_2$H
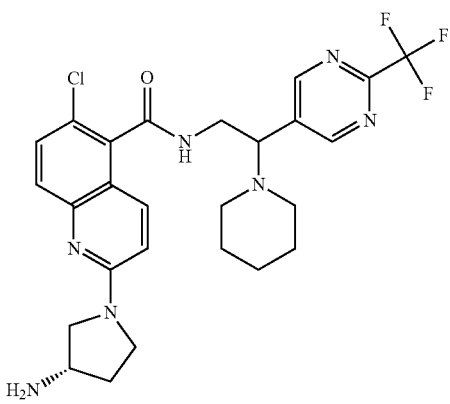
Co. No. 544; Ex. B.31; CF$_3$CO$_2$H
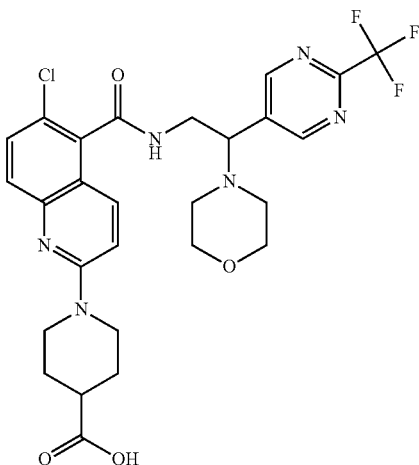 [SMILES: O=C(NCC(c1cnc(C(F)(F)F)nc1)N1CCOCC1)c1c(Cl)ccc2nc(N3CCC(C(=O)O)CC3)ccc12]
Co. No. 464; Ex. B.31; CF$_3$CO$_2$H
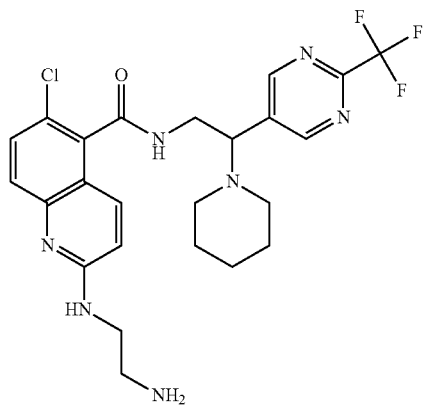
Co. No. 545; Ex. B.31; CF$_3$CO$_2$H
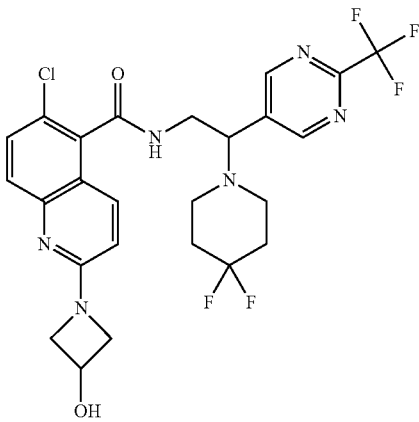 [SMILES: O=C(NCC(c1cnc(C(F)(F)F)nc1)N1CCC(F)(F)CC1)c1c(Cl)ccc2nc(N3CC(O)C3)ccc12]
Co. No. 465; Ex. B.31; CF$_3$CO$_2$H
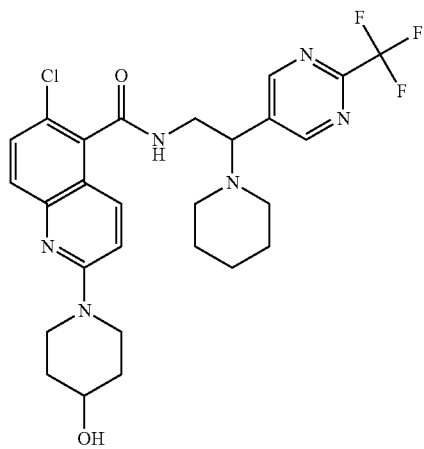 [SMILES: O=C(NCC(c1cnc(C(F)(F)F)nc1)N1CCCCC1)c1c(Cl)ccc2nc(N3CCC(O)CC3)ccc12]
Co. No. 546; Ex. B.31; CF$_3$CO$_2$H TABLE F-3-continued
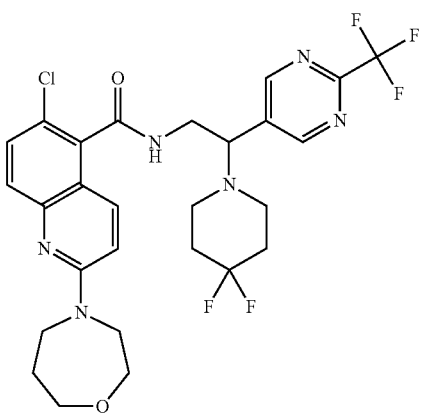 [SMILES: O=C(NCC(c1cnc(C(F)(F)F)nc1)N1CCC(F)(F)CC1)c1c(Cl)ccc2nc(N3CCCOCC3)ccc12]
Co. No. 466; Ex. B.31; CF₃CO₂H
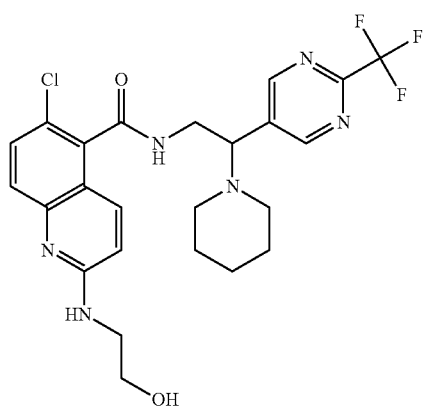 [SMILES: O=C(NCC(c1cnc(C(F)(F)F)nc1)N1CCCCC1)c1c(Cl)ccc2nc(NCCO)ccc12]
Co. No. 547; Ex. B.31; CF₃CO₂H
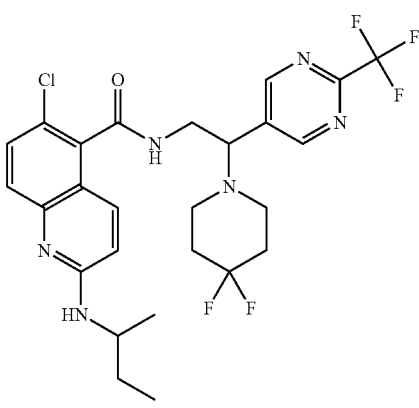 [SMILES: CCC(C)Nc1ccc2c(C(=O)NCC(c3cnc(C(F)(F)F)nc3)N3CCC(F)(F)CC3)c(Cl)ccc2n1]
Co. No. 467; Ex. B.31; CF₃CO₂H
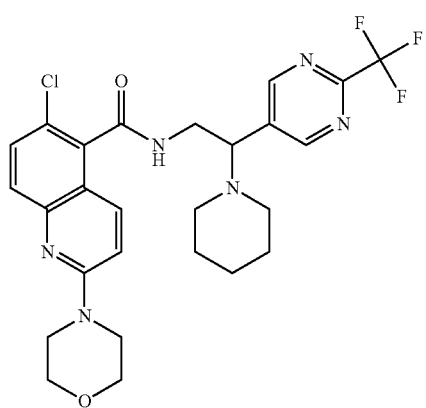 [SMILES: O=C(NCC(c1cnc(C(F)(F)F)nc1)N1CCCCC1)c1c(Cl)ccc2nc(N3CCOCC3)ccc12]
Co. No. 548; Ex. B.31; CF₃CO₂H
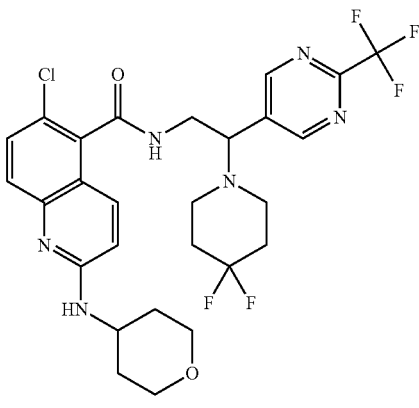 [SMILES: O=C(NCC(c1cnc(C(F)(F)F)nc1)N1CCC(F)(F)CC1)c1c(Cl)ccc2nc(NC3CCOCC3)ccc12]
Co. No. 468; Ex. B.31; CF₃CO₂H
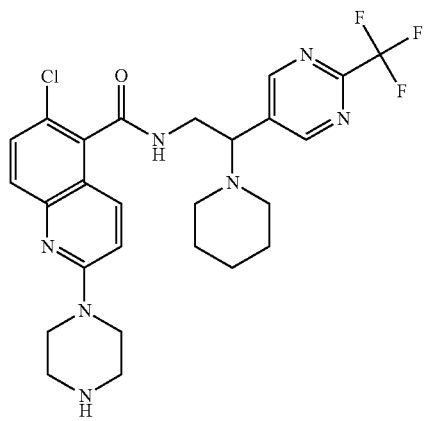 [SMILES: O=C(NCC(c1cnc(C(F)(F)F)nc1)N1CCCCC1)c1c(Cl)ccc2nc(N3CCNCC3)ccc12]
Co. No. 549; Ex. B.31; CF₃CO₂H TABLE F-3-continued
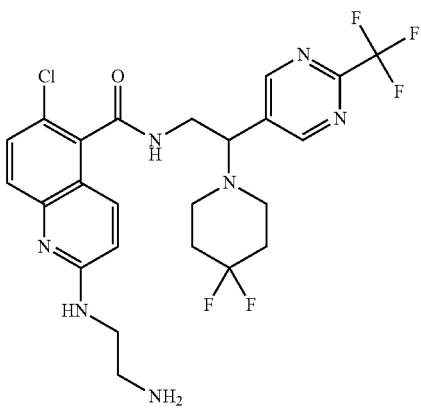 [SMILES: NCCNc1ccc2c(C(=O)NCC(c3cnc(C(F)(F)F)nc3)N3CCC(F)(F)CC3)c(Cl)ccc2n1]
Co. No. 469; Ex. B.31; CF$_3$CO$_2$H
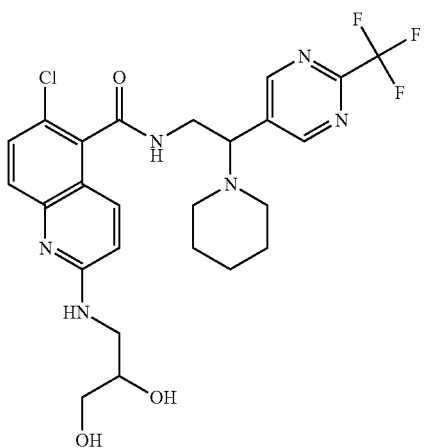 [SMILES: O=C(NCC(c1cnc(C(F)(F)F)nc1)N1CCCCC1)c1c(Cl)ccc2nc(NCC(O)CO)ccc12]
Co. No. 550; Ex. B.31; CF$_3$CO$_2$H
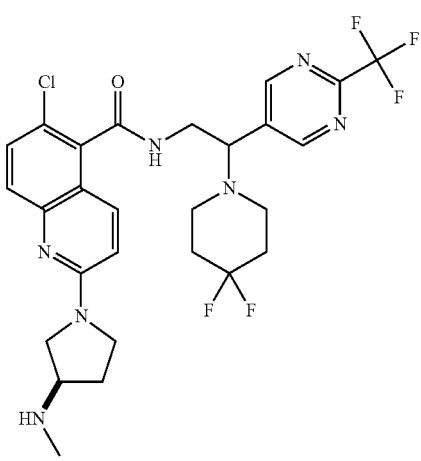 [SMILES: CN[C@@H]1CCN(c2ccc3c(C(=O)NCC(c4cnc(C(F)(F)F)nc4)N4CCC(F)(F)CC4)c(Cl)ccc3n2)C1]
Co. No. 470; Ex. B.31; CF$_3$CO$_2$H
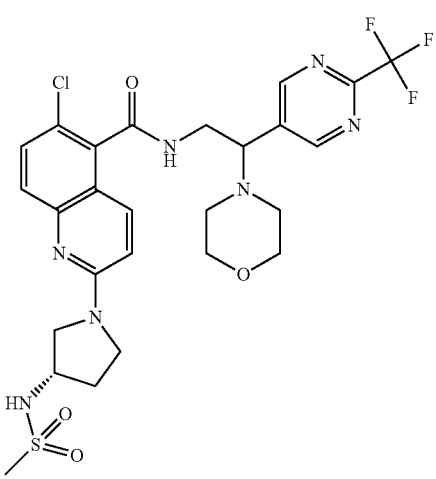 [SMILES: CS(=O)(=O)N[C@H]1CCN(c2ccc3c(C(=O)NCC(c4cnc(C(F)(F)F)nc4)N4CCOCC4)c(Cl)ccc3n2)C1]
Co. No. 551; Ex. B.31; CF$_3$CO$_2$H
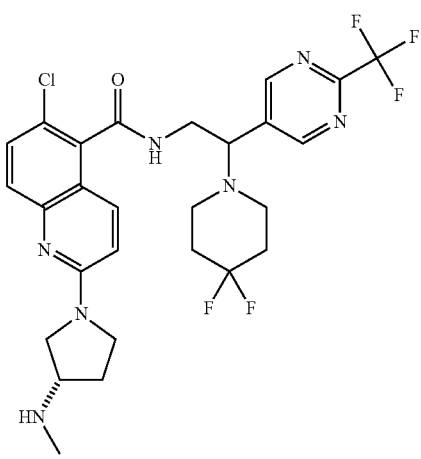 [SMILES: CN[C@H]1CCN(c2ccc3c(C(=O)NCC(c4cnc(C(F)(F)F)nc4)N4CCC(F)(F)CC4)c(Cl)ccc3n2)C1]
Co. No. 471; Ex. B.31; CF$_3$CO$_2$H
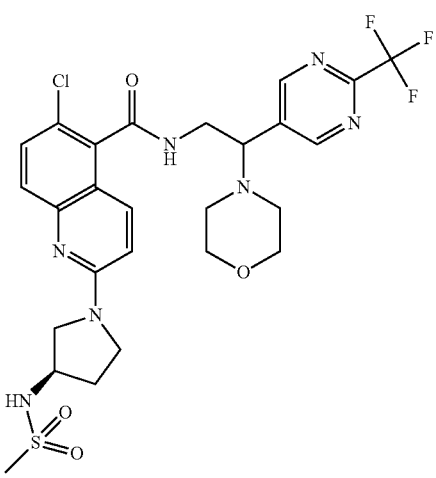 [SMILES: CS(=O)(=O)N[C@@H]1CCN(c2ccc3c(C(=O)NCC(c4cnc(C(F)(F)F)nc4)N4CCOCC4)c(Cl)ccc3n2)C1]
Co. No. 552; Ex. B.31; CF$_3$CO$_2$H TABLE F-3-continued
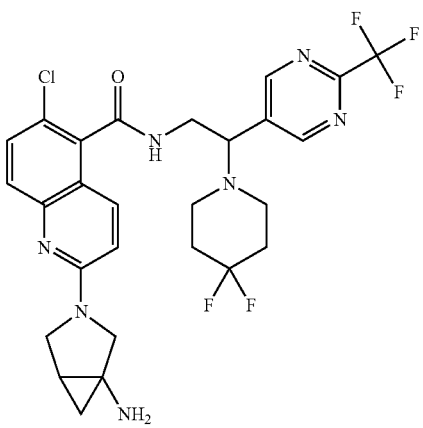 [SMILES: NC12CC1CN(c1ccc3c(C(=O)NCC(c4cnc(C(F)(F)F)nc4)N4CCC(F)(F)CC4)c(Cl)ccc3n1)C2]
Co. No. 472; Ex. B.31; CF$_3$CO$_2$H
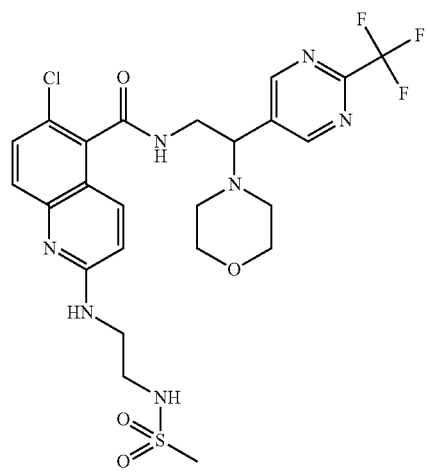 [SMILES: CS(=O)(=O)NCCNc1ccc2c(C(=O)NCC(c3cnc(C(F)(F)F)nc3)N3CCOCC3)c(Cl)ccc2n1]
Co. No. 553; Ex. B.31; CF$_3$CO$_2$H
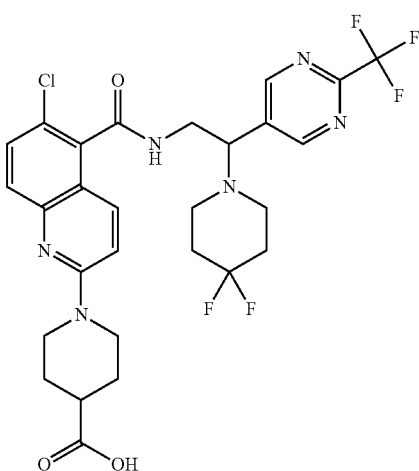 [SMILES: O=C(NCC(c1cnc(C(F)(F)F)nc1)N1CCC(F)(F)CC1)c1c(Cl)ccc2nc(N3CCC(C(=O)O)CC3)ccc12]
Co. No. 473; Ex. B.31; CF$_3$CO$_2$H
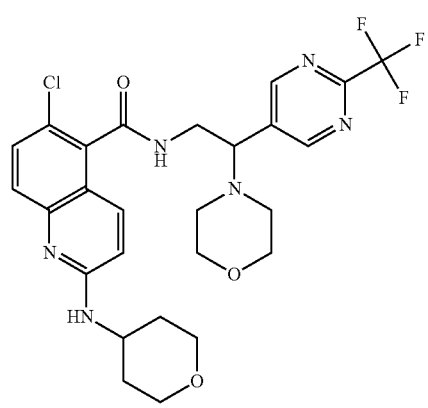 [SMILES: O=C(NCC(c1cnc(C(F)(F)F)nc1)N1CCOCC1)c1c(Cl)ccc2nc(NC3CCOCC3)ccc12]
Co. No. 554; Ex. B.31; CF$_3$CO$_2$H
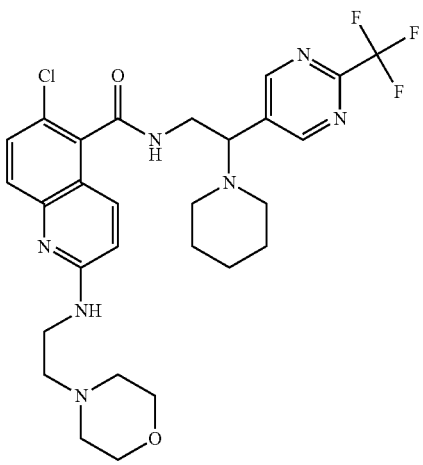 [SMILES: O=C(NCC(c1cnc(C(F)(F)F)nc1)N1CCCCC1)c1c(Cl)ccc2nc(NCCN3CCOCC3)ccc12]
Co. No. 474; Ex. B.31; CF$_3$CO$_2$H
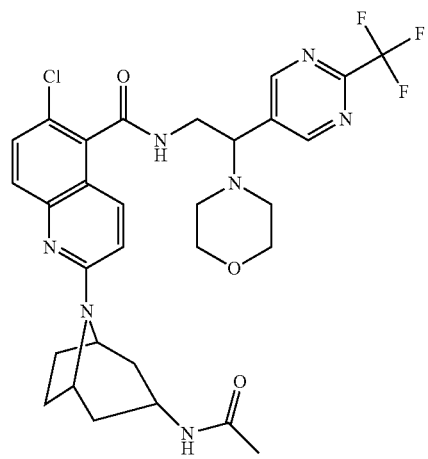 [SMILES: CC(=O)NC1CC2CCC(C1)N2c1ccc2c(C(=O)NCC(c3cnc(C(F)(F)F)nc3)N3CCOCC3)c(Cl)ccc2n1]
Co. No. 555; Ex. B.31; CF$_3$CO$_2$H TABLE F-3-continued
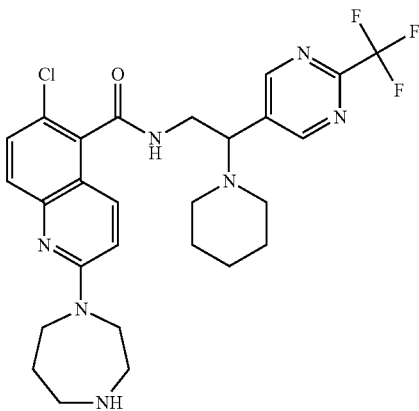 [SMILES: O=C(NCC(c1cnc(C(F)(F)F)nc1)N1CCCCC1)c1c(Cl)ccc2nc(N3CCCNCC3)ccc12]
Co. No. 475; Ex. B.31; CF$_3$CO$_2$H
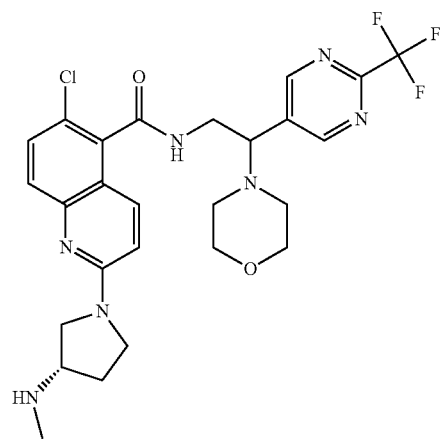 [SMILES: CN[C@H]1CCN(c2ccc3c(C(=O)NCC(c4cnc(C(F)(F)F)nc4)N4CCOCC4)c(Cl)ccc3n2)C1]
Co. No. 556; Ex. B.31; CF$_3$CO$_2$H
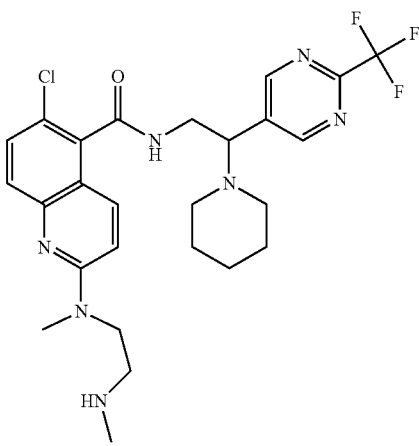 [SMILES: CNCCN(C)c1ccc2c(C(=O)NCC(c3cnc(C(F)(F)F)nc3)N3CCCCC3)c(Cl)ccc2n1]
Co. No. 476; Ex. B.31; CF$_3$CO$_2$H
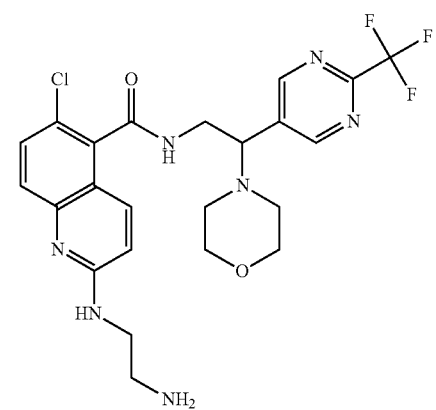 [SMILES: NCCNc1ccc2c(C(=O)NCC(c3cnc(C(F)(F)F)nc3)N3CCOCC3)c(Cl)ccc2n1]
Co. No. 557; Ex. B.31; CF$_3$CO$_2$H
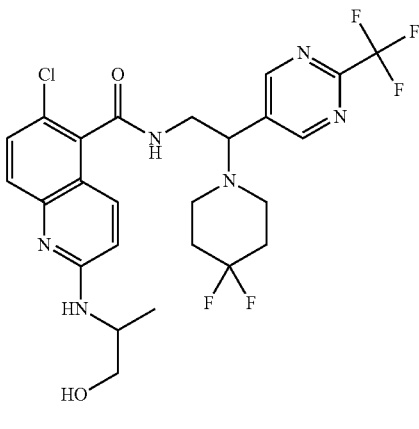 [SMILES: CC(CO)Nc1ccc2c(C(=O)NCC(c3cnc(C(F)(F)F)nc3)N3CCC(F)(F)CC3)c(Cl)ccc2n1]
Co. No. 477; Ex. B.31; CF$_3$CO$_2$H
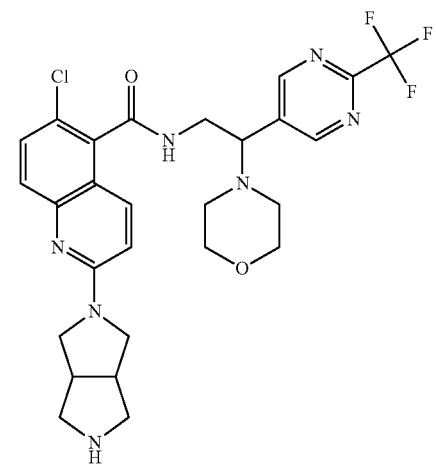 [SMILES: O=C(NCC(c1cnc(C(F)(F)F)nc1)N1CCOCC1)c1c(Cl)ccc2nc(N3CC4CNCC4C3)ccc12]
Co. No. 558; Ex. B.31; CF$_3$CO$_2$H TABLE F-3-continued
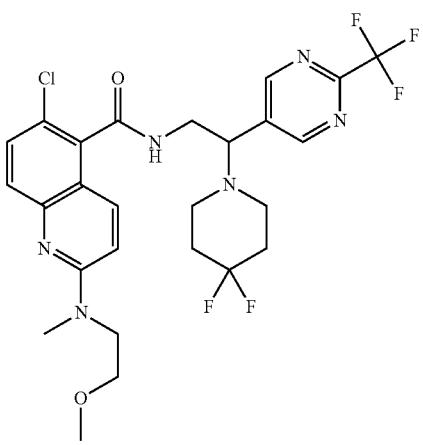 [SMILES: COCCN(C)c1ccc2c(C(=O)NCC(c3cnc(C(F)(F)F)nc3)N3CCC(F)(F)CC3)c(Cl)ccc2n1]
Co. No. 478; Ex. B.31; CF₃CO₂H
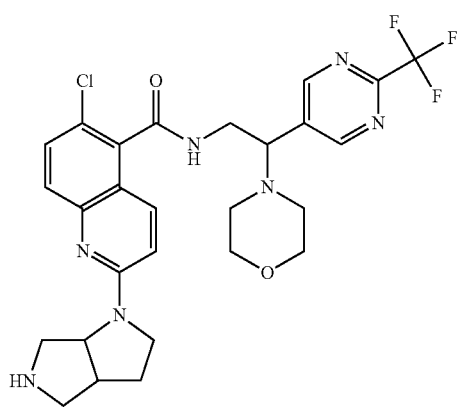 [SMILES: O=C(NCC(c1cnc(C(F)(F)F)nc1)N1CCOCC1)c1c(Cl)ccc2nc(N3CCC4CNCC43)ccc12]
Co. No. 559; Ex. B.31; CF₃CO₂H
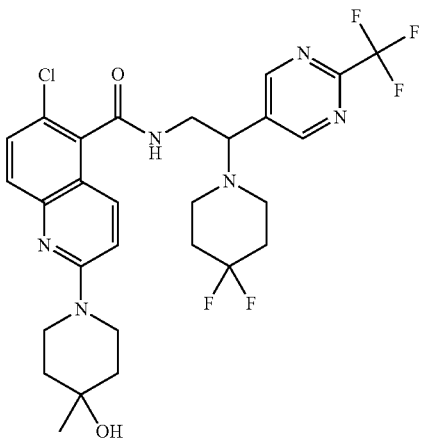 [SMILES: CC1(O)CCN(c2ccc3c(C(=O)NCC(c4cnc(C(F)(F)F)nc4)N4CCC(F)(F)CC4)c(Cl)ccc3n2)CC1]
Co. No. 479; Ex. B.31; CF₃CO₂H
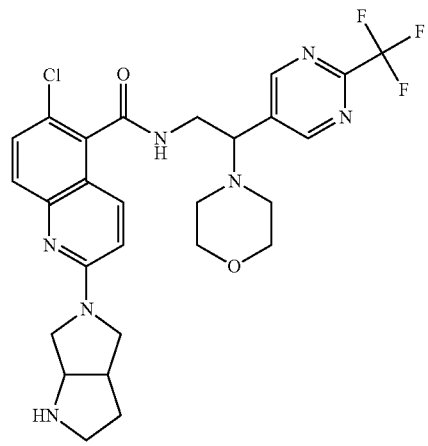 [SMILES: O=C(NCC(c1cnc(C(F)(F)F)nc1)N1CCOCC1)c1c(Cl)ccc2nc(N3CC4CCNC4C3)ccc12]
Co. No. 560; Ex. B.31; CF₃CO₂H
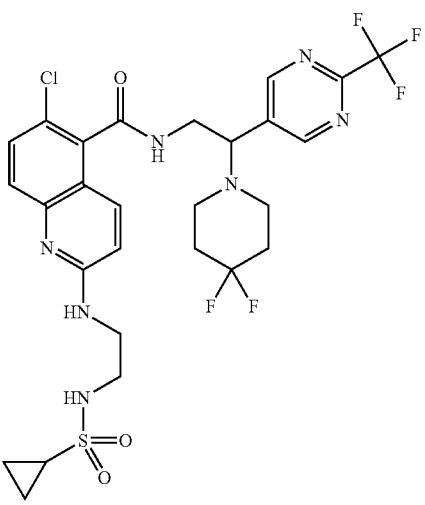 [SMILES: O=C(NCC(c1cnc(C(F)(F)F)nc1)N1CCC(F)(F)CC1)c1c(Cl)ccc2nc(NCCNS(=O)(=O)C3CC3)ccc12]
Co. No. 480; Ex. B.31; CF₃CO₂H
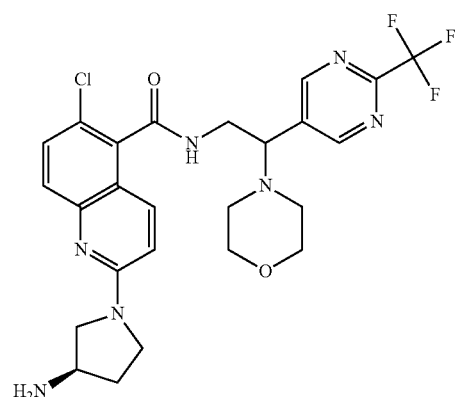
Co. No. 561; Ex. B.31; CF₃CO₂H TABLE F-3-continued
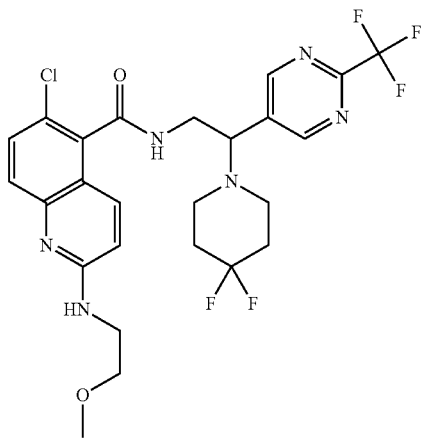 [SMILES: COCCNc1ccc2c(C(=O)NCC(c3cnc(C(F)(F)F)nc3)N3CCC(F)(F)CC3)c(Cl)ccc2n1]
Co. No. 481; Ex. B.31; CF₃CO₂H
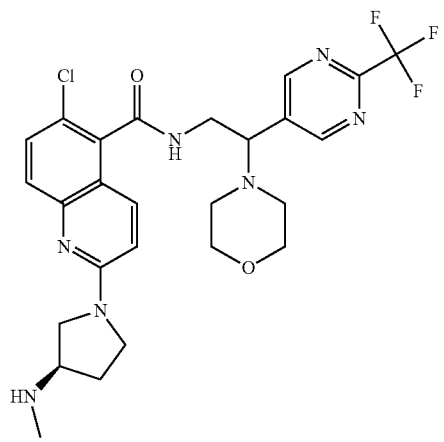 [SMILES: CN[C@@H]1CCN(c2ccc3c(C(=O)NCC(c4cnc(C(F)(F)F)nc4)N4CCOCC4)c(Cl)ccc3n2)C1]
Co. No. 562; Ex. B.31; CF₃CO₂H
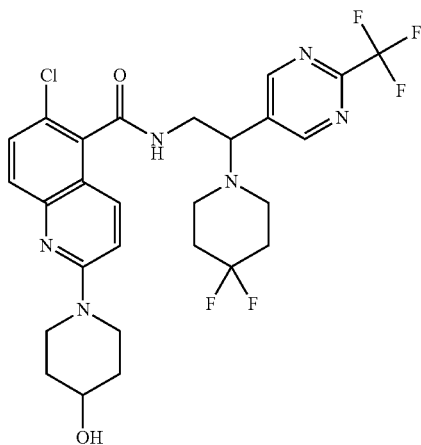 [SMILES: O=C(NCC(c1cnc(C(F)(F)F)nc1)N1CCC(F)(F)CC1)c1c(Cl)ccc2nc(N3CCC(O)CC3)ccc12]
Co. No. 482; Ex. B.31; CF₃CO₂H
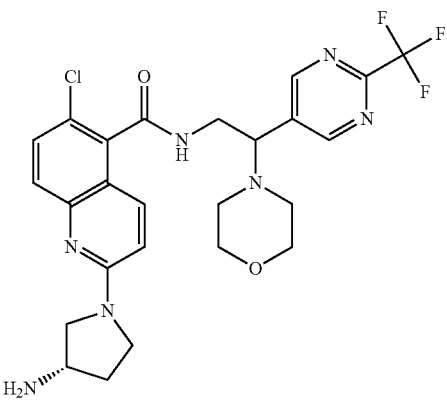 [SMILES: N[C@H]1CCN(c2ccc3c(C(=O)NCC(c4cnc(C(F)(F)F)nc4)N4CCOCC4)c(Cl)ccc3n2)C1]
Co. No. 563; Ex. B.31; CF₃CO₂H
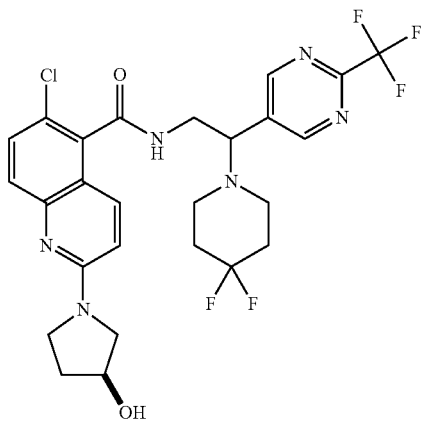 [SMILES: O=C(NCC(c1cnc(C(F)(F)F)nc1)N1CCC(F)(F)CC1)c1c(Cl)ccc2nc(N3CC[C@H](O)C3)ccc12]
Co. No. 483; Ex. B.31; CF₃CO₂H
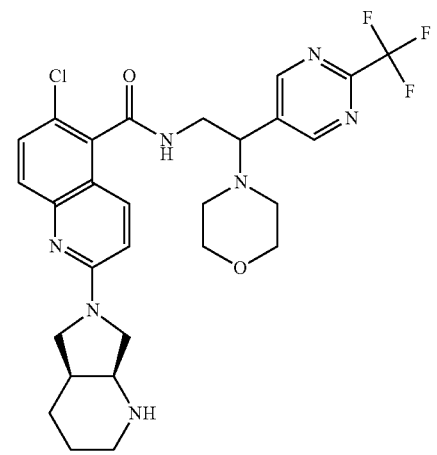 [SMILES: O=C(NCC(c1cnc(C(F)(F)F)nc1)N1CCOCC1)c1c(Cl)ccc2nc(N3C[C@@H]4CCCN[C@@H]4C3)ccc12]
Co. No. 564; Ex. B.31; CF₃CO₂H TABLE F-3-continued
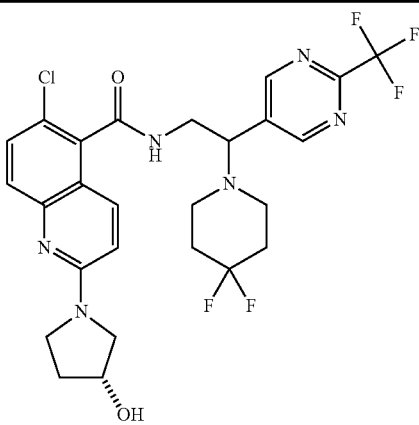
Co. No. 484; Ex. B.31
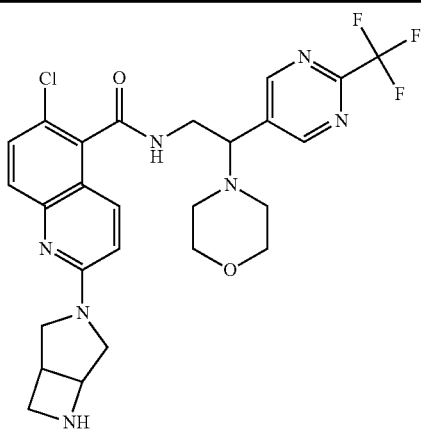
Co. No. 565; Ex. B.31; CF₃CO₂H
| TABLE F-4 | TABLE F-4-continued |
|---|---|
| 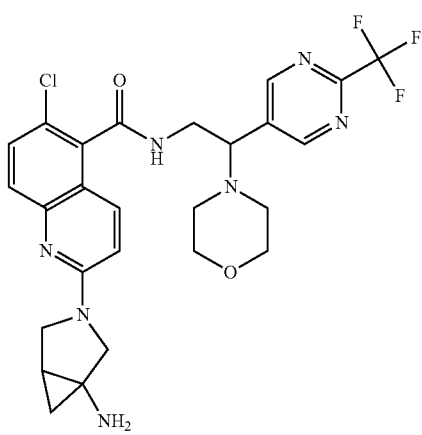 [SMILES: O=C(NCC(c1cnc(C(F)(F)F)nc1)N1CCOCC1)c1c(Cl)ccc2nc(N3CC4CNC4C3)ccc12]<br>Co. No. 566; Ex. B.31; CF₃CO₂H | 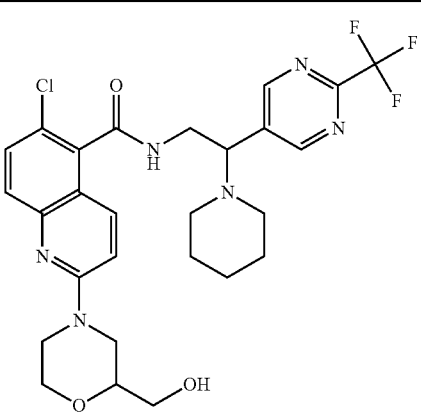<br>Co. No. 568; Ex. B.31; CF₃CO₂H |
| 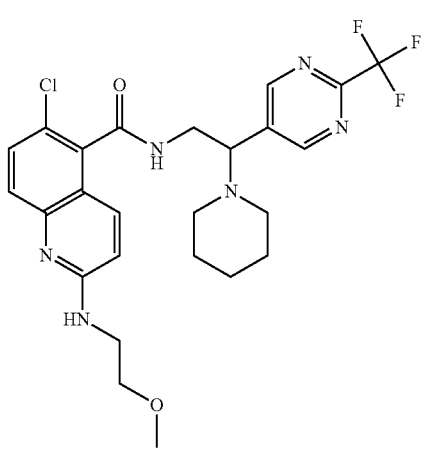<br>Co. No. 567; Ex. B.31; CF₃CO₂H | 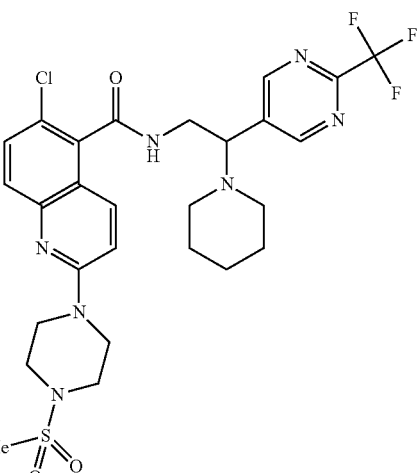<br>Co. No. 569; Ex. B.31; CF₃CO₂H |

TABLE F-4-continued
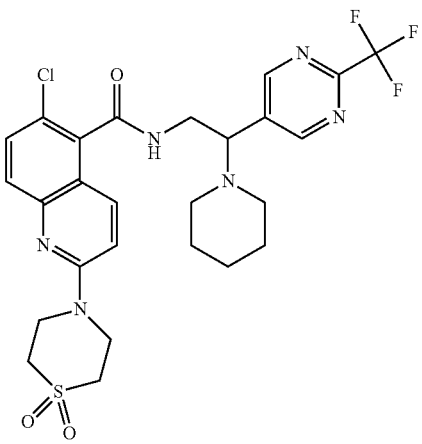
Co. No. 570; Ex. B.31; CF$_3$CO$_2$H
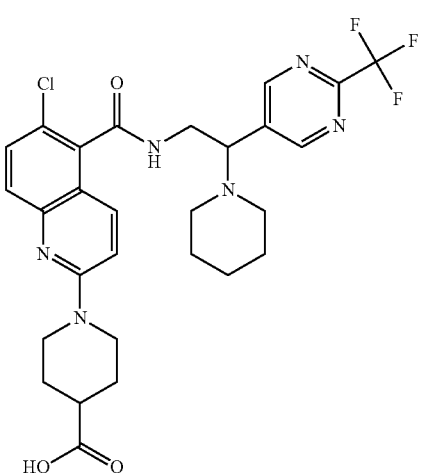
Co. No. 571; Ex. B.31; CF$_3$CO$_2$H
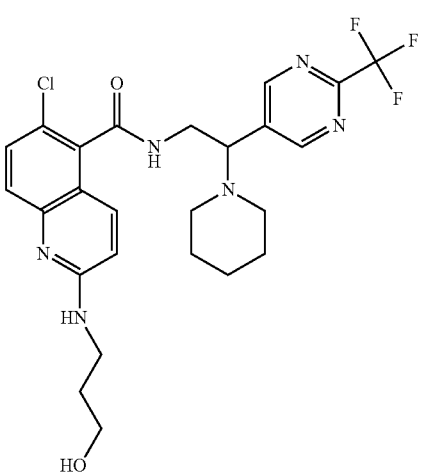
Co. No. 572; Ex. B.31; CF$_3$CO$_2$H
TABLE F-4-continued
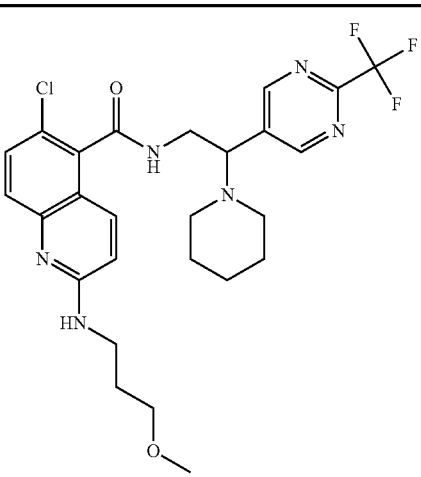
Co. No. 573; Ex. B.31; CF$_3$CO$_2$H
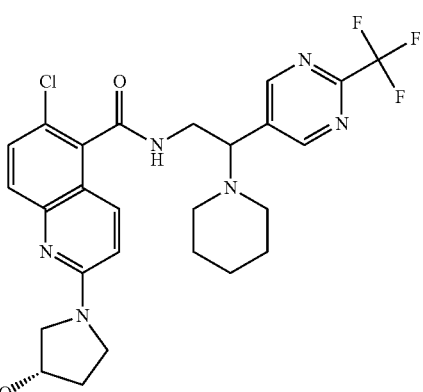
Co. No. 574; Ex. B.31; CF$_3$CO$_2$H
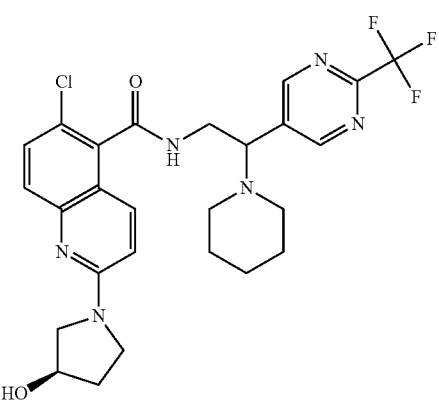
Co. No. 575; Ex. B.31; CF$_3$CO$_2$H TABLE F-4-continued
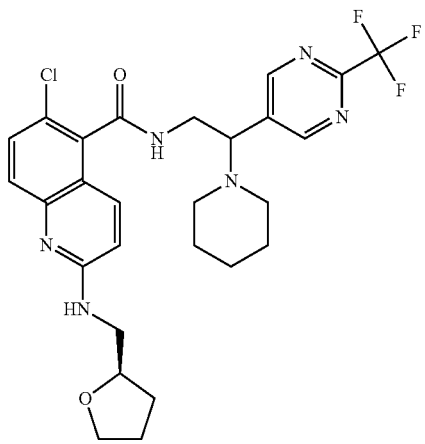
Co. No. 576; Ex. B.31; CF$_3$CO$_2$H
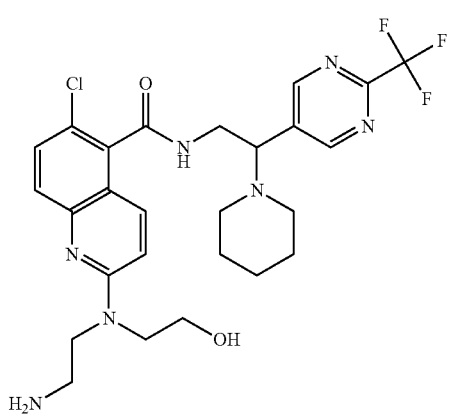
Co. No. 577; Ex. B.31; CF$_3$CO$_2$H
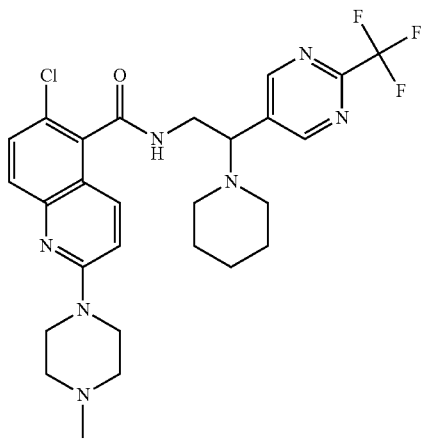
Co. No. 578; Ex. B.31; CF$_3$CO$_2$H
TABLE F-4-continued
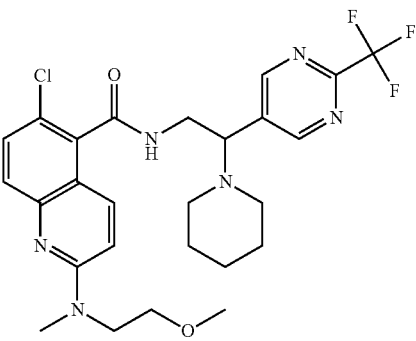
Co. No. 579; Ex. B.31; CF$_3$CO$_2$H
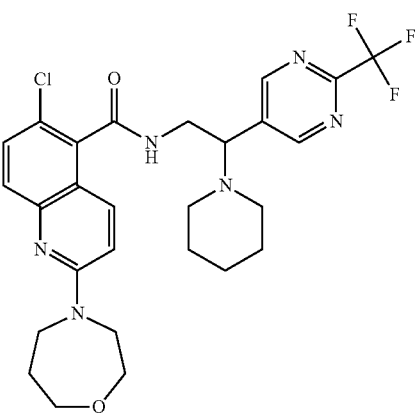
Co. No. 580; Ex. B.31; CF$_3$CO$_2$H
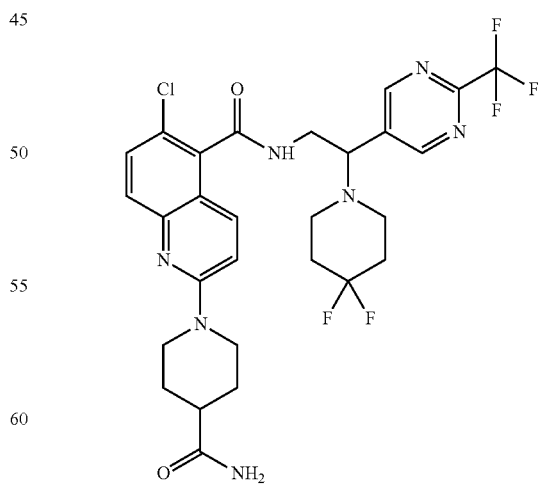
Co. No. 581; Ex. B.31; CF$_3$CO$_2$H TABLE F-4-continued
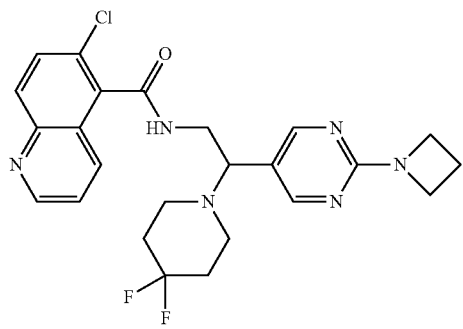
Co. No. 585; Ex. B.34; CF3CO2H
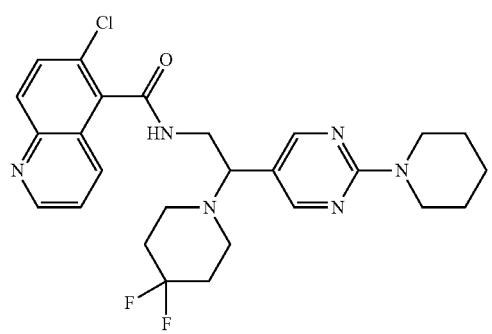
Co. No. 586; Ex. B.34; CF3CO2H
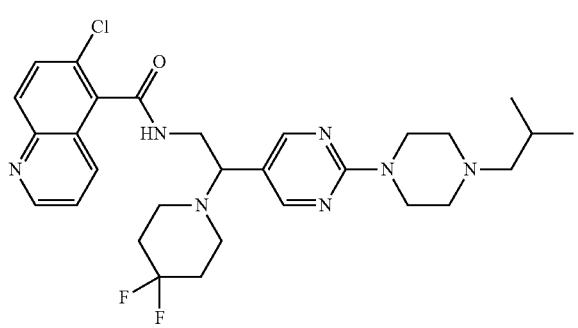
Co. No. 587; Ex. B.34; CF3CO2H
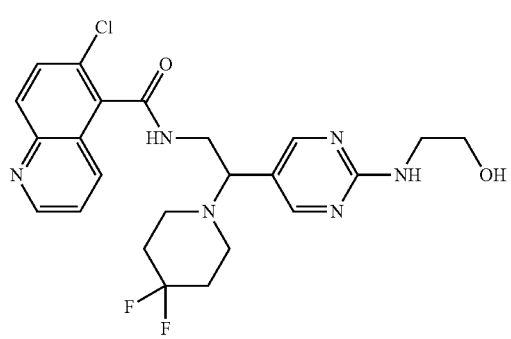
Co. No. 588; Ex. B.34; CF3CO2H
TABLE F-4-continued
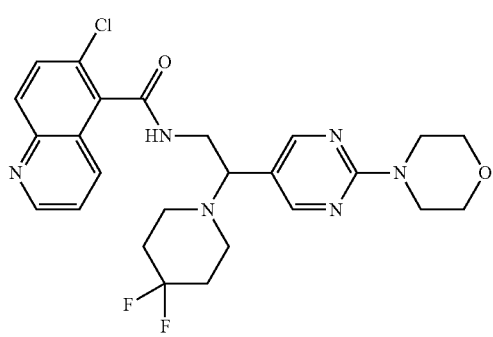
Co. No. 589; Ex. B.34; CF3CO2H
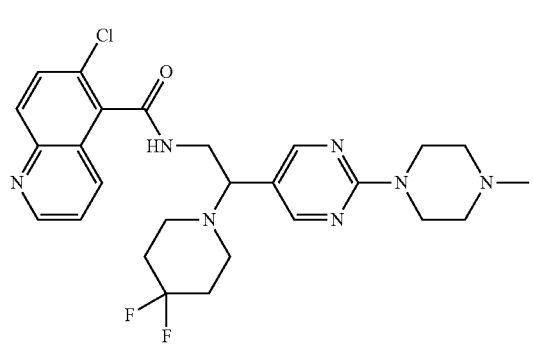
Co. No. 590; Ex. B.34; CF3CO2H
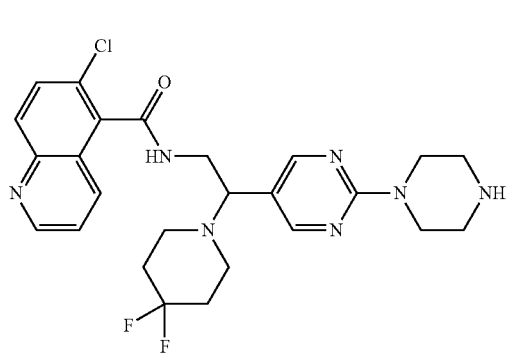
Co. No. 591; Ex. B.34; CF3CO2H
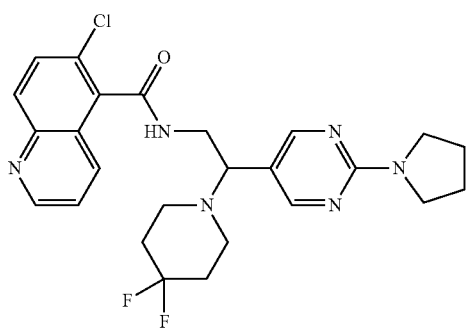
Co. No. 592; Ex. B.34; CF3CO2H TABLE F-4-continued
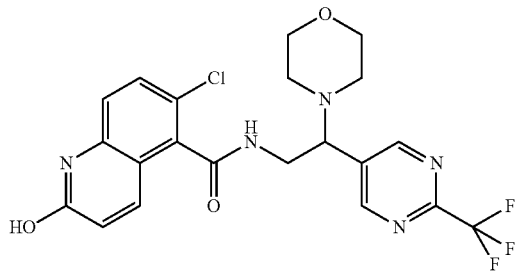
Co. No. 594; Ex. B.35; CF3CO2H
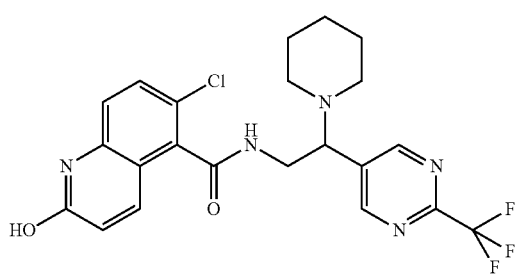
Co. No. 595; Ex. B.35; CF3CO2H
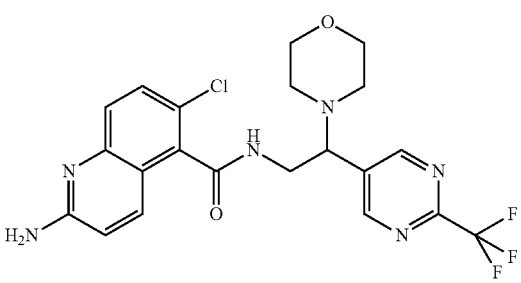
Co. No. 597; Ex. B.36; CF3CO2H
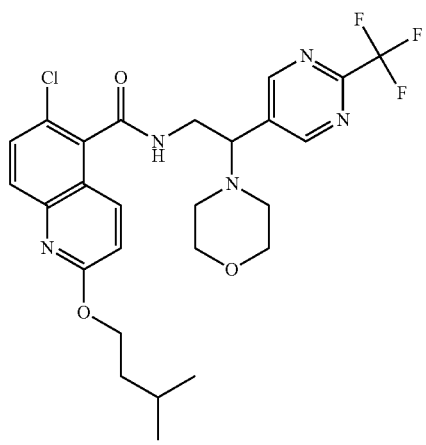
Co. No. 599; Ex. B.37; CF3CO2H
TABLE F-4-continued
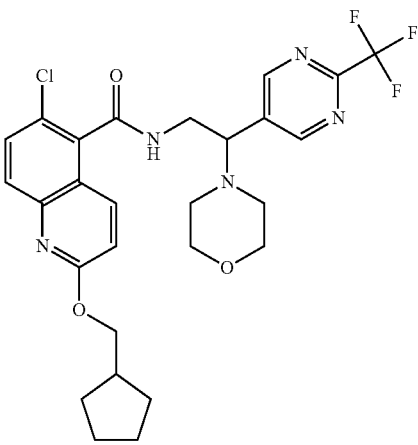
Co. No. 600; Ex. B.37; CF3CO2H
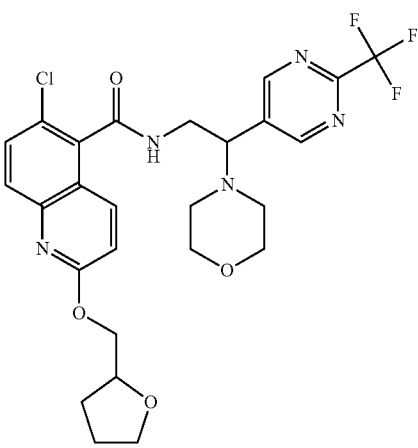
Co. No. 601; Ex. B.37; CF3CO2H
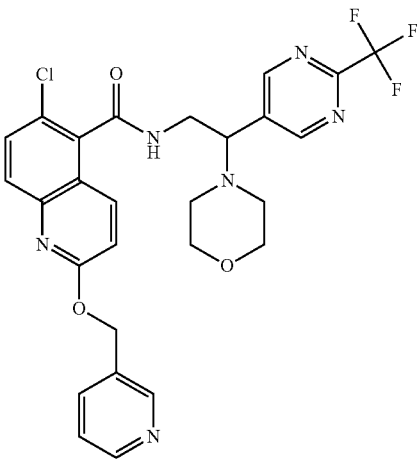
Co. No. 602; Ex. B.37; CF3CO2H TABLE F-4-continued
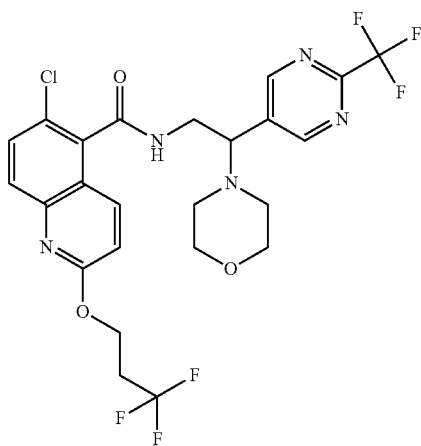
Co. No. 603; Ex. B.37; CF3CO2H
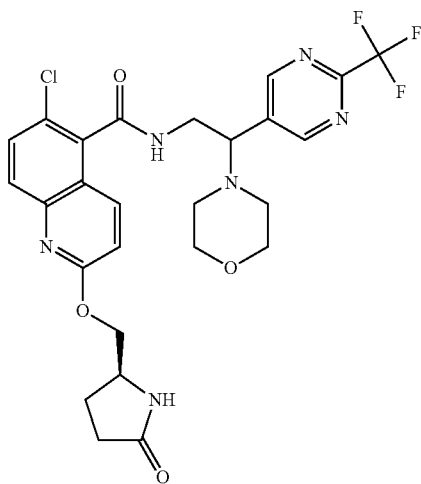
Co. No. 604; Ex. B.37; CF3CO2H
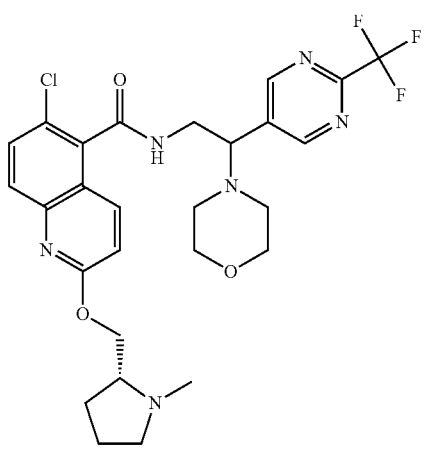
Co. No. 605; Ex. B.37; CF3CO2H
TABLE F-4-continued
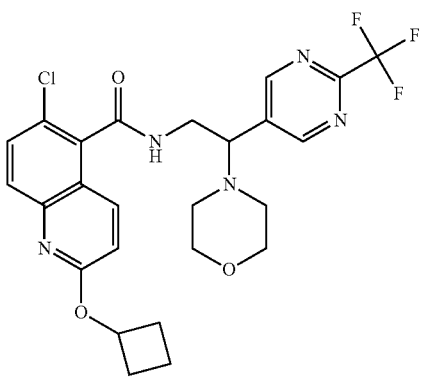
Co. No. 606; Ex. B.37; CF3CO2H
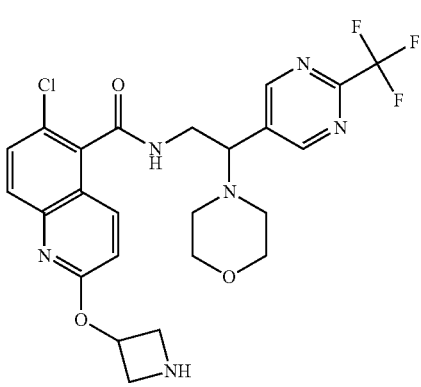
Co. No. 607; Ex. B.37; CF3CO2H
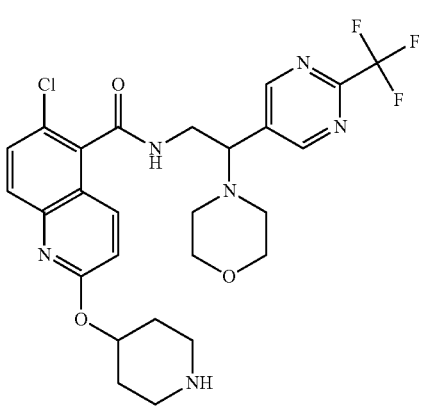
Co. No. 608; Ex. B.37; CF3CO2H TABLE F-4-continued
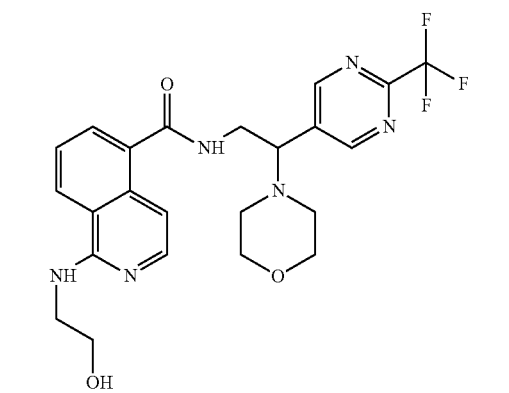
Co. No. 610; Ex. B.38;
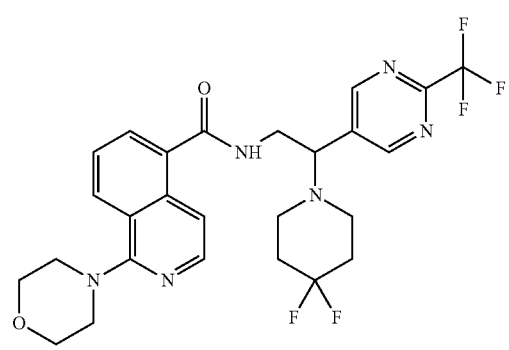
Co. No. 611; Ex. B.38;
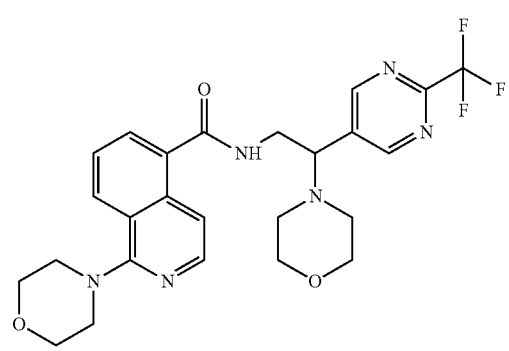
Co. No. 612; Ex. B.38
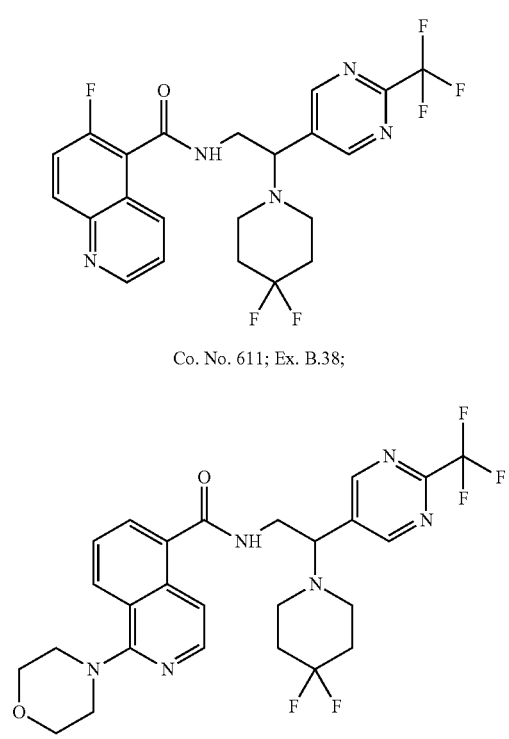
Co. No. 613; Ex. B.38
TABLE F-4-continued
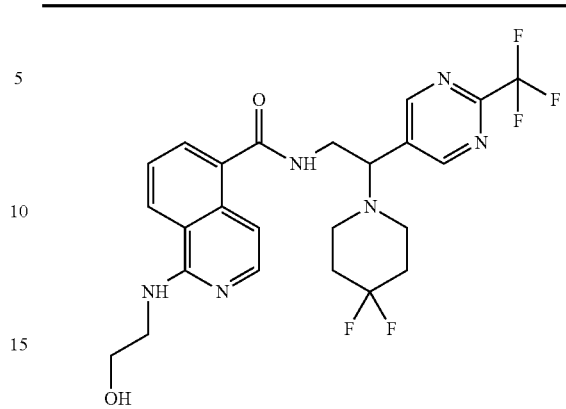
Co. No. 614; Ex. B.38
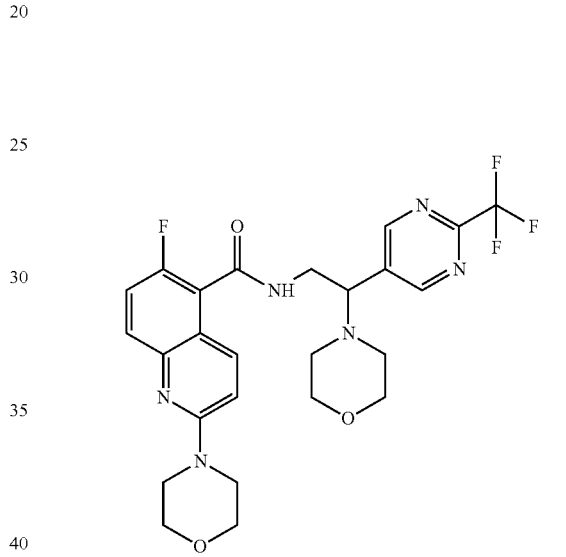
Co. No. 615; Ex. B.38
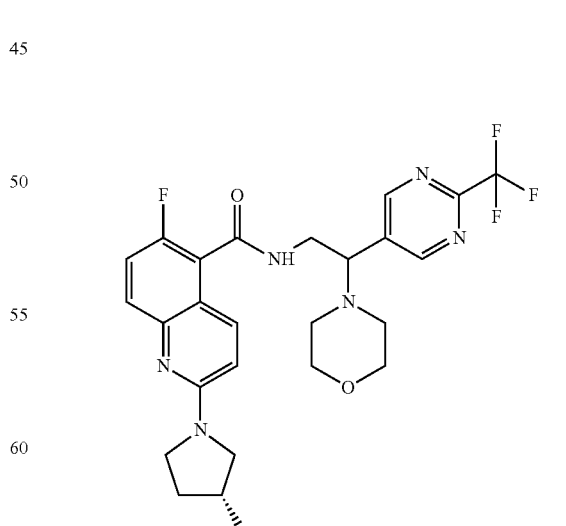
Co. No. 616; Ex. B.38; CF₃CO₂H TABLE F-4-continued
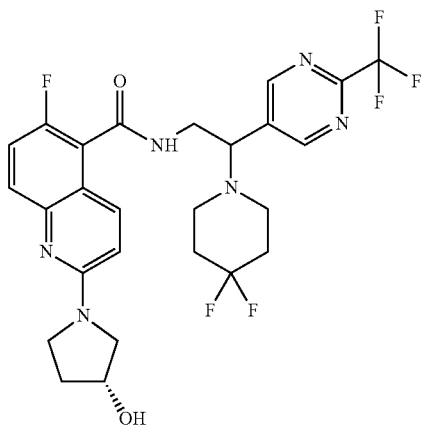
Co. No. 617; Ex. B.38; CF$_3$CO$_2$H
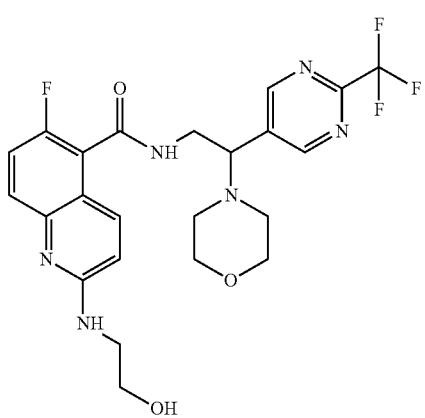
Co. No. 618; Ex. B.38; CF$_3$CO$_2$H
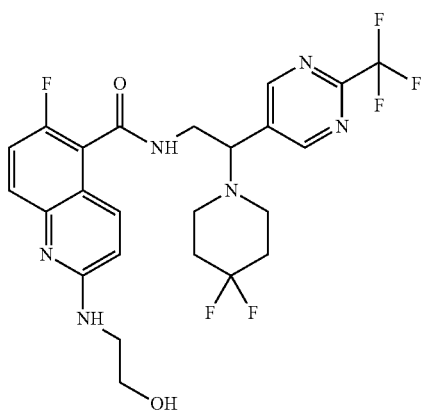
Co. No. 619; Ex. B.38; CF$_3$CO$_2$H
TABLE F-4-continued
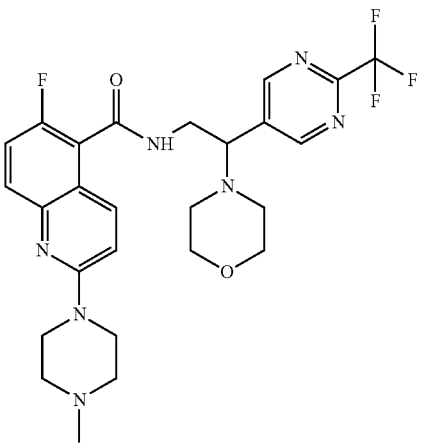
Co. No. 620; Ex. B.38; CF$_3$CO$_2$H
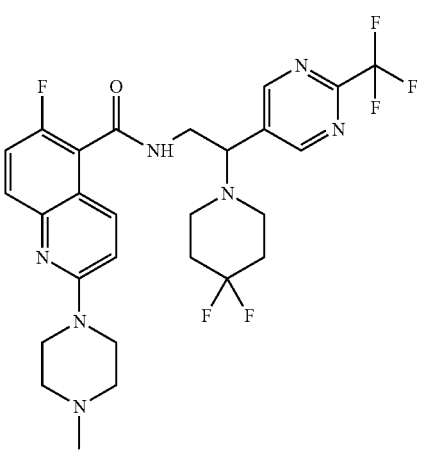
Co. No. 621; Ex. B.38; CF$_3$CO$_2$H
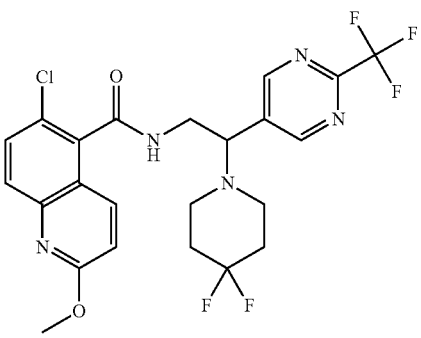
Co. No. 622; Ex. 37

TABLE F-4-continued
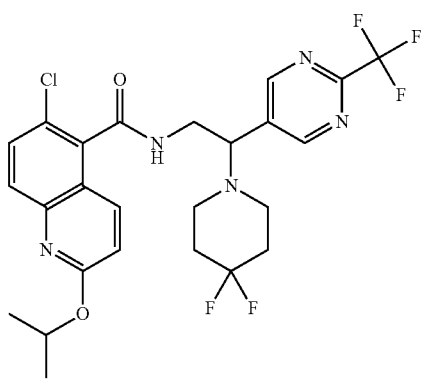
Co. No. 623; Ex. 37
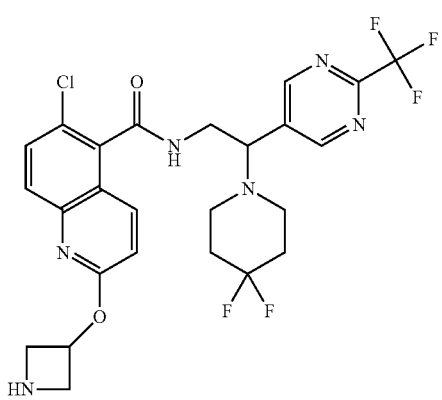
Co. No. 624; Ex. B.37; CF3CO2H
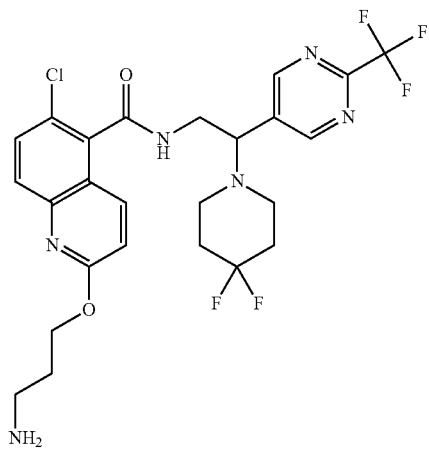
Co. No. 625; Ex. B.37
TABLE F-4-continued
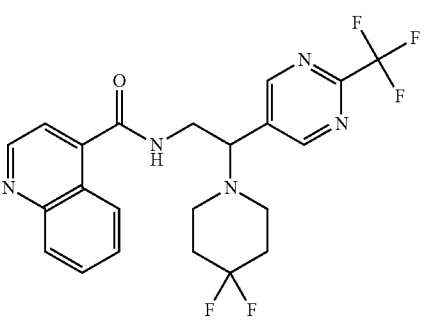
Co. No. 626; Ex. B.30
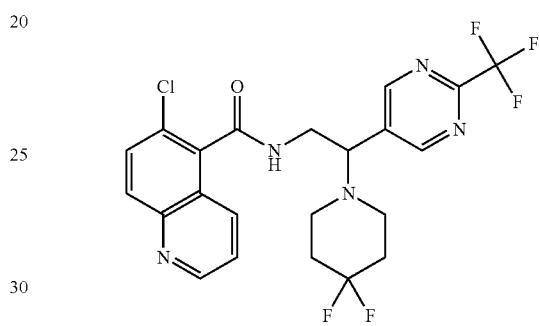
Co. No. 627; Ex. B.30
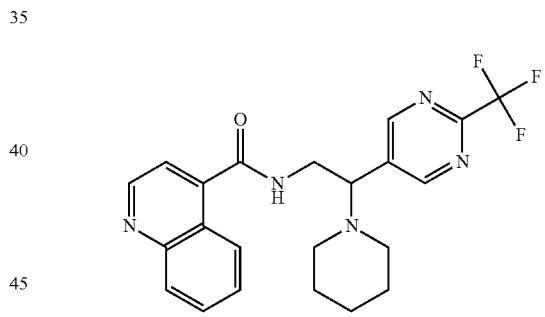
Co. No. 628; Ex. B.30
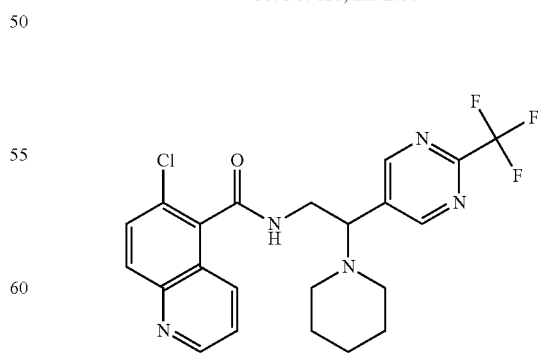
Co. No. 629; Ex. B.30

TABLE F-4-continued
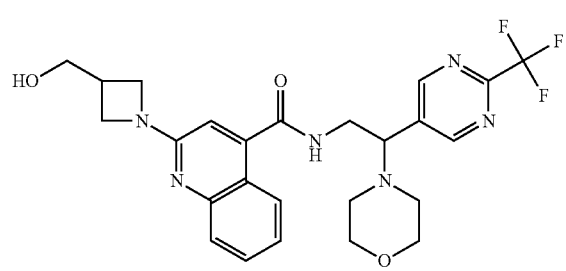
Co. No. 630; Ex. B.31
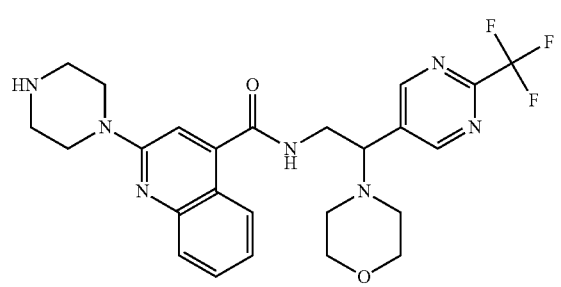
Co. No. 631; Ex. B.31; CF$_3$CO$_2$H
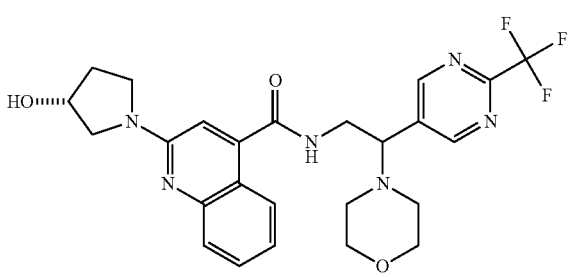
Co. No. 632; Ex. B.31; CF$_3$CO$_2$H
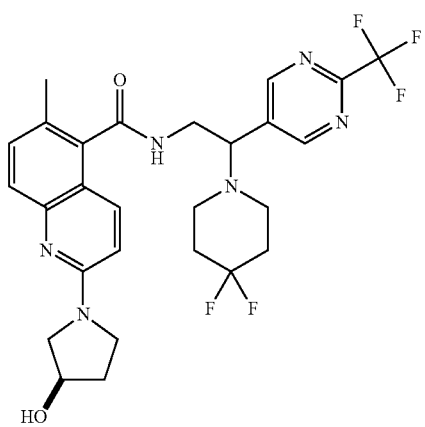
Co. No. 633; Ex. B.31; CF$_3$CO$_2$H
TABLE F-4-continued
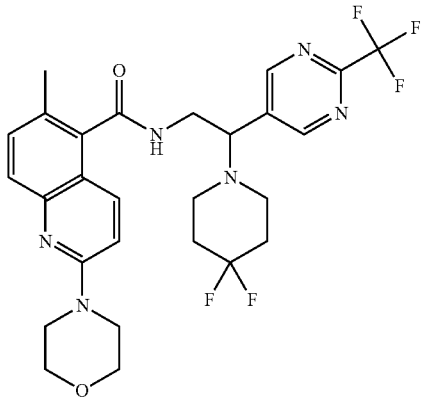
Co. No. 634; Ex. B.31; CF$_3$CO$_2$H
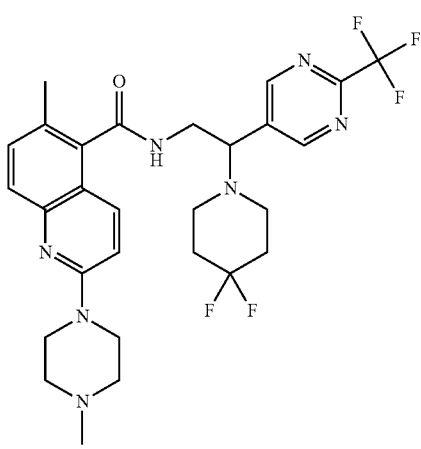
Co. No. 635; Ex. B.31; CF$_3$CO$_2$H
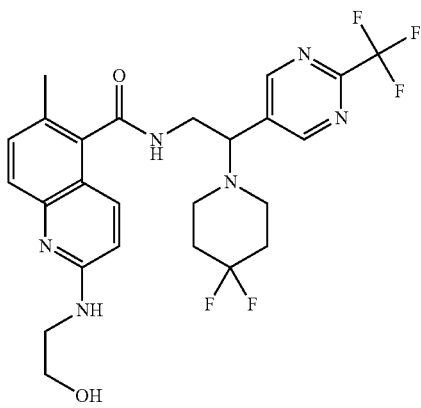
Co. No. 636; Ex. B.31; CF$_3$CO$_2$H TABLE F-4-continued
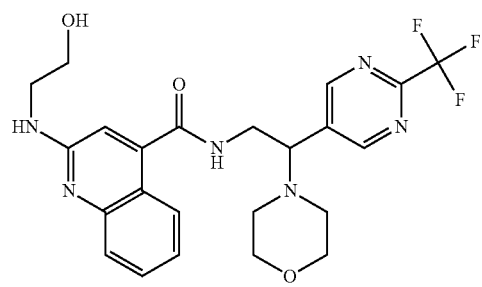
Co. No. 637; Ex. B.31; CF$_3$CO$_2$H
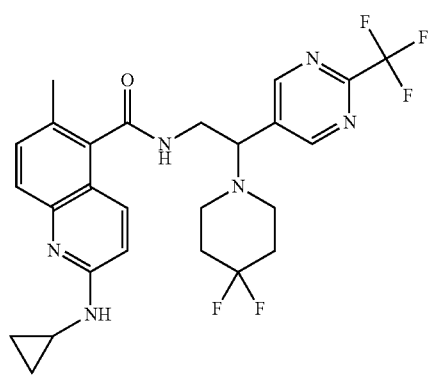
Co. No. 638; Ex. B.31; CF$_3$CO$_2$H
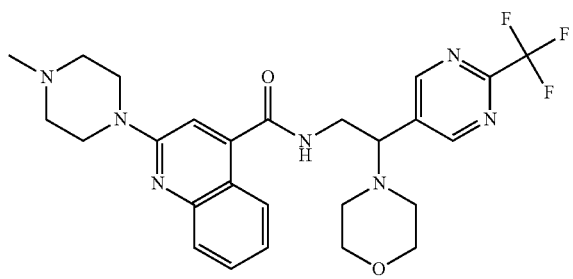
Co. No. 639; Ex. B.31; CF$_3$CO$_2$H
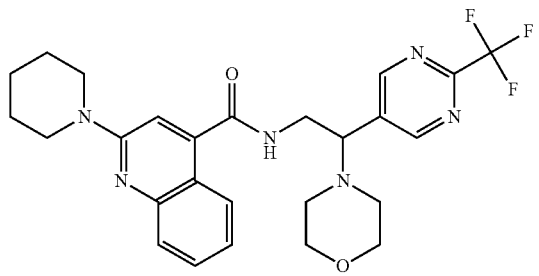
Co. No. 640; Ex. B.31; CF$_3$CO$_2$H
TABLE F-4-continued
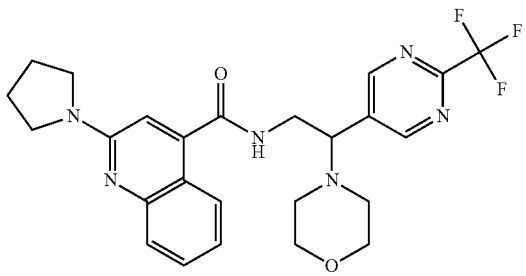
Co. No. 641; Ex. B.31; CF$_3$CO$_2$H
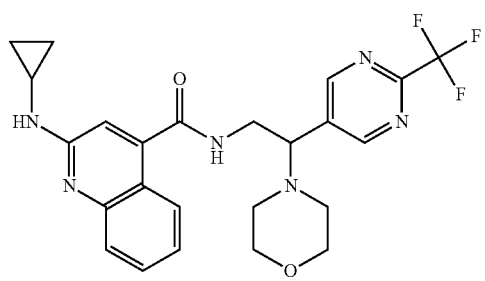
Co. No. 642; Ex. B.31; CF$_3$CO$_2$H
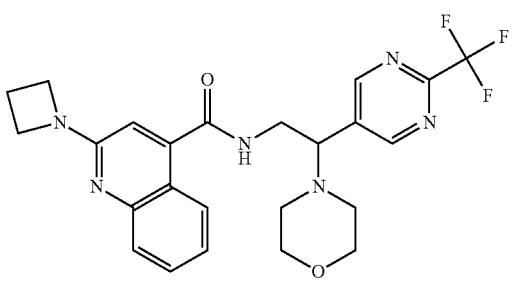
Co. No. 643; Ex. B.31; CF$_3$CO$_2$H
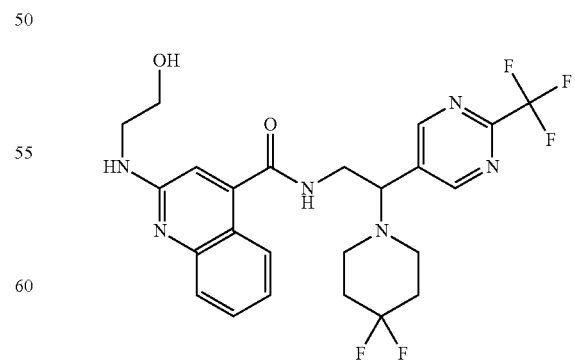
Co. No. 644; Ex. B.31; CF$_3$CO$_2$H TABLE F-4-continued
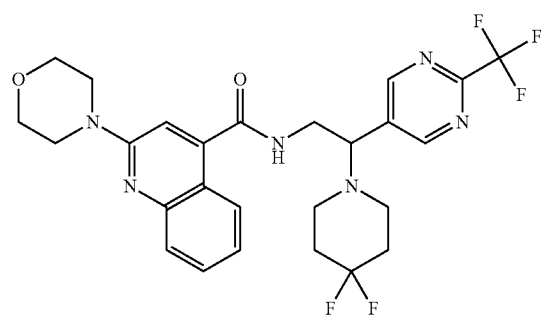
Co. No. 645; Ex. B.31; CF₃CO₂H
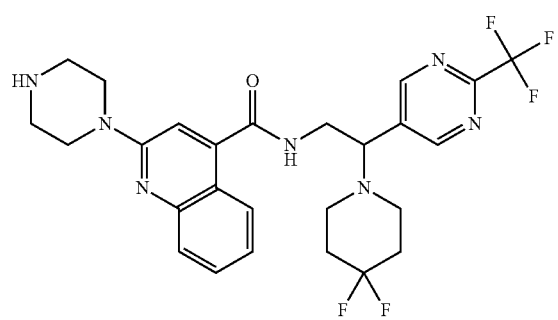
Co. No. 646; Ex. B.31; CF₃CO₂H
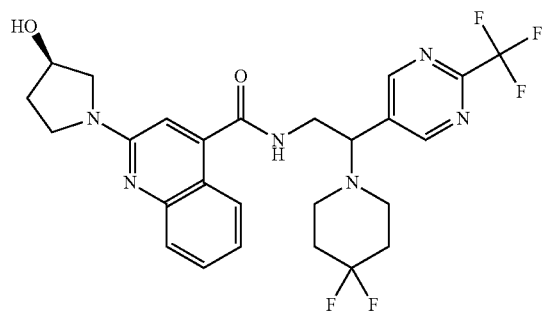
Co. No. 647; Ex. B.31; CF₃CO₂H
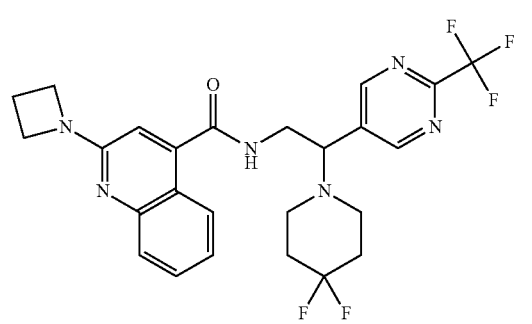
Co. No. 648; Ex. B.31; CF₃CO₂H
TABLE F-4-continued
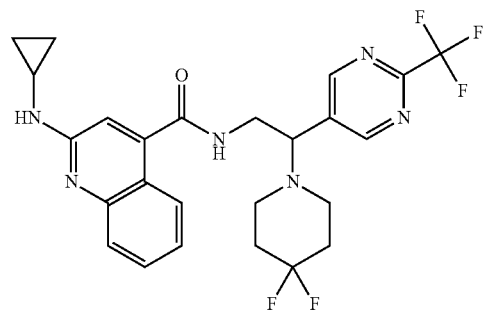
Co. No. 649; Ex. B.31; CF₃CO₂H
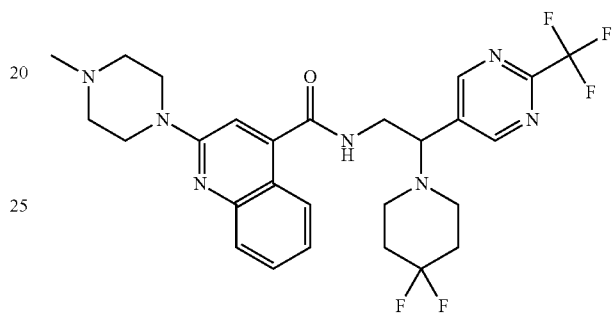
Co. No. 650; Ex. B.31; CF₃CO₂H
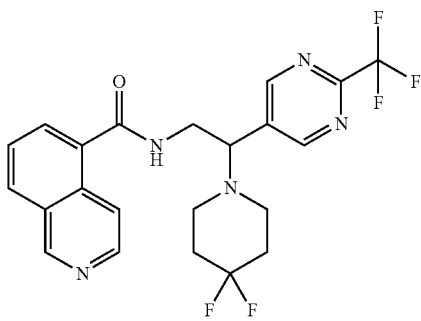
Co. No. 651; Ex. B.30; CF₃CO₂H
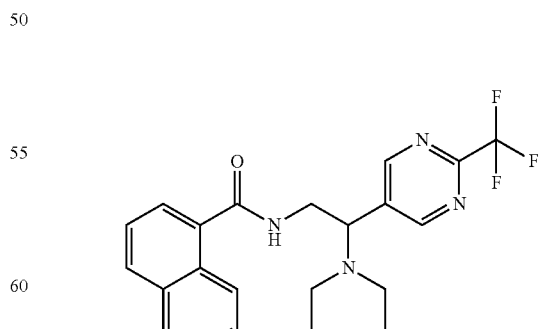
Co. No. 652; Ex. B.30; CF₃CO₂H TABLE F-4-continued

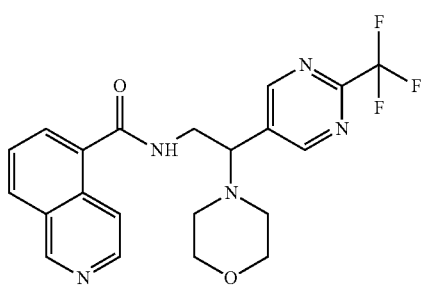

Co. No. 653; Ex. B.30; $CF_3CO_2H$

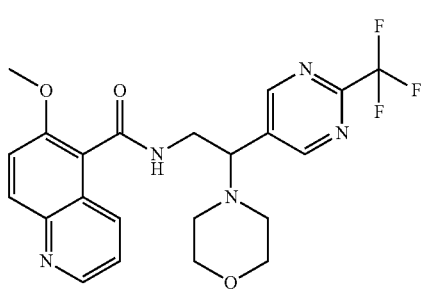

Co. No. 654; Ex. B.38; $CF_3CO_2H$

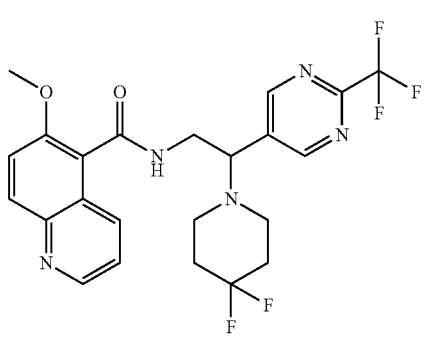

Co. No. 655; Ex. B.38; $CF_3CO_2H$

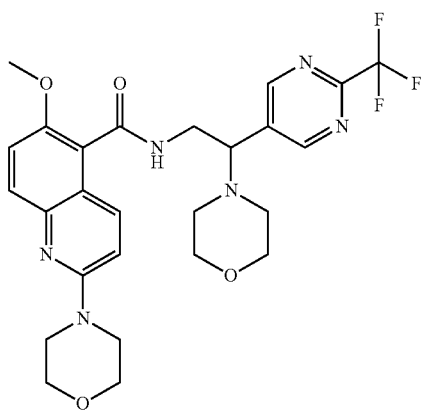

Co. No. 656; Ex. B.38; $CF_3CO_2H$

TABLE F-4-continued

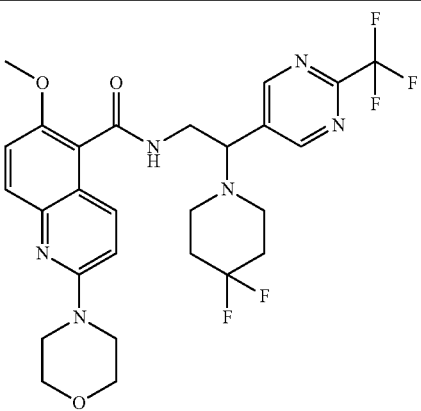

Co. No. 657; Ex. B.38; $CF_3CO_2H$

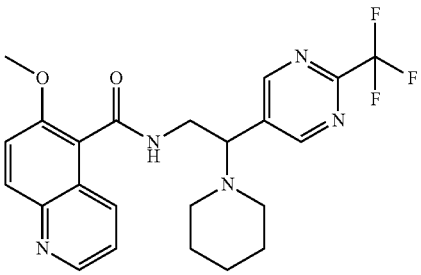

Co. No. 658; Ex. B.38; $CF_3CO_2H$

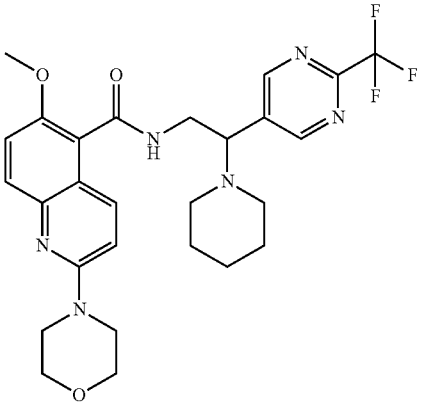

Co. No. 659; Ex. B.38; $CF_3CO_2H$

C. Analytical Part

C.1 Melting Points (a) For a number of compounds, melting points (m.p.) were determined with a DSC823e (Mettler-Toledo). Melting points were measured with a temperature gradient of 30° C./minute. The reported values are peak values.

(b) For a number of compounds, melting points (m.p.) were determined with a WRS-2A melting point apparatus that was purchased from Shanghai Precision and Scientific Instrument Co. Ltd. Melting points were measured with a linear heating up rate of 0.2-5.0° C./minute The reported values are melt ranges. The maximum temperature was 300° C.

(c) For a number of compounds, melting points were obtained with a Kofler hot bench, consisting of a heated plate with linear temperature gradient, a sliding pointer and a temperature scale in degrees Celsius.

Values were obtained with experimental uncertainties that are commonly associated with this analytical method.

TABLE F-5 melting points

| Co. No. | m.p. (° C.) |
|---|---|
| 1 | 199.1 (a) |
| 4 | 179 (c) |
| 5 | 176 (c) |
| 6 | 173 (c) |
| 7 | 187.3 (a) |
| 8 | 198 (c) |
| 10 | 208.9 (a) |
| 11 | 208.7 (a) |
| 26 | 175.8-176.2 (b) |
| 28 | 165.3-165.7 (b) |
| 29 | 155.0-162.2 (b) |
| 32 | 191.0-195.4 (b) |
| 33 | 219.2 (a) |
| 34 | 253.7-254.3 (b) |
| 35 | 183.6 (a) |
| 36 | 206.6 (a) |
| 37 | 211.9 (a) |
| 38 | 116.8 (a) |
| 39 | 125.3 (a) |
| 43 | 208.3 (a) |
| 44 | 180.9 (a) |
| 46 | 217.7 (a) |
| 47 | 217.7 (a) |
| 48 | 181.0 (a) |
| 49 | 159.8 (a) |
| 50 | 120.2 (a) |
| 51 | 199.6 (a) |
| 54 | 162.9 (a) |
| 55 | 151.0 (a) |
| 57 | 202.9 (a) |
| 58 | 231.6 (a) |
| 59 | 156.6 (a) |
| 60 | 228.3 (a) |
| 61 | 184.6 (a) |
| 62 | 177.9 (a) |
| 63 | 190.4 (a) |
| 64 | 154.3 (a) |
| 65 | 219.6 (a) |
| 67 | 171.2 (a) |
| 68 | 173.8 (a) |
| 69 | 160.6 (a) |
| 70 | 160.9 (a) |
| 74 | 218.2 (a) |
| 75 | 169.4 (a) |
| 76 | 214.6 (a) |
| 77 | 206.9 (a) |
| 78 | 202.9 (a) |
| 79 | 186.2 (a) |
| 80 | 210.8 (a) |
| 81 | 212.8 (a) |
| 82 | 212.9 (a) |
| 83 | 247.1 (a) |
| 84 | 246.3 (a) |
| 86 | 177.0 (a) |
| 88 | 231.2 (a) |
| 91 | 200.7 (a) |
| 92 | 167.2 (a) |
| 93 | 218.1 (a) |
| 96 | 160.0 (a) |
| 97 | 125.3 (a) |
| 99 | 190.3 (a) |
| 100 | 143.2 (a) |
| 101 | 165.0 (a) |
| 102 | 234.3 (a) |
| 103 | 141.3 (a) |
| 104 | 225.2 (a) |
| 105 | 207.6 (a) |

TABLE F-5-continued melting points

| Co. No. | m.p. (° C.) |
|---|---|
| 106 | 159.7 (a) |
| 108 | 163.1 (a) |
| 110 | 213.2 (a) |
| 111 | 215.9 (a) |
| 114 | 239.3 (a) |
| 123 | 126.1-127.0 (b) |
| 129 | 200.4 (a) |
| 130 | 192.4 (a) |
| 133 | 217.4 (a) |
| 134 | 236.3 (a) |
| 136 | 193.6 (a) |
| 137 | 189.0 (a) |
| 138 | 136.4 (a) |
| 139 | 225.0 (a) |
| 140 | 191.5 (a) |
| 141 | 204.6 (a) |
| 143 | 222.9 (a) |
| 145 | 193.6-196.0 (b) |
| 148 | 214.5 (a) |
| 150 | 128.3 (a) |
| 151 | 196.4 (a) |
| 152 | 187.1 (a) |
| 153 | 158.1 (a) |
| 157 | 122.7-126.5 (b) |
| 158 | 158.2-161.0 (b) |
| 159 | 120.8-124.0 (b) |
| 160 | 186.6-187.3 (b) |
| 165 | 214.4 (a) |
| 315 | 2461-253.9 (b) |

C.2 LCMS

LCMS General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS General Procedure C

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50V. Drying gas temperature was maintained at 350° C. at a flow of 10 l/min.

LCMS—Procedure 1

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µA was used. Cone voltage was 10 V for positive ionization mode and 20 V for negative ionization mode.

LCMS—Procedure 2

In addition to general procedure A: Reversed phase HPLC was carried out on an Atlantis C18 column (3.5 µm, 4.6×100 mm) (3.5 µm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 µl was used. Cone voltage was 10 V for positive ionization mode and 20 V for negative ionization mode.

LCMS—Procedure 3

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µA was used. Cone voltage was 10 V for positive ionization mode and 20 V for negative ionization mode.

LCMS—Procedure 4

In addition to general procedure C: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 µl were used. Oven temperature was 50° C. (MS polarity: positive)

LCMS—Procedure 5

In addition to general procedure B: Reversed phase HPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

LCMS—Procedure 6

In addition to general procedure C: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 70% A and 30% B in 4.5 minutes and hold for 2 minutes. Typical injection volumes of 2 µl were used. Oven temperature was 50° C. (MS polarity: positive).

LCMS—Procedure 7

In addition to general procedure C: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive).

LCMS—Procedure 8

In addition to general procedure A: Reversed phase HPLC was carried out on an Ultimate XB-C18, 50×2.1 mm 5 µm column with a flow rate of 0.8 ml/min. Two mobile phases (mobile phase C: 10 mmol/L $NH_4HCO_3$; mobile phase D: acetonitrile) were used. First, 100% C was hold for 1 minute. Then a gradient was applied to 40% C and 60% D in 4 minutes and hold for 2.5 minutes. Typical injection volumes of 2 µl were used. Oven temperature was 50° C. (MS polarity: positive).

TABLE F-6

Retention time ($R_t$) in minutes, $[M + H]^+$ peak, LCMS procedure

| Co. No. | $R_t$ | $[M + H]^+$ | LCMS Procedure |
|---|---|---|---|
| 3 | 4.56 | 431 | 3 |
| 12 | 1.44 | 495 | 5 |
| 5 | 1.28 | 465 | 5 |
| 14 | 1.39 | 465 | 5 |
| 15 | 3.30 | 386 | 7 |
| 16 | 1.11 | 465 | 5 |
| 18 | 1.34 | 507 | 5 |
| 19 | 1.22 | 465 | 5 |
| 24 | 1.25 | 507 | 5 |
| 25 | 3.45 | 397 | 7 |
| 27 | 3.36 | 505 | 4 |
| 29 | 3.29 | 555 | 4 |
| 31 | 4.40 | 431 | 1 |
| 41 | 8.00 | 496 | 2 |
| 42 | 6.46 | 535 | 2 |
| 45 | 4.86 | 416 | 1 |
| 52 | 5.00 | 444 | 2 |
| 66 | 5.18 | 466 | 1 |
| 71 | 5.06 | 448 | 1 |
| 72 | 4.62 | 446 | 1 |
| 73 | 5.82 | 444 | 1 |
| 87 | 5.06 | 531 | 2 |
| 89 | 4.37 | 505 | 2 |
| 90 | 4.63 | 519 | 2 |
| 94 | 5.31 | 559 | 2 |
| 95 | 5.10 | 501 | 2 |
| 96 | 5.14 | 497 | 2 |
| 98 | 3.58 | 461 | 7 |
| 106 | 7.52 | 650 | 2 |
| 107 | 6.83 | 628 | 2 |
| 109 | 5.22 | 528 | 3 |
| 113 | 6.35 | 478 | 2 |
| 116 | 3.21 | 490 | 7 |
| 117 | 4.46 | 436 | 7 |
| 118 | 3.29 | 504 | 7 |
| 119 | 3.71 | 475 | 7 |
| 120 | 3.60 | 491 | 7 |
| 121 | 4.17 | 422 | 7 |
| 122 | 3.34 | 463 | 7 |
| 124 | 0.91 | 550 | 5 |

TABLE F-6-continued

Retention time ($R_t$) in minutes, [M + H]$^+$ peak, LCMS procedure

| Co. No. | $R_t$ | [M + H]$^+$ | LCMS Procedure |
|---|---|---|---|
| 127 | 5.61 | 550 | 2 |
| 128 | 4.13 | 530 | 2 |
| 132 | 4.05 | 485 | 1 |
| 135 | 4.71 | 446 | 3 |
| 142 | 7.77 | 482 | 2 |
| 144 | 3.29 | 499 | 7 |
| 146 | 6.33 | 579 | 2 |
| 155 | 4.61 | 519 | 3 |
| 161 | 4.07 | 545 | 7 |
| 162 | 4.13 | 501 | 7 |
| 163 | 3.12 | 515 | 4 |
| 164 | 8.39 | 500 | 2 |
| 166 | 5.15 | 476 | 7 |
| 167 | 4.57 | 530 | 6 |
| 168 | 4.09 | 489 | 7 |
| 175 | 5.57 | 521 | 1 |
| 176 | 3.9 | 552 | 7 |
| 177 | 4.53 | 551 | 7 |
| 178 | 4.03 | 531 | 7 |
| 179 | 3.3 | 515 | 4 |
| 180 | 3.27 | 503 | 4 |
| 181 | 5.15 | 558 | 6 |
| 182 | 4.46 | 547 | 7 |
| 183 | 5.91 | 501 | 6 |
| 184 | 5.52 | 489 | 8 |
| 185 | 4.09 | 519 | 7 |
| 186 | 6.13 | 536 | 8 |
| 187 | 4.8 | 498 | 8 |
| 188 | 5.51 | 526 | 8 |
| 189 | 5.21 | 538 | 8 |
| 190 | 5.52 | 522 | 8 |
| 191 | 3.41 | 559 | 4 |
| 192 | 3.69 | 483 | 7 |
| 193 | 3.49 | 529 | 4 |
| 194 | 4.7 | 468 | 8 |
| 195 | 3.8 | 496 | 7 |
| 196 | 3.64 | 557 | 4 |
| 197 | 4.8 | 560 | 8 |
| 198 | 3.58 | 530 | 7 |
| 199 | 4.83 | 533 | 8 |
| 200 | 5.4 | 554 | 8 |
| 201 | 6.19 | 600 | 8 |
| 202 | 4.86 | 537 | 8 |
| 203 | 5.57 | 609 | 8 |
| 204 | 6.19 | 537 | 8 |
| 205 | 5.39 | 538 | 8 |
| 206 | 5.53 | 510 | 8 |
| 207 | 4.31 | 447 | 8 |
| 208 | 5.09 | 467 | 8 |
| 209 | 5.56 | 567 | 8 |
| 210 | 4.9 | 475 | 8 |
| 211 | 5.27 | 467 | 8 |
| 212 | 5.57 | 511 | 8 |
| 213 | 5.97 | 592 | 8 |
| 214 | 5.82 | 523 | 8 |
| 215 | 5.63 | 593 | 8 |
| 216 | 5.27 | 522 | 8 |
| 217 | 5.56 | 495 | 8 |
| 218 | 4.74 | 476 | 8 |
| 219 | 4.85 | 502 | 8 |
| 220 | 5.27 | 511 | 8 |
| 221 | 5.22 | 481 | 8 |
| 222 | 5.21 | 593 | 8 |
| 223 | 5.17 | 551 | 8 |
| 224 | 5.54 | 552 | 8 |
| 225 | 5.61 | 536 | 8 |
| 226 | 4.88 | 482 | 8 |
| 227 | 5.29 | 491 | 8 |
| 228 | 4.74 | 493 | 8 |
| 229 | 4.67 | 463 | 8 |
| 230 | 4.79 | 491 | 8 |
| 231 | 4.76 | 461 | 8 |
| 232 | 4.66 | 492 | 8 |
| 233 | 4.6 | 462 | 8 |
| 234 | 6.05 | 537 | 8 |
| 235 | 5.72 | 541 | 8 |
| 236 | 5.66 | 511 | 8 |
| 237 | 6.37 | 543 | 8 |
| 238 | 5.86 | 521 | 8 |
| 239 | 5.87 | 553 | 8 |
| 240 | 5.41 | 593 | 8 |
| 241 | 4.97 | 507 | 8 |
| 242 | 4.91 | 477 | 8 |
| 243 | 5.04 | 477 | 8 |
| 244 | 5.12 | 475 | 8 |
| 245 | 4.97 | 476 | 8 |
| 246 | 5.8 | 553 | 8 |
| 247 | 5.74 | 523 | 8 |
| 248 | 5.98 | 525 | 8 |
| 249 | 5.93 | 551 | 8 |
| 250 | 5.13 | 609 | 8 |
| 251 | 5.07 | 579 | 8 |
| 252 | 5.7 | 552 | 8 |
| 253 | 5.52 | 527 | 8 |
| 254 | 5.46 | 497 | 8 |
| 255 | 4.81 | 518 | 8 |
| 256 | 4.92 | 453 | 8 |
| 257 | 5.8 | 511 | 8 |
| 258 | 5.87 | 509 | 8 |
| 259 | 4.74 | 488 | 8 |
| 260 | 5.56 | 497 | 8 |
| 261 | 5.53 | 495 | 8 |
| 262 | 5.86 | 536 | 8 |
| 263 | 5.49 | 522 | 8 |
| 264 | 5.1 | 502 | 8 |
| 265 | 5.6 | 525 | 8 |
| 266 | 5.76 | 510 | 8 |
| 267 | 5.06 | 482 | 8 |
| 268 | 4.97 | 483 | 8 |
| 269 | 5.47 | 568 | 8 |
| 270 | 5.14 | 508 | 8 |
| 271 | 3.47 | 530 | 7 |
| 272 | 3.98 | 503 | 7 |
| 273 | 3.31 | 543 | 4 |
| 274 | 3.58 | 544 | 7 |
| 275 | 5.89 | 529 | 8 |
| 276 | 3.66 | 571 | 4 |
| 277 | 4.28 | 573 | 7 |
| 278 | 3.89 | 519 | 7 |
| 279 | 3.99 | 503 | 7 |
| 280 | 6.41 | 572 | 8 |
| 281 | 3.68 | 574 | 7 |
| 282 | 5.38 | 495 | 8 |
| 283 | 6.23 | 543 | 8 |
| 284 | 5.07 | 491 | 8 |
| 285 | 4.96 | 559 | 8 |
| 286 | 5.38 | 497 | 8 |
| 287 | 4.95 | 567 | 8 |
| 288 | 4.99 | 532 | 8 |
| 289 | 5.15 | 548 | 8 |
| 290 | 3.37 | 461 | 7 |
| 291 | 5.93 | 594 | 8 |
| 292 | 5.42 | 552 | 8 |
| 293 | 5.98 | 535 | 8 |
| 294 | 5.96 | 537 | 8 |
| 295 | 4.74 | 518 | 8 |
| 296 | 4.68 | 461 | 8 |
| 297 | 5.14 | 524 | 8 |
| 298 | 5.64 | 568 | 8 |
| 299 | 5.69 | 566 | 8 |
| 300 | 5.98 | 594 | 8 |
| 301 | 3.28 | 551 | 7 |
| 302 | 4.97 | 539 | 8 |
| 303 | 4.85 | 477 | 8 |
| 304 | 5.92 | 537 | 8 |
| 305 | 5.83 | 525 | 8 |
| 306 | 5.85 | 582 | 8 |
| 307 | 5.99 | 535 | 8 |
| 308 | 5.66 | 509 | 8 |
| 309 | 5.28 | 650 | 8 |

TABLE F-6-continued

Retention time ($R_t$) in minutes, $[M + H]^+$ peak, LCMS procedure

| Co. No. | $R_t$ | $[M + H]^+$ | LCMS Procedure |
|---|---|---|---|
| 310 | 4.94 | 534 | 8 |
| 311 | 4.38 | 477 | 8 |
| 312 | 5.33 | 608 | 8 |
| 313 | 3.67 | 519 | 7 |
| 314 | 3.78 | 517 | 7 |

TABLE F-7

Retention time ($R_t$) in minutes, $[M - H]^-$ peak, LCMS procedure

| Co. No. | $R_t$ | $[M - H]^-$ | LCMS Procedure |
|---|---|---|---|
| 56 | 4.83 | 549 | 3 |
| 112 | 5.53 | 498 | 3 |
| 154 | 5.66 | 531 | 2 |
| 40 | 4.72 | 537 | 3 |

C.3 Optical Rotation

The optical rotation was measured using a Perkin Elmer 341 polarimeter. $[\alpha]_D^{20}$ indicates the optical rotation measured with light at the wavelength of the D-line of sodium (589 nm) at a temperature of 20° C.*. The cell pathlength is 10 cm. Behind the actual value the concentration and solvent of the solution which was used to measure the optical rotation are mentioned.

*The optical rotation of compound (10) was measured at 23° C. (measured without temperature regulator).

TABLE F-8 optical rotation

| Co. No. | $[\alpha]_D^{20}$ | concentration | solvent |
|---|---|---|---|
| 10 | +7.70° | 0.4418 w/v % | DMF (23° C.) |
| 46 | +8.07° | 0.2726 w/v % | MeOH |
| 47 | −9.13° | 0.4052 w/v % | MeOH |
| 67 | +9.09° | 0.3850 w/v % | MeOH |
| 68 | −11.25° | 0.4444 w/v % | MeOH |
| 69 | +8.31° | 0.4212 w/v % | MeOH |
| 70 | −11.28° | 0.3636 w/v % | MeOH |
| 83 | +9.77° | 0.5934 w/v % | MeOH |
| 84 | −10.70° | 0.3926 w/v % | MeOH |
| 114 | +9.56° | 0.3662 w/v % | MeOH |
| 124 | −8.08° | 0.3838 w/v % | MeOH |
| 169 | −9.35° | 0.3744 w/v % | MeOH |
| 174 | −10.88° | 0.3954 w/v % | MeOH |
| 175 | +9.98° | 0.4310 w/v % | MeOH |

C.4 SEC-MS

For some compounds SFC-MS (Supercritical fluid chromatography-mass spectrometry) was measured with an analytical SFC system from Berger Instruments (Newark, Del., USA) comprising a dual pump control module (FCM-1200) for delivery of carbon dioxide ($CO_2$) and modifier, a thermal control module for column heating (TCM2100) with temperature control in the range of 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

For Co. No. (10) an enantiomeric excess of 100.0% was detected when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed to run a gradient from 10% B to 40% B at a rate of 1.6%/minute. Then a gradient was applied from 40% B to 50% B in 2 minutes and hold for 3.6 minutes. Column temperature was set at 50° C. This measurement was compared against the racemic mixture.

For Co. No. (67) an enantiomeric excess of 100.0% was detected when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed. First 30% B (and 70% A) was hold for 18.5 minutes. Then a gradient was applied from 30% B to 50% B in 2 minutes and hold for 4.1 minutes. Column temperature was set at 50° C. This measurement was compared against the racemic mixture.

Identical SFC-MS conditions as for Co. No. (67), were used for the SFC-MS measurements of Co. No. (68), (69), (70).

For Co. No. (83) an enantiomeric excess of 100.0% was detected when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed. First 40% B (and 60% A) was hold for 19.5 minutes. Then a gradient was applied from 40% B to 50% B in 2 minutes and hold for 4.1 minutes. Column temperature was set at 50° C. This measurement was compared against the racemic mixture.

Identical SFC-MS conditions as for Co. No. (83), were used for the SFC-MS measurements of Co. No. (84).

For Co. No. (110) an enantiomeric excess of 100.0% was detected when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed. First 35% B (and 65% A) was hold for 19.0 minutes. Then a gradient was applied from 35% B to 50% B in 1.5 minutes and hold for 4.1 minutes. Column temperature was set at 50° C. This measurement was compared against the racemic mixture.

Identical SFC-MS conditions as for Co. No. (110), were used for the SFC-MS measurements of Co. No. (111).

For Co. No. (114) an enantiomeric excess of 100.0% was detected when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: ethanol containing 0.2% 2-propylamine) were employed. First 25% B (and 75% A) was hold for 18.0 minutes. Then a gradient was applied from 25% B to 50% B in 2.5 minutes and hold for 4.1 minutes. Column temperature was set at 50° C. This measurement was compared against the racemic mixture.

Identical SFC-MS conditions as for Co. No. (114), were used for the SFC-MS measurement of Co. No. (124).

For Co. No. (115) an enantiomeric excess of 100.0% was detected when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed. First 40% B (and 60% A) was hold for 19.5 minutes. Then a gradient was applied from 40% B to 50% B in 1 minute and hold for 4.1 minutes. Column temperature was set at 50° C. This measurement was compared against the racemic mixture.

For Co. No. (138) an enantiomeric excess was found of 100% when a screening (no racemic mixture available to compare) was performed with 4 different columns (Chiralcel OJ-H, Chiralpak AD-H, Chiralcel OD-H, Chiralpak AS-H; 500×4.6 mm; Daicel Chemical Industries Ltd) and 3 different solvents (MeOH, EtOH, 2-propanol; the solvent is containing 0.2% 2-propylamine). SFC-MS was carried out with one of the columns mentioned above with a flow rate of 3 ml/min. Two mobile phases (mobile phase A: $CO_2$; mobile phase B: one of the solvents mentioned above containing 0.2% 2-propylamine) were employed to run a condition from 10% B to 40% B in 18.75 minutes. Then a gradient was applied from 40% B to 50% B in 2 minutes and hold for 3.6 minutes. Column temperature was set at 50° C.

C.5 NMR

For a number of compounds, $^1$H NMR spectra were recorded on a Bruker DPX-360, on a Bruker DPX-400 or on a Bruker Avance 500 spectrometer with standard pulse sequences, operating at 360 MHz, 400 MHz and 500 MHz respectively, using CHLOROFORM-d or DMSO-$d_6$ as solvents. Chemical shifts (δ) are reported in parts per million (ppm) relative to tetramethylsilane (TMS), which was used as internal standard.

| Co. No. | Solvent | NMR data |
|---|---|---|
| 83 | CDCl3 | δ ppm 1.98-2.10 (m, 4 H), 2.59-2.73 (m, 4 H), 3.73 (t, J = 4.8 Hz, 4 H), 3.85 (t, J = 4.8 Hz, 4 H), 3.89-4.08 (m, 3 H), 6.26 (t, J = 5.3 Hz, 1 H), 6.98 (d, J = 9.5 Hz, 1 H), 7.25 (d, J = 7.1 Hz, 1 H), 7.51 (t, J = 7.8 Hz, 1 H), 7.79 (d, J = 8.5 Hz, 1 H), 8.28 (d, J = 9.5 Hz, 1 H), 8.88 (s, 2 H) |
| 127 | CDCl3 | δ ppm 1.76-1.96 (m, 4 H), 2.46-2.53 (m, 1 H), 2.56-2.64 (m, 1 H), 2.65-2.72 (m, 1 H), 2.82 (q, J = 10.9 Hz, 1 H), 3.00-3.05 (m, 4 H), 3.72-3.80 (m, 4 H), 3.95-4.01 (m, 2 H), 4.04-4.08 (m, 1 H), 6.46 (t, J = 5.4 Hz, 1 H), 7.01 (d, J = 9.5 Hz, 1 H), 7.31 (d, J = 7.2 Hz, 1 H), 7.50 (dd, J = 8.5, 7.1 Hz, 1 H), 7.79 (d, J = 8.4 Hz, 1 H), 8.37 (d, J = 9.5 Hz, 1 H), 8.87 (s, 2 H) |
| 175 | CDCl3 | δ ppm 0.59-0.65 (m, 2 H), 0.85-0.92 (m, 2 H), 1.97-2.11 (m, 4 H), 2.58-2.74 (m, 5 H), 3.89-4.08 (m, 3 H), 5.37 (br. s., 1 H), 6.32 (t, J = 5.2 Hz, 1 H), 7.09 (d, J = 9.3 Hz, 1 H), 7.23 (dd, J = 7.1, 1.1 Hz, 1 H), 7.49 (dd, J = 8.5, 7.1 Hz, 1 H), 7.71 (d, J = 8.5 Hz, 1 H), 8.28 (d, J = 9.3 Hz, 1 H), 8.88 (s, 1 H) |
| 403 | (CD3)2SO | 9.12 (s, 2H), 8.72 (s, 1H), 7.76 (d, J = 9.4, 1H), 7.56 (d, J = 9.0, 1H), 7.51 (d, J = 9.0, 1H), 7.24 (d, J = 9.5, 1H), 4.19 (t, J = 7.3, 1H), 4.06-3.95 (m, J = 16.3, 6.6, 1H), 3.95-3.84 (m, 1H), 3.75-3.69 (m, J = 5.1, 4H), 3.68-3.62 (m, J = 5.2, 4H), 2.71-2.60 (m, 2H), 2.60-2.52 (m, 2H), 2.05-1.91 (m, 4H). |
| 404 | CD3OD | 9.11 (s, 2H), 8.07-7.72 (m, 3H), 7.16 (br s, 1H), 4.33-4.08 (m, 3H), 3.79 (t, J = 4.6, 4H), 3.68 (d, J = 7.4, 2H), 3.58 (dd, J = 11.9, 7.9, 1H), 3.46 (ddd, J = 8.1, 6.5, 3.3, 1H), 3.37-3.33 (m, 1H), 3.19-3.05 (m, 1H), 2.97-2.74 (m, 5H), 2.35 (td, J = 12.8, 7.6, 1H), 1.86 (dq, J = 13.4, 8.4, 1H). |
| 406 | CD3OD | 9.09 (s, 2H), 8.05 (d, J = 9.7, 1H), 7.96-7.84 (m, 1H), 7.74 (d, J = 9.1, 1H), 7.22 (d, J = 9.7, 1H), 4.37-3.97 (m, 7H), 3.89-3.71 (m, 5H), 3.03 (s, 6H), 2.90-2.64 (m, 5H), 2.53-2.37 (m, 1H). |
| 407 | CD3OD | 9.15 (s, 2H), 8.11 (d, J = 9.8, 1H), 7.95 (d, J = 9.1, 1H), 7.77 (d, J = 9.1, 1H), 7.28 (d, J = 9.8, 1H), 4.45 (dd, J = 8.9, 5.5, 1H), 4.38-4.03 (m, 6H), 3.93-3.77 (m, 5H), 3.10-2.96 (m, 7H), 2.96-2.81 (m, 2H), 2.80-2.64 (m, 1H), 2.56-2.41 (m, 1H). |
| 408 | CD3OD | 9.09 (s, 2H), 7.83 (d, J = 9.4, 1H), 7.68 (dd, J = 9.1, 0.6, 1H), 7.54 (d, J = 9.0, 1H), 7.27 (d, J = 9.4, 1H), 4.35-4.03 (m, 3 H), 3.82-3.75 (m, 4H), 3.71-3.33 (m, 8H), 3.07 (d, J = 7.3, 2H), 2.93-2.69 (m, 4H), 2.23 (dt, J = 13.6, 6.8, 1H), 1.09 (d, J = 6.6, 6H). |
| 409 | CD3OD | 9.11 (s, 2H), 7.84 (d, J = 9.4, 1H), 7.70 (d, J = 9.1, 1H), 7.54 (d, J = 9.0, 1H), 7.30 (d, J = 9.5, 1H), 4.34 (dd, J = 8.9, 5.5, 1H), 4.26-3.87 (m, 5H), 3.87-3.73 (m, 4H), 3.66-3.50 (m, 4H), 3.04-2.72 (m, 6H), 1.16-0.92 (m, 4H). |
| 410 | CD3OD | 9.12 (s, 2H), 7.83 (d, J = 9.5, 1H), 7.69 (d, J = 9.1, 1H), 7.54 (d, J = 9.0, 1H), 7.28 (d, J = 9.4, 1H), 4.35 (dd, J = 8.9, 5.5, 1H), 4.18 (ddd, J = 22.7, 13.7, 7.2, 2H), 3.87-3.75 (m, 4H), 3.73-3.37 (m, 9H), 3.04-2.75 (m, 4H), 1.41 (d, J = 6.6, 6H). |
| 411 | CD3OD | 9.07 (s, 2H), 7.83 (d, J = 9.4, 1H), 7.68 (d, J = 9.1, 1H), 7.54 (d, J = 9.0, 1H), 7.27 (d, J = 9.4, 1H), 4.27-4.02 (m, 3H), 3.83 3.15 (m, 14H), 2.88-2.62 (m, 4H), 1.40 (t, J = 7.3, 3H). |
| 412 | CD3OD | 9.10 (s, 2H), 7.76 (d, J = 9.2, 1H), 7.71 (d, J = 9.0, 1H), 7.61 (d, J = 9.0, 1H), 6.97 (d, J = 9.3, 1H), 4.27 (dd, J = 8.7, 5.5, 1H), 4.23-4.03 (m, 2H), 3.94-3.86 (m, 2H), 3.81-3.71 (m, 4H), 3.52-3.43 (m, 2H), 3.01 (s, 6H), 2.92-2.81 (m, 2H), 2.82-2.70 (m, 2H). |

| Co. No. | Solvent | NMR data |
| --- | --- | --- |
| 413 | CD3OD | 9.14 (s, 2H), 7.89 (d, J = 9.6, 1H), 7.77 (d, J = 9.0, 1H), 7.60 (d, J = 9.0, 1H), 7.35 (d, J = 9.7, 1H), 4.51 (d, J = 13.3, 1H), 4.46-4.36 (m, 1H), 4.26 (dd, J = 13.7, 5.4, 1H), 4.18 (dd, J = 13.6, 9.4, 1H), 4.05 (d, J = 13.8, 1H), 3.88-3.75 (m, 4H), 3.66-3.39 (m, 3H), 3.09-2.96 (m, 2H), 2.95-2.81 (m, 2H), 2.25-2.11 (m, 1H), 2.04-1.88 (m, 1H), 1.86-1.67 (m, 2H). |
| 414 | CD3OD | 9.02 (s, 2H), 7.66-7.51 (m, 2H), 7.43 (d, J = 9.0, 1H), 7.12 (d, J = 9.5, 1H), 4.13-3.91 (m, 3H), 3.82-3.61 (m, 8H), 2.69-2.46 (m, 4H), 1.79-1.53 (m, 6H). |
| 415 | (CD3)2SO | 9.04 (s, J = 20.3, 2H), 8.66 (t, J = 5.5, 1H), 7.63 (d, J = 9.3, 1H), 7.51 (d, J = 9.0, 1H), 7.44 (d, J = 9.0, 1H), 6.86 (d, J = 9.3, 1H), 4.06-3.78 (m, 3H), 3.68-3.44 (m, 8H), 2.56-2.43 (m, 4H), 2.03-1.85 (m, 4H). |
| 416 | (CD3)2SO | 9.06 (s, 2H), 8.65 (t, J = 5.5, 1H), 7.66 (d, J = 9.2, 1H), 7.53 (d, J = 9.1, 1H), 7.46 (d, J = 9.1, 1H), 6.68 (d, J = 9.2, 1H), 4.09 (app t, J = 7.5, 4H), 4.04-3.78 (m, 3H), 3.64-3.50 (m, 4H), 2.47-2.24 (m, 6H). |
| 417 | (CD3)2SO | 9.12 (s, J = 10.6, 2H), 8.81-8.75 (m, 1H), 7.81-7.73 (m, 1H), 7.69-7.54 (m, 2H), 7.41-7.30 (m, 1H), 4.27-4.20 (m, 1H), 4.06-3.98 (m, 1H), 3.95-3.88 (m, 1H), 3.79-3.71 (m, 4H), 2.72-2.64 (m, 2H), 2.63-2.56 (m, 2H), 2.04-1.95 (m, 4H), 1.71-1.65 (m, 2H), 1.64-1.58 (m, 4H). |
| 418 | (CD3)2SO | 9.13 (s, 2H), 8.92-8.84 (m, 1H), 8.00-7.80 (m, 2H), 7.78-7.69 (m, 1H), 7.28-7.10 (m, 1H), 4.22 (t, J = 7.2, 1H), 4.06-4.00 (m, 1H), 3.96-3.89 (m, 1H), 3.68 (s, 4H), 2.69-2.63 (m, 2H), 2.60-2.54 (m, 2H), 2.09-2.03 (m, 4H), 2.03-1.94 (m, 4H). |
| 419 | (CD3)2SO | 9.13 (s, 2H), 8.89 (t, J = 5.7, 1H), 7.90 (d, J = 9.4, 1H), 7.77-7.69 (m, 2H), 6.94 (d, J = 9.3, 1H), 4.42-4.33 (m, 4H), 4.23 (t, J = 7.3, 1H), 4.07-3.99 (m, 1H), 3.94-3.87 (m, 1H), 2.70-2.55 (m, 3H), 2.49-2.44 (m, 3H), 2.03-1.93 (m, 4H). |
| 420 | (CD3)2SO | 10.01 (s, 1H), 9.13 (s, 2H), 8.78 (t, J = 5.8, 1H), 7.77 (d, J = 9.2, 1H), 7.61 (d, J = 9.0, 1H), 7.56 (d, J = 9.0, 1H), 6.98 (d, J = 9.3, 1H), 4.24 (t, J = 7.4, 1H), 4.07-3.97 (m, 3H), 3.96-3.89 (m, 1H), 3.86-3.79 (m, 1H), 3.56 (dd, J = 18.5, 8.2, 1H), 2.89 (s, J = 4.3, 6H), 2.72-2.54 (m, 4H), 2.29-2.19 (m, 1H), 2.04-1.96 (m, 4H). |
| 421 | (CD3)2SO | 10.00-9.89 (m, 1H), 9.13 (s, 2H), 8.77 (t, J = 5.8, 1H), 7.77 (d, J = 7.1, 1H), 7.60 (d, J = 9.1, 1H), 7.55 (d, J = 9.0, 1H), 6.97 (d, J = 9.3, 1H), 4.26-4.20 (m, 1H), 4.07-3.98 (m, 3H), 3.96-3.88 (m, 1H), 3.87-3.78 (m, 1H), 3.75-3.65 (m, 1H), 3.55 (dd, J = 18.4, 8.2, 1H), 2.89 (s, J = 5.0, 6H), 2.71-2.55 (m, 4H), 2.29-2.21 (m, 1H), 2.04-1.95 (m, 4H). |
| 422 | (CD3)2SO | 9.71-9.53 (m, 1H), 9.14 (d, J = 6.1, 2H), 8.78 (t, J = 5.8, 1H), 7.67 (d, J = 9.3, 1H), 7.62-7.52 (m, 2H), 6.87 (d, J = 9.3, 1H), 4.25 (t, J = 7.1, 1H), 4.10-3.98 (m, 1H), 3.95-3.83 (m, 1H), 3.81-3.71 (m, 2H), 3.38-3.29 (m, 2H), 2.88 (s, 6H), 2.76-2.56 (m, 4H), 2.08-1.93 (m, 4H). |
| 423 | (CD3)2SO | 9.14 (s, 2H), 8.77 (t, J = 5.8, 1H), 8.03-7.96 (m, 2H), 7.77 (d, J = 9.4, 1H), 7.60-7.51 (m, 2H), 7.27 (d, J = 9.5, 1H), 4.55-4.43 (m, 1H), 4.31-4.20 (m, 1H), 4.10-3.98 (m, 2H), 3.97-3.86 (m, 1H), 3.30-3.18 (m, 3H), 2.77-2.56 (m, 4H), 2.08-1.94 (m, 5H), 1.90-1.79 (m, 1H), 1.70-1.49 (m, 2H). |
| 424 | (CD3)2SO | 9.14 (s, 2H), 8.77 (t, J = 5.7, 1H), 8.04-7.97 (m, 2H), 7.77 (d, J = 9.4, 1H), 7.59-7.51 (m, 2H), 7.27 (d, J = 9.5, 1H), 4.50 (d, J = 9.2, 1H), 4.30-4.20 (m, 1H), 4.12-3.97 (m, 2H), 3.96-3.88 (m, 1H), 3.31-3.18 (m, 3H), 2.76-2.56 (m, 4H), 2.10-1.94 (m, 5H), 1.90-1.79 (m, 1H), 1.69-1.48 (m, 2H). |
| 425 | (CD3)2SO | 9.14 (s, 2H), 8.79 (t, J = 5.8, 1H), 7.85 (d, J = 9.5, 1H), 7.64-7.60 (m, 1H), 7.57 (d, J = 9.0, 1H), 7.38 (d, J = 9.5, 1H), 4.83-4.53 (m, 2H), 4.26 (t, J = 7.1, 1H), 4.09-3.88 (m, 2H), 3.74-3.51 (m, 2H), 3.44-3.14 (m, 4H), 2.99-2.88 (m, 1H), 2.77-2.55 (m, 4H), 2.01 (t, J = 14.0, 4H), 1.05-0.96 (m, 2H), 0.91-0.81 (m, 2H). |
| 426 | (CD3)2SO | 9.41 (s, 1H), 9.14 (s, 2H), 8.78 (t, J = 5.9, 1H), 7.84 (d, J = 9.4, 1H), 7.61 (d, J = 9.1, 1H), 7.57 (d, J = 9.0, 1H), 7.35 (d, J = 9.5, 1H), 4.59 (d, J = 14.0, 2H), 4.24 (t, J = 7.1, 1H), 4.08-3.87 (m, 2H), 3.62 (d, J = 11.6, 2H), 3.44-3.33 (m, 2H), 3.17-2.97 (m, 4H), 2.74-2.55 (m, 4H), 2.18-2.07 (m, 1H), 2.05-1.94 (m, 4H), 0.99 (d, J = 6.6, 6H). |
| 427 | (CD3)2SO | 9.55 (s, 1H), 9.13 (s, 2H), 8.78 (t, J = 5.9, 1H), 7.84 (d, J = 9.5, 1H), 7.59 (m, 2H), 7.36 (d, J = 9.5, 1H), 4.70 (d, J = 13.9, 2H), 4.23 (t, J = 7.2, 1H), 4.08-3.86 (m, 2H), 3.62-3.49 (m, 3H), 3.33-3.19 (m, 2H), 3.18-3.04 (m, 2H), 2.75-2.53 (m, 4H), 2.05-1.94 (m, 4H), 1.29 (d, J = 6.6, 6H). |
| 428 | (CD3)2SO | 9.65 (s, 1H), 9.13 (s, 2H), 8.78 (t, J = 5.9, 1H), 7.85 (d, J = 9.4, 1H), 7.65-7.54 (m, 2H), 7.36 (d, J = 9.5, 1H), 4.65 (d, J = 14.2, 2H), 4.24 (t, J = 7.2, 1H), 4.08-3.86 (m, 2H), 3.62 (d, J = 11.9, 2H), 3.34-3.14 (m, 4H), 3.07 (d, J = 11.6, 2H), 2.64 (d, J = 22.2, 4H), 2.00 (t, J = 14.0, 4H), 1.26 (t, J = 7.3, 3H). |
| 429 | (CD3)2SO | 9.74-9.62 (m, 1H), 9.13 (s, 2H), 8.73 (t, J = 5.1, 1H), 7.77 (d, J = 9.4, 1H), 7.58 (d, J = 9.0, 1H), 7.54 (d, J = 9.0, 1H), 7.29 (d, J = 9.5, 1H), 4.68 (d, J = 12.7, 1H), 4.29-4.22 (m, 1H), 4.21-4.14 (m, 1H), 4.08-3.86 (m, 2H), 3.47-3.37 (m, 1H), 3.35-3.25 (m, 1H), 3.21-3.11 (m, 1H), 2.87 (s, 6H), 2.74-2.57 (m, 4H), 2.15-2.07 (m, 1H), 2.06-1.95 (m, 4H), 1.92-1.83 (m, 1H), 1.83-1.74 (m, 1H), 1.59-1.46 (m, 1H). |

| Co. No. | Solvent | NMR data |
|---|---|---|
| 430 | CD3OD | 1H NMR (600 MHz, MeOD) δ 9.06 (s, 2H), 8.00-7.91 (m, 1H), 7.84-7.74 (m, 2H), 7.17 (d, J = 8.5, 1H), 4.20-4.11 (m, 2H), 4.10-4.02 (m, 1H), 3.99-3.90 (m, 1H), 3.75 (t, J = 4.7, 4H), 3.73-3.63 (m, 3H), 3.61-3.55 (m, 1H), 3.37-3.34 (m, 1H), 2.79-2.70 (m, 2H), 2.70-2.63 (m, 2H). |
| 431 | CD3OD | 1H NMR (600 MHz, MeOD) δ 9.09 (s, 2H), 7.91 (d, J = 9.3, 1H), 7.84 (d, J = 8.5, 1H), 7.76 (d, J = 9.0, 1H), 7.11 (d, J = 9.4, 1H), 4.25-4.15 (m, 2H), 4.14-4.05 (m, 1H), 3.77 (t, J = 4.6, 4H), 3.73 (t, J = 5.9, 2H), 3.67 (t, J = 6.9, 2H), 2.87-2.76 (m, 2H), 2.76-2.69 (m, 2H), 2.02-1.91 (m, 2H). |
| 432 | CD3OD | 1H NMR (600 MHz, MeOD) δ 9.06 (s, 2H), 7.95 (d, J = 7.5, 1H), 7.83 (d, J = 7.5, 1H), 7.78 (d, J = 8.9, 1H), 7.16 (d, J = 7.5, 1H), 4.24-4.09 (m, 3H), 4.09-4.01 (m, 1H), 3.95-3.85 (m, 2H), 3.83-3.71 (m, 6H), 3.66-3.52 (m, 1H), 2.79-2.58 (m, 4H), 2.22-2.09 (m, 1H), 2.04-1.91 (m, 3H), 1.78-1.67 (m, 1H). |
| 433 | CD3OD | 1H NMR (600 MHz, MeOD) δ 9.16 (s, 2H), 8.01 (d, J = 9.8, 1H), 7.92 (d, J = 9.1, 1H), 7.71 (d, J = 9.1, 1H), 7.40 (d, J = 9.9, 1H), 4.48-4.41 (m, 1H), 4.31-4.16 (m, 2H), 3.94-3.87 (m, 2H), 3.82 (t, J = 4.7, 4H), 3.40 (s, 3H), 3.14-3.08 (m, 2H), 3.06-2.99 (m, 2H), 2.94-2.86 (m, 2H), 2.71 (s, 3H), 2.18-2.08 (m, 2H). |
| 434 | CD3OD | 1H NMR (400 MHz, MeOD) δ 9.01 (s, 2H), 7.58 (dd, J = 9.1, 3.7, 2H), 7.50-7.18 (m, 6H), 6.82 (d, J = 9.2, 1H), 4.66 (s, 2H), 4.14-3.95 (m, 3H), 3.82-3.67 (m, 4H), 2.70-2.51 (m, 4H). |
| 435 | CD3OD | 1H NMR (600 MHz, MeOD) δ 9.11 (s, 2H), 8.88 (s, 1H), 8.73 (d, J = 5.1, 1H), 8.49 (d, J = 8.1, 1H), 7.92 (dd, J = 8.0, 5.5, 1H), 7.87 (d, J = 9.3, 1H), 7.74 (d, J = 9.1, 1H), 7.65 (d, J = 9.0, 1H), 7.10 (d, J = 8.7, 1H), 4.95 (s, 2H), 4.32-4.26 (m, 1H), 4.23-4.10 (m, 2H), 3.78 (t, J = 4.6, 4H), 2.93-2.84 (m, 2H), 2.82-2.74 (m, 2H). |
| 436 | CD3OD | 1H NMR (600 MHz, MeOD) δ 9.12 (s, 2H), 7.85 (d, J = 9.5, 1H), 7.69 (dt, J = 5.8, 2.9, 1H), 7.53 (d, J = 9.0, 1H), 7.33 (d, J = 9.5, 1H), 4.80-4.73 (m, 2H), 4.39-4.31 (m, 1H), 4.25-4.19 (m, 1H), 4.19-4.11 (m, 1H), 3.80 (t, J = 4.7, 4H), 3.49-3.40 (m, 2H), 3.04-2.91 (m, 4H), 2.87-2.78 (m, 2H), 1.42 (d, J = 6.6, 6H). |
| 437 | CD3OD | 1H NMR (600 MHz, MeOD) δ 9.06 (s, 2H), 8.01-7.94 (m, 1H), 7.91-7.85 (m, 1H), 7.79 (d, J = 9.0, 1H), 7.38-7.22 (m, 6H), 7.16 (d, J = 9.6, 1H), 4.74 (s, 2H), 4.20-4.11 (m, 2H), 4.10-4.03 (m, 1H), 3.75 (t, J = 4.6, 4H), 2.78-2.63 (m, 4H), 2.40 (s, 4H), 2.37-2.31 (m, 1H). |
| 438 | CD3OD | 1H NMR (400 MHz, MeOD) δ 9.01 (s, 2H), 7.58 (d, J = 9.3, 2H), 7.49-7.35 (m, 3H), 7.07-6.98 (m, 2H), 6.81 (d, J = 9.3, 1H), 4.64 (s, 2H), 4.13-3.94 (m, 3H), 3.71 (t, J = 4.5, 4H), 2.69-2.51 (m, 4H). |
| 439 | CD3OD | 1H NMR (600 MHz, MeOD) δ 9.08 (s, 2H), 7.78 (d, J = 9.3, 1H), 7.74 (d, J = 9.1, 1H), 7.62 (d, J = 9.0, 1H), 6.98 (d, J = 9.3, 1H), 4.25-4.20 (m, 1H), 4.20-4.14 (m, 1H), 4.14-4.07 (m, 1H), 3.96 (t, J = 5.9, 2H), 3.94-3.92 (m, 4H), 3.77 (t, J = 4.6, 4H), 3.50 (t, J = 5.9, 2H), 3.48-3.43 (m, 4H), 2.87-2.79 (m, 2H), 2.78-2.71 (m, 2H). |
| 440 | CD3OD | 1H NMR (600 MHz, MeOD) δ 9.10 (s, 2H), 8.06-7.91 (m, 1H), 7.91-7.82 (m, 1H), 7.78 (d, J = 9.0, 1H), 7.19-7.10 (m, 1H), 6.97-6.90 (m, 2H), 6.89-6.83 (m, 1H), 6.04-5.95 (m, 2H), 4.64 (d, J = 21.3, 2H), 4.32-4.17 (m, 2H), 4.15-4.06 (m, 1H), 3.77 (t, J = 4.6, 4H), 2.89-2.80 (m, 2H), 2.80-2.68 (m, 2H). |
| 441 | CD3OD | 1H NMR (600 MHz, MeOD) δ 9.13 (s, 2H), 8.04 (d, J = 9.9, 1H), 7.88 (d, J = 9.1, 1H), 7.74 (d, J = 9.1, 1H), 7.53 (d, J = 10.0, 1H), 4.43-4.34 (m, 1H), 4.29-4.22 (m, 1H), 4.22-4.14 (m, 1H), 4.00-3.96 (m, 4H), 3.94-3.90 (m, 4H), 3.81 (t, J = 4.6, 4H), 3.03-2.92 (m, 2H), 2.89-2.82 (m, 2H), 2.16-2.11 (m, 4H), 1.82-1.70 (m, 2H). |
| 442 | CD3OD | 1H NMR (600 MHz, MeOD) δ 9.12 (s, 2H), 8.07 (d, J = 10.0, 1H), 7.88 (dd, J = 9.1, 0.6, 1H), 7.75 (d, J = 9.1, 1H), 7.55 (d, J = 10.0, 1H), 4.61-4.54 (m, 2H), 4.36-4.30 (m, 1H), 4.30-4.20 (m, 2H), 4.18-4.11 (m, 1H), 3.80 (t, J = 4.7, 4H), 3.51-3.39 (m, 4H), 2.96-2.87 (m, 2H), 2.86-2.78 (m, 2H), 2.40 (t, J = 8.1, 2H), 2.09-2.01 (m, 2H), 1.98-1.89 (m, 4H). |
| 443 | CD3OD | 1H NMR (600 MHz, MeOD) δ 9.09 (s, 2H), 8.13-8.06 (m, 1H), 7.97-7.85 (m, 1H), 7.77 (dd, J = 9.0, 2.6, 1H), 7.67-7.23 (m, 1H), 5.02-4.87 (m, 2H), 4.29-4.17 (m, 2H), 4.16-4.04 (m, 2H), 4.01-3.84 (m, 3H), 3.78 (t, J = 4.6, 4H), 3.75-3.70 (m, 1H), 2.92-2.80 (m, 2H), 2.80-2.71 (m, 2H), 2.26-2.15 (m, 3H), 2.15-1.90 (m, 4H). |
| 444 | CD3OD | 1H NMR (600 MHz, MeOD) δ 9.12 (s, 2H), 7.85 (d, J = 9.6, 1H), 7.74 (d, J = 9.1, 1H), 7.58 (d, J = 9.0, 1H), 7.26 (d, J = 9.6, 1H), 4.36-4.29 (m, 1H), 4.25-4.11 (m, 4H), 3.94 (t, J = 6.1, 2H), 3.80 (t, J = 4.6, 4H), 3.55-3.49 (m, 2H), 3.36-3.34 (m, 2H), 2.98-2.88 (m, 2H), 2.86-2.78 (m, 2H), 2.31-2.21 (m, 2H). |
| 445 | CD3OD | 1H NMR (600 MHz, MeOD) δ 9.02 (s, 2H), 7.68 (d, J = 9.4, 1H), 7.59 (dd, J = 9.0, 0.6, 1H), 7.46 (d, J = 9.0, 1H), 7.18 (d, J = 9.5, 1H), 4.63-4.57 (m, 2H), 4.09-3.96 (m, 3H), 3.71 (t, J = 4.6, 4H), 3.17-3.10 (m, 2H), 2.93-2.84 (m, 1H), 2.66-2.50 (m, 4H), 2.07-2.01 (m, 2H), 1.80-1.69 (m, 2H). |

| Co. No. | Solvent | NMR data |
|---|---|---|
| 446 | CD3OD | 1H NMR (600 MHz, MeOD) δ 9.10 (s, 2H), 8.07 (d, J = 9.9, 1H), 7.87 (d, J = 9.1, 1H), 7.83 (s, 1H), 7.74 (d, J = 9.0, 1H), 7.55 (d, J = 10.0, 1H), 4.64 (d, J = 13.8, 2H), 4.35-4.25 (m, 2H), 4.25-4.19 (m, 1H), 4.17-4.08 (m, 1H), 3.78 (t, J = 4.6, 4H), 3.49 (t, J = 12.3, 2H), 2.94-2.83 (m, 2H), 2.83-2.74 (m, 2H), 2.28-2.19 (m, 2H), 2.18-2.06 (m, 2H). |
| 447 | CD3OD | 1H NMR (600 MHz, MeOD) δ 9.05 (s, 2H), 7.98 (d, J = 9.3, 1H), 7.81 (d, J = 9.0, 1H), 7.75 (d, J = 9.0, 1H), 7.15 (d, J = 9.6, 1H), 7.10-7.04 (m, 2H), 6.99-6.93 (m, 1H), 4.80 (s, 2H), 4.17-4.01 (m, 3H), 3.73 (t, J = 4.6, 4H), 2.72-2.66 (m, 2H), 2.66-2.59 (m, 2H). |
| 448 | CD3OD | 1H NMR (400 MHz, MeOD) δ 9.28 (s, 2H), 7.94-7.81 (m, 2H), 7.72 (d, J = 9.0, 1H), 7.09 (d, J = 9.3, 1H), 4.96-4.85 (m, 1H), 4.58-4.31 (m, 2H), 3.42-3.21 (m, 4H), 3.18 (s, 3H), 1.97-1.83 (m, 4H), 1.63 (s, 2H). |
| 449 | CD3OD | 1H NMR (400 MHz, MeOD) δ 9.30 (s, 2H), 7.99 (d, J = 10.0, 1H), 7.92 (d, J = 9.1, 1H), 7.72 (d, J = 9.1, 1H), 7.39 (d, J = 10.0, 1H), 4.94 (dd, J = 10.3, 4.9, 1H), 4.63-4.29 (m, 2H), 3.44 (s, 6H), 3.42-3.25 (m, 4H), 1.93 (d, J = 5.0, 4H), 1.65 (s, 2H). |
| 450 | CD3OD | 1H NMR (400 MHz, MeOD) δ 9.30 (s, 2H), 7.93 (d, J = 9.6, 1H), 7.84 (d, J = 9.1, 1H), 7.66 (dd, J = 9.1, 1.1, 1H), 7.17 (d, J = 9.6, 1H), 4.95 (dd, J = 10.1, 5.0, 1H), 4.55-4.35 (m, 2H), 4.16-3.83 (m, 5H), 3.56-3.30 (m, 4H), 2.83 (d, J = 1.1, 3H), 2.70-2.56 (m, 1H), 2.48-2.33 (m, 1H), 2.00-1.88 (m, 4H), 1.76-1.58 (m, 2H). |
| 451 | CD3OD | 1H NMR (400 MHz, MeOD) δ 9.30 (s, 2H), 7.94 (dd, J = 9.6, 1.8, 1H), 7.85 (d, J = 9.1, 1H), 7.66 (d, J = 9.1, 1H), 7.17 (d, J = 9.7, 1H), 4.95 (dd, J = 10.2, 5.2, 1H), 4.60-4.35 (m, 2H), 4.21-3.82 (m, 6H), 3.59-3.30 (m, 4H), 2.83 (s, 3H), 2.72-2.57 (m, 1H), 2.49-2.33 (m, 1H), 1.99-1.84 (m, 4H), 1.73-1.55 (m, 2H). |
| 452 | CD3OD | 9.13-8.94 (m, 2H), 8.11-7.96 (m, 1H), 7.91-7.80 (m, 1H), 7.80-7.72 (m, 1H), 7.57-7.41 (m, 1H), 4.21-3.97 (m, 6H), 3.85-3.68 (m, 6H), 2.70 (d, J = 25.6, 4H), 2.06 (s, 2H), 1.81-1.67 (m, 2H) |
| 453 | CD3OD | 9.07 (s, 2H), 8.06 (d, J = 9.9, 1H), 7.79 (dd, J = 52.8, 9.1, 2H), 7.49 (d, J = 9.9, 1H), 4.40-4.22 (m, 2H), 4.21-4.13 (m, 2H), 4.12-4.02 (m, 2H), 3.81-3.68 (m, 6H), 3.46-3.35 (m, 1H), 3.10-3.01 (m, 1H), 2.84-2.60 (m, 4H), 1.29 (d, J = 6.2, 3H) |
| 454 | CD3OD | 9.04 (s, 2H), 8.04 (d, J = 10.0, 1H), 7.81 (dd, J = 42.0, 9.1, 2H), 7.52 (d, J = 10.0, 1H), 4.18-3.87 (m, 7H), 3.84-3.69 (m, 5H), 2.74-2.57 (m, 4H), 2.05 (t, J = 15.4, 2H), 1.79 (d, J = 14.7, 2H) |
| 455 | CD3OD | 8.98 (s, 2H), 7.74 (d, J = 9.5, 1H), 7.59 (d, J = 9.0, 1H), 7.44 (d, J = 9.0, 1H), 7.18 (d, J = 9.5, 1H), 4.17-3.94 (m, 3H), 3.89-3.77 (m, 2H), 3.68 (t, J = 4.5, 4H), 3.60-3.21 (m, 10H), 2.82-2.56 (m, 4H) |
| 456 | CD3OD | 9.12-9.01 (m, 2H), 8.01-7.87 (m, 1H), 7.86-7.73 (m, 2H), 7.21-7.07 (m, 1H), 4.32-4.20 (m, 1H), 4.19-3.97 (m, 3H), 3.87-3.66 (m, 5H), 3.66-3.55 (m, 1H), 2.77-2.58 (m, 4H), 1.40-1.30 (m, 3H) |
| 457 | CD3OD | 9.22-8.91 (m, 2H), 8.07-7.67 (m, 3H), 7.20-6.97 (m, 1H), 4.20-3.96 (m, 4H), 3.81-3.67 (m, 4H), 2.75-2.54 (m, 4H), 1.81-1.67 (m, 2H), 1.42-1.30 (m, 3H), 1.11-0.97 (m, 3H) |
| 458 | CD3OD | 9.10-8.99 (m, 2H), 8.08-7.98 (m, 1H), 7.83-7.69 (m, 2H), 7.05-6.95 (m, 1H), 4.76-4.65 (m, 2H), 4.33-4.22 (m, 2H), 4.19-3.99 (m, 3H), 3.79-3.67 (m, 4H), 2.76-2.55 (m, 4H) |
| 459 | CD3OD | 9.06 (s, 2H), 8.05 (d, J = 9.9, 1H), 7.84 (dd, J = 71.9, 9.1, 2H), 7.47 (d, J = 10.0, 1H), 4.19-3.93 (m, 9H), 3.86-3.79 (m, 2H), 3.74 (t, J = 4.6, 4H), 2.76-2.58 (m, 4H), 2.12-2.02 (m, 2H) |
| 460 | CD3OD | 9.10 (s, 2H), 7.96-7.87 (m, 1H), 7.70 (dd, J = 51.7, 9.1, 2H), 7.13 (d, J = 9.3, 1H), 5.32-5.23 (m, 1H), 4.69-4.62 (m, 1H), 4.32-4.06 (m, 3H), 3.98-3.81 (m, 2H), 3.81-3.73 (m, 4H), 3.53-3.46 (m, 2H), 2.93-2.69 (m, 4H), 2.27 (dd, J = 69.9, 11.2, 2H) |
| 461 | CD3OD | 9.04 (s, 2H), 8.14-8.01 (m, 1H), 7.90-7.73 (m, 2H), 5.33-5.21 (m, 1H), 5.13-5.05 (m, 1H), 4.99-4.90 (m, 1H), 4.17-3.51 (m, 10H), 2.71-2.54 (m, 4H), 2.31-2.14 (m, 3H), 2.04-1.95 (m, 2H) |
| 462 | CD3OD | 9.05 (s, 2H), 8.01 (d, J = 10.0, 1H), 7.87 (dd, J = 68.4, 9.1, 2H), 7.38 (d, J = 10.0, 1H), 4.19-3.99 (m, 3H), 3.83 (q, J = 7.2, 4H), 3.73 (t, J = 4.6, 4H), 2.62 (dt, J = 11.5, 8.9, 4H), 1.37 (t, J = 7.2, 6H) |
| 463 | CD3OD | 9.03 (s, 2H), 8.06-7.67 (m, 3H), 7.24-7.01 (m, 1H), 4.19-3.94 (m, 3H), 3.72 (t, J = 4.5, 4H), 3.66-3.53 (m, 2H), 2.68-2.45 (m, 6H), 2.13-1.96 (m, 2H) |
| 464 | CD3OD | 9.04 (s, 2H), 8.05 (d, J = 9.9, 1H), 7.81 (dd, J = 38.4, 9.1, 2H), 7.52 (d, J = 10.0, 1H), 4.42-4.28 (m, 2H), 4.19-3.96 (m, 3H), 3.74 (t, J = 4.6, 4H), 3.57 (t, J = 10.9, 2H), 2.91-2.75 (m, 1H), 2.75-2.55 (m, 4H), 2.27-2.11 (m, 2H), 2.00-1.81 (m, 2H) |
| 465 | CD3OD | 9.04 (s, 2H), 8.02 (d, J = 9.7, 1H), 7.77 (dd, J = 19.7, 9.0, 2H), 6.99 (d, J = 9.7, 1H), 4.75-4.64 (m, 3H), 4.36-3.97 (m, 5H), 2.80-2.61 (m, 4H), 2.11-1.92 (m, 4H) |
| 466 | CD3OD | 9.05 (s, 2H), 8.05 (d, J = 10.0, 1H), 7.84 (dd, J = 55.4, 9.1, 2H), 7.46 (d, J = 10.0, 1H), 4.25-4.16 (m, 1H), 4.14-3.93 (m, 8H), 3.86-3.77 (m, 2H), 2.79-2.62 (m, 4H), 2.13-1.93 (m, 6H) |

-continued

| Co. No. | Solvent | NMR data |
|---|---|---|
| 467 | CD3OD | 9.04 (s, 2H), 8.01-7.71 (m, 3H), 7.18-7.00 (m, 1H), 4.27-3.95 (m, 4H), 2.81-2.59 (m, 4H), 2.13-1.93 (m, 4H), 1.82-1.66 (m, 2H), 1.36 (d, J = 6.4, 3H), 1.03 (t, J = 7.4, 3H) |
| 468 | CD3OD | 9.05 (s, 2H), 8.00-7.74 (m, 3H), 7.16-7.04 (m, 1H), 4.23-3.98 (m, 6H), 3.66-3.50 (m, 2H), 2.81-2.60 (m, 4H), 2.12-1.95 (m, 6H), 1.81-1.63 (m, 2H) |
| 469 | CD3OD | 9.05 (s, 2H), 7.81 (d, J = 9.3, 1H), 7.69 (dd, J = 52.3, 9.0, 2H), 6.98 (d, J = 9.4, 1H), 4.26-4.16 (m, 1H), 4.15-4.00 (m, 2H), 3.82 (t, J = 5.7, 2H), 3.30-3.24 (m, 2H), 2.83-2.62 (m, 4H), 2.12-1.95 (m, 4H) |
| 470 | CD3OD | 9.05 (s, 2H), 7.96 (dd, J = 9.6, 4.0, 1H), 7.76 (dd, J = 55.3, 9.1, 2H), 7.14 (d, J = 9.6, 1H), 4.26-3.79 (m, 8H), 2.83 (s, 3H), 2.80-2.55 (m, 5H), 2.46-2.32 (m, 1H), 2.11-1.93 (m, 4H) |
| 471 | CD3OD | 9.05 (s, 2H), 7.98 (dd, J = 9.6, 3.8, 1H), 7.84 (d, J = 9.1, 1H), 7.70 (d, J = 9.1, 1H), 7.15 (d, J = 9.6, 1H), 4.26-3.76 (m, 8H), 2.84 (s, 3H), 2.79-2.53 (m, 5H), 2.46-2.31 (m, 1H), 2.13-1.89 (m, 4H) |
| 472 | CD3OD | 9.05 (s, 2H), 7.93 (d, J = 9.6, 1H), 7.82 (d, J = 9.1, 1H), 7.68 (d, J = 9.1, 1H), 7.09 (d, J = 9.6, 1H), 4.36 (d, J = 10.7, 1H), 4.22 (t, J = 7.1, 1H), 4.15-3.99 (m, 2H), 3.98-3.83 (m, 3H), 2.82-2.62 (m, 4H), 2.35-2.17 (m, 1H), 2.15-1.92 (m, 4H), 1.53-1.41 (m, 1H), 1.11-0.93 (m, 1H) |
| 473 | CD3OD | 9.05 (s, 2H), 8.07 (d, J = 10.0, 1H), 7.87 (d, J = 9.1, 1H), 7.78 (d, J = 9.1, 1H), 7.53 (d, J = 10.0, 1H), 4.40-4.26 (m, 2H), 4.26-4.16 (m, 1H), 4.17-3.91 (m, 2H), 3.65-3.51 (m, 2H), 2.90-2.49 (m, 5H), 2.26-2.11 (m, 2H), 2.11-1.81 (m, 6H) |
| 474 | CD3OD | 9.28 (s, 2H), 7.72-7.47 (m, 3H), 6.89 (d, J = 9.3, 1H), 4.92 (dd, J = 10.2, 5.4, 1H), 4.48-4.31 (m, 2H), 3.95-3.86 (m, 6H), 3.53-3.41 (m, 6H), 3.41-3.20 (m, 4H), 1.92 (s, 4H), 1.64 (s, 2H) |
| 475 | CD3OD | 9.29 (s, 2H), 7.76-7.44 (m, 3H), 7.16 (d, J = 9.5, 1H), 4.98-4.90 (m, 1H), 4.51-4.33 (m, 2H), 4.22-4.12 (m, 2H), 3.90 (t, J = 6.1, 2H), 3.51-3.45 (m, 2H), 3.44-3.21 (m, 6H), 2.30-2.17 (m, 2H), 1.99-1.87 (m, 4H), 1.72-1.59 (m, 2H) |
| 476 | CD3OD | 9.30 (s, 2H), 7.74-7.64 (m, 2H), 7.48 (d, J = 9.1, 1H), 7.13 (d, J = 9.5, 1H), 5.01-4.91 (m, 1H), 4.51-4.34 (m, 2H), 4.10-3.99 (m, 2H), 3.49-3.26 (m, 6H), 3.23 (s, 3H), 2.77 (s, 3H), 1.93 (s, 4H), 1.66 (s, 2H) |
| 477 | CD3OD | 9.04 (s, 2H), 8.01-7.90 (m, 1H), 7.86-7.73 (m, 2H), 7.20-7.07 (m, 1H), 4.31-3.98 (m, 4H), 3.86-3.76 (m, 1H), 3.67-3.56 (m, 1H), 2.81-2.60 (m, 4H), 2.12-1.94 (m, 4H), 1.34 (d, J = 6.6, 3H) |
| 478 | CD3OD | 9.05 (s, 2H), 8.05 (d, J = 9.9, 1H), 7.86 (dd, J = 51.4, 9.1, 2H), 7.49 (d, J = 10.1, 1H), 4.24-3.97 (m, 5H), 3.74 (t, J = 4.9, 2H), 3.46 (s, 3H), 3.36 (s, 3H), 2.79-2.61 (m, 4H), 2.10-1.94 (m, 4H) |
| 479 | CD3OD | 9.05 (s, 2H), 8.05 (d, J = 9.9, 1H), 7.90-7.73 (m, 2H), 7.54 (d, J = 10.1, 1H), 4.27-4.15 (m, 3H), 4.15-4.00 (m, 2H), 3.82-3.69 (m, 2H), 2.80-2.62 (m, 4H), 2.12-1.94 (m, 4H), 1.89-1.74 (m, 4H), 1.31 (s, 3H) |
| 480 | CD3OD | 9.04 (s, 2H), 8.06-7.75 (m, 3H), 7.23-7.10 (m, 1H), 4.24-3.97 (m, 3H), 3.75 (t, J = 5.6, 2H), 3.51-3.42 (m, 2H), 2.80-2.61 (m, 4H), 2.61-2.53 (m, 1H), 2.10-1.94 (m, 4H), 1.08-0.96 (m, 4H) |
| 481 | CD3OD | 9.05 (s, 2H), 8.02-7.76 (m, 3H), 7.22-7.11 (m, 1H), 4.24-3.98 (m, 3H), 3.73 (dt, J = 9.7, 4.3, 4H), 3.41 (s, 3H), 2.80-2.61 (m, 4H), 2.11-1.95 (m, 4H) |
| 482 | (CD3)2SO | δ 9.14 (s, 2H), 8.80 (dd, J = 15.1, 9.4, 1H), 7.80 (d, J = 9.4, 1H), 7.69 (d, J = 8.8, 1H), 7.61 (d, J = 8.7, 1H), 7.40 (d, J = 9.0, 1H), 4.27 (t, J = 6.9, 1H), 4.18-4.09 (m, 2H), 4.09-4.00 (m, 2H), 4.00-3.89 (m, 1H), 3.88-3.78 (m, 1H), 3.54-3.37 (m, 2H), 2.79-2.57 (m, 4H), 2.08-1.95 (m, 5H), 1.90-1.81 (m, 2H), 1.51-1.41 (m, 2H). |
| 483 | (CD3)2SO | 9.11 (d, J = 10.2, 2H), 8.72 (t, J = 5.7, 1H), 7.63 (d, J = 9.3, 1H), 7.52 (d, J = 9.0, 1H), 7.46 (d, J = 9.0, 1H), 6.85 (d, J = 9.3, 1H), 4.98 (s, 1H), 4.42 (s, 1H), 4.20 (t, J = 7.3, 1H), 4.04-3.85 (m, 2H), 3.69-3.52 (m, 3H), 3.51-3.39 (m, 1H), 2.72-2.52 (m, 4H), 2.07-1.88 (m, 6H). |
| 484 | (CD3)2SO | 9.11 (d, J = 10.2, 2H), 8.72 (t, J = 5.7, 1H), 7.63 (d, J = 9.3, 1H), 7.52 (d, J = 9.0, 1H), 7.46 (d, J = 9.0, 1H), 6.85 (d, J = 9.3, 1H), 4.98 (s, 1H), 4.42 (s, 1H), 4.20 (t, J = 7.3, 1H), 4.04-3.85 (m, 2H), 3.69-3.52 (m, 3H), 3.51-3.39 (m, 1H), 2.72-2.52 (m, 4H), 2.07-1.88 (m, 6H). |
| 485 | (CD3)2SO | 9.14 (s, 2H), 8.95 (s, 2H), 8.79 (s, 1H), 7.83 (d, J = 9.4, 1H), 7.61 (d, J = 9.0, 1H), 7.56 (d, J = 9.0, 1H), 7.33 (d, J = 9.5, 1H), 4.35-4.21 (m, 1H), 4.13-3.99 (m, 1H), 3.99-3.83 (m, 5H), 3.33-3.11 (m, 4H), 2.79-2.58 (m, J = 23.7, 4H), 2.13-1.92 (m, 4H). |
| 486 | (CD3)2SO | 9.14 (s, 2H), 8.91-8.79 (m, 1H), 8.29 (bs, 2H), 7.87-7.77 (m, 1H), 7.75-7.65 (m, 1H), 7.62 (d, J = 9.0, 1H), 7.11-6.97 (m, 1H), 4.32-4.21 (m, 1H), 4.10-4.00 (m, 2H), 3.99-3.91 (m, 1H), 3.91-3.84 (m, 1H), 3.83-3.64 (m, 3H), 2.79-2.57 (m, J = 32.3, 4H), 2.44-2.32 (m, 1H), 2.23-2.12 (m, 1H), 2.07-1.94 (m, 4H). |
| 487 | (CD3)2SO | 10.10 (s, 1H), 9.14 (s, 2H), 8.79 (t, J = 5.9, 1H), 7.85 (d, J = 9.5, 1H), 7.61 (d, J = 9.0, 1H), 7.57 (d, J = 9.0, 1H), 7.36 (d, J = 9.5, 1H), 4.74-4.52 (m, J = 13.8, 2H), 4.37-4.21 (m, 1H), 4.11-4.00 (m, 1H), 4.00-3.86 (m, 1H), 3.66-3.49 (m, 2H), 3.36-3.21 (m, 2H), 3.21-3.00 (m, 2H), 2.86 (s, 3H), 2.79-2.55 (m, J = 32.4, 4H), 2.10-1.93 (m, 4H). |

| Co. No. | Solvent | NMR data |
|---|---|---|
| 488 | (CD3)2SO | 9.15 (s, 2H), 8.79 (t, J = 5.9, 1H), 7.79 (d, J = 9.5, 1H), 7.63 (d, J = 9.0, 1H), 7.57 (d, J = 9.0, 1H), 7.32 (d, J = 9.5, 1H), 4.41-4.34 (m, J = 12.7, 1H), 4.33-4.25 (m, J = 13.1, 2H), 4.12-4.00 (m, 1H), 4.00-3.87 (m, J = 8.1, 2H), 3.65-3.50 (m, J = 12.9, 10.3, 2H), 3.12-2.92 (m, 1H), 2.83-2.60 (m, 4H), 2.13-1.92 (m, 4H), 1.19 (d, J = 6.2, 3H) |
| 489 | (CD3)2SO | 9.14 (s, 2H), 9.05 (s, 1H), 8.87-8.77 (m, 1H), 8.64 (d, J = 4.7, 1H), 8.10-7.94 (m, 1H), 7.87-7.79 (m, 1H), 7.67-7.61 (m, 3H), 7.56-7.45 (m, 1H), 7.15 (d, J = 9.4, 1H), 4.89 (s, 2H), 4.30-4.19 (m, 1H), 4.10-4.00 (m, 1H), 3.95-3.86 (m, J = 7.6, 1H), 2.76-2.55 (m, J = 39.2, 4H), 2.07-1.91 (m, 4H |
| 490 | | |
| 491 | (CD3)2SO | 9.17-9.09 (m, 2H), 8.91-8.78 (m, 1H), 7.96-7.64 (m, 3H), 7.13-6.92 (m, 1H), 4.26-4.17 (m, 3H), 4.09-4.01 (m, 2H), 3.91-3.83 (m, 2H), 3.70-3.60 (m, 1H), 2.75-2.52 (m, 5H), 2.07-1.90 (m, 5H), 1.30-1.25 (m, 6H). |
| 492 | (CD3)2SO | 9.21-9.05 (m, 2H), 8.90 (t, J = 5.8, 1H), 7.94-7.80 (m, 2H), 7.77 (d, J = 8.7, 1H), 7.17-7.00 (m, 1H), 4.23 (t, J = 7.3, 1H), 4.10-3.98 (m, 1H), 3.97-3.81 (m, 1H), 3.09 (s, 3H), 2.75-2.52 (m, 4H), 2.06-1.91 (m, 4H). |
| 493 | (CD3)2SO | 9.18-9.09 (m, 2H), 8.73 (s, 1H), 7.68-7.34 (m, 4H), 6.85 (s, 1H), 4.20 (t, J = 7.3, 1H), 4.04-3.96 (m, 1H), 3.93-3.84 (m, 1H), 2.79 (s, 1H), 2.69-2.53 (m, 4H), 2.04-1.90 (m, 4H), 0.85-0.65 (m, 2H), 0.57-0.39 (m, 2H). |
| 494 | (CD3)2SO | 9.14 (s, 2H), 8.82-8.72 (m, 1H), 7.78 (d, J = 9.5, 1H), 7.61 (d, J = 8.9, 1H), 7.55 (d, J = 9.0, 1H), 7.32 (d, J = 9.5, 1H), 4.45-4.32 (m, J = 12.8, 2H), 4.32-4.21 (m, 1H), 4.10-4.00 (m, 1H), 3.99-3.88 (m, 1H), 3.72-3.59 (m, 2H), 2.79-2.54 (m, 6H), 2.13-1.92 (m, 4H), 1.19 (d, J = 6.2, 6H). |
| 495 | (CD3)2SO | 9.92-9.26 (m, 1H), 9.14 (s, 2H), 8.90 (t, J = 5.9, 1H), 7.97-7.80 (m, 2H), 7.77 (d, J = 8.9, 1H), 7.28-7.11 (m, 1H), 4.31-4.17 (m, J = 7.2, 1H), 4.13-4.00 (m, 1H), 3.95-3.77 (m, J = 7.3, 1H), 3.78-3.65 (m, 2H), 3.65-3.51 (m, 2H), 2.76-2.55 (m, 4H), 2.08-1.89 (m, 5H). |
| 496 | (CD3)2SO | 9.13 (s, 2H), 8.91-8.79 (m, 1H), 7.97-7.64 (m, 3H), 7.16-6.97 (m, 1H), 4.29-4.14 (m, 2H), 4.14-4.06 (m, 1H), 3.97-3.83 (m, 1H), 3.65 (s, 4H), 2.76-2.55 (m, 4H), 1.28 (d, J = 6.4, 6H). |
| 497 | (CD3)2SO | 9.12 (s, J = 21.1, 2H), 8.93-8.81 (m, 1H), 7.96-7.78 (m, 2H), 7.74 (d, J = 8.9, 1H), 7.24-7.10 (m, 1H), 4.27-4.15 (m, 1H), 4.14-4.08 (m, 1H), 3.97-3.86 (m, 1H), 3.70-3.62 (m, 4H), 3.38 (d, J = 6.3, 2H), 2.74-2.57 (m, 4H), 1.16 (td, J = 7.5, 3.9, 1H), 0.63-0.53 (m, 2H), 0.37-0.30 (m, 2H). |
| 498 | (CD3)2SO | 9.07 (s, 2H), 8.65 (t, J = 5.6, 1H), 7.55 (d, J = 9.2, 1H), 7.50-7.43 (m, 1H), 7.42 (d, J = 9.0, 1H), 7.32-7.26 (m, 1H), 6.84 (d, J = 9.2, 1H), 4.78 (t, J = 5.3, 1H), 4.03-3.94 (m, 2H), 3.89-3.78 (m, 1H), 3.65-3.53 (m, 6H), 3.51-3.41 (m, 2H), 2.50-2.39 (m, 4H). |
| 499 | (CD3)2SO | 9.06 (s, J = 9.1, 2H), 8.69 (d, J = 5.6, 1H), 7.63 (d, J = 9.3, 1H), 7.51 (d, J = 9.1, 1H), 7.45 (d, J = 9.0, 1H), 6.86 (d, J = 9.3, 1H), 5.00 (s, 1H), 4.49-4.33 (m, 1H), 4.08-3.93 (m, 2H), 3.92-3.83 (m, 1H), 3.71-3.53 (m, 7H), 3.53-3.39 (m, 1H), 2.50-2.39 (m, 4H), 2.12-2.00 (m, 1H), 1.97-1.87 (m, 1H). |
| 500 | (CD3)2SO | 9.12 (s, 2H), 8.86 (s, 1H), 7.87 (d, J = 19.3, 2H), 7.75 (s, 1H), 7.09 (s, 1H), 4.18-4.02 (m, 2H), 4.02 (bs, 2H), 3.95-3.81 (m, 1H), 3.72-3.57 (m, 4H), 3.08 (s, 3H), 2.69-2.52 (m, 4H) |
| 501 | (CD3)2SO | 9.84 (bs, 1H), 9.13 (s, 2H), 8.88 (t, J = 5.6, 1H), 8.10-7.84 (m, 2H), 7.79 (d, J = 8.6, 1H), 7.16-7.00 (m, 1H), 4.29-4.03 (m, 3H), 3.99-3.82 (m, 1H), 3.72-3.55 (m, 4H), 2.98-2.86 (m, 1H), 2.74-2.54 (m, 4H), 1.06-0.92 (m, 2H), 0.81-0.68 (m, 2H). |
| 502 | (CD3)2SO | 9.07 (s, 2H), 8.69 (t, J = 5.6, 1H), 7.80 (d, J = 9.5, 1H), 7.58-7.53 (m, 1H), 7.51 (d, J = 9.0, 1H), 7.26 (d, J = 9.5, 1H), 4.05-3.94 (m, 2H), 3.93-3.82 (m, 1H), 3.76-3.69 (m, 4H), 3.69-3.63 (m, 4H), 3.63-3.56 (m, 4H), 2.50-2.40 (m, 4H). |
| 503 | (CD3)2SO | 9.16 (s, 2H), 8.80 (s, 1H), 7.76 (d, J = 9.2, 1H), 7.61 (d, J = 9.0, 1H), 7.54 (d, J = 9.0, 1H), 7.33 (d, J = 9.6, 1H), 5.80 (bs, 2H), 4.38 (d, J = 12.9, 3H), 4.22-4.09 (m, 1H), 4.07-3.94 (m, 1H), 3.71 (s, 4H), 3.65-3.57 (m, 2H), 3.01-2.70 (m, 3H), 2.64-2.55 (m, 2H), 1.22-1.15 (m, 6H). |
| 504 | (CD3)2SO | 9.14 (s, 2H), 8.91 (s, 2H), 8.77 (s, 1H), 7.83 (d, J = 9.4, 1H), 7.60 (dd, J = 9.0, 0.5, 1H), 7.55 (d, J = 9.0, 1H), 7.33 (d, J = 9.5, 1H), 4.38-4.19 (m, 1H), 4.18-4.03 (m, 1H), 4.04-3.94 (m, 1H), 3.94-3.85 (m, 4H), 3.76-3.60 (m, 4H), 3.27-3.17 (m, 4H), 2.88-2.63 (m, 4H). |
| 505 | (CD3)2SO | 10.04 (s, 1H), 9.14 (s, 2H), 8.78 (t, J = 5.6, 1H), 7.85 (d, J = 9.4, 1H), 7.61 (dd, J = 9.0, 0.6, 1H), 7.58-7.53 (m, 1H), 7.36 (d, J = 9.5, 1H), 6.60 (bs, J = 528.3, 1H), 4.64 (d, J = 13.6, 2H), 4.31 (s, 1H), 4.18-4.04 (m, 1H), 4.05-3.90 (m, 1H), 3.69 (d, J = 11.3, 2H), 3.57 (d, J = 11.3, 2H), 3.32-3.19 (m, 2H), 3.15-3.02 (m, 2H), 2.86 (s, 3H), 2.86-2.61 (m, 4H). |
| 506 | (CD3)2SO | 9.13 (s, 2H), 8.88 (t, J = 5.7, 1H), 7.93 (d, J = 9.6, 1H), 7.88 (d, J = 9.0, 1H), 7.74 (d, J = 9.0, 1H), 7.23 (d, J = 9.6, 1H), 5.74 (bs, 2H), 4.52 (s, 1H), 4.22 (s, 1H), 4.16-4.03 (m, 1H), 4.03-3.90 (m, 1H), 3.90-3.71 (m, 3H), 3.71 (s, 5H), 2.86-2.56 (m, 4H), 2.21-1.96 (m, 2H). |

| Co. No. | Solvent | NMR data |
|---|---|---|
| 507 | (CD3)2SO | 10.28-9.18 (m, 1H), 9.14 (s, 2H), 8.89 (s, 1H), 7.99-7.66 (m, 3H), 7.16 (s, 1H), 4.31-4.15 (m, 1H), 4.05 (dm, J = 6.5, 1H), 3.88 (s, 1H), 3.38 (s, 2H), 2.62 (d, J = 35.4, 4H), 2.00 (s, 4H), 1.16 (s, 1H), 0.59 (d, J = 7.1, 2H), 0.34 (d, J = 5.0, 2H). |
| 508 | (CD3)2SO | 9.83-9.42 (m, 1H), 9.15 (s, 2H), 9.01-8.84 (m, 1H), 8.03-7.71 (m, 3H), 7.38-7.20 (m, 1H), 4.33-4.22 (m, 1H), 4.06 (s, 1H), 3.90 (s, 1H), 3.80 (s, 1H), 3.65 (s, 1H), 3.50 (dd, J = 10.9, 5.1, 2H), 3.45-3.35 (m, 1H), 2.76-2.53 (m, 4H), 2.09-1.88 (m, 4H). |
| 509 | (CD3)2SO | 9.14 (s, 2H), 8.81 (t, J = 5.8, 1H), 7.83 (d, J = 9.2, 1H), 7.65 (d, J = 9.1, 1H), 7.60 (d, J = 9.0, 1H), 7.58-7.41 (m, 1H), 6.91 (d, J = 9.3, 1H), 4.45 (d, J = 10.3, 3H), 4.33-4.23 (m, 1H), 4.19 (d, J = 10.3, 2H), 4.12-3.98 (m, 1H), 3.98-3.87 (m, 1H), 2.78-2.55 (m, 4H), 2.10-1.92 (m, 4H). |
| 510 | (CD3)2SO | 9.17-9.07 (m, 2H), 8.90 (t, J = 5.6, 1H), 7.91 (d, J = 9.4, 1H), 7.81-7.67 (m, 2H), 6.98 (d, J = 9.6, 1H), 4.49-4.31 (m, 2H), 4.23 (t, J = 7.2, 1H), 4.20-4.09 (m, 2H), 4.08-4.01 (m, 1H), 3.97-3.86 (m, 1H), 3.63 (d, J = 5.7, 2H), 3.00-2.87 (m, 1H), 2.72-2.63 (m, 2H), 2.63-2.55 (m, 2H), 2.05-1.92 (m, 4H). |
| 511 | CD3OD | 9.04 (s, 2H), 7.76-7.60 (m, 2H), 7.58-7.43 (m, 1H), 6.86 (d, J = 9.3, 1H), 4.27-4.12 (m, 1H), 4.13-3.99 (m, 2H), 3.85-3.71 (m, 2H), 3.55-3.45 (m, 2H), 2.78 (s, 3H), 2.76-2.62 (m, 4H), 2.15-1.91 (m, 4H) |
| 512 | CD3OD | 9.01 (s, 2H), 7.71-7.52 (m, 2H), 7.48 (d, J = 9.0, 1H), 6.69 (d, J = 9.0, 1H), 4.40 (dd, J = 8.7, 7.6, 2H), 4.11-3.90 (m, 4H), 3.90-3.80 (m, 2H), 3.71 (t, J = 4.6, 4H), 2.66-2.48 (m, 4H) |
| 513 | CD3OD | 9.04 (s, 2H), 7.70 (dd, J = 12.5, 9.2, 2H), 7.57 (d, J = 9.0, 1H), 6.89 (d, J = 9.3, 1H), 4.26-4.12 (m, 1H), 4.12-4.01 (m, 2H), 3.97-3.88 (m, 6H), 3.54-3.41 (m, 6H), 2.81-2.60 (m, 4H), 2.12-1.92 (m, 4H) |
| 514 | CD3OD | 9.01 (s, 2H), 7.58 (dd, J = 15.6, 9.2, 2H), 7.55-7.42 (m, 1H), 6.78 (d, J = 9.2, 1H), 4.14-3.93 (m, 2H), 3.88-3.75 (m, 1H), 3.76-3.58 (m, 8H), 3.00-2.87 (m, 2H), 2.82 (t, J = 5.5, 2H), 2.66-2.47 (m, 4H) |
| 515 | CD3OD | 9.05 (s, 2H), 8.05 (d, J = 10.0, 1H), 7.85 (d, J = 9.0, 1H), 7.76 (d, J = 9.0, 1H), 7.52 (d, J = 10.0, 1H), 4.52-4.38 (m, 2H), 4.19 (dd, J = 7.7, 6.4, 1H), 4.14-3.96 (m, 2H), 3.65-3.52 (m, 2H), 3.11-2.99 (m, 1H), 2.81-2.54 (m, 4H), 2.31-2.14 |
| 516 | CD3OD | 9.02 (s, 2H), 7.63 (d, J = 9.9, 1H), 7.57 (dd, J = 9.1, 0.6, 1H), 7.44 (d, J = 9.1, 1H), 7.15 (d, J = 9.5, 1H), 4.14-3.94 (m, 5H), 3.76-3.66 (m, 4H), 3.61-3.45 (m, 2H), 2.65-2.44 (m, 4H), 1.64 (dt, J = 13.7, 8.9, 4H), 1.26 (s, 3H) |
| 517 | CD3OD | 9.04 (s, 2H), 7.93 (d, J = 9.1, 1H), 7.84 (d, J = 9.0, 1H), 7.67 (d, J = 9.0, 1H), 7.08 (d, J = 9.1, 1H), 4.88-4.81 (m, 2H), 4.18 (d, J = 6.4, 1H), 4.12-4.03 (m, 2H), 3.71-3.60 (m, 2H), 3.01 (s, 6H), 2.79-2.59 (m, 4H), 2.02 (t, J = 13.6, 4H). |
| 518 | CD3OD | 9.05 (s, 2H), 8.03 (d, J = 9.6, 1H), 7.87-7.78 (m, 2H), 7.73 (d, J = 9.1, 1H), 7.50 (d, J = 10.0, 1H), 4.69-4.60 (m, 2H), 4.36-4.23 (m, 1H), 4.23-4.14 (m, 1H), 4.14-4.00 (m, 2H), 3.51-3.42 (m, 2H), 2.80-2.61 (m, 4H), 2.27-2.16 (m, 2H), 2.16-1.95 (m, 6H) |
| 519 | CD3OD | 9.02 (s, 2H), 7.74-7.55 (m, 2H), 7.44 (d, J = 9.1, 1H), 6.86 (d, J = 9.4, 1H), 4.13-3.92 (m, 3H), 3.81-3.66 (m, 6H), 3.65-3.47 (m, 2H), 3.11-2.90 (m, 2H), 2.69-2.40 (m, 4H), 2.21-2.02 (m, 2H), 2.01-1.77 (m, 4H) |
| 520 | CD3OD | 9.02 (s, 2H), 7.70-7.56 (m, 2H), 7.45 (d, J = 9.0, 1H), 6.87 (d, J = 9.0, 1H), 4.11-3.90 (m, 3H), 3.80-3.50 (m, 8H), 2.96-2.69 (m, 2H), 2.67-2.44 (m, 4H), 2.18-1.94 (m, 2H), 1.80-1.41 (m, 6H) |
| 521 | CD3OD | 9.38 (s, 2H), 8.14-7.96 (m, 3H), 7.72 (d, J = 9.1, 1H), 7.58 (d, J = 10.0, 1H), 4.58 (d, J = 13.4, 2H), 4.50-4.36 (m, 2H), 4.01-3.87 (m, 4H), 3.56-3.35 (m, 4H), 3.25-3.08 (m, 2H), 2.99-2.89 (m, 2H), 2.28-1.99 (m, 3H), 1.67-1.45 (m, 2H) |
| 522 | CD3OD | 9.00 (s, 2H), 7.69-7.57 (m, 2H), 7.48 (d, J = 9.0, 1H), 6.70 (d, J = 9.0, 1H), 4.40-4.28 (m, 2H), 4.09-3.95 (m, 3H), 3.95-3.86 (m, 2H), 3.75-3.64 (m, 5H), 2.65-2.47 (m, 4H), 2.38 (s, 3H) |
| 523 | CDCl3 | 8.90 (s, 2H), 7.40-7.32 (m, 1H), 7.33-7.28 (m, 1H), 7.08-6.99 (m, 1H), 6.68-6.50 (m, 1H), 4.10-3.81 (m, 3H), 3.78-3.55 (m, 7H), 3.25-3.09 (m, 2H), 2.79-2.65 (m, 2H), 2.59-2.42 (m, 4H) |
| 524 | CD3OD | 9.02 (s, 2H), 7.76-7.57 (m, 2H), 7.53-7.44 (m, 1H), 6.77-6.63 (m, 1H), 4.30-3.79 (m, 9H), 3.71 (t, J = 4.5, 4H), 2.57 (s, 4H) |
| 525 | CD3OD | 9.02 (s, 2H), 7.70-7.58 (m, 2H), 7.46 (d, J = 9.0, 1H), 6.90 (d, J = 9.0, 1H), 4.11-3.91 (m, 5H), 3.87-3.76 (m, 2H), 3.76-3.67 (m, 6H), 3.62-3.53 (m, 2H), 3.18-3.09 (m, 2H), 2.67-2.47 (m, 4H) |
| 526 | CD3OD | 8.99 (s, 2H), 7.66 (d, J = 9.3, 1H), 7.63-7.58 (m, 1H), 7.46 (d, J = 9.0, 1H), 6.88 (d, J = 9.3, 1H), 5.10-5.01 (m, 1H), 4.75-4.69 (m, 1H), 4.09-3.94 (m, 3H), 3.91 (dd, J = 7.4, 1.4, 1H), 3.83 (d, J = 7.4, 1H), 3.71 (t, J = 4.6, 4H), 3.66-3.59 (m, 1H), 3.49 (d, J = 10.0, 1H), 2.66-2.44 (m, 4H), 2.05-1.97 (m, 2H). |
| 527 | CD3OD | 9.01 (s, 2H), 7.66-7.54 (m, 2H), 7.43 (d, J = 9.0, 1H), 6.78 (d, J = 9.0, 1H), 4.11-3.87 (m, 5H), 3.71 (t, J = 4.6, 4H), 3.40 (dd, J = 17.6, 5.9, 2H), 3.36 (d, J = 6.9, 2H), 2.65-2.48 (m, 4H), 1.99-1.85 (m, 1H), 1.80-1.66 (m, 2H), 1.39-1.31 (m, 2H). |

| Co. No. | Solvent | NMR data |
|---|---|---|
| 528 | CD3OD | 9.05 (s, 2H), 7.91 (d, J = 9.8, 1H), 7.78 (d, J = 9.0, 1H), 7.66 (d, J = 9.0, 1H), 7.39 (d, J = 9.8, 1H), 4.24-4.14 (m, 1H), 4.12-4.00 (m, 2H), 3.35-3.21 (m, 4H), 2.91 (d, J = 6.8, 2H), 2.79-2.57 (m, 4H), 2.12-1.81 (m, 7H), 1.51-1.32 (m, 2H) |
| 529 | CD3OD | 9.04 (s, 2H), 7.89-7.80 (m, 1H), 7.75 (d, J = 9.0, 1H), 7.61 (d, J = 9.1, 1H), 7.08-6.98 (m, 1H), 4.23-4.01 (m, 4H), 3.96-3.68 (m, 3H), 3.39-3.32 (m, 2H), 2.79-2.61 (m, 4H), 2.56-2.28 (m, 2H), 2.12-1.71 (m, 10H) |
| 530 | CD3OD | 9.04 (s, 2H), 8.05 (d, J = 9.8, 1H), 7.88-7.72 (m, 2H), 7.48-7.13 (m, 1H), 5.25 (s, 1H), 4.88 (s, 1H), 4.23-3.86 (m, 5H), 3.88-3.64 (m, 2H), 2.81-2.57 (m, 4H), 2.26-2.10 (m, 2H), 2.10-1.86 (m, 4H) |
| 531 | CD3OD | 9.04 (s, 2H), 7.85 (dd, J = 9.4, 5.3, 1H), 7.73 (d, J = 9.1, 1H), 7.60 (d, J = 9.1, 1H), 7.02 (d, J = 9.4, 1H), 4.24-4.01 (m, 4H), 3.97-3.68 (m, 3H), 3.54-3.42 (m, 2H), 2.81-2.56 (m, 4H), 2.49 (t, J = 7.5, 2H), 2.35-2.11 (m, 4H), 2.13-1.83 (m, 4H) |
| 532 | CD3OD | 9.04 (s, 2H), 8.08 (d, J = 9.9, 1H), 7.91 (d, J = 9.1, 1H), 7.80 (d, J = 9.1, 1H), 7.28 (d, J = 9.9, 1H), 4.65-4.52 (m, 1H), 4.18-3.99 (m, 4H), 3.98-3.84 (m, 2H), 3.79-3.59 (m, 5H), 2.73-2.52 (m, 4H), 2.49-2.35 (m, 1H), 2.29-2.12 (m, 1H), 1.97 (s, 3H). |
| 533 | CD3OD | 9.05 (s, 2H), 8.09 (d, J = 9.8, 1H), 7.91 (d, J = 9.0, 1H), 7.80 (d, J = 9.0, 1H), 7.27 (d, J = 9.8, 1H), 5.28-5.11 (m, 1H), 4.18-3.96 (m, 5H), 3.87-3.67 (m, 6H), 3.13-2.86 (m, 3H), 2.73-2.55 (m, 4H), 2.48-2.30 (m, 2H), 2.28-2.07 (m, 3H) |
| 534 | CD3OD | 9.02 (s, 2H), 7.64-7.49 (m, 2H), 7.42 (d, J = 9.0, 1H), 6.86 (d, J = 9.4, 1H), 4.36-4.22 (m, 1H), 4.07-3.93 (m, 3H), 3.75-3.63 (m, 4H), 3.58-3.42 (m, 1H), 2.66-2.40 (m, 4H), 2.22-1.93 (m, 4H), 1.86-1.73 (m, 1H), 1.26 (d, J = 6.3, 3H) |
| 535 | CD3OD | 9.04 (s, 2H), 8.06 (d, J = 9.9, 1H), 7.92-7.75 (m, 2H), 7.54-7.28 (m, 1H), 4.61-4.43 (m, 1H), 4.19-3.97 (m, 3H), 3.95-3.64 (m, 8H), 2.74-2.53 (m, 4H), 2.34-1.97 (m, 4H) |
| 536 | CD3OD | 9.04 (s, 2H), 8.06 (d, J = 9.8, 1H), 7.94-7.69 (m, 2H), 7.55-7.25 (m, 1H), 4.53 (s, 1H), 4.20-3.98 (m, 3H), 3.94-3.59 (m, 8H), 2.72-2.50 (m, 4H), 2.39-1.94 (m, 4H). |
| 537 | CD3OD | 9.04 (s, 2H), 8.08-7.96 (m, 1H), 7.92-7.83 (m, 1H), 7.79 (d, J = 9.0, 1H), 7.50-7.34 (m, 1H), 4.70-4.60 (m, 1H), 4.17-3.97 (m, 3H), 3.95-3.85 (m, 1H), 3.82-3.52 (m, 7H), 3.38 (s, 3H), 2.70-2.54 (m, 4H), 2.34-2.00 (m, 4H) |
| 538 | CD3OD | 9.04 (s, 2H), 8.08-7.98 (m, 1H), 7.93-7.84 (m, 1H), 7.79 (d, J = 8.9, 1H), 7.47-7.31 (m, 1H), 4.72-4.56 (m, 1H), 4.15-4.08 (m, 1H), 4.07-3.97 (m, 2H), 3.95-3.85 (m, 1H), 3.83-3.51 (m, 7H), 3.38 (s, 3H), 2.69-2.53 (m, 4H), 2.34-1.99 (m, 4H) |
| 539 | CD3OD | 9.03 (s, 2H), 8.03 (d, J = 9.9, 1H), 7.85 (d, J = 9.2, 1H), 7.76 (d, J = 9.2, 1H), 7.58 (d, J = 9.9, 1H), 4.31-4.17 (m, 1H), 4.15-3.98 (m, 4H), 3.82-3.63 (m, 5H), 2.67-2.52 (m, 4H), 2.00-1.86 (m, 2H), 1.80-1.65 (m, 4H) |
| 540 | CD3OD | 9.02 (s, 2H), 7.84 (d, J = 9.3, 1H), 7.67 (d, J = 9.0, 1H), 7.52 (d, J = 9.0, 1H), 7.31 (d, J = 9.3, 1H), 4.38-4.24 (m, 4H), 4.15-3.89 (m, 3H), 3.72 (t, J = 4.3, 4H), 3.23-3.05 (m, 4H), 2.71-2.47 (m, 4H) |
| 541 | CD3OD | 9.04 (s, 2H), 8.10 (d, J = 9.8, 1H), 7.91 (d, J = 9.1, 1H), 7.81 (d, J = 9.1, 1H), 7.29 (d, J = 9.8, 1H), 4.74-4.61 (m, 1H), 4.22-3.86 (m, 6H), 3.84-3.63 (m, 5H), 2.76-2.56 (m, 4H), 2.56-2.42 (m, 1H), 2.41-2.20 (m, 1H). |
| 542 | CD3OD | 9.26 (s, 2H), 7.94-7.81 (m, 2H), 7.76-7.70 (m, 1H), 7.17-7.04 (m, 1H), 4.44-4.35 (m, 2H), 3.86-3.77 (m, 2H), 3.28-3.15 (m, 4H), 2.83-2.77 (m, 2H), 1.94-1.84 (m, 4H), 1.69-1.55 (m, 2H) |
| 543 | CD3OD | 9.30 (s, 2H), 7.93-7.87 (m, 1H), 7.82 (d, J = 9.1, 1H), 7.64 (d, J = 9.1, 1H), 7.14 (d, J = 9.6, 1H), 4.99-4.91 (m, 2H), 4.54-4.36 (m, 2H), 4.20-4.13 (m, 1H), 4.12-4.04 (m, 1H), 3.99-3.80 (m, 3H), 3.44 (dd, J = 30.5, 28.9, 2H), 3.27-3.09 (m, 1H), 2.66-2.52 (m, 1H), 2.38-2.26 (m, 1H), 1.99-1.84 (m, 4H), 1.73-1.54 (m, 2H) |
| 544 | CD3OD | 9.30 (s, 2H), 7.86 (d, J = 9.6, 1H), 7.79 (d, J = 9.2, 1H), 7.62 (d, J = 9.2, 1H), 7.11 (d, J = 9.6, 1H), 4.96-4.91 (m, 1H), 4.51-4.35 (m, 2H), 4.18-4.11 (m, 1H), 4.09-4.00 (m, 1H), 3.96-3.79 (m, 3H), 3.51-3.35 (m, 2H), 3.28-3.10 (m, 2H), 2.63-2.52 (m, 1H), 2.34-2.26 (m, 1H), 1.98-1.85 (m, 4H), 1.72-1.54 (m, 2H) |
| 545 | CD3OD | 9.29 (s, 2H), 7.69 (d, J = 9.0, 1H), 7.62 (d, J = 9.3, 1H), 7.52 (d, J = 9.0, 1H), 6.91 (d, J = 9.3, 1H), 5.00-4.92 (m, 1H), 4.49-4.33 (m, 2H), 3.80-3.74 (m, 2H), 3.55-3.34 (m, 2H), 3.26-3.21 (m, 2H), 3.21-3.05 (m, 2H), 1.96-1.85 (m, 4H), 1.73-1.54 (m, 2H) |
| 546 | CD3OD | 9.31 (s, 2H), 7.98 (d, J = 10.0, 1H), 7.85 (d, J = 9.1, 1H), 7.69 (d, J = 9.1, 1H), 7.52 (d, J = 10.0, 1H), 4.99-4.93 (m, 1H), 4.52-4.37 (m, 2H), 4.20-4.09 (m, 2H), 4.07-4.01 (m, 1H), 3.79-3.69 (m, 2H), 3.50-3.32 (m, 2H), 3.28-3.14 (m, 2H), 2.11-1.99 (m, 2H), 1.96-1.87 (m, 4H), 1.80-1.57 (m, 4H) |
| 547 | CD3OD | 9.27 (s, 2H), 7.94-7.85 (m, 1H), 7.81-7.76 (m, 1H), 7.74-7.70 (m, 1H), 7.20-7.10 (m, 1H), 4.84-4.79 (m, 1H), 4.44-4.33 (m, 2H), 3.86 (t, J = 5.0, 2H), 3.69 (t, J = 5.0, 2H), 3.42-3.33 (m, 2H), 3.27-3.14 (m, 2H), 1.97-1.82 (m, 4H), 1.71-1.55 (m, 2H) |

| Co. No. | Solvent | NMR data |
|---|---|---|
| 548 | CD3OD | 9.30 (s, 2H), 7.87 (d, J = 9.7, 1H), 7.75 (d, J = 9.1, 1H), 7.60 (d, J = 9.1, 1H), 7.35 (d, J = 9.7, 1H), 4.99-4.92 (m, 1H), 4.51-4.35 (m, 2H), 3.83 (m, 8H), 3.52-3.32 (m, 2H), 3.28-3.12 (m, 2H), 2.01-1.84 (m, 4H), 1.73-1.55 (m, 2H) |
| 549 | CD3OD | 9.30 (s, 2H), 7.76 (d, J = 9.1, 1H), 7.67 (d, J = 9.1, 1H), 7.49 (d, J = 9.1, 1H), 7.27 (d, J = 9.1, 1H), 4.99-4.93 (m, 1H), 4.51-4.35 (m, 2H), 4.07-3.96 (m, 4H), 3.54-3.32 (m, 6H), 3.28-3.14 (m, 2H), 2.00-1.87 (m, 4H), 1.73-1.54 (m, 2H) |
| 550 | CD3OD | 9.30 (s, 2H), 7.95-7.83 (m, 1H), 7.80-7.74 (m, 1H), 7.72-7.69 (m, 1H), 7.27-7.08 (m, 1H), 5.00-4.93 (m, 1H), 4.52-4.34 (m, 2H), 3.98-3.87 (m, 1H), 3.76-3.54 (m, 4H), 3.51-3.33 (m, 2H), 3.28-3.07 (m, 2H), 2.00-1.81 (m, 4H), 1.73-1.51 (m, 2H) |
| 551 | CD3OD | 9.07 (s, 2H), 8.11 (d, J = 9.8, 1H), 7.93 (d, J = 9.1, 1H), 7.81 (d, J = 9.1, 1H), 7.30 (d, J = 9.8, 1H), 4.37-4.27 (m, 1H), 4.22-4.03 (m, 4H), 4.00-3.83 (m, 2H), 3.82-3.70 (m, 5H), 3.05 (s, 3H), 2.79-2.71 (m, 2H), 2.70-2.63 (m, 2H), 2.55-2.44 (m, 1H), 2.30-2.16 (m, 1H) |
| 552 | CD3OD | 9.04 (s, 2H), 8.10 (d, J = 9.8, 1H), 7.92 (d, J = 9.0, 1H), 7.81 (d, J = 9.0, 1H), 7.29 (d, J = 9.8, 1H), 4.35-4.28 (m, 1H), 4.16-3.99 (m, 4H), 3.97-3.82 (m, 2H), 3.82-3.75 (m, 1H), 3.75-3.68 (m, 4H), 3.05 (s, 3H), 2.68-2.54 (m, 4H), 2.52-2.43 (m, 1H), 2.29-2.16 (m, 1H) |
| 553 | CD3OD | 9.05 (s, 2H), 8.07-7.90 (m, 1H), 7.89-7.75 (m, 2H), 7.27-7.05 (m, 1H), 4.20-3.99 (m, 3H), 3.81-3.68 (m, 6H), 3.46-3.38 (m, 2H), 2.96 (s, 3H), 2.75-2.56 (m, 4H) |
| 554 | CD3OD | 9.06 (s, 2H), 7.99-7.82 (m, 2H), 7.80-7.75 (m, 1H), 7.16-7.03 (m, 1H), 4.23-3.98 (m, 6H), 3.80-3.68 (m, 4H), 3.61-3.52 (m, 2H), 2.79-2.59 (m, 4H), 2.06-1.98 (m, 2H), 1.79-1.63 (m, 2H) |
| 555 | CD3OD | 9.05 (s, 2H), 8.06 (d, J = 9.9, 1H), 7.86 (d, J = 9.0, 1H), 7.78 (d, J = 9.0, 1H), 7.43 (d, J = 9.9, 1H), 4.98-4.88 (m, 2H), 4.18-4.01 (m, 3H), 3.99-3.90 (m, 1H), 3.79-3.70 (m, 4H), 2.77-2.59 (m, 4H), 2.40-2.19 (m, 6H), 2.12-2.04 (m, 2H), 1.99 (s, 3H) |
| 556 | CD3OD | 9.09 (s, 2H), 8.05 (d, J = 9.7, 1H), 7.89 (d, J = 9.1, 1H), 7.75 (d, J = 9.1, 1H), 7.23 (d, J = 9.7, 1H), 4.23-3.86 (m, 8H), 3.79-3.74 (m, 4H), 2.84 (s, 3H), 2.83-2.77 (m, 2H), 2.75-2.58 (m, 3H), 2.48-2.38 (m, 1H) |
| 557 | CD3OD | 9.11 (s, 2H), 7.90 (d, J = 9.4, 1H), 7.85-7.80 (d, J = 9.0 1H), 7.68 (d, J = 9.0, 1H), 7.09 (d, J = 9.4, 1H), 4.32-4.26 (m, 1H), 4.25-4.18 (m, 1H), 4.16-4.09 (m, 1H), 3.91-3.84 (m, 2H), 3.82-3.76 (m, 4H), 3.29-3.33 (m, 2H), 2.96-2.84 (m, 2H), 2.82-2.75 (m, 2H) |
| 558 | CD3OD | 9.06 (s, 2H), 8.05 (d, J = 9.8, 1H), 7.89 (d, J = 9.1, 1H), 7.76 (d, J = 9.1, 1H), 7.22 (d, J = 9.8, 1H), 4.18-4.02 (m, 5H), 3.90-3.83 (m, 2H), 3.78-3.72 (m, 4H), 3.69-3.61 (m, 2H), 3.49-3.40 (m, 2H), 3.39-3.34 (m, 2H), 2.71 (m, 2H), 2.66 (m, 2H) |
| 559 | CD3OD | 9.09 (s, 2H), 7.83 (d, J = 9.5, 1H), 7.74 (d, J = 9.1, 1H), 7.59 (d, J = 9.1, 1H), 7.07 (d, J = 9.5, 1H), 4.24-4.06 (m, 3H), 3.91-3.82 (m, 1H), 3.82-3.69 (m, 7H), 3.65-3.53 (m, 2H), 3.38-3.32 (m, 2H), 2.88-2.77 (m, 2H), 2.76-2.67 (m, 2H), 2.45-2.30 (m, 1H), 2.19-2.05 (m, 1H) |
| 560 | CD3OD | 9.08 (s, 2H), 7.98 (d, J = 9.6, 1H), 7.84 (d, J = 9.1, 1H), 7.70 (d, J = 9.1, 1H), 7.18 (d, J = 9.6, 1H), 4.56-4.49 (m, 1H), 4.32-4.26 (m, 1H), 4.21-3.96 (m, 5H), 3.81-3.70 (m, 5H), 3.55-3.38 (m, 3H), 2.84-2.75 (m, 2H), 2.74-2.66 (m, 2H), 2.46-2.34 (m, 1H), 2.18-2.06 (m, 1H) |
| 561 | CD3OD | 9.12 (s, 2H), 8.08 (d, J = 9.8, 1H), 7.93 (d, J = 9.1, 1H), 7.77 (d, J = 9.1, 1H), 7.26 (d, J = 9.8, 1H), 4.35-4.28 (m, 1H), 4.27-4.10 (m, 4H), 4.05-3.91 (m, 3H), 3.83-3.75 (m, 4H), 2.96-2.85 (m, 2H), 2.84-2.75 (m, 2H), 2.68-2.56 (m, 1H), 2.43-2.31 (m, 1H) |
| 562 | CD3OD | 9.05 (s, 2H), 7.91-7.85 (m, 1H), 7.77 (d, J = 9.1, 1H), 7.64 (d, J = 9.1, 1H), 7.11-7.06 (m, 1H), 4.14-4.01 (m, 5H), 3.99-3.77 (m, 3H), 3.76-3.69 (m, 4H), 2.83 (s, 3H), 2.74-2.55 (m, 5H), 2.41-2.30 (m, 1H) |
| 563 | CD3OD | 9.13 (s, 2H), 8.09 (d, J = 9.8, 1H), 7.93 (d, J = 9.1, 1H), 7.78 (d, J = 9.1, 1H), 7.26 (d, J = 9.8, 1H), 4.37-4.31 (m, 1H), 4.28-4.11 (m, 4H), 4.07-3.91 (m, 3H), 3.85-3.76 (m, 4H), 3.00-2.88 (m, 2H), 2.87-2.78 (m, 2H), 2.68-2.57 (m, 1H), 2.43-2.33 (m, 1H) |
| 564 | CD3OD | 9.08 (s, 2H), 8.07-8.00 (m, 1H), 7.87 (d, J = 9.0, 1H), 7.73 (d, J = 9.0, 1H), 7.22-7.17 (m, 1H), 4.23-4.13 (m, 2H), 4.12-4.03 (m, 4H), 4.01-3.91 (m, 1H), 3.83-3.73 (m, 5H), 3.44-3.35 (m, 1H), 3.16-3.05 (m, 1H), 3.03-2.96 (m, 1H), 2.83-2.73 (m, 2H), 2.72-2.64 (m, 2H), 2.05-1.82 (m, 4H) |
| 565 | CD3OD | 9.11 (s, 2H), 7.97 (d, J = 9.5, 1H), 7.84 (d, J = 9.1, 1H), 7.67 (d, J = 9.1, 1H), 7.30 (d, J = 9.5, 1H), 5.17-5.12 (m, 1H), 4.62 (m, 1H), 4.36-4.25 (m, 3H), 4.24-4.07 (m, 2H), 3.85-3.75 (m, 5H), 3.72-3.53 (m, 3H), 2.95-2.83 (m, 2H), 2.81-2.74 (m, 2H) |
| 566 | CD3OD | 9.07 (s, 2H), 7.91 (d, J = 9.6, 1H), 7.81 (d, J = 9.2, 1H), 7.66 (d, J = 9.2, 1H), 7.09 (d, J = 9.6, 1H), 4.35 (m, 1H), 4.21-4.02 (m, 3H), 3.98-3.87 (m, 3H), 3.81-3.71 (m, 4H), 2.83-2.73 (m, 2H), 2.73-2.65 (m, 2H), 2.31-2.23 (m, 1H), 1.51-1.44 (m, 1H), 1.08-1.01 (m, 1H) |
| 567 | CD3OD | 9.26 (s, 2H), 7.89 (d, J = 9.7, 1H), 7.81 (d, J = 9.1, 1H), 7.72 (d, J = 9.1, 1H), 7.15 (d, J = 9.7, 1H), 4.82-4.76 (m, 1H), 4.43-4.30 (m, 2H), 3.77-3.72 (m, 2H), 3.70-3.65 (m, 2H), 3.40 (s, 3H), 3.28-3.02 (m, 4H), 1.97-1.76 (m, 4H), 1.69-1.51 (m, 2H) |

| Co. No. | Solvent | NMR data |
|---|---|---|
| 568 | CD3OD | 9.30 (s, 2H), 7.89 (d, J = 9.7, 1H), 7.76 (d, J = 9.1, 1H), 7.61 (d, J = 9.1, 1H), 7.38 (d, J = 9.7, 1H), 4.99-4.92 (m, 1H), 4.49-4.34 (m, 3H), 4.31-4.26 (m, 1H), 4.13-4.06 (m, 1H), 3.78-3.69 (m, 1H), 3.69-3.61 (m, 3H), 3.54-3.32 (m, 3H), 3.29-3.19 (m, 2H), 3.16-3.07 (m, 1H), 2.01-1.85 (m, 4H), 1.71-1.58 (m, 2H) |
| 569 | CD3OD | 9.27 (s, 2H), 7.73 (d, J = 9.6, 1H), 7.65 (d, J = 9.0, 1H), 7.48 (d, J = 9.0, 1H), 7.25 (d, J = 9.6, 1H), 4.97-4.91 (m, 1H), 4.47-4.31 (m, 2H), 3.92-3.86 (m, 4H), 3.45-3.32 (m, 8H), 2.86 (s, 3H), 2.01-1.80 (m, 4H), 1.72-1.56 (m, 2H) |
| 570 | CD3OD | 9.30 (s, 2H), 7.77 (d, J = 9.4, 1H), 7.67 (d, J = 9.0, 1H), 7.49 (d, J = 9.0, 1H), 7.32 (d, J = 9.4, 1H), 5.02-4.95 (m, 1H), 4.46-4.39 (m, 2H), 4.34-4.27 (m, 4H), 3.57-3.32 (m, 3H), 3.28-3.23 (m, 1H), 3.20-3.11 (m, 4H), 2.00-1.83 (m, 4H), 1.76-1.54 (m, 2H) |
| 571 | CD3OD | 9.28 (s, 2H), 7.91 (d, J = 9.8, 1H), 7.79 (d, J = 9.1, 1H), 7.65 (d, J = 9.1, 1H), 7.44 (d, J = 9.8, 1H), 4.97-4.89 (m, 1H), 4.43-4.32 (m, 4H), 3.56-3.35 (m, 4H), 3.28-3.09 (m, 2H), 2.84-2.72 (m, 1H), 2.21-2.06 (m, 2H), 1.99-1.75 (m, 6H), 1.72-1.50 (m, 2H) |
| 572 | CD3OD | 9.29 (s, 2H), 7.94-7.85 (m, 1H), 7.81 (d, J = 9.0, 1H), 7.72 (d, J = 9.0, 1H), 7.17-7.05 (m, 1H), 4.98-4.91 (m, 1H), 4.50-4.33 (m, 2H), 3.75-3.69 (m, 2H), 3.67-3.64 (m, 2H), 3.37 (m, 2H), 3.28-3.16 (m, 2H), 2.01-1.84 (m, 6H), 1.63 (m, 2H) |
| 573 | CD3OD | 9.27 (s, 2H), 7.96-7.77 (m, 2H), 7.74-7.71 (m, 1H), 7.17-7.03 (m, 1H), 4.85-4.76 (m, 1H), 4.50-4.33 (m, 2H), 3.68-3.59 (m, 2H), 3.57-3.49 (m, 2H), 3.34 (s, 3H), 3.26-3.05 (m, 4H), 2.05-1.95 (m, 2H), 1.94-1.82 (m, 4H), 1.69-1.53 (m, 2H) |
| 574 | CD3OD | 9.29 (s, 2H), 8.05-7.99 (m, 1H), 7.89 (d, J = 9.1, 1H), 7.75 (d, J = 9.1, 1H), 7.35-7.22 (m, 1H), 4.99-4.91 (m, 1H), 4.71-4.62 (m, 1H), 4.51-4.36 (m, 2H), 4.00-3.82 (m, 3H), 3.79-3.66 (m, 1H), 3.48-3.12 (m, 4H), 2.34-2.15 (m, 2H), 1.98-1.85 (m, 4H), 1.71-1.57 (m, 2H) |
| 575 | CD3OD | 9.28 (s, 2H), 8.02 (d, J = 9.7, 1H), 7.89 (d, J = 9.1, 1H), 7.75 (d, J = 9.1, 1H), 7.28 (d, J = 9.7, 1H), 4.95-4.90 (m, 1H), 4.72-4.62 (m, 1H), 4.49-4.34 (m, 2H), 3.99-3.82 (m, 3H), 3.78-3.68 (m, 1H), 3.43-3.17 (m, 4H), 2.34-2.17 (m, 2H), 1.98-1.83 (m, 4H), 1.71-1.54 (m, 2H) |
| 576 | CD3OD | 9.27 (s, 2H), 7.95-7.85 (m, 1H), 7.80 (d, J = 9.1, 1H), 7.73 (d, J = 9.1, 1H), 7.24-7.08 (m, 1H), 4.84-4.75 (m, 1H), 4.46-4.32 (m, 2H), 4.24-4.11 (m, 1H), 3.93-3.84 (m, 1H), 3.82-3.73 (m, 2H), 3.57 (m, 7.2, 1H), 3.36-3.13 (m, 4H), 2.23-2.09 (m, 1H), 2.04-1.93 (m, 2H), 1.92-1.79 (m, 4H), 1.77-1.67 (m, 1H), 1.65-1.50 (m, 2H) |
| 577 | CD3OD | 9.29 (s, 2H), 7.76 (d, J = 9.0, 1H), 7.62 (d, J = 9.3, 1H), 7.51 (d, J = 9.0, 1H), 6.91 (d, J = 9.3, 1H), 4.99-4.91 (m, 1H), 4.50-4.31 (m, 2H), 3.85-3.76 (m, 4H), 3.58-3.38 (m, 3H), 3.41-3.33 (m, 3H), 3.23-3.15 (m, 2H), 2.00-1.84 (m, 4H), 1.72-1.56 (m, 2H) |
| 578 | CD3OD | 9.30 (s, 2H), 7.76 (d, J = 9.4, 1H), 7.67 (d, J = 9.1, 1H), 7.49 (d, J = 9.1, 1H), 7.27 (d, J = 9.4, 1H), 5.00-4.92 (m, 1H), 4.85-4.52 (m, 2H), 4.49-4.37 (m, 2H), 3.76-3.08 (m, 10H), 2.96 (s, 3H), 1.98-1.88 (m, 4H), 1.73-1.58 (m, 2H) |
| 579 | CD3OD | 9.28 (s, 2H), 7.96 (d, J = 10.0, 1H), 7.89 (d, J = 9.1, 1H), 7.71 (d, J = 9.1, 1H), 7.45 (d, J = 10.0, 1H), 4.96-4.90 (m, 1H), 4.48-4.35 (m, 2H), 4.04-3.96 (m, 2H), 3.73-3.70 (m, 2H), 3.42 (s, 3H), 3.35 (s, 3H), 3.33-3.13 (m, 4H), 1.96-1.84 (m, 4H), 1.68-1.55 (m, 2H) |
| 580 | CD3OD | 9.30 (s, 2H), 7.96 (d, J = 9.9, 1H), 7.87 (d, J = 9.1, 1H), 7.68 (d, J = 9.1, 1H), 7.42 (d, J = 9.9, 1H), 4.99-4.91 (m, 1H), 4.49-4.37 (m, 2H), 4.08-3.99 (m, 4H), 3.96-3.91 (m, 2H), 3.83-3.77 (m, 2H), 3.52-3.10 (m, 4H), 2.12-2.00 (m, 2H), 1.95-1.87 (m, 4H), 1.72-1.56 (m, 2H) |
| 582 | CD3OD | 8.98 (dd, J = 4.5, 1.5, 1H), 8.77 (s, 1H), 8.15-8.07 (m, 2H), 7.84 (d, J = 9.1, 1H), 7.70 (dd, J = 8.6, 4.5, 1H), 4.56 (dd, J = 9.4, 6.0, 1H), 4.33-4.19 (m, 2H), 3.29-3.13 (m, 5H), 2.62 (s, 3H), 2.33-2.19 (m, 4H). |
| 583 | CD3OD | 9.08 (s, 2H), 9.01 (dd, J = 4.6, 1.6, 1H), 8.42-8.31 (m, 1H), 8.12 (dd, J = 9.1, 0.7, 1H), 7.88 (d, J = 9.1, 1H), 7.77 (dd, J = 8.6, 4.6, 1H), 4.35 (t, J = 7.0, 1H), 4.22 (dd, J = 13.8, 6.4, 1H), 4.11 (dd, J = 13.6, 8.0, 1H), 2.99 (s, J = 1.4, 3H), 2.94-2.78 (m, 4H), 2.09 (ddd, J = 20.9, 13.2, 6.7, 4H). |
| 585 | CD3OD | 8.96 (dd, J = 4.4, 1.6, 1H), 8.54 (s, 2H), 8.16-8.02 (m, 2H), 7.81 (d, J = 9.1, 1H), 7.64 (dd, J = 8.6, 4.4, 1H), 4.57 (dd, J = 10.1, 5.3, 1H), 4.34-4.12 (m, 6H), 3.41-3.30 (m, 4H), 2.51-2.39 (m, 2H), 2.38-2.19 (m, 4H). |
| 586 | CD3OD | 8.93 (dd, J = 4.4, 1.6, 1H), 8.51 (s, 2H), 8.12-7.96 (m, 2H), 7.79 (d, J = 9.1, 1H), 7.59 (dd, J = 8.6, 4.4, 1H), 4.68-4.56 (m, 1H), 4.36-4.15 (m, 2H), 3.92-3.82 (m, 4H), 3.50-3.34 (m, 4H), 2.43-2.25 (m, 4H), 1.82-1.69 (m, 2H), 1.66-1.52 (m, 4H). |
| 587 | CD3OD | 8.96-8.89 (m, 1H), 8.56 (s, 2H), 8.14 (d, J = 8.2, 1H), 8.07 (d, J = 9.6, 1H), 7.78 (d, J = 9.1, 1H), 7.59 (dd, J = 8.6, 4.3, 1H), 4.98-4.89 (m, 2H), 4.41-4.29 (m, 1H), 4.19-4.07 (m, 2H), 3.74-3.60 (m, 3H), 3.51-3.36 (m, 2H), 3.19-2.95 (m, 8H), 2.26-2.10 (m, 5H), 1.09 (d, J = 6.6, 6H). |
| 588 | CD3OD | 8.95 (dd, J = 4.4, 1.6, 1H), 8.54 (br s, 2H), 8.10-8.07 (m, 2H), 7.81 (d, J = 9.1, 1H), 7.65 (dd, J = 8.6, 4.4, 1H), 4.58 (dd, J = 9.9, 5.8, 1H), 4.29-4.22 (m, 2H), 3.72 (t, J = 5.7, 2H), 3.58 (t, J = 5.7, 2H), 3.40-3.33 (m, 4H), 2.38-2.28 (m, 4H). |

| Co. No. | Solvent | NMR data |
|---|---|---|
| 589 | CD3OD | 8.97 (dd, J = 4.5, 1.6, 1H), 8.57 (s, 2H), 8.13-8.07 (m, 2H), 7.83 (d, J = 9.1, 1H), 7.65 (dd, J = 8.6, 4.5, 1H), 4.70 (dd, J = 10.4, 5.4, 1H), 4.36-4.26 (m, 2H), 3.89-3.84 (m, 4H), 3.76-3.72 (m, 4H), 3.56-3.40 (m, 4H), 2.44-2.34 (m, 4H). |
| 590 | CD3OD | 8.94-8.90 (m, 1H), 8.59 (s, 2H), 8.14 (d, J = 8.4, 1H), 8.07 (d, J = 9.1, 1H), 7.78 (d, J = 9.1, 1H), 7.60 (dd, J = 8.6, 4.4, 1H), 5.05-4.95 (m, 2H), 4.43 (s, 1H), 4.24-4.16 (m, 2H), 3.66-3.56 (m, 4H), 3.26-3.07 (m, 8H), 2.97 (s, 3H), 2.28-2.18 (m, 4H). |
| 591 | CD3OD | 8.94 (dd, J = 4.4, 1.6, 1H), 8.61 (s, 2H), 8.13 (d, J = 8.3, 1H), 8.08 (d, J = 9.1, 1H), 7.79 (d, J = 9.1, 1H), 7.62 (dd, J = 8.6, 4.4, 1H), 4.56 (t, J = 7.7, 1H), 4.28-4.23 (m, 2H), 4.18-4.11 (m, 4H), 3.29-3.22 (m, 8H), 2.36-2.26 (m, 4H). |
| 592 | CD3OD | 8.95 (dd, J = 4.4, 1.6, 1H), 8.57 (s, 2H), 8.13 (d, J = 8.2, 1H), 8.08 (d, J = 9.1, 1H), 7.81 (d, J = 9.1, 1H), 7.62 (dd, J = 8.6, 4.4, 1H), 4.57 (dd, J = 10.1, 5.4, 1H), 4.30-4.17 (m, 2H), 3.67-3.60 (m, 4H), 3.37-3.32 (m, 4H), 2.36-2.25 (m, 4H), 2.12-2.02 (m, 4H). |
| 593 | (CD3)2SO | 11.96 (s, 1H), 9.13 (s, 2H), 8.79 (t, J = 5.8, 1H), 7.55 (m, 2H), 7.31 (d, J = 8.9, 1H), 6.53 (d, J = 9.8, 1H), 4.25-4.22 (m, 1H), 3.94-3.82 (m, 2H), 2.75-2.54 (m, 4H), 2.06-1.93 (m, 4H). |
| 594 | (CD3)2SO | 11.96 (s, 1H), 9.12 (s, 2H), 8.77 (s, 1H), 7.54 (d, J = 8.8, 2H), 7.30 (d, J = 8.9, 1H), 6.54 (d, J = 9.8, 1H), 4.35-3.80 (m, 8H), 2.82-2.55 (m, 4H). |
| 595 | (CD3)2SO | 11.97 (s, 1H), 9.30 (s, 2H), 8.91 (s, 1H), 7.52 (d, J = 8.9, 1H), 7.42 (d, J = 9.6, 1H), 7.30 (d, J = 8.9, 1H), 6.52 (d, J = 9.8, 1H), 4.82 (s, 1H), 4.27 (s, 2H), 2.90 (s, 2H), 2.01-1.20 (m, 8H). |
| 596 | CDCl3 | 8.90 (s, 2H), 7.95 (d, J = 9.3, 1H), 7.89 (d, J = 9.2, 1H), 7.68 (d, J = 9.0, 1H), 6.82 (d, J = 9.5, 1H), 6.55-6.47 (m, 1H), 4.08 (d, J = 3.7, 3H), 2.70 (d, J = 23.7, 4H), 2.07 (d, J = 2.3, 4H). |
| 597 | CDCl3 | 8.99 (s, 2H), 7.92-7.86 (m, 2H), 7.67 (d, J = 9.0, 1H), 7.52 (s, 1H), 6.99 (s, 1H), 4.19 (s, 3H), 3.84 (s, 4H), 2.91-2.74 (m, 4H). |
| 598 | CD3OD | 1H NMR (400 MHz, MeOD) δ 9.02 (s, 2H), 7.87 (d, J = 9.1, 1H), 7.79 (dd, J = 8.9, 0.4, 1H), 7.60 (d, J = 9.0, 1H), 7.01 (d, J = 9.1, 1H), 4.61 (d, J = 6.4, 2H), 4.14-3.96 (m, 4H), 3.81 (t, J = 8.3, 2H), 3.71 (t, J = 4.6, 4H), 3.63 (t, J = 7.4, 2H), 3.28-3.19 (m, 1H), 2.66-2.49 (m, 4H). |
| 599 | CD3OD | 1H NMR (600 MHz, MeOD) δ 9.12 (s, 2H), 7.82 (d, J = 9.1, 1H), 7.78 (d, J = 9.0, 1H), 7.58 (d, J = 9.0, 1H), 6.96 (d, J = 9.1, 1H), 4.48 (t, J = 6.7, 2H), 4.44-4.34 (m, 1H), 4.29-4.20 (m, 1H), 4.18-4.09 (m, 1H), 3.81 (t, J = 4.6, 4H), 3.01-2.92 (m, 2H), 2.91-2.80 (m, 2H), 1.87-1.77 (m, 1H), 1.77-1.64 (m, 2H), 0.99 (d, J = 6.6, 6H). |
| 600 | CD3OD | 1H NMR (600 MHz, MeOD) δ 9.12 (s, 2H), 7.82 (d, J = 9.1, 1H), 7.78 (dd, J = 9.0, 0.7, 1H), 7.58 (d, J = 9.0, 1H), 6.97 (d, J = 9.1, 1H), 4.42-4.35 (m, 1H), 4.32 (d, J = 7.1, 2H), 4.27-4.19 (m, 1H), 4.16-4.08 (m, 1H), 3.81 (t, J = 4.6, 4H), 3.01-2.91 (m, 2H), 2.91-2.81 (m, 2H), 2.47-2.35 (m, 1H), 1.91-1.81 (m, 2H), 1.77-1.57 (m, 4H), 1.48-1.33 (m, 2H). |
| 601 | CD3OD | 1H NMR (600 MHz, MeOD) δ 9.09 (s, 2H), 7.86 (d, J = 9.1, 1H), 7.79 (d, J = 9.0, 1H), 7.59 (d, J = 9.0, 1H), 7.01 (d, J = 9.1, 1H), 4.55-4.47 (m, 1H), 4.46-4.37 (m, 1H), 4.37-4.25 (m, 2H), 4.25-4.17 (m, 1H), 4.15-4.07 (m, 1H), 3.98-3.89 (m, 1H), 3.85-3.75 (m, 6H), 2.93-2.82 (m, 2H), 2.82-2.73 (m, 2H), 2.18-2.06 (m, 1H), 2.07-1.90 (m, 2H), 1.84-1.75 (m, 1H). |
| 602 | CD3OD | 1H NMR (600 MHz, MeOD) δ 9.06 (s, 2H), 9.02 (s, 1H), 8.76 (d, J = 5.4, 1H), 8.67 (d, J = 8.1, 1H), 8.00 (dd, J = 8.0, 5.6, 1H), 7.93 (d, J = 9.1, 1H), 7.82 (d, J = 9.0, 1H), 7.63 (d, J = 9.0, 1H), 7.12 (d, J = 9.1, 1H), 5.75 (s, 2H), 4.19-4.12 (m, 2H), 4.12-4.03 (m, 1H), 3.75 (t, J = 4.6, 4H), 2.80-2.63 (m, 4H). |
| 603 | CD3OD | 1H NMR (600 MHz, MeOD) δ 9.11 (s, 2H), 7.87 (d, J = 9.1, 1H), 7.81 (dd, J = 9.0, 0.7, 1H), 7.61 (d, J = 9.0, 1H), 7.00 (d, J = 9.1, 1H), 4.69 (t, J = 6.2, 2H), 4.35-4.29 (m, 1H), 4.22 (dd, J = 13.7, 5.6, 1H), 4.17-4.09 (m, 1H), 3.79 (t, J = 4.6, 4H), 2.95-2.87 (m, 2H), 2.85-2.69 (m, 4H). |
| 604 | CD3OD | 1H NMR (600 MHz, MeOD) δ 9.11 (s, 2H), 7.87 (dd, J = 9.1, 1.2, 1H), 7.80 (dd, J = 9.0, 0.6, 1H), 7.60 (d, J = 9.0, 1H), 7.04 (d, J = 9.1, 1H), 4.55 (dd, J = 11.1, 4.1, 1H), 4.39-4.32 (m, 2H), 4.26-4.20 (m, 1H), 4.17-4.09 (m, 2H), 3.80 (t, J = 4.6, 4H), 2.98-2.90 (m, 2H), 2.84 (dd, J = 10.5, 5.4, 2H), 2.52-2.40 (m, 1H), 2.40-2.30 (m, 2H), 2.12-1.92 (m, 1H). |
| 605 | CD3OD | 1H NMR (600 MHz, MeOD) δ 9.05 (s, 2H), 7.94 (dd, J = 9.1, 4.3, 1H), 7.84 (d, J = 9.0, 1H), 7.66 (d, J = 9.0, 1H), 7.12 (d, J = 9.1, 1H), 4.67 (dd, J = 12.8, 6.8, 1H), 4.15-4.03 (m, 3H), 3.98-3.89 (m, 1H), 3.77-3.71 (m, 5H), 3.29-3.21 (m, 1H), 3.09 (s, 3H), 2.73-2.67 (m, 2H), 2.67-2.58 (m, 2H), 2.50-2.39 (m, 1H), 2.29-2.18 (m, 2H), 2.17-2.00 (m, 2H). |
| 606 | CD3OD | 1H NMR (500 MHz, MeOD) δ 9.11 (s, 2H), 7.81 (d, J = 9.1, 1H), 7.75 (d, J = 9.0, 1H), 7.57 (d, J = 9.0, 1H), 6.93 (d, J = 9.1, 1H), 5.40-5.31 (m, 1H), 4.33 (dd, J = 8.5, 5.8, 1H), 4.27-4.18 (m, 1H), 4.18-4.07 (m, 1H), 3.79 (t, J = 4.5, 4H), 2.99-2.88 (m, 2H), 2.88-2.75 (m, 2H), 2.59-2.45 (m, 2H), 2.26-2.09 (m, 2H), 1.95-1.82 (m, 1H), 1.82-1.69 (m, 1H). |

| Co. No. | Solvent | NMR data |
|---|---|---|
| 607 | CD3OD | 1H NMR (500 MHz, MeOD) δ 9.09 (s, 2H), 8.78 (d, J = 9.5, 1H), 8.16 (d, J = 9.1, 1H), 8.03 (d, J = 9.2, 1H), 7.72 (d, J = 9.5, 1H), 6.03-5.91 (m, 1H), 5.37 (t, J = 11.0, 1H), 5.06-4.96 (m, 1H), 4.27-4.16 (m, 2H), 4.16-4.05 (m, 1H), 3.76 (t, J = 4.5, 4H), 3.74-3.69 (m, 2H), 3.69-3.63 (m, 1H), 2.86-2.64 (m, 4H). |
| 608 | CD3OD | 1H NMR (400 MHz, MeOD) δ 9.02 (s, 2H), 7.88-7.81 (m, 1H), 7.76 (dd, J = 9.0, 0.5, 1H), 7.58 (d, J = 9.0, 1H), 6.95 (d, J = 9.1, 1H), 5.44-5.33 (m, 1H), 4.17-3.96 (m, 3H), 3.71 (t, J = 4.6, 4H), 3.16-3.04 (m, 2H), 2.84-2.75 (m, 2H), 2.66-2.46 (m, 4H), 2.17-2.06 (m, 2H), 1.82-1.68 (m, 2H). |
| 609 | CD3OD | 9.02 (s, 2H), 8.87 (dd, J = 4.3, 1.5, 1H), 8.22 (ddd, J = 8.7, 1.5, 0.8, 1H), 8.13 (dd, J = 9.4, 5.2, 1H), 7.66-7.49 (m, 2H), 4.18-4.08 (m, 1H), 4.00-3.89 (m, 2H), 3.72 (t, J = 4.6, 4H), 2.69-2.45 (m, 4H) |
| 610 | CD3OD | 9.00 (s, J = 11.8, 2H), 8.21 (d, J = 8.4, 1H), 7.76 (d, J = 6.3, 1H), 7.58 (dd, J = 7.2, 1.2, 1H), 7.50 (dd, J = 8.4, 7.2, 1H), 6.87 (dd, J = 6.3, 0.8, 1H), 4.10-3.98 (m, 1H), 3.97-3.85 (m, 2H), 3.84-3.76 (m, 2H), 3.72 (t, J = 4.6, 4H), 3.69-3.61 (m, 2H), 2.65-2.48 (m, 4H) |
| 611 | CD3OD | 9.03 (s, J = 4.2, 2H), 8.89-8.80 (m, 1H), 8.24 (ddd, J = 8.7, 1.6, 0.8, 1H), 8.13 (dd, J = 9.4, 5.2, 1H), 7.62 (t, J = 9.2, 1H), 7.57 (dd, J = 8.6, 4.3, 1H), 4.20-4.06 (m, 2H), 4.03-3.92 (m, 1H), 2.78-2.59 (m, 4H), 2.12-1.87 (m, 4H) |
| 612 | CD3OD | 9.04 (s, 2H), 8.29 (d, J = 8.4, 1H), 8.05 (d, J = 6.1, 1H), 7.68 (dd, J = 7.1, 1.2, 1H), 7.59 (dd, J = 8.4, 7.2, 1H), 7.39 (dd, J = 6.1, 0.7, 1H), 4.16-4.03 (m, 2H), 3.99-3.87 (m, 5H), 3.38-3.32 (m, 4H), 2.78-2.63 (m, 4H), 2.10-1.94 (m, 4H). |
| 613 | CD3OD | 9.04 (s, 2H), 8.31 (d, J = 8.4, 1H), 8.07 (d, J = 6.1, 1H), 7.68 (dd, J = 7.1, 1.0, 1H), 7.61 (dd, J = 8.4, 7.2, 1H), 7.37 (dd, J = 6.1, 1.0, 1H), 4.15-4.03 (m, 1H), 4.00-3.93 (m, 6H), 3.75 (t, J = 4.6, 4H), 3.42-3.35 (m, 4H), 2.71-2.52 (m, 4H) |
| 614 | CD3OD | 9.03 (s, 2H), 8.20 (d, J = 8.4, 1H), 7.77 (d, J = 6.3, 1H), 7.59 (dd, J = 7.2, 1.2, 1H), 7.50 (dd, J = 8.4, 7.2, 1H), 6.90 (dd, J = 6.3, 1.2, 1H), 4.17-4.00 (m, 2H), 3.96-3.87 (m, 1H), 3.81 (t, J = 5.5, 2H), 3.66 (t, J = 5.5, 2H), 2.77-2.59 (m, 4H), 2.11-1.93 (m, 4H) |
| 615 | CD3OD | 9.01 (s, 2H), 7.85 (d, J = 9.4, 1H), 7.70 (dd, J = 9.0, 5.4, 1H), 7.34 (t, J = 9.3, 1H), 7.16 (d, J = 9.5, 1H), 4.15-4.00 (m, 1H), 3.97-3.86 (m, 2H), 3.84-3.75 (m, 4H), 3.75-3.58 (m, 9H), 2.67-2.47 (m, 4H) |
| 616 | CD3OD | 9.05 (s, 2H), 8.22 (d, J = 9.9, 1H), 7.98 (dd, J = 9.3, 4.4, 1H), 7.64 (t, J = 9.1, 1H), 7.30 (d, J = 9.1, 1H), 4.74-4.60 (m, 1H), 4.22-4.13 (m, 1H), 4.12-4.04 (m, 1H), 4.04-3.81 (m, 4H), 3.75 (t, J = 4.6, 5H), 2.78-2.59 (m, 4H), 2.36-2.14 (m, 2H). |
| 617 | CD3OD | 9.04 (s, 2H), 8.24 (d, J = 9.9, 1H), 7.99 (dd, J = 9.2, 4.3, 1H), 7.65 (t, J = 9.1, 1H), 7.39-7.16 (m, 1H), 4.72-4.65 (m, 1H), 4.23-4.07 (m, 2H), 4.06-3.64 (m, 5H), 2.82-2.63 (m, 4H), 2.37-2.13 (m, 2H), 2.12-1.90 (m, 4H) |
| 618 | CD3OD | 9.04 (s, 2H), 8.15-8.00 (m, 1H), 7.96-7.80 (m, 1H), 7.61 (t, J = 9.1, 1H), 7.24-7.01 (m, 1H), 4.19-4.10 (m, 1H), 4.09-3.93 (m, 2H), 3.87 (t, J = 5.0, 2H), 3.79-3.63 (m, 6H), 2.79-2.57 (m, 4H) |
| 619 | CD3OD | 9.03 (s, 2H), 8.14-8.04 (m, 1H), 7.93-7.81 (m, 1H), 7.62 (t, J = 9.1, 1H), 7.22-7.08 (m, 1H), 4.19-4.05 (m, 2H), 4.02-3.92 (m, 1H), 3.87 (t, J = 5.0, 2H), 3.70 (t, J = 5.1, 2H), 2.78-2.61 (m, 4H), 2.14-1.93 (m, 4H) |
| 620 | CD3OD | 9.04 (s, 2H), 7.99 (d, J = 9.4, 1H), 7.83-7.68 (m, 1H), 7.49-7.33 (m, 1H), 7.29 (d, J = 9.4, 1H), 4.24-4.11 (m, 2H), 4.11-3.95 (m, 1H), 3.78 (t, J = 4.3, 4H), 3.58-3.22 (m, 8H), 3.03-2.93 (m, 3H), 2.93-2.61 (m, 4H) |
| 621 | CD3OD | 9.05 (s, 2H), 8.02 (d, J = 9.5, 1H), 7.78 (dd, J = 9.3, 5.1, 1H), 7.42 (t, J = 9.3, 1H), 7.30 (d, J = 9.5, 1H), 4.26-4.05 (m, 2H), 4.04-3.92 (m, 1H), 3.58-3.25 (m, 8H), 2.97 (s, 3H), 2.84-2.73 (m, 4H), 2.16-1.95 (m, 4H) |
| 622 | (CD3)2SO | 9.16-9.10 (m, 2H), 8.87-8.78 (m, 1H), 7.93 (d, J = 9.1, 1H), 7.80 (dd, J = 9.0, 0.6, 1H), 7.69 (d, J = 9.0, 1H), 7.06 (d, J = 9.1, 1H), 4.22 (t, J = 7.4, 1H), 4.07-4.00 (m, 1H), 3.99 (s, J = 8.8, 3H), 3.95-3.84 (m, 1H), 2.63 (t, J = 9.5, 2H), 2.59-2.51 (m, 2H), 2.05-1.91 (m, 4H). |
| 623 | (CD3)2SO | 9.11 (d, J = 19.9, 2H), 8.79 (t, J = 5.9, 1H), 7.92 (d, J = 9.1, 1H), 7.75 (dd, J = 9.0, 0.6, 1H), 7.66 (d, J = 8.9, 1H), 6.98 (d, J = 9.1, 1H), 5.54-5.36 (m, 1H), 4.20 (t, J = 7.3, 1H), 4.08-3.97 (m, 1H), 3.94-3.82 (m, 1H), 2.70-2.58 (m, 2H), 2.59-2.50 (m, 2H), 2.05-1.90 (m, 4H), 1.41-1.30 (m, 6H). |
| 624 | (CD3)2SO | 9.22-9.14 (m, 3H), 8.77-8.68 (m, 1H), 8.46 (s, 3H), 8.28 (dt, J = 14.1, 7.0, 1H), 8.09 (d, J = 9.1, 1H), 7.84 (dd, J = 9.5, 5.3, 1H), 5.99-5.82 (m, 1H), 5.27 (t, J = 10.9, 1H), 4.97 (dd, J = 11.9, 7.8, 1H), 4.35-4.23 (m, 1H), 4.13 (dt, J = 12.9, 6.3, 1H), 3.96 (dd, J = 7.8, 4.7, 1H), 3.60 (s, 2H), 2.70 (s, 2H), 2.59 (d, J = 31.3, 2H), 2.01 (s, 4H). |
| 625 | (CD3)2SO | 9.15 (s, 2H), 8.85 (t, J = 5.9, 1H), 7.95 (d, J = 9.1, 1H), 7.84-7.73 (m, 4H), 7.70 (d, J = 9.0, 1H), 7.06 (t, J = 9.4, 1H), 4.48 (t, J = 6.2, 2H), 4.25 (t, J = 7.3, 1H), 4.13-3.99 (m, 1H), 3.97-3.86 (m, 1H), 3.05-2.93 (m, 2H), 2.74-2.53 (m, 4H), 2.13-1.92 (m, 6H). |

| Co. No. | Solvent | NMR data |
|---|---|---|
| 626 | (CD3)2SO | 9.14 (s, 2H), 8.96 (d, J = 4.3, 1H), 8.84 (t, J = 5.9, 1H), 8.07 (d, J = 8.1, 1H), 7.93-7.87 (m, 1H), 7.81 (ddd, J = 8.4, 6.9, 1.4, 1H), 7.57 (ddd, J = 8.2, 6.9, 1.2, 1H), 7.43 (d, J = 4.3, 1H), 4.18 (t, J = 7.2, 1H), 4.05 (dt, J = 13.1, 6.4, 1H), 3.92-3.74 (m, 1H), 2.72-2.62 (m, 2H), 2.60-2.54 (m, 2H), 2.06-1.93 (m, 4H). |
| 627 | (CD3)2SO | 9.10 (s, 2H), 8.96 (dd, J = 4.2, 1.6, 1H), 8.80 (t, J = 5.7, 1H), 8.09 (d, J = 8.5, 1H), 8.05 (dd, J = 9.0, 0.6, 1H), 7.78 (d, J = 9.0, 1H), 7.59 (dd, J = 8.5, 4.2, 1H), 4.12-3.96 (m, 2H), 3.93-3.80 (m, 1H), 3.61 (t, J = 4.5, 4H), 2.54-2.40 (m, 4H). |
| 630 | (CD3)2SO | 9.08 (s, 2H), 8.63 (t, J = 5.8, 1H), 7.62-7.50 (m, 3H), 7.22-7.10 (m, 1H), 7.01 (s, 1H), 4.04-3.88 (m, 2H), 3.79-3.68 (m, 5H), 3.66-3.58 (m, 8H), 2.58-2.40 (m, 4H). |
| 633 | (CD3)2SO | 12.60 (s, 1H), 9.15 (s, 2H), 8.80 (t, J = 5.8, 1H), 8.04 (d, J = 9.7, 1H), 7.90 (d, J = 8.6, 1H), 7.65 (d, J = 8.7, 1H), 7.24 (d, J = 10.6, 1H), 5.70 (bs, J = 69.0, 1H), 4.62-4.46 (m, 1H), 4.33-4.19 (m, 1H), 4.16-3.99 (m, 1H), 3.96-3.72 (m, 4H), 3.70-3.58 (m, 1H), 2.73-2.63 (m, 2H), 2.63-2.53 (m, 2H), 2.27-2.18 (m, 3H), 2.18-1.89 (m, 6H). |
| 634 | (CD3)2SO | 9.15 (s, 2H), 8.76-8.63 (m, 1H), 8.05-7.87 (m, 1H), 7.79-7.63 (m, 1H), 7.59-7.46 (m, 1H), 7.45-7.29 (m, 1H), 4.95 (bs, 1H), 4.35-4.20 (m, 1H), 4.16-3.99 (m, 1H), 3.97-3.83 (m, 1H), 3.83-3.68 (m, 8H), 2.77-2.65 (m, 2H), 2.65-2.54 (m, 2H), 2.19 (s, 3H), 2.11-1.94 (m, 4H). |
| 635 | (CD3)2SO | 9.94 (s, 1H), 9.15 (s, 2H), 8.61 (t, J = 5.8, 1H), 7.85 (d, J = 9.4, 1H), 7.57 (d, J = 8.6, 1H), 7.43 (d, J = 8.8, 1H), 7.27 (d, J = 9.4, 1H), 4.60 (d, J = 13.4, 2H), 4.28 (t, J = 7.1, 1H), 4.15-3.98 (m, 1H), 3.98-3.82 (m, 1H), 3.65-3.44 (m, 2H), 3.36-3.18 (m, 2H), 3.18-3.01 (m, 2H), 2.87 (s, 3H), 2.80-2.54 (m, 4H), 2.18 (s, 3H), 2.11-1.91 (m, 4H). |
| 636 | (CD3)2SO | 12.76 (bs, 1H), 9.72 (s, 1H), 9.13 (s, 2H), 8.88-8.72 (m, 1H), 7.95 (d, J = 8.8, 1H), 7.83 (d, J = 7.7, 1H), 7.71-7.56 (m, 1H), 7.29-7.08 (m, 1H), 6.16 (bs, 1H), 4.26 (t, J = 7.2, 1H), 4.16-4.02 (m, 1H), 3.94-3.77 (m, 1H), 3.77-3.66 (m, 2H), 3.66-3.53 (m, 2H), 2.81-2.63 (m, 2H), 2.64-2.53 (m, 2H), 2.21 (s, 3H), 2.11-1.87 (m, 4H). |
| 637 | (CD3)2SO | 9.80 (s, 1H), 9.13 (s, 2H), 9.10-8.97 (m, 1H), 8.01-7.83 (m, 1H), 7.79 (dd, J = 7.3, 1H), 7.61 (d, J = 8.0, 1H), 7.41 (dd, J = 8.1, 1H), 7.06 (s, 1H), 5.00 (bs, 2H), 4.22-4.00 (m, 2H), 3.93-3.77 (m, 1H), 3.75-3.57 (m, 8H), 2.74-2.53 (m, 4H). |
| 638 | (CD3)2SO | 9.91 (s, 1H), 9.14 (s, 2H), 8.76 (t, J = 5.8, 1H), 7.97 (s, 2H), 7.65 (d, J = 8.7, 1H), 7.02 (s, 1H), 4.33-4.16 (m, 1H), 4.17-3.99 (m, 1H), 3.95-3.73 (m, 1H), 2.96-2.84 (m, 1H), 2.75-2.59 (m, 2H), 2.60-2.51 (m, 2H), 2.23 (s, 3H), 2.09-1.87 (m, 4H), 1.10-0.93 (m, 2H), 0.82-0.70 (m, 2H). |
| 639 | (CD3)2SO | 9.93 (s, 1H), 9.14 (s, 2H), 8.76 (s, 1H), 7.67-7.57 (m, 2H), 7.54 (d, J = 8.2, 1H), 7.22 (ddd, J = 8.2, 6.5, 1.6, 1H), 7.18 (s, 1H), 4.61 (d, J = 13.9, 2H), 4.16 (s, 1H), 4.13-3.99 (m, 1H), 3.94-3.79 (m, 1H), 3.76-3.60 (m, 4H), 3.55 (d, J = 11.0, 2H), 3.25 (t, J = 13.1, 2H), 3.10 (s, 2H), 2.86 (s, 3H), 2.82-2.57 (m, 4H). |
| 640 | (CD3)2SO | 9.14 (s, 2H), 8.87 (s, 1H), 7.75 (d, J = 36.8, 2H), 7.57 (d, J = 8.1, 1H), 7.31 (s, 2H), 4.27-4.00 (m, 2H), 3.92-3.72 (m, 5H), 3.73-3.56 (m, 4H), 2.87-2.52 (m, 4H), 1.79-1.53 (m, 6H). |
| 641 | (CD3)2SO | 9.13 (s, 2H), 9.02-8.89 (m, 1H), 7.96 (sm, 1H), 7.87-7.73 (m, 1H), 7.73-7.64 (m, 1H), 7.51-7.31 (m, 1H), 7.11 (s, 1H), 4.16-4.00 (m, 2H), 3.96 (bs, 1H), 3.84-3.75 (m, 1H), 3.71 (s, 2H), 3.67-3.58 (m, 2H), 2.73-2.51 (m, 8H), 2.15-1.99 (m, 4H). |
| 642 | (CD3)2SO | 13.64-12.34 (m, 1H), 10.08 (s, 1H), 9.12 (s, 2H), 9.08-8.97 (m, 1H), 8.17-7.91 (m, 1H), 7.90-7.75 (m, 1H), 7.66 (d, J = 7.9, 1H), 7.45 (dd, J = 7.6, 1H), 6.94 (s, 1H), 4.19-4.01 (m, 2H), 3.94-3.73 (m, 1H), 3.64 (s, 4H), 2.92 (s, 1H), 2.68-2.51 (m, 4H), 1.09-0.96 (m, 2H), 0.79-0.66 (m, 2H). |
| 643 | (CD3)2SO | 9.13 (s, 2H), 9.01-8.91 (m, 1H), 7.85-7.75 (m, 2H), 7.63 (d, J = 8.1, 1H), 7.47-7.32 (m, 1H), 6.88 (s, 1H), 4.43 (bs, 1H), 4.50-4.34 (m, 4H), 4.17-4.03 (m, 2H), 3.89-3.72 (m, 1H), 3.71-3.58 (m, 4H), 2.74-2.50 (m, 6H). |
| 644 | (CD3)2SO | 9.84 (s, 1H), 9.15 (s, 2H), 9.06 (t, J = 5.8, 1H), 8.00-7.86 (m, 1H), 7.83-7.76 (m, 1H), 7.67 (d, J = 8.0, 1H), 7.46-7.38 (m, 1H), 7.07 (s, 1H), 5.57 (bs, 2H), 4.73-4.60 (m, 1H), 4.27-4.17 (m, 1H), 4.15-4.00 (m, 1H), 4.00-3.88 (m, 0H), 3.88-3.75 (m, 1H), 3.75-3.58 (m, 3H), 2.78-2.54 (m, 4H), 2.08-1.93 (m, 4H). |
| 645 | (CD3)2SO | 9.16 (s, 2H), 8.86 (t, J = 5.7, 1H), 7.73 (d, J = 8.2, 1H), 7.69-7.58 (m, 2H), 7.32-7.18 (m, 2H), 5.46 (bs, 1H), 4.24 (d, J = 7.0, 1H), 4.06 (dt, J = 12.7, 6.3, 1H), 3.82 (dt, J = 21.3, 6.8, 1H), 3.78 (s, 8H), 2.71 (s, 4H), 2.04 (dd, J = 22.3, 8.4, 4H). |
| 648 | (CD3)2SO | 9.15 (s, 2H), 8.99 (t, J = 5.5, 1H), 7.88-7.74 (m, 2H), 7.68 (d, J = 8.1, 1H), 7.43-7.29 (m, 1H), 6.89 (s, 1H), 4.41 (t, J = 7.6, 4H), 4.20 (t, J = 7.2, 1H), 4.13-4.02 (m, 1H), 3.86-3.70 (m, 1H), 2.74-2.62 (m, 2H), 2.63-2.53 (m, 2H), 2.53-2.44 (m, 2H), 2.08-1.92 (m, 4H). |

-continued

| Co. No. | Solvent | NMR data |
|---|---|---|
| 649 | (CD3)2SO | 10.41-9.67 (m, 1H), 9.14 (s, 2H), 9.08-8.96 (m, 1H), 8.15-7.90 (m, 1H), 7.82 (t, J = 7.6, 1H), 7.70 (d, J = 8.1, 1H), 7.44 (dd, J = 7.4, 1H), 7.05-6.79 (m, 1H), 4.19 (t, J = 7.1, 1H), 4.13-4.03 (m, 1H), 3.87-3.73 (m, 1H), 2.99-2.84 (m, 1H), 2.73-2.60 (m, 2H), 2.61-2.50 (m, 2H), 2.07-1.90 (m, 4H), 1.10-0.94 (m, 2H), 0.82-0.69 (m, 3H). |
| 650 | (CD3)2SO | 10.02 (s, 1H), 9.16 (s, 2H), 8.79 (t, J = 5.9, 1H), 7.70-7.54 (m, 3H), 7.30-7.15 (m, 2H), 4.63 (d, J = 13.3, 2H), 4.24 (t, J = 7.1, 1H), 4.11-3.94 (m, 1H), 3.92-3.71 (m, 1H), 3.65-3.45 (m, 2H), 3.37-3.15 (m, 2H), 3.16-2.97 (m, 2H), 2.87 (s, 3H), 2.78-2.57 (m, 4H), 2.13-1.91 (m, 4H). |
| 651 | CD3OD | 9.76 (s, 1H), 9.09 (s, 2H), 8.61-8.52 (m, 3H), 8.20 (dd, J = 7.2, 1.1, 1H), 8.02 (dd, J = 8.3, 7.3, 1H), 4.29-4.15 (m, 2H), 4.03-3.97 (m, 1H), 2.89-2.76 (m, 4H), 2.16-2.00 (m, 4H) |
| 652 | CD3OD | 9.74 (s, 1H), 9.31 (s, 2H), 8.63-8.51 (m, 3H), 8.20-8.15 (m, 1H), 8.01-7.92 (m, 1H), 4.99 (m, 1H), 4.48-4.42 (m, 1H), 4.39-4.32 (m, 1H), 3.64-3.33 (m, 3H), 3.29-3.15 (m, 1H), 2.01-1.89 (m, 4H), 1.83-1.53 (m, 2H) |
| 653 | CD3OD | 9.29 (s, 1H), 9.06 (s, 2H), 8.44 (d, J = 6.1, 1H), 8.24 (d, J = 8.2, 1H), 7.89-7.78 (m, 2H), 7.78-7.64 (m, 1H), 4.17-4.05 (m, 1H), 4.04-3.91 (m, 2H), 3.76 (t, J = 4.6, 4H), 2.75-2.51 (m, 4H) |
| 654 | CD3OD | 1H NMR (600 MHz, MeOD) δ 9.04 (s, 2H), 8.71 (dd, J = 4.2, 1.4, 1H), 8.07 (t, J = 9.3, 2H), 7.69 (d, J = 9.4, 1H), 7.47 (dd, J = 8.5, 4.3, 1H), 4.17-4.06 (m, 1H), 3.97-3.93 (m, 5H), 3.72 (t, J = 4.6, 4H), 2.74-2.59 (m, 2H), 2.59-2.49 (m, 2H). |
| 655 | CD3OD | 1H NMR (500 MHz, MeOD) δ 9.10 (s, 2H), 8.98 (dd, J = 5.0, 1.3, 1H), 8.68 (d, J = 8.7, 1H), 8.25 (dd, J = 9.5, 0.6, 1H), 7.99 (d, J = 9.5, 1H), 7.87 (dd, J = 8.7, 5.0, 1H), 4.30-4.24 (m, 1H), 4.21-4.14 (m, 1H), 4.10-4.01 (m, 1H), 2.88-2.76 (m, 4H), 2.15-1.99 (m, 5H). |
| 656 | CD3OD | 1H NMR (400 MHz, MeOD) δ 9.01 (s, 2H), 7.74 (d, J = 9.4, 1H), 7.70 (d, J = 9.3, 1H), 7.40 (d, J = 9.3, 1H), 7.09 (d, J = 9.4, 1H), 4.10-3.97 (m, 1H), 3.96-3.87 (m, 2H), 3.83 (s, 3H), 3.82-3.77 (m, 4H), 3.70 (t, J = 4.6, 4H), 3.65-3.60 (m, 4H), 2.66-2.57 (m, 2H), 2.56-2.46 (m, 2H). |
| 657 | CD3OD | 1H NMR (400 MHz, MeOD) δ 9.02 (s, 2H), 7.76 (d, J = 9.4, 1H), 7.70 (d, J = 9.3, 1H), 7.40 (d, J = 9.3, 1H), 7.09 (d, J = 9.4, 1H), 4.15-4.08 (m, 1H), 4.06-3.88 (m, 2H), 3.82-3.78 (m, 7H), 3.67-3.58 (m, 4H), 2.71-2.65 (m, 4H), 2.05-1.96 (m, 4H). |
| 658 | CD3OD | 1H NMR (400 MHz, MeOD) δ 9.33 (s, 2H), 9.06 (s, 1H), 8.96 (dd, J = 4.9, 1.2, 1H), 8.60 (dd, J = 8.7, 0.7, 1H), 8.24 (d, J = 9.5, 1H), 7.92 (d, J = 9.6, 1H), 7.83 (dd, J = 8.7, 5.0, 1H), 4.99 (t, J = 7.3, 1H), 4.53-4.37 (m, 3H), 3.92 (s, 3H), 2.96-2.77 (m, 1H), 2.75-2.62 (m, 1H), 2.01-1.90 (m, 4H), 1.81-1.62 (m, 3H), 1.57-1.37 (m, 1H). |
| 659 | (CD3)2SO | 1H NMR (400 MHz, DMSO) δ 9.04 (s, 2H), 8.31 (t, J = 5.7, 1H), 7.72 (d, J = 9.4, 1H), 7.60 (d, J = 9.2, 1H), 7.41 (d, J = 9.3, 1H), 7.13 (d, J = 9.4, 1H), 4.09-3.98 (m, 1H), 3.98-3.76 (m, 3H), 3.76-3.68 (m, 7H), 3.64-3.51 (m, 4H), 2.47-2.28 (m, 4H), 1.62-1.43 (m, 4H), 1.43-1.23 (m, 2H). |

D. Pharmacological Examples

D.1 P2X7 Antagonism

Extracellular binding of ATP to P2X7 that is expressed in the cell-membrane opens the ligand gated cation channel and allows $Ca^{2+}$ entry into the cell. This ligand-induced $Ca^{2+}$ flux was measured in 1321N1 astrocytoma cells overexpressing hP2X7 for the compounds of the present invention.

The calcium assay kit used (Molecular Devices, R8090), provides a $Ca^{2+}$ sensitive dye together with a quenching dye. However, no specifications are given by the manufacturer. The kit most likely consists of a membrane permeable acetoxymethyl (AM) ester of a fluorescent $Ca^{2+}$ indicator, such as fluo-4 or fluo-3. Upon cellular uptake, the AM esters get cleaved by esterases, liberating the $Ca^{2+}$-sensitive dye which can then bind calcium. The dyes have an absorption spectrum compatible with excitation at 488 nm by argon laser sources and a large fluorescence intensity increase in response to $Ca^{2+}$ binding without an accompanying spectral shift. Emission wavelength is in the range of 510-560 nm.

The fluorescence, and thus the changes in intracellular $[Ca^{2+}]$ in the 1321N1 cells was monitored in time before and after addition of the agonist. The effect of the antagonist was measured as % control and as $IC_{50}$. The pIC50 values ($=-\log (IC_{50})$ values) are listed in Table F-9.

TABLE F-9 mean pIC50 values

| Co. No. | hP2RX7pIC50 |
|---|---|
| 1 | 7.23 |
| 2 | 7.67 |
| 3 | 5.44 |
| 4 | 6.74 |
| 5 | 5.92 |
| 6 | 6.05 |
| 7 | 7.6 |
| 8 | <5 |
| 10 | 7.36 |
| 11 | 7.28 |
| 12 | 5.49 |
| 13 | 7.03 |
| 14 | 6.75 |
| 16 | 6.65 |
| 17 | 6.99 |
| 18 | 7.26 |
| 19 | 5.91 |
| 24 | 5.28 |
| 25 | <5 |

TABLE F-9-continued mean pIC50 values

| Co. No. | hP2RX7pIC50 |
|---|---|
| 27 | <5 |
| 28 | 5.17 |
| 29 | <5 |
| 31 | 6.97 |
| 32 | 5.59 |
| 33 | 7.48 |
| 34 | <5 |
| 35 | 7.67 |
| 36 | 7.4 |
| 37 | 7.34 |
| 39 | 7.47 |
| 40 | 7.46 |
| 41 | 7.34 |
| 42 | 7.42 |
| 43 | 7.49 |
| 44 | 7.41 |
| 45 | 6.02 |
| 46 | 7.56 |
| 47 | 7.42 |
| 48 | 7.2 |
| 49 | 7.42 |
| 50 | 7.41 |
| 51 | 7.37 |
| 52 | 7.72 |
| 53 | 6.76 |
| 54 | 7.37 |
| 55 | 7.55 |
| 56 | 7.31 |
| 57 | 7.4 |
| 58 | 7.45 |
| 59 | 7.41 |
| 60 | 7.44 |
| 61 | 7.4 |
| 62 | 7.49 |
| 63 | 7.46 |
| 64 | 7.47 |
| 65 | 7.55 |
| 66 | 7.74 |
| 67 | 7.44 |
| 68 | 7.33 |
| 69 | 7.47 |
| 70 | 7.41 |
| 71 | 7.51 |
| 72 | 6.52 |
| 73 | 7.3 |
| 74 | 6.62 |
| 75 | 7.54 |
| 76 | 7.54 |
| 77 | 6.65 |
| 78 | 7.59 |
| 79 | 7.22 |
| 80 | 7.33 |
| 81 | 7.23 |
| 82 | 7.3 |
| 83 | 7.41 |
| 84 | 7.43 |
| 86 | 7.03 |
| 87 | 7.35 |
| 88 | 7.34 |
| 89 | 7.07 |
| 90 | 7.06 |
| 91 | 7.48 |
| 92 | 7.53 |
| 93 | 6.84 |
| 94 | 7.09 |
| 95 | 7.35 |
| 96 | 7.32 |
| 97 | 5.1 |
| 98 | 7.28 |
| 99 | 6.81 |
| 100 | 7.49 |
| 101 | 7.47 |
| 102 | 7.14 |
| 103 | 7.39 |
| 104 | 7.44 |
| 105 | 7.06 |
| 106 | 6.86 |
| 107 | 6.41 |
| 108 | 7.28 |
| 109 | 7.65 |
| 110 | 7.3 |
| 111 | 7.29 |
| 114 | 7.52 |
| 116 | 6.73 |
| 117 | 6.74 |
| 118 | 6.79 |
| 119 | 7.05 |
| 120 | 6.43 |
| 121 | 6.6 |
| 122 | 6.94 |
| 123 | 5.99 |
| 124 | 7.58 |
| 126 | 7.41 |
| 127 | 7.85 |
| 128 | 7.33 |
| 129 | 7.32 |
| 130 | 7.48 |
| 131 | 7.23 |
| 132 | 7.2 |
| 136 | 7.19 |
| 138 | 7.45 |
| 139 | 6.67 |
| 140 | 7.04 |
| 141 | 7.38 |
| 143 | 7.46 |
| 144 | 5.98 |
| 145 | 7.4 |
| 146 | 7.32 |
| 148 | 7.07 |
| 150 | 7.38 |
| 151 | 7.41 |
| 152 | 7.32 |
| 153 | 6.61 |
| 155 | 7.19 |
| 157 | 6.86 |
| 158 | 7 |
| 159 | 7.35 |
| 160 | 7.02 |
| 161 | 7.33 |
| 162 | 7.34 |
| 163 | 7.43 |
| 165 | 7.49 |
| 166 | 7.31 |
| 167 | 6.93 |
| 168 | 7.12 |
| 169 | 7.21 |
| 171 | 7.57 |
| 172 | 6.84 |
| 173 | 7.15 |
| 174 | 7.18 |
| 175 | 7.35 |
| 176 | 6.73 |
| 177 | 7.32 |
| 178 | 7.04 |
| 179 | 7.05 |
| 180 | 7.17 |
| 181 | 7.03 |
| 182 | 6.95 |
| 183 | 7.27 |
| 184 | 7.21 |
| 185 | 6.89 |
| 187 | 7.06 |
| 188 | 7.16 |
| 189 | 6.96 |
| 190 | 7.11 |
| 191 | 7.19 |
| 192 | 7.26 |
| 193 | 7.21 |
| 194 | 6.75 |
| 195 | 7.14 |
| 196 | 6.71 |
| 197 | 6.92 |

TABLE F-9-continued mean pIC50 values

| Co. No. | hP2RX7pIC50 |
|---|---|
| 198 | 7.11 |
| 199 | 6.39 |
| 200 | 7.29 |
| 201 | 6.94 |
| 202 | 6.94 |
| 203 | 7.17 |
| 204 | 7.32 |
| 205 | 7.19 |
| 206 | 6.98 |
| 207 | 6.86 |
| 208 | 7.34 |
| 209 | 6.93 |
| 210 | 6.43 |
| 211 | 7.1 |
| 212 | 7.38 |
| 213 | 7 |
| 214 | 7.47 |
| 215 | 6.76 |
| 216 | 7 |
| 217 | 7.32 |
| 218 | 6.5 |
| 219 | 6.9 |
| 220 | 7.08 |
| 221 | 7.17 |
| 222 | 7.18 |
| 223 | 6.71 |
| 224 | 6.94 |
| 225 | 6.99 |
| 226 | 6.79 |
| 227 | 7.48 |
| 228 | 7.29 |
| 229 | 7.16 |
| 230 | 6.85 |
| 231 | 6.94 |
| 232 | 6.77 |
| 233 | 6.83 |
| 234 | 7.57 |
| 235 | 7.25 |
| 236 | 7.46 |
| 237 | 7.05 |
| 238 | 7.41 |
| 239 | 7.27 |
| 240 | 7.24 |
| 241 | 6.93 |
| 242 | 6.94 |
| 243 | 7.3 |
| 244 | 7.1 |
| 245 | 6.77 |
| 246 | 7.49 |
| 247 | 7.68 |
| 248 | 7.48 |
| 249 | 7.29 |
| 250 | 7.11 |
| 251 | 7.19 |
| 252 | 7.31 |
| 253 | 7.44 |
| 254 | 7.53 |
| 256 | 7.35 |
| 257 | 7.58 |
| 258 | 7.35 |
| 259 | 7.01 |
| 260 | 7.56 |
| 261 | 7.43 |
| 262 | 7.25 |
| 263 | 7.43 |
| 264 | 7.11 |
| 265 | 7.19 |
| 266 | 7.3 |
| 267 | 6.94 |
| 268 | 7.48 |
| 269 | 6.64 |
| 270 | 6.99 |
| 271 | 6.97 |
| 272 | 7.22 |
| 273 | 6.95 |
| 274 | 6.84 |

TABLE F-9-continued mean pIC50 values

| Co. No. | hP2RX7pIC50 |
|---|---|
| 275 | 7.15 |
| 276 | 6.09 |
| 277 | 7.33 |
| 278 | 7.06 |
| 279 | 7.11 |
| 280 | 7.02 |
| 281 | 7.12 |
| 282 | 7.12 |
| 283 | 6.94 |
| 284 | 7.17 |
| 285 | 6.8 |
| 286 | 7.42 |
| 287 | 6.98 |
| 288 | 6.87 |
| 289 | 7.19 |
| 290 | 6.87 |
| 291 | 7.33 |
| 292 | 6.94 |
| 293 | 6.98 |
| 294 | 7.17 |
| 295 | 6.68 |
| 296 | 6.91 |
| 297 | 7.49 |
| 298 | 7.34 |
| 299 | 6.96 |
| 300 | 7.43 |
| 301 | 6.78 |
| 302 | 7.09 |
| 303 | 7.28 |
| 304 | 7.55 |
| 305 | 7 |
| 306 | 7.33 |
| 307 | 7.34 |
| 308 | 7.31 |
| 309 | 7.13 |
| 310 | 7.25 |
| 311 | 6.95 |
| 312 | 6.98 |
| 313 | 6.93 |
| 314 | 6.82 |
| 315 | 7.37 |

D.2 THP-1 YoPro Uptake Assay

The human monocytic cell line THP-1 was grown as a suspension culture in RPMI medium supplemented with 10% fetal bovine serum, penicillin/streptomycin (50 units/mL), 2 mM L-glutamine, and 20 μM 2-mercaptoethanol. Cells were maintained at a density below 0.5 million per mL. On the day of the assay, cells were washed twice with assay buffer, and then resuspended at 2 million per mL in assay buffer containing 2 μM Yo-Pro-1 (Invitrogen). The assay buffer contained (in mM): 280 sucrose, 5 KCl, 10 glucose, 10 HEPES, 5 N-methyl-D-glucamine. The cells were added at 200 k/well into poly-D-lysine-coated black-walled 96-well plates (Biocoat, Becton-Dickinson). Test compounds were dissolved in DMSO, and then added at the test concentration to each well of the 96-well plate. Concentration dependence of block was determined by exposing each well of cells in duplicate rows of a 96-well plate to a serial dilution of test compound. The concentration series usually started at 10 μM with a three-fold decrement in concentration. The final DMSO concentration seen by the cells was less than 0.5%. Cells were incubated with test compounds for 30 minutes at 37° C. A background reading was taken using a Gemini SpectraMax with 490 nm excitation and 530 nm emission. Then, 504/well of the dye/stimulation buffer containing 2 μM Yo-Pro-1 and 200 μM BzATP was added (final concentration seen by the cells was 2

μM Yo-Pro-1 and 50 μM BzATP). After incubation for 60 minutes at 37° C., an endpoint read was taken in the Spectra-Max plate reader. The amount of block of the response was determined by comparing the fluorescence intensity in each well to the average of control wells on each plate. The control wells contained either a known antagonist of P2X7 (positive controls) or a concentration of DMSO equal to that in the test wells. Data were analyzed using a nonlinear regression program (Origin, OriginLab, MA). Results are reported as the −log of the $IC_{50}$ ($pIC_{50}$).

TABLE F-10 mean pIC50 values for P2X7 antagonism

| Co. No. | pIC50 |
|---|---|
| 403 | 7.83 |
| 406 | 8.06 |
| 407 | 8.13 |
| 408 | 8.17 |
| 409 | 8.47 |
| 410 | 8.30 |
| 411 | 8.25 |
| 412 | 8.29 |
| 413 | 8.29 |
| 414 | 8.38 |
| 415 | 8.62 |
| 416 | 8.76 |
| 423 | 8.95 |
| 424 | 8.65 |
| 425 | 8.20 |
| 426 | 8.24 |
| 427 | 8.47 |
| 428 | 8.49 |
| 430 | 7.65 |
| 431 | 7.47 |
| 432 | 4.00 |
| 433 | 7.94 |
| 434 | 7.84 |
| 435 | 7.11 |
| 436 | 7.50 |
| 437 | 6.81 |
| 438 | 7.64 |
| 439 | 7.39 |
| 440 | 7.43 |
| 441 | 7.61 |
| 442 | 6.65 |
| 443 | 6.55 |
| 444 | 7.59 |
| 445 | 7.63 |
| 446 | 7.46 |
| 447 | 6.51 |
| 452 | 7.71 |
| 453 | 7.68 |
| 454 | 7.72 |
| 455 | 7.59 |
| 456 | 8.14 |
| 457 | 9.02 |
| 458 | 8.52 |
| 459 | 8.58 |
| 460 | 8.05 |
| 461 | 6.97 |
| 462 | 8.04 |
| 463 | 6.42 |
| 464 | 6.93 |
| 465 | 8.11 |
| 466 | 8.09 |
| 467 | 8.16 |
| 468 | 7.65 |
| 484 | 8.11 |
| 485 | 8.65 |
| 491 | 8.42 |
| 492 | 8.61 |
| 493 | 8.06 |
| 494 | 7.85 |
| 495 | 8.13 |
| 496 | 8.18 |
| 497 | 8.21 |
| 498 | 8.04 |
| 499 | 7.68 |
| 500 | 7.99 |
| 501 | 7.99 |
| 502 | 7.86 |
| 503 | 7.43 |
| 504 | 8.16 |
| 505 | 8.29 |
| 506 | 7.74 |
| 507 | 7.87 |
| 508 | 7.59 |
| 509 | 7.75 |
| 510 | 8.46 |
| 511 | 8.32 |
| 512 | 8.27 |
| 513 | 8.29 |
| 514 | 8.12 |
| 515 | 8.25 |
| 516 | 8.01 |
| 517 | 8.07 |
| 518 | 7.99 |
| 519 | 8.15 |
| 520 | 8.02 |
| 521 | 7.86 |
| 522 | 7.61 |
| 523 | 7.80 |
| 524 | 7.52 |
| 525 | 7.28 |
| 526 | 7.25 |
| 527 | 7.11 |
| 528 | 8.34 |
| 529 | 8.25 |
| 530 | 8.58 |
| 531 | 8.52 |
| 545 | 8.84 |
| 546 | 8.32 |
| 547 | 8.46 |
| 548 | 8.72 |
| 549 | 8.47 |
| 550 | 8.63 |
| 551 | 7.83 |
| 552 | 7.75 |
| 553 | 7.76 |
| 554 | 7.90 |
| 555 | 7.79 |
| 556 | 8.94 |
| 557 | 8.95 |
| 558 | 8.60 |
| 559 | 8.44 |
| 560 | 8.31 |
| 561 | 8.87 |
| 562 | 8.31 |
| 563 | 9.07 |
| 564 | 8.13 |
| 565 | 8.59 |
| 566 | 8.40 |
| 581 | 7.59 |
| 582 | 7.97 |
| 585 | 8.65 |
| 586 | 8.36 |
| 587 | 7.90 |
| 588 | 6.51 |
| 589 | 7.92 |
| 590 | 6.63 |
| 591 | 4.90 |
| 592 | 8.21 |
| 593 | 6.95 |
| 594 | 6.79 |
| 595 | 6.78 |
| 596 | 8.45 |
| 597 | 8.14 |
| 599 | 7.31 |
| 600 | 7.60 |
| 601 | 7.50 |
| 602 | 8.45 |
| 603 | 7.31 |

TABLE F-10-continued mean pIC50 values for P2X7 antagonism

| Co. No. | pIC50 |
|---|---|
| 604 | 7.51 |
| 605 | 7.81 |
| 609 | 7.48 |
| 610 | 6.47 |
| 611 | 7.84 |
| 612 | 6.86 |
| 613 | 5.94 |
| 622 | 7.86 |
| 623 | 8.05 |
| 624 | 6.63 |
| 625 | 8.20 |
| 626 | 7.25 |
| 627 | 7.64 |
| 630 | 7.38 |
| 631 | 7.61 |
| 632 | 7.57 |
| 633 | 8.36 |
| 634 | 7.88 |
| 635 | 8.24 |
| 636 | 8.43 |
| 653 | 6.62 |
| 654 | 4.67 |

What is claimed is:

1. A compound of formula (I)

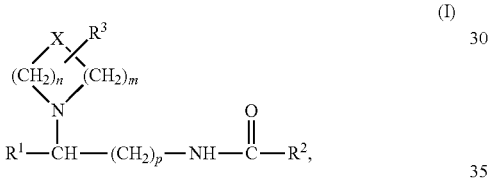

(I)

including any stereochemically isomeric form thereof, wherein n is an integer 1, 2 or 3;

m is an integer 1, 2 or 3;

p is an integer 1 or 2;

$R^3$ is hydrogen, halo, $C_{1-4}$alkyl or $C_{1-4}$alkyloxy;

X represents O, S, $SO_2$, $CR^4R^5$ or $NR^6$;

wherein $R^4$ and $R^5$ are each independently from another selected from hydrogen, halo, hydroxy, $C_{1-4}$alkyl, $C_{1-4}$alkyloxy, or aryl;

wherein $R^6$ is hydrogen, phenyl, —CO—$R^7$, or —CO—O—$R^7$, wherein $R^7$ is $C_{1-6}$alkyl or amino;

$R^1$ is a heterocycle selected from pyridinyl or pyrimidinyl, wherein said heterocycle is substituted with one or two substituents each independently from another selected from hydrogen, halo, hydroxy, $C_{1-6}$alkyl, $C_{1-6}$alkyloxy, polyhalo$C_{1-4}$alkyl, phenyl, $C_{3-6}$cycloalkyl, $C_{3-6}$cycloalkyloxy, $C_{3-6}$cycloalkyl$C_{1-4}$alkyloxy, or $NR^8R^9$;

wherein $R^8$ and $R^9$ are independently from another selected from hydrogen, $C_{1-6}$alkyl, hydroxy$C_{1-6}$alkyl, $C_{3-6}$cycloalkyl, and wherein $R^8$ and $R^9$ may be taken together with the nitrogen atom to which they are attached to form a azetidinyl, pyrrolidinyl, piperidinyl, piperazinyl or morpholinyl ring which may be optionally substituted with one or two substituents each independently from another selected from $C_{1-4}$alkyl, $C_{1-4}$alkyloxy, halo, hydroxy, or $C_{1-4}$alkylcarbonyl;

$R^2$ is a heterocycle selected from quinolinyl or isoquinolinyl, wherein said heterocycle is substituted with one or two substituents each independently from another selected from hydrogen, halo, hydroxy, $C_{1-6}$alkyl, $C_{1-6}$alkyloxy, $C_{3-6}$cycloalkyl, $C_{3-6}$cycloalkyloxy, polyhalo$C_{1-4}$alkyl, $NR^{10}R^{11}$, and $OR^{12}$;

wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, piperidinyl, N-(1,5-dioxa-9-aza-spiro[5.5]undec-9-yl), N-(1,7-diaza-spiro[4.4]non-7-yl), N-(2,6-diaza-spiro[4.5]dec-2-yl), and $C_{1-6}$alkyl substituted with one or two substituents selected from hydroxy, halo, aryl$^1$, $C_{1-4}$alkyloxy, $C_{3-6}$cycloalkyl, hydroxycarbonyl, $C_{1-4}$alkylsulfonylamino, $C_{3-6}$cycloalkylsulfonylamino, tetrahydrofuranyl, tetrahydropyranyl, pyrrolidinyl, pyridinyl, morpholinyl, amino, mono- or di($C_{1-4}$alkyl)amino, amino substituted with $C_{1-4}$alkyl substituted with hydroxy; and wherein $R^{10}$ and $R^{11}$ may be taken together with the nitrogen atom to which they are attached to form a azetidinyl, pyrrolidinyl, piperidinyl, piperazinyl, azepanyl, N-[1,4]-oxazepanyl, morpholinyl, N-(2,6-diaza-spiro[3.3]hept-2-yl), 6-acetyl-2,6-diaza-bicyclo[2.2.2]octane-2-yl, 2-(tetrahydro-furo[3,4-c]pyrrol-5-yl), 2-(2-oxa-5-aza-bicyclo[2.2.1]hept-5-yl), 1,1-dioxo-thiomorpholin-4-yl, 2-(2,6-diaza-bicyclo[2.2.1]hept-2-yl), 1-(1-amino-3-aza-bicyclo[3.1.0]hex-3-yl), N-(3-acetylamino-8-aza-bicyclo[3.2.1]oct-8-yl), N-[1,4]-diazepanyl, 2-(hexahydro-pyrrolo[3,4-c]pyrrol-2-yl), 2-(hexahydro-pyrrolo[3,4-b]pyrrol-1-yl), 2-(hexahydro-pyrrolo[3,4-b]pyrrol-5-yl), 2-(octahydro-pyrrolo[3,4-b]pyridin-6-yl), or 2-(3,6-diaza-bicyclo[3.2.0]hept-3-yl), 1-amino-3-aza-bicyclo[3.1.0]hex-3-yl ring; which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino, $C_{1-6}$alkyl substituted with hydroxy; trifluoromethyl, amino, mono- or di($C_{1-4}$alkyl)amino, amino, mono- or di($C_{1-4}$alkyl)amino, trifluoromethyl, N-(2-oxo-pyrrolidin-1-yl), 2,4-dihydro-[1,2,4]triazolone-5-yl, $C_{1-4}$alkylcarbonylamino, 2,4-dihydro-[1,2,4]triazolone-4-yl, ($C_{1-4}$alkylcarbonyl)($C_{1-4}$alkyl)amino, trifluoromethylcarbonylamino, hydroxycarbonyl, methylsulfonylamino, aminocarbonyl;

wherein $R^{12}$ is azetidinyl, pyrrolidinyl, piperidinyl, or $C_{1-6}$alkyl substituted with amino, $C_{3-6}$cycloalkyl, trifluoromethyl, trifluoroethyl, tetrahydrofuranyl, N-(1-methylpyrrolidinyl), N-(5-oxo-pyrrolidin-2-yl), or pyridinyl;

aryl is phenyl or phenyl substituted with one substituent selected from halo, $C_{1-4}$alkyl, $C_{1-4}$alkyloxy or hydroxy;

aryl$^1$ is phenyl or phenyl substituted with one substituent selected from halo, $C_{1-4}$alkyl, $C_{1-4}$alkyloxy or hydroxy;

or a pharmaceutically acceptable acid addition salt thereof.

2. The compound as claimed in claim 1 wherein n is an integer 1, 2 or 3;

m is an integer 1, 2 or 3;

p is an integer 1 or 2;

$R^3$ is hydrogen, halo, $C_{1-4}$alkyl or $C_{1-4}$alkyloxy;

X represents O, S, $SO_2$, $CR^4R^5$ or $NR^6$;

wherein $R^4$ and $R^5$ are each independently from another selected from hydrogen, halo, hydroxy, $C_{1-4}$alkyl, $C_{1-4}$alkyloxy, or aryl;

wherein $R^6$ is hydrogen, phenyl, —CO—$R^7$, or —CO—O—$R^7$, wherein $R^7$ is $C_{1-6}$alkyl or amino;

R¹ is a heterocycle selected from pyridinyl or pyrimidinyl, wherein said heterocycle is substituted with one or two substituents each independently from another selected from hydrogen, halo, hydroxy, $C_{1-6}$alkyl, $C_{1-6}$alkyloxy, polyhalo$C_{1-4}$alkyl, phenyl, $C_{3-6}$cycloalkyl, $C_{3-6}$cycloalkyloxy, $C_{3-6}$cycloalkyl$C_{1-4}$alkyloxy, or $NR^8R^9$;
  wherein $R^8$ and $R^9$ are independently from another selected from hydrogen, $C_{1-6}$alkyl, $C_{3-6}$cycloalkyl, and
  wherein $R^8$ and $R^9$ may be taken together with the nitrogen atom to which they are attached to form a pyrrolidinyl, piperidinyl, piperazinyl or morpholinyl ring which may be optionally substituted with one or two substituents each independently from another selected from $C_{1-4}$alkyl, $C_{1-4}$alkyloxy, halo, hydroxy, or $C_{1-4}$alkylcarbonyl;
R² is a heterocycle selected from quinolinyl or isoquinolinyl, wherein said heterocycle is substituted with one or two substituents each independently from another selected from hydrogen, halo, hydroxy, $C_{1-6}$alkyl, $C_{1-6}$alkyloxy, $C_{3-6}$cycloalkyl, $C_{3-6}$cycloalkyloxy, polyhalo$C_{1-4}$alkyl, and $NR^{10}R^{11}$;
  wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, or $C_{1-6}$alkyl substituted with hydroxy, halo, phenyl, $C_{1-4}$alkyloxy, $C_{3-6}$cycloalkyl, tetrahydrofuranyl, tetrahydropyranyl, or morpholinyl; and
  wherein $R^{10}$ and $R^{11}$ may be taken together with the nitrogen atom to which they are attached to form a azetidinyl, pyrrolidinyl, piperidinyl, piperazinyl, azepanyl, N-[1,4]-oxazepanyl or morpholinyl ring which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino or $C_{1-6}$alkylsubstituted with hydroxy;
aryl is phenyl or phenyl substituted with one substituent selected from halo, $C_{1-4}$alkyl, $C_{1-4}$alkyloxy or hydroxy; or a pharmaceutically acceptable acid addition salt thereof.

3. The compound as claimed in claim 1 wherein R¹ is a heterocycle selected from pyridinyl or pyrimidinyl wherein said heterocycle is substituted with one substituent selected from hydrogen, halo, hydroxy, $C_{1-6}$alkyl, $C_{1-6}$alkyloxy, polyhalo$C_{1-4}$alkyl or phenyl.

4. The compound as claimed in claim 1 wherein R² is a heterocycle selected from quinolinyl or isoquinolinyl, wherein said heterocycle is substituted with one or two substituents each independently from another selected from hydrogen, halo, hydroxy, $C_{1-6}$alkyl or $C_{1-6}$alkyloxy.

5. The compound as claimed in claim 1 wherein R² is a heterocycle selected from quinolinyl or isoquinolinyl, wherein said heterocycle is substituted with $NR^{10}R^{11}$ wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, or $C_{1-6}$alkyl substituted with hydroxy, halo, phenyl, $C_{1-4}$alkyloxy, $C_{3-6}$cycloalkyl, tetrahydrofuranyl, tetrahydropyranyl, or morpholinyl.

6. The compound as claimed in claim 1 wherein R² is a heterocycle selected from quinolinyl or isoquinolinyl, wherein said heterocycle is substituted with $NR^{10}R^{11}$ wherein $R^{10}$ and $R^{11}$ are taken together with the nitrogen atom to which they are attached to form a azetidinyl, pyrrolidinyl, piperidinyl, piperazinyl, azepanyl, N-[1,4]-oxazepanyl or morpholinyl ring which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino or $C_{1-6}$alkylsubstituted with hydroxy.

7. The compound as claimed in claim 1 wherein R³ is hydrogen, n is an integer 2, m is an integer 3, and X represents O.

8. The compound as claimed in claim 1 wherein n is an integer 2, m is an integer 2, and X represents $CR^4R^5$ wherein $R^4$ and $R^5$ are each fluoro.

9. The compound as claimed in claim 1 wherein n is an integer 1, m is an integer 3, and X represents $CR^4R^5$ wherein $R^4$ and $R^5$ are each fluoro.

10. The compound as claimed in claim 1 wherein R¹ is 2-trifluoro-methylpyridin-5-yl or R¹ is 2-trifluoromethylpyrimidin-5-yl.

11. A pharmaceutical composition comprising a pharmaceutically acceptable carrier and a therapeutically effective amount of a compound as claimed in formula (I)

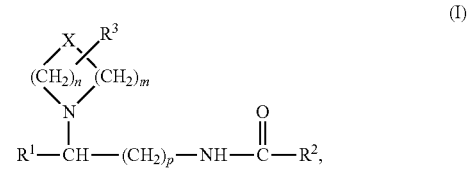

including any stereochemically isomeric form thereof, wherein
n is an integer 1, 2 or 3;
m is an integer 1, 2 or 3;
p is an integer 1 or 2;
R³ is hydrogen, halo, $C_{1-4}$alkyl or $C_{1-4}$alkyloxy;
X represents O, S, $SO_2$, $CR^4R^5$ or $NR^6$;
  wherein $R^4$ and $R^5$ are each independently from another selected from hydrogen, halo, hydroxy, $C_{1-4}$alkyl, $C_{1-4}$alkyloxy, or aryl;
  wherein $R^6$ is hydrogen, phenyl, —CO—R⁷, or —CO—O—R⁷, wherein $R^7$ is $C_{1-6}$alkyl or amino;
R¹ is a heterocycle selected from pyridinyl or pyrimidinyl, wherein said heterocycle is substituted with one or two substituents each independently from another selected from hydrogen, halo, hydroxy, $C_{1-6}$alkyl, $C_{1-6}$alkyloxy, polyhalo$C_{1-4}$alkyl, phenyl, $C_{3-6}$cycloalkyl, $C_{3-6}$cycloalkyloxy, $C_{3-6}$cycloalkyl$C_{1-4}$alkyloxy, or $NR^8R^9$;
  wherein $R^8$ and $R^9$ are independently from another selected from hydrogen, $C_{1-6}$alkyl, hydroxy$C_{1-6}$alkyl, $C_{3-6}$cycloalkyl, and
  wherein $R^8$ and $R^9$ may be taken together with the nitrogen atom to which they are attached to form a azetidinyl, pyrrolidinyl, piperidinyl, piperazinyl or morpholinyl ring which may be optionally substituted with one or two substituents each independently from another selected from $C_{1-4}$alkyl, $C_{1-4}$alkyloxy, halo, hydroxy, or $C_{1-4}$alkylcarbonyl;
R² is a heterocycle selected from quinolinyl or isoquinolinyl, wherein said heterocycle is substituted with one or two substituents each independently from another selected from hydrogen, halo, hydroxy, $C_{1-6}$alkyl, $C_{1-6}$alkyloxy, $C_{3-6}$cycloalkyl, $C_{3-6}$cycloalkyloxy, polyhalo$C_{1-4}$alkyl, $NR^{10}R^{11}$, and $OR^{12}$;
  wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, piperidinyl, N-(1,5-dioxa-9-aza-spiro[5.5]undec-9-yl), N-(1,7-diaza-spiro[4.4]non-7-yl), N-(2,6-diaza-spiro[4.5]dec-2-yl), and $C_{1-6}$alkyl substituted with one or two substituents selected from hydroxy, halo, aryl$^1$, $C_{1-4}$alkyloxy, $C_{3-6}$cycloalkyl, hydroxycarbonyl, $C_{1-4}$alkylsulfonylamino, $C_{3-6}$cycloalkylsulfonylamino, tetrahydrofuranyl, tetrahydropyranyl, pyrrolidinyl, pyridinyl, morpholinyl, amino, mono- or di($C_{1-4}$alkyl)amino, amino substituted with $C_{1-4}$alkyl substituted with hydroxy; and wherein $R^{10}$ and $R^{11}$ may be taken together with the nitrogen atom to which they are attached to form a azetidinyl, pyrrolidinyl, piperidinyl, piperazinyl, azepanyl, N-[1,4]-oxazepanyl, morpholinyl, N-(2,6-diaza-spiro[3.3]hept-2-yl), 6-acetyl-2,6-diaza-bicyclo[2.2.2]octane-2-yl, 2-(tetrahydro-furo[3,4-c]pyrrol-5-yl), 2-(2-oxa-5-aza-bicyclo[2.2.1]hept-5-yl), 1,1-dioxo-thiomorpholin-4-yl, 2-(2,6-diaza-bicyclo[2.2.1]hept-2-yl), 1-(1-amino-3-aza-bicyclo[3.1.0]hex-3-yl), N-(3-acetylamino-8-aza-bicyclo[3.2.1]oct-8-yl), N-[1,4]-diazepanyl, 2-(hexahydro-pyrrolo[3,4-c]pyrrol-2-yl), 2-(hexahydro-pyrrolo[3,4-b]pyrrol-1-yl), 2-(hexahydro-pyrrolo[3,4-b]pyrrol-5-yl), 2-(octahydro-pyrrolo[3,4-b]pyridin-6-yl), or 2-(3,6-diaza-bicyclo[3.2.0]hept-3-yl), 1-amino-3-aza-bicyclo[3.1.0]hex-3-yl ring; which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino, $C_{1-6}$alkyl substituted with hydroxy; trifluoromethyl, amino, mono- or di($C_{1-4}$alkyl)amino, amino, mono- or di($C_{1-4}$alkyl)amino, trifluoromethyl, N-(2-oxo-pyrrolidin-1-yl), 2,4-dihydro-[1,2,4]triazolone-5-yl, $C_{1-4}$alkylcarbonylamino, 2,4-dihydro-[1,2,4]triazolone-4-yl, ($C_{1-4}$alkylcarbonyl)($C_{1-4}$alkyl)amino, trifluoromethylcarbonylamino, hydroxycarbonyl, methylsulfonylamino, aminocarbonyl;

wherein $R^{12}$ is azetidinyl, pyrrolidinyl, piperidinyl, or $C_{1-6}$alkyl substituted with amino, $C_{3-6}$cycloalkyl, trifluoromethyl, trifluoroethyl, tetrahydrofuranyl, N-(1-methylpyrrolidinyl), N-(5-oxo-pyrrolidin-2-yl), or pyridinyl;

aryl is phenyl or phenyl substituted with one substituent selected from halo, $C_{1-4}$alkyl, $C_{1-4}$alkyloxy or hydroxy;
aryl$^1$ is phenyl or phenyl substituted with one substituent selected from halo, $C_{1-4}$alkyl, $C_{1-4}$alkyloxy or hydroxy;
or a pharmaceutically acceptable acid addition salt thereof.

12. A process for preparing a compound of formula (I)

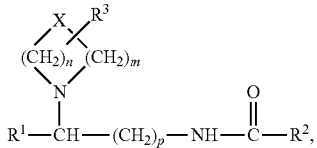

(I)

including any stereochemically isomeric form thereof, wherein
n is an integer 1, 2 or 3;
m is an integer 1, 2 or 3;
p is an integer 1 or 2;
$R^3$ is hydrogen, halo, $C_{1-4}$alkyl or $C_{1-4}$alkyloxy;
X represents O, S, SO$_2$, CR$^4$R$^5$ or NR$^6$;

wherein $R^4$ and $R^5$ are each independently from another selected from hydrogen, halo, hydroxy, $C_{1-4}$alkyl, $C_{1-4}$alkyloxy, or aryl;
wherein $R^6$ is hydrogen, phenyl, —CO—R$^7$, or —CO—O—R$^7$, wherein R$^7$ is $C_{1-6}$alkyl or amino;

$R^1$ is a heterocycle selected from pyridinyl or pyrimidinyl, wherein said heterocycle is substituted with one or two substituents each independently from another selected from hydrogen, halo, hydroxy, $C_{1-6}$alkyl, $C_{1-6}$alkyloxy, polyhalo$C_{1-4}$alkyl, phenyl, $C_{3-6}$cycloalkyl, $C_{3-6}$cycloalkyloxy, $C_{3-6}$cycloalkyl$C_{1-4}$alkyloxy, or NR$^8$R$^9$;

wherein R$^8$ and R$^9$ are independently from another selected from hydrogen, $C_{1-6}$alkyl, hydroxy$C_{1-6}$alkyl, $C_{3-6}$cycloalkyl, and wherein R$^8$ and R$^9$ may be taken together with the nitrogen atom to which they are attached to form a azetidinyl, pyrrolidinyl, piperidinyl, piperazinyl or morpholinyl ring which may be optionally substituted with one or two substituents each independently from another selected from $C_{1-4}$alkyl, $C_{1-4}$alkyloxy, halo, hydroxy, or $C_{1-4}$alkylcarbonyl;

$R^2$ is a heterocycle selected from quinolinyl or isoquinolinyl, wherein said heterocycle is substituted with one or two substituents each independently from another selected from hydrogen, halo, hydroxy, $C_{1-6}$alkyl, $C_{1-6}$alkyloxy, $C_{3-6}$cycloalkyl, $C_{3-6}$cycloalkyloxy, polyhalo$C_{1-4}$alkyl, NR$^{10}$R$^{11}$, and OR$^{12}$;

wherein $R^{10}$ and $R^{11}$ are independently from another selected from hydrogen, $C_{1-6}$alkyl, $C_{3-6}$cycloalkyl, polyhalo$C_{1-4}$alkyl, tetrahydrofuranyl, tetrahydropyranyl, piperidinyl, N-(1,5-dioxa-9-aza-spiro[5.5]undec-9-yl), N-(1,7-diaza-spiro[4.4]non-7-yl), N-(2,6-diaza-spiro[4.5]dec-2-yl), and $C_{1-6}$alkyl substituted with one or two substituents selected from hydroxy, halo, aryl$^1$, $C_{1-4}$alkyloxy, $C_{3-6}$cycloalkyl, hydroxycarbonyl, $C_{1-4}$alkylsulfonylamino, $C_{3-6}$cycloalkylsulfonylamino, tetrahydrofuranyl, tetrahydropyranyl, pyrrolidinyl, pyridinyl, morpholinyl, amino, mono- or di($C_{1-4}$alkyl)amino, amino substituted with $C_{1-4}$alkyl substituted with hydroxy; and wherein $R^{10}$ and $R^{11}$ may be taken together with the nitrogen atom to which they are attached to form a azetidinyl, pyrrolidinyl, piperidinyl, piperazinyl, azepanyl, N-[1,4]-oxazepanyl, morpholinyl, N-(2,6-diaza-spiro[3.3]hept-2-yl), 6-acetyl-2,6-diaza-bicyclo[2.2.2]octane-2-yl, 2-(tetrahydro-furo[3,4-c]pyrrol-5-yl), 2-(2-oxa-5-aza-bicyclo[2.2.1]hept-5-yl), 1,1-dioxo-thiomorpholin-4-yl, 2-(2,6-diaza-bicyclo[2.2.1]hept-2-yl), 1-(1-amino-3-aza-bicyclo[3.1.0]hex-3-yl), N-(3-acetylamino-8-aza-bicyclo[3.2.1]oct-8-yl), N-[1,4]-diazepanyl, 2-(hexahydro-pyrrolo[3,4-c]pyrrol-2-yl), 2-(hexahydro-pyrrolo[3,4-b]pyrrol-1-yl), 2-(hexahydro-pyrrolo[3,4-b]pyrrol-5-yl), 2-(octahydro-pyrrolo[3,4-b]pyridin-6-yl), or 2-(3,6-diaza-bicyclo[3.2.0]hept-3-yl), 1-amino-3-aza-bicyclo[3.1.0]hex-3-yl ring; which may be optionally substituted with one or two substituents each independently from another selected from halo, hydroxy, $C_{1-4}$alkyl, $C_{1-4}$alkyloxy, $C_{1-4}$alkyloxy$C_{1-4}$alkyl, $C_{3-6}$cycloalkyl, $C_{1-4}$alkylcarbonyl, $C_{1-4}$alkyloxycarbonyl, $C_{1-4}$alkyloxycarbonylamino, $C_{1-6}$alkyl substituted with hydroxy; trifluoromethyl, amino, mono- or di($C_{1-4}$alkyl)amino, amino, mono- or di($C_{1-4}$alkyl)amino, trifluoromethyl, N-(2-oxo-pyrrolidin-1-yl), 2,4-dihydro-[1,2,4]triazolone-5-yl, $C_{1-4}$alkylcarbonylamino, 2,4-dihydro-[1,2,4]triazolone-4-yl, ($C_{1-4}$alkylcarbonyl)($C_{1-4}$alkyl)amino, trifluoromethylcarbonylamino, hydroxycarbonyl, methylsulfonylamino, aminocarbonyl;

wherein R$^{12}$ is azetidinyl, pyrrolidinyl, piperidinyl, or C$_{1-6}$alkyl substituted with amino, C$_{3-6}$cycloalkyl, trifluoromethyl, trifluoroethyl, tetrahydrofuranyl, N-(1-methylpyrrolidinyl), N-(5-oxo-pyrrolidin-2-yl), or pyridinyl;

aryl is phenyl or phenyl substituted with one substituent selected from halo, C$_{1-4}$alkyl, C$_{1-4}$alkyloxy or hydroxy;

aryl$^1$ is phenyl or phenyl substituted with one substituent selected from halo, C$_{1-4}$alkyl, C$_{1-4}$alkyloxy or hydroxy;

or a pharmaceutically acceptable acid addition salt thereof wherein a) an intermediate of formula (II) is reacted with an intermediate of formula (III), in at least one reaction-inert solvent and optionally in the presence of at least one suitable coupling reagent and/or a suitable base;

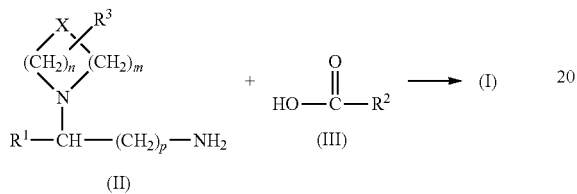

b) an intermediate of formula (II) is reacted with an intermediate of formula (IV), wherein W is an appropriate leaving group in a reaction-inert solvent and optionally in the presence of a suitable base;

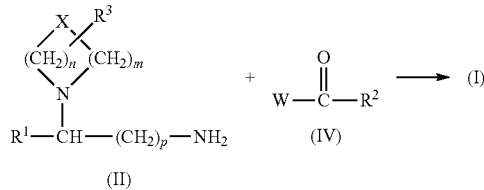

or c) compounds of formula (I) are converted into each other following art-known transformation reactions; or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

* * * * *

UNITED STATES PATENT AND TRADEMARK OFFICE
CERTIFICATE OF CORRECTION

| | | |
|---|---|---|
| PATENT NO. | : 8,431,704 B2 | Page 1 of 1 |
| APPLICATION NO. | : 12/988891 | |
| DATED | : April 30, 2013 | |
| INVENTOR(S) | : Love et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Second Day of December, 2014

Michelle K. Lee
*Deputy Director of the United States Patent and Trademark Office*